United States Patent
van Duzer et al.

(10) Patent No.: US 10,774,056 B2
(45) Date of Patent: Sep. 15, 2020

(54) SUBSTITUTED PIPERAZINES AS SELECTIVE HDAC1,2 INHIBITORS

(71) Applicant: REGENACY PHARMACEUTICALS, LLC, Waltham, MA (US)

(72) Inventors: John H. van Duzer, Concord, MA (US); Ralph Mazitschek, Weston, MA (US)

(73) Assignee: REGENACY PHARMACEUTICALS, INC., Waltham, MA (US)

(*) Notice: Subject to any disclaimer, the term of this patent is extended or adjusted under 35 U.S.C. 154(b) by 0 days.

(21) Appl. No.: 16/507,727

(22) Filed: Jul. 10, 2019

(65) Prior Publication Data
US 2019/0330169 A1 Oct. 31, 2019

Related U.S. Application Data

(62) Division of application No. 15/820,827, filed on Nov. 22, 2017, now Pat. No. 10,385,031.

(60) Provisional application No. 62/506,344, filed on May 15, 2017, provisional application No. 62/425,938, filed on Nov. 23, 2016.

(51) Int. Cl.
| | | |
|---|---|---|
| A61K 31/496 | (2006.01) |
| C07D 295/00 | (2006.01) |
| C07D 295/155 | (2006.01) |
| A61P 35/02 | (2006.01) |
| C07D 405/12 | (2006.01) |
| C07D 401/12 | (2006.01) |
| C07D 213/82 | (2006.01) |
| C07D 409/12 | (2006.01) |
| C07D 333/20 | (2006.01) |
| C07D 307/52 | (2006.01) |
| C07D 213/40 | (2006.01) |
| C07D 417/12 | (2006.01) |
| C07D 277/56 | (2006.01) |
| C07D 413/12 | (2006.01) |
| C07D 263/48 | (2006.01) |
| A61P 35/00 | (2006.01) |
| A61P 7/00 | (2006.01) |
| C07D 215/48 | (2006.01) |
| C07D 401/04 | (2006.01) |
| C07D 401/14 | (2006.01) |
| C07D 405/14 | (2006.01) |
| C07D 409/14 | (2006.01) |
| C07D 413/04 | (2006.01) |
| C07D 417/14 | (2006.01) |

(52) U.S. Cl.
CPC ............ *C07D 295/155* (2013.01); *A61P 7/00* (2018.01); *A61P 35/00* (2018.01); *A61P 35/02* (2018.01); *C07D 213/40* (2013.01); *C07D 213/82* (2013.01); *C07D 215/48* (2013.01); *C07D 263/48* (2013.01); *C07D 277/56* (2013.01); *C07D 307/52* (2013.01); *C07D 333/20* (2013.01); *C07D 401/04* (2013.01); *C07D 401/12* (2013.01); *C07D 401/14* (2013.01); *C07D 405/12* (2013.01); *C07D 405/14* (2013.01); *C07D 409/12* (2013.01); *C07D 409/14* (2013.01); *C07D 413/04* (2013.01); *C07D 413/12* (2013.01); *C07D 417/12* (2013.01); *C07D 417/14* (2013.01)

(58) Field of Classification Search
CPC ........................... A61K 31/496; C07D 295/00
USPC ...................................... 514/252.12; 544/358
See application file for complete search history.

(56) References Cited

U.S. PATENT DOCUMENTS

| | | | |
|---|---|---|---|
| 8,598,168 B2 | 12/2013 | Moradei | |
| 9,096,549 B2* | 8/2015 | van Duzer | ........... C07D 235/06 |
| 2014/0128391 A1 | 5/2014 | Van Duzer et al. | |

FOREIGN PATENT DOCUMENTS

| | | |
|---|---|---|
| WO | 2007118137 A1 | 10/2007 |
| WO | 2009033281 A1 | 3/2009 |

OTHER PUBLICATIONS

Jordan, V.C. Nature Reviews: Drug Discovery, 2, 2003, 2005.
Hackam, et al., JAMA, 296(14), 2006, 1731-1732.
International Search Report and Written Opinion of PCT/US2017/063037 dated Apr. 25, 2018 (19 pages).

* cited by examiner

*Primary Examiner* — Douglas M Willis
(74) *Attorney, Agent, or Firm* — Brian C. Trinque; Lathrop GPM LLP

(57) ABSTRACT

Provided herein are substituted piperazine compounds, pharmaceutical compositions comprising such compounds, and methods of using such compounds to treat diseases or disorders associated with HDAC1 and/or HDAC2 activity.

4 Claims, No Drawings

SUBSTITUTED PIPERAZINES AS SELECTIVE HDAC1,2 INHIBITORS

CROSS-REFERENCE TO RELATED APPLICATIONS

This application is a divisional of U.S. application Ser. No. 15/820,827, filed Nov. 22, 2017, which claims the benefit of U.S. Provisional Application No. 62/425,938, filed Nov. 23, 2016, and U.S. Provisional Application No. 62/506,344, filed May 15, 2017. The entire contents of these applications are incorporated herein in their entireties.

BACKGROUND

A biological target of current interest is histone deacetylase (HDAC) (see, for example, a discussion of the use of inhibitors of histone deacetylases for the treatment of cancer: Marks et al. *Nature Reviews Cancer* 2001, 7, 194; Johnstone et al. *Nature Reviews Drug Discovery* 2002, 287). Post-translational modification of proteins through acetylation and deacetylation of lysine residues plays a critical role in regulating their cellular functions. HDACs are zinc hydrolases that modulate gene expression through deacetylation of the N-acetyl-lysine residues of histone proteins and other transcriptional regulators (Hassig et al. *Curr. Opin. Chem. Biol.* 1997, 1, 300-308). HDACs participate in cellular pathways that control cell shape and differentiation, and an HDAC inhibitor has been shown to be effective in treating an otherwise recalcitrant cancer (Warrell et al. *J. Natl. Cancer Inst.* 1998, 90, 1621-1625).

Eleven human HDACs, which use Zn as a cofactor, have been identified (Taunton et al. *Science* 1996, 272, 408-411; Yang et al. *J. Biol. Chem.* 1997, 272, 28001-28007. Grozinger et al. *Proc. Natl. Acad. Sci. U.S.A.* 1999, 96, 4868-4873; Kao et al. *Genes Dev.* 2000, 14, 55-66. Hu et al. *J. Biol. Chem.* 2000, 275, 15254-15264; Zhou et al. *Proc. Natl. Acad. Sci U.S.A.* 2001, 98, 10572-10577; Venter et al. *Science* 2001, 291, 1304-1351) and these members fall into three classes (class I, II, and IV) based on sequence homology to their yeast orthologues (O. Witt et al. *Cancer Letters*, 2009, 277, 8-21). Class I HDACs include HDAC1, HDAC2, HDAC3, and HDAC8, and are referred to as "classical" HDACs, which implies a catalytic pocket with a $Zn^{2+}$ ion at its base.

There remains a need for preparing structurally diverse HDAC inhibitors, particularly ones that are potent and/or selective inhibitors of particular classes of HDACs and individual HDACs.

SUMMARY

Provided herein are compounds and methods of using these compounds to treat disorders related to HDAC1 or HDAC2 function, including cancer, myelodysplastic syndrome or hemoglobinopathy.

Thus, in an aspect, provided herein are compounds of Formula I:

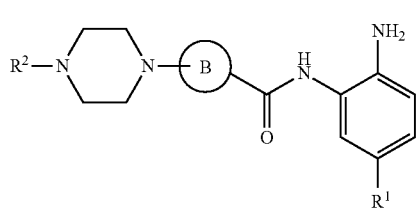

or a pharmaceutically acceptable salt thereof.

Also provided herein is a pharmaceutical composition comprising a compound of Formula I, or a pharmaceutically acceptable salt thereof, together with a pharmaceutically acceptable carrier.

In another aspect, provided herein are compounds of Formula II:

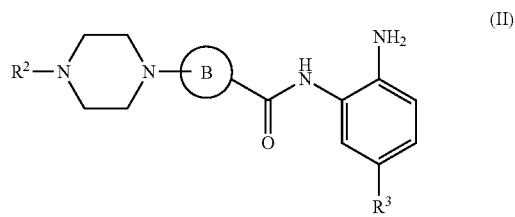

or a pharmaceutically acceptable salt thereof.

Also provided herein is a pharmaceutical composition comprising a compound of Formula II, or a pharmaceutically acceptable salt thereof, together with a pharmaceutically acceptable carrier.

In a further aspect, provided here are compounds of Formula III:

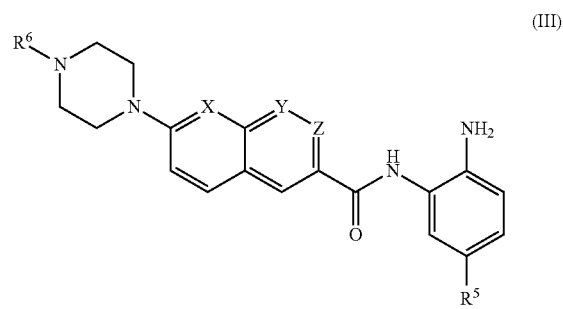

or a pharmaceutically acceptable salt thereof.

Also provided herein is a pharmaceutical composition comprising a compound of Formula III, or a pharmaceutically acceptable salt thereof, together with a pharmaceutically acceptable carrier.

In yet another aspect, provided herein are compounds of Formula IV:

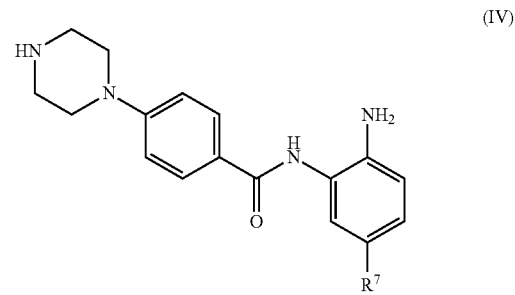

or a pharmaceutically acceptable salt thereof.

Also provided herein is a pharmaceutical composition comprising a compound of Formula III, or a pharmaceutically acceptable salt thereof, together with a pharmaceutically acceptable carrier.

In an aspect, provided herein is a method of inhibiting the activity of HDAC1 and/or HDAC2 in a subject in need thereof, comprising administering to the subject a compound of Formula I, or a pharmaceutically acceptable salt thereof.

In an aspect, provided herein is a method of inhibiting the activity of HDAC1 and/or HDAC2 in a subject in need thereof, comprising administering to the subject a compound of Formula II, Formula III, Formula IV, or a pharmaceutically acceptable salt thereof.

In another aspect, provided herein is a method of treating a disease mediated by HDAC1 and/or HDAC2 in a subject in need thereof, comprising administering to the subject a compound of Formula I, or a pharmaceutically acceptable salt thereof.

In another aspect, provided herein is a method of treating a disease mediated by HDAC1 and/or HDAC2 in a subject in need thereof, comprising administering to the subject a compound of Formula II, Formula III, Formula IV, or a pharmaceutically acceptable salt thereof.

In yet another aspect, provided herein is a method of treating a myelodysplastic syndrome in a subject in need thereof, comprising administering to the subject a compound of Formula I, or a pharmaceutically acceptable salt thereof.

In yet another aspect, provided herein is a method of treating a myelodysplastic syndrome in a subject in need thereof, comprising administering to the subject a compound of Formula II, Formula III, Formula IV, or a pharmaceutically acceptable salt thereof.

In another aspect, provided herein is a method of treating a hemoglobinopathy in a subject in need thereof, comprising administering to the subject a compound of Formula I, or a pharmaceutically acceptable salt thereof. In an embodiment, the hemoglobinopathy is sickle-cell disease or beta-thalassemia.

In another aspect, provided herein is a method of treating a hemoglobinopathy in a subject in need thereof, comprising administering to the subject a compound of Formula II, Formula III, Formula IV, or a pharmaceutically acceptable salt thereof. In an embodiment, the hemoglobinopathy is sickle-cell disease or beta-thalassemia.

In another aspect, provided herein is a method of treating a cancer in a subject in need thereof, comprising administering to the subject a compound of Formula I, or a pharmaceutically acceptable salt thereof. In an embodiment, the cancer is lung cancer, colon cancer, breast cancer, neuroblastoma, leukemia, or lymphoma. In a further embodiment, the cancer is acute myelogenous leukemia or acute megakaryocytic leukemia. In yet another embodiment, the cancer is neuroblastoma.

In another aspect, provided herein is a method of treating a cancer in a subject in need thereof, comprising administering to the subject a compound of Formula II, Formula III, Formula IV, or a pharmaceutically acceptable salt thereof. In an embodiment, the cancer is lung cancer, colon cancer, breast cancer, neuroblastoma, leukemia, or lymphoma. In a further embodiment, the cancer is acute myelogenous leukemia or acute megakaryocytic leukemia. In yet another embodiment, the cancer is neuroblastoma.

In a further aspect, provided herein is a method for treating sickle cell disease, beta thalassemia, myelodysplastic syndrome, acute myelogenous leukemia, neuroblastoma, or acute megakaryocytic leukemia in a subject in need thereof, comprising administering to the subject a therapeutically effective amount of a compound of a compound of Formula I, or a pharmaceutically acceptable salt thereof.

In a further aspect, provided herein is a method for treating sickle cell disease, beta thalassemia, myelodysplastic syndrome, acute myelogenous leukemia, neuroblastoma, or acute megakaryocytic leukemia in a subject in need thereof, comprising administering to the subject a therapeutically effective amount of a compound of a compound of Formula II, Formula III, Formula IV, or a pharmaceutically acceptable salt thereof.

DETAILED DESCRIPTION

Provided herein are compounds, e.g., the compounds of Formula I or pharmaceutically acceptable salts thereof, that are useful in the treatment of cancer, myelodysplastic syndrome or hemoglobinopathy in a subject.

In a non-limiting aspect, these compounds can inhibit histone deacetylases. In a particular embodiment, the compounds provided herein are considered HDAC1 and/or HDAC2 inhibitors. As such, in one aspect, the compounds provided herein are useful in the treatment of cancer, myelodysplastic syndrome or hemoglobinopathy in a subject by acting as a HDAC1 and/or HDAC2 inhibitor.

Definitions

Listed below are definitions of various terms used to describe this invention. These definitions apply to the terms as they are used throughout this specification and claims, unless otherwise limited in specific instances, either individually or as part of a larger group.

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and peptide chemistry are those well-known and commonly employed in the art.

As used herein, the articles "a" and "an" refer to one or to more than one (i.e., to at least one) of the grammatical object of the article. By way of example, "an element" means one element or more than one element. Furthermore, use of the term "including" as well as other forms, such as "include," "includes," and "included," is not limiting.

As used herein, the term "about" will be understood by persons of ordinary skill in the art and will vary to some extent on the context in which it is used. As used herein when referring to a measurable value such as an amount, a temporal duration, and the like, the term "about" is meant to encompass variations of ±20% or ±10%, including ±5%, ±1%, and ±0.1% from the specified value, as such variations are appropriate to perform the disclosed methods.

The term "treat," "treated," "treating," or "treatment" includes the diminishment or alleviation of at least one symptom associated or caused by the state, disorder or disease being treated. In certain embodiments, the treatment comprises bringing into contact with HDAC1 and/or HDAC2 an effective amount of a compound of the invention for conditions related to cancers, hemoglobinopathies, or myelodysplastic syndrome.

As used herein, the term "prevent" or "prevention" means no disorder or disease development if none had occurred, or no further disorder or disease development if there had already been development of the disorder or disease. Also considered is the ability of one to prevent some or all of the symptoms associated with the disorder or disease.

The phrase "jointly therapeutically active" or "joint therapeutic effect" as used herein means that the therapeutic agents can be given separately (in a chronologically staggered manner, especially a sequence-specific manner) in such time intervals that they prefer, in the warm-blooded animal, especially human, to be treated, still show an (preferably synergistic) interaction (joint therapeutic effect). Whether this is the case can, inter alia, be determined by following the blood levels of the compounds, showing that both compounds are present in the blood of the human to be treated at least during certain time intervals.

As used herein, the term "resistant" or "refractive" to a therapeutic agent when referring to a cancer patient means that the cancer has innate, or achieved resistance to, the effects of the therapeutic agent as a result of contact with the therapeutic agent. Stated alternatively, the cancer is resistant to the ordinary standard of care associated with the particular therapeutic agent.

As used herein, the term "patient," "individual," or "subject" refers to a human or a non-human mammal. Non-human mammals include, for example, livestock and pets, such as ovine, bovine, porcine, canine, feline and marine mammals. Preferably, the patient, subject, or individual is human.

As used herein, the terms "effective amount," "pharmaceutically effective amount," and "therapeutically effective amount" refer to a nontoxic but sufficient amount of an agent to provide the desired biological result. That result may be reduction or alleviation of the signs, symptoms, or causes of a disease, or any other desired alteration of a biological system. An appropriate therapeutic amount in any individual case may be determined by one of ordinary skill in the art using routine experimentation.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the term "pharmaceutically acceptable salt" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. The phrase "pharmaceutically acceptable salt" is not limited to a mono, or 1:1, salt. For example, "pharmaceutically acceptable salt" also includes bis-salts, such as a bis-hydrochloride salt. Lists of suitable salts are found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in its entirety.

As used herein, the term "composition" or "pharmaceutical composition" refers to a mixture of at least one compound useful within the invention with a pharmaceutically acceptable carrier. The pharmaceutical composition facilitates administration of the compound to a patient or subject. Multiple techniques of administering a compound exist in the art including, but not limited to, intravenous, oral, aerosol, parenteral, ophthalmic, pulmonary, and topical administration.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations.

As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example, in Remington's Pharmaceutical Sciences (Genaro, Ed., Mack Publishing Co., 1985, Easton, Pa.), which is incorporated herein by reference.

The terms "combination," "therapeutic combination," or "pharmaceutical combination" as used herein refer to either a fixed combination in one dosage unit form, or non-fixed combination, or a kit of parts for the combined administration where two or more therapeutic agents may be administered independently, at the same time or separately within time intervals, especially where these time intervals allow that the combination partners show a cooperative, e.g., synergistic, effect.

The term "combination therapy" refers to the administration of two or more therapeutic agents to treat a therapeutic condition or disorder described in the present disclosure. Such administration encompasses co-administration of these therapeutic agents in a substantially simultaneous manner, such as in a single formulation having a fixed ratio of active ingredients or in separate formulations (e.g., capsules and/or intravenous formulations) for each active ingredient. In addition, such administration also encompasses use of each type of therapeutic agent in a sequential or separate manner, either at approximately the same time or at different times. Regardless of whether the active ingredients are administered as a single formulation or in separate formulations, the drugs are administered to the same patient as part of the same course of therapy. In any case, the treatment regimen will provide beneficial effects in treating the conditions or disorders described herein.

An "oral dosage form" includes a unit dosage form prescribed or intended for oral administration. In an embodiment of the pharmaceutical combinations provided herein, the HDAC6 inhibitor (e.g., Compounds A or B) is administered as an oral dosage form.

The term "HDAC" refers to histone deacetylases, which are enzymes that remove the acetyl groups from the lysine residues in core histones, thus leading to the formation of a condensed and transcriptionally silenced chromatin. There are currently 18 known histone deacetylases, which are classified into four groups. Class I HDACs, which include HDAC1, HDAC2, HDAC3, and HDAC8, are related to the yeast RPD3 gene. Class II HDACs, which include HDAC4, HDAC5, HDAC6, HDAC7, HDAC9, and HDAC10, are related to the yeast Hda1 gene. Class III HDACs, which are also known as the sirtuins are related to the Sir2 gene and include SIRT1-7. Class IV HDACs, which contains only HDAC11, has features of both Class I and II HDACs. The term "HDAC" refers to any one or more of the 18 known histone deacetylases, unless otherwise specified.

As used herein, the term "alkyl," by itself or as part of another substituent means, unless otherwise stated, a straight or branched chain hydrocarbon having the number of carbon atoms designated (i.e., $C_1$-$C_6$-alkyl means an alkyl having one to six carbon atoms) and includes straight and branched chains. In an embodiment, $C_1$-$C_6$ alkyl groups are provided herein. Examples include methyl, ethyl, propyl, isopropyl, butyl, isobutyl, tert-butyl, pentyl, neopentyl, and hexyl. Other examples of $C_1$-$C_6$-alkyl include ethyl, methyl, isopropyl, isobutyl, n-pentyl, and n-hexyl.

As used herein, the term "alkoxy," refers to the group —O-alkyl, wherein alkyl is as defined herein. Alkoxy includes, by way of example, methoxy, ethoxy, n-propoxy, isopropoxy, n-butoxy, sec-butoxy, t-butoxy and the like. In an embodiment, $C_1$-$C_6$ alkoxy groups are provided herein.

As used herein, the term "halo" or "halogen" alone or as part of another substituent means, unless otherwise stated, a fluorine, chlorine, bromine, or iodine atom, preferably, fluorine, chlorine, or bromine, more preferably, fluorine or chlorine.

As used herein, the term "cycloalkyl" means a non-aromatic carbocyclic system that is partially or fully saturated having 1, 2 or 3 rings wherein such rings may be fused. The term "fused" means that a second ring is present (i.e., attached or formed) by having two adjacent atoms in common (i.e., shared) with the first ring. Cycloalkyl also includes bicyclic structures that may be bridged or spirocyclic in nature with each individual ring within the bicycle varying from 3-8 atoms. The term "cycloalkyl" includes, but is not limited to, cyclopropyl, cyclobutyl, cyclopentyl, cyclohexyl, bicyclo[3.1.0]hexyl, spiro[3.3]heptanyl, and bicyclo[1.1.1]pentyl. In an embodiment, $C_4$-$C_7$ cycloalkyl groups are provided herein.

As used herein, the term "heterocycloalkyl" means a non-aromatic carbocyclic system containing 1, 2, 3 or 4 heteroatoms selected independently from N, O, and S and having 1, 2 or 3 rings wherein such rings may be fused, wherein fused is defined above. Heterocycloalkyl also includes bicyclic structures that may be bridged or spirocyclic in nature with each individual ring within the bicycle varying from 3-8 atoms, and containing 0, 1, or 2 N, O, or S atoms. The term "heterocycloalkyl" includes cyclic esters (i.e., lactones) and cyclic amides (i.e., lactams) and also specifically includes, but is not limited to, epoxidyl, oxetanyl, tetrahydrofuranyl, tetrahydropyranyl (i.e., oxanyl), pyranyl, dioxanyl, aziridinyl, azetidinyl, pyrrolidinyl, 2,5-dihydro-1H-pyrrolyl, oxazolidinyl, thiazolidinyl, piperidinyl, morpholinyl, piperazinyl, thiomorpholinyl, 1,3-oxazinanyl, 1,3-thiazinanyl, 2-azabicyclo[2.1.1]hexanyl, 5-azabicyclo[2.1.1]hexanyl, 6-azabicyclo[3.1.1]heptanyl, 2-azabicyclo[2.2.1]heptanyl, 3-azabicyclo[3.1.1]heptanyl, 2-azabicyclo[3.1.1]heptanyl, 3-azabicyclo[3.1.0]hexanyl, 2-azabicyclo[3.1.0]hexanyl, 3-azabicyclo[3.2.1]octanyl, 8-azabicyclo[3.2.1]octanyl, 3-oxa-7-azabicyclo[3.3.1]nonanyl, 3-oxa-9-azabicyclo[3.3.1]nonanyl, 2-oxa-5-azabicyclo[2.2.1]heptanyl, 6-oxa-3-azabicyclo[3.1.1]heptanyl, 2-azaspiro[3.3]heptanyl, 2-oxa-6-azaspiro[3.3]heptanyl, 2-oxaspiro[3.3]heptanyl, 2-oxaspiro[3.5]nonanyl, 3-oxaspiro[5.3]nonanyl, and 8-oxabicyclo[3.2.1]octanyl. In an embodiment, $C_2$-$C_7$ heterocycloalkyl groups are provided herein.

As used herein, the term "aromatic" refers to a carbocycle or heterocycle with one or more polyunsaturated rings and having aromatic character, i.e., having (4n+2) delocalized π (pi) electrons, where n is an integer.

As used herein, the term "aryl" means an aromatic carbocyclic system containing 1, 2 or 3 rings, wherein such rings may be fused, wherein fused is defined above. If the rings are fused, one of the rings must be fully unsaturated and the fused ring(s) may be fully saturated, partially unsaturated or fully unsaturated. The term "aryl" includes, but is not limited to, phenyl, naphthyl, indanyl, and 1,2,3,4-tetrahydronaphthalenyl. In some embodiments, aryl groups have 6 carbon atoms. In some embodiments, aryl groups have from six to ten carbon atoms. In some embodiments, aryl groups have from six to sixteen carbon atoms. In an embodiment, $C_5$-$C_7$ aryl groups are provided herein.

As used herein, the term "heteroaryl" means an aromatic carbocyclic system containing 1, 2, 3, or 4 heteroatoms selected independently from N, O, and S and having 1, 2, or 3 rings wherein such rings may be fused, wherein fused is defined above. The term "heteroaryl" includes, but is not limited to, furanyl, thiophenyl, oxazolyl, thiazolyl, imidazolyl, pyrazolyl, triazolyl, tetrazolyl, isoxazolyl, isothiazolyl, oxadiazolyl, thiadiazolyl, pyridinyl, pyridazinyl, pyrimidinyl, pyrazinyl, imidazo[1,2-a]pyridinyl, pyrazolo[1,5-a]pyridinyl, 5,6,7,8-tetrahydroisoquinolinyl, 5,6,7,8-tetrahydroquinolinyl, 6,7-dihydro-5H-cyclopenta[b]pyridinyl, 6,7-dihydro-5H-cyclopenta[c]pyridinyl, 1,4,5,6-tetrahydrocyclopenta[c]pyrazolyl, 2,4,5,6-tetrahydrocyclopenta[c]pyrazolyl, 5,6-dihydro-4H-pyrrolo[1,2-b]pyrazolyl, 6,7-dihydro-5H-pyrrolo[1,2-b][1,2,4]triazolyl, 5,6,7,8-tetrahydro-[1,2,4]triazolo[1,5-a]pyridinyl, 4,5,6,7-tetrahydropyrazolo[1,5-a]pyridinyl, 4,5,6,7-tetrahydro-1H-indazolyl and 4,5,6,7-tetrahydro-2H-indazolyl. In an embodiment, $C_2$-$C_7$ heteroaryl groups are provided herein.

As used herein, the term "polycyclic ring" means two or more carbocyclic rings in which two or more carbons are common to two adjoining rings (the rings are "fused rings") wherein at least one of the rings is aromatic, e.g., the other cyclic rings may be cycloalkyls, and/or aryls. The term "polycyclic ring" includes, but is not limited to, fluorene, anthracene, 9,10-dihydroanthracene, phenanthrene, 9,10-dihydrophenanthrene, phenalene, and 2,3-dihydrophenalene. In an embodeiment, $C_9$-$C_{16}$ polycyclic rings are provided herein.

As used herein, the term "bicyclic heteroaryl" means 7 to 11 membered bicyclic aromatic groups which have at least one heteroatom in at least one carbon atom-containing ring. Each ring of the heteroaryl group containing a heteroatom may have 1, 2, 3, or 4 heteroatoms selected from nitrogen atoms, oxygen atoms and/or sulfur atoms, where the nitrogen and/or sulfur heteroatoms may optionally be oxidized and the nitrogen heteroatoms may optionally be quaternized. Exemplary bicyclic heteroaryl groups include benzothiazolyl, benzoxazolyl, benzoxadiazolyl, benzothienyl, quinolinyl, chromenyl, indolyl, indazolyl, isoquinolinyl, benzimidazolyl, benzopyranyl, benzofuryl, benzofurazanyl, benzopyranyl, cinnolinyl, quinoxalinyl, pyrrolopyridyl, furopyridinyl (such as furo[2,3-c]pyridinyl, furo[3,2-b]pyridinyl] or furo[2,3-b]pyridinyl), triazinylazepinyl, and the like. In an embodiment, $C_5$-$C_{15}$ biciclic heteroaryl groups are provided herein.

It is to be understood that if an aryl, heteroaryl, cycloalkyl, or heterocycloalkyl moiety may be bonded or otherwise attached to a designated moiety through differing ring atoms (i.e., shown or described without denotation of a specific point of attachment), then all possible points are intended, whether through a carbon atom or, for example, a trivalent nitrogen atom. For example, the term "pyridinyl" means 2-, 3- or 4-pyridinyl, the term "thiophenyl" means 2- or 3-thiophenyl, and so forth.

As used herein, the term "substituted" means that an atom or group of atoms has replaced hydrogen as the substituent attached to another group.

Compounds of the Invention

In an embodiment, the invention provides a compound of Formula I:

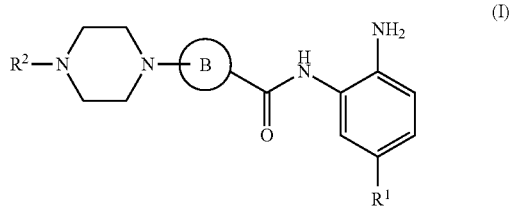

or a pharmaceutically acceptable salt thereof; wherein $R^1$ is H, furan, pyridine, phenyl or thiophene, wherein phenyl is optionally substituted with halogen;

$R^2$ is H or $C_{1-4}$ alkyl, wherein the $C_{1-4}$ alkyl group is optionally, independently substituted one or more times with halo, —CN, —$NO_2$, —$C_1$-$C_6$ alkoxy, —$C_1$-$C_6$ alkyl, —$C_1$-$C_6$ haloalkyl, and C(O)—$C_1$-$C_6$ alkyl; and B is oxazole, phenyl, pyridine, thiophene, thiazole or quinoline, wherein the thiazole is optionally substituted with $CH_3$, and wherein if $R^1$ is thiophene, B is not 2-(piperazin-1-yl)quinoline.

In another embodiment of Formula I, $R^1$ is H, furan, pyridine, phenyl or thiophene, wherein phenyl is optionally substituted with halogen;

$R^2$ is H or $CH_3$; and

B is phenyl, pyridine, thiophene, thiazole or quinoline, wherein the thiazole is optionally substituted with $CH_3$, and wherein if $R^1$ is thiophene, B is not 2-(piperazin-1-yl)quinoline.

In further embodiment of Formula I, $R^1$ is furan, pyridine, phenyl or thiophene, wherein phenyl is optionally substituted with halogen.

In a specific embodiment, including pharmaceutically acceptable salts thereof, Formula I is:

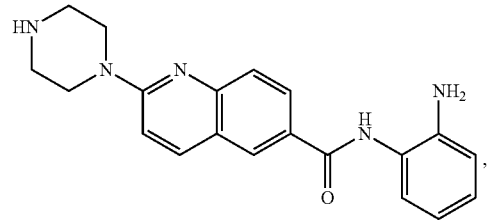

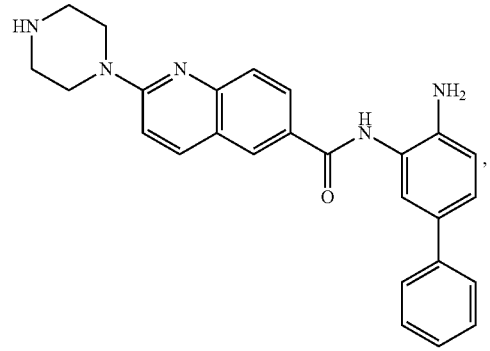

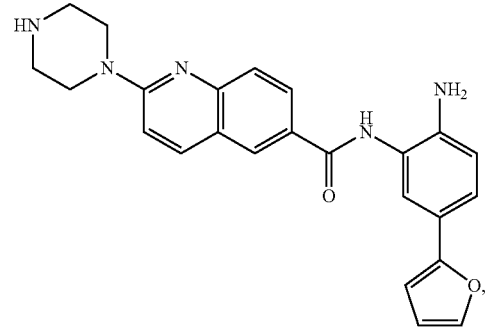

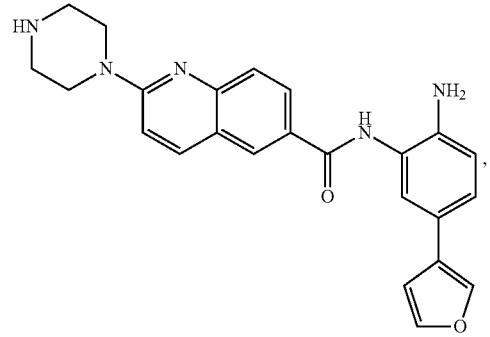

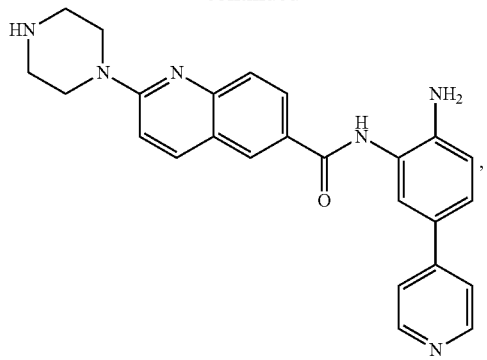
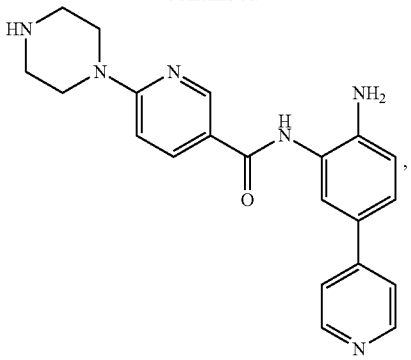

-continued
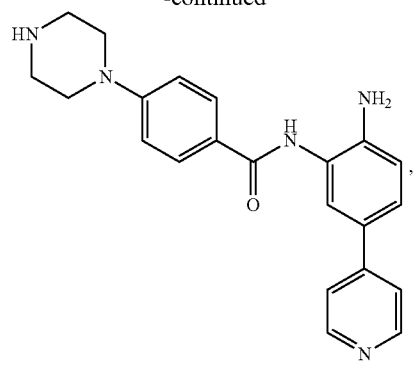
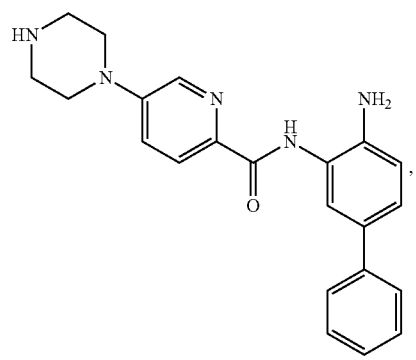
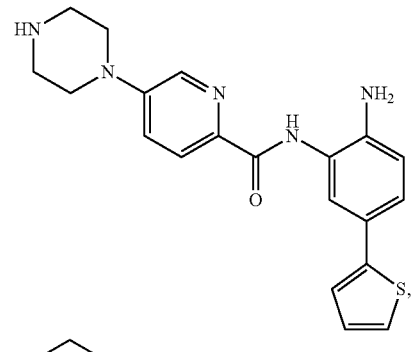
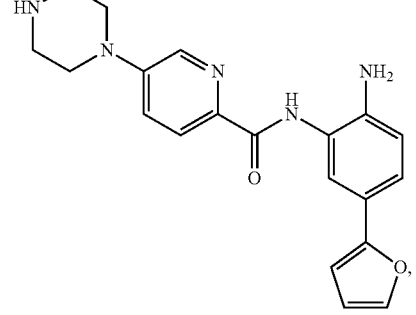
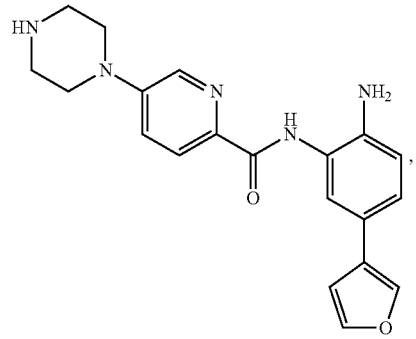
-continued
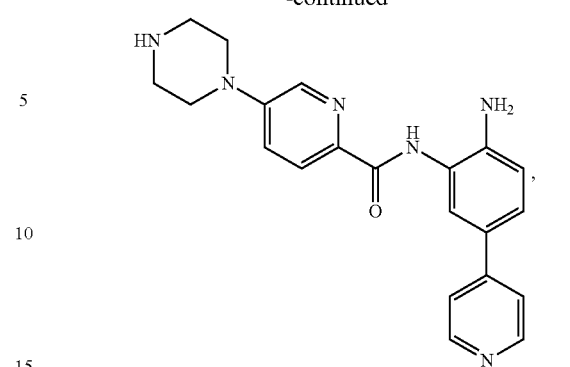
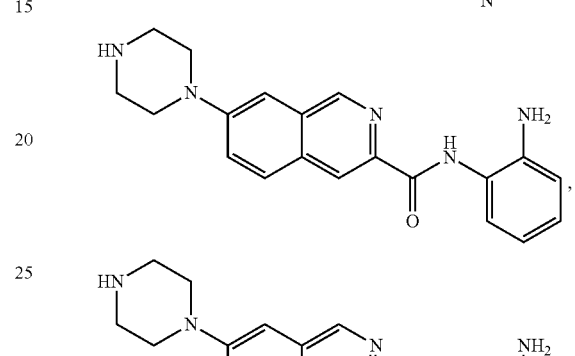
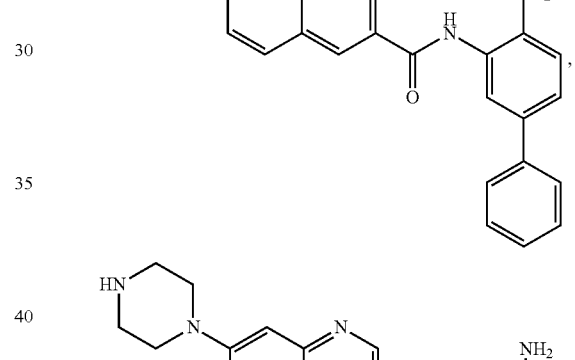
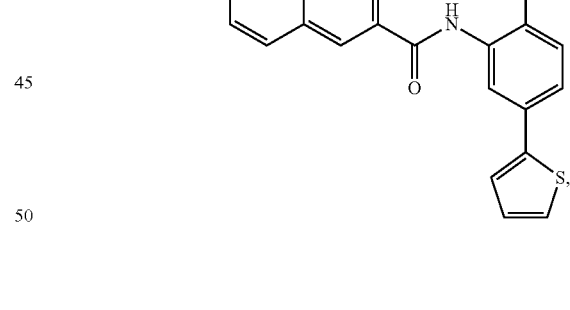
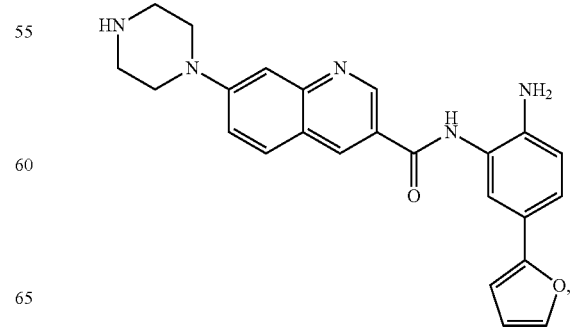

-continued
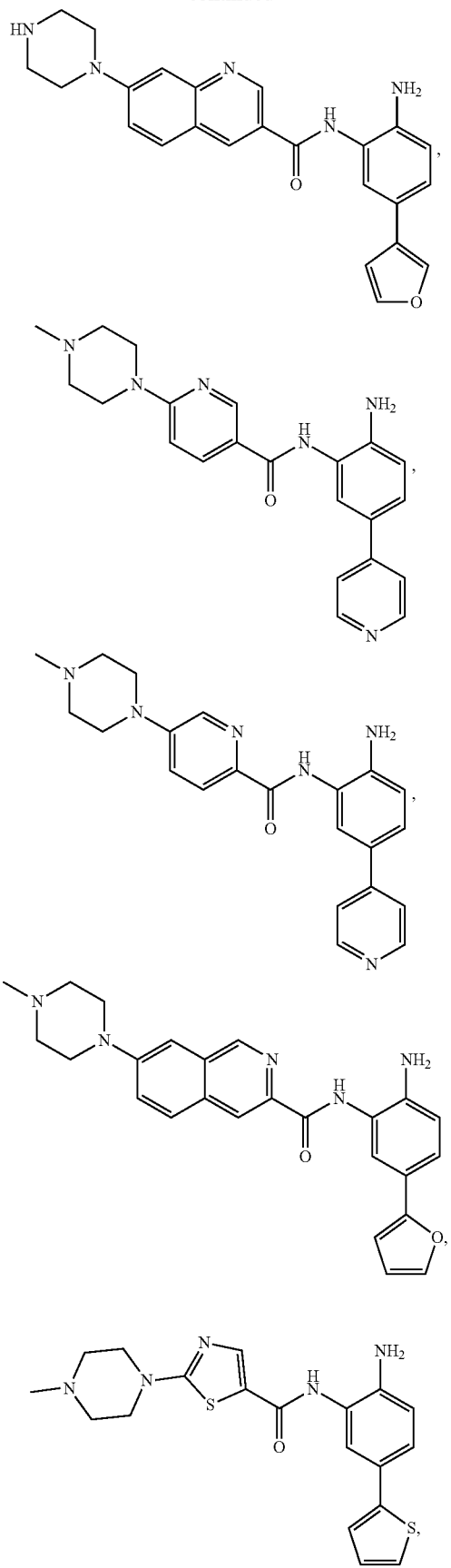
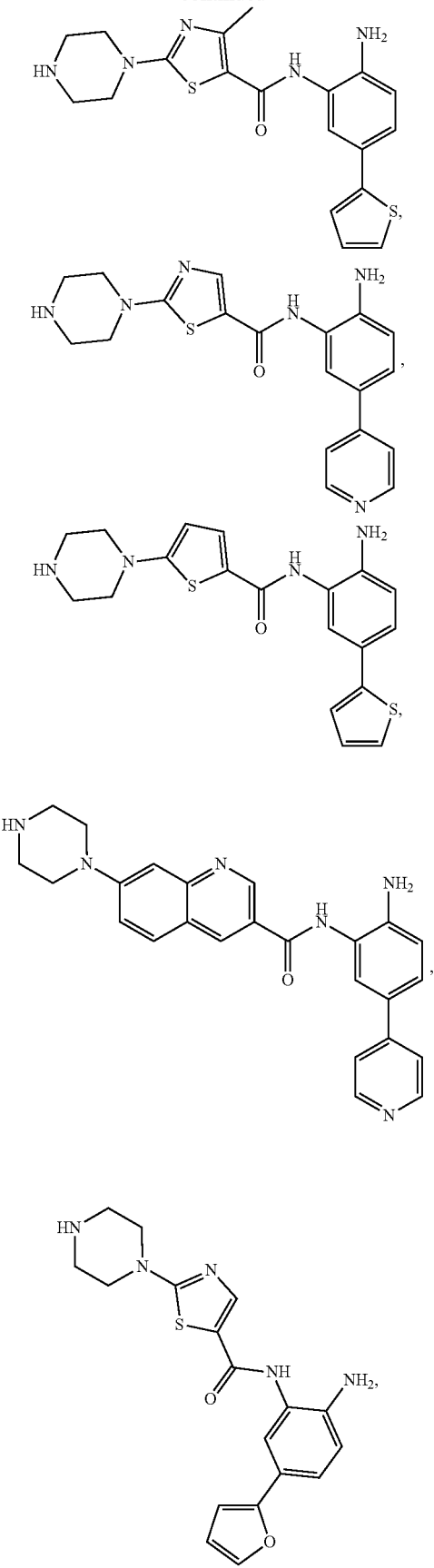

-continued

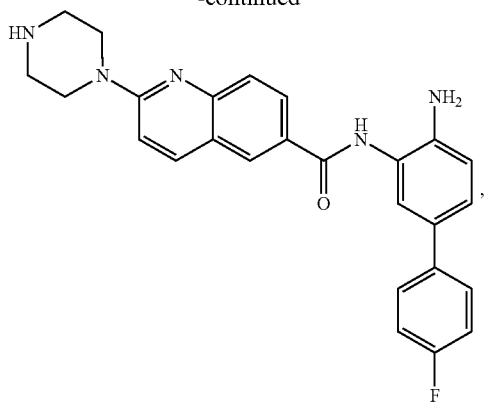

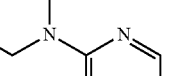

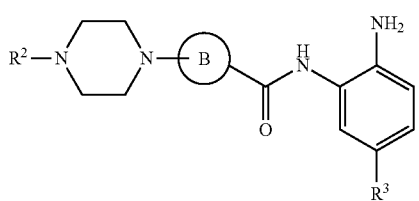

In an embodiment, the invention provides a compound of Formula II:

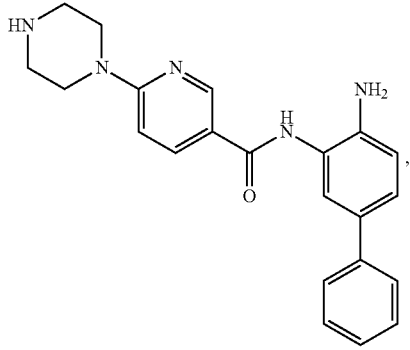

(II)

or a pharmaceutically acceptable salt thereof;
wherein
$R^3$ is furan, pyridine, phenyl or thiophene, wherein phenyl is optionally substituted with halogen;

$R^4$ is H or $C_{1-4}$ alkyl, wherein the $C_{1-4}$ alkyl group is optionally, independently substituted one or more times with halo, —CN, —NO$_2$, —$C_1$-$C_6$ alkoxy, —$C_1$-$C_6$ alkyl, —$C_1$-$C_6$ haloalkyl, or C(O)—$C_1$-$C_6$ alkyl; and B is pyrazine, oxazole, pyridine, thiophene, or thiazole.

In another embodiment of Formula II, $R^3$ is furan, pyridine, phenyl or thiophene, wherein phenyl is optionally substituted with halogen;

$R^4$ is H or CH$_3$; and

B is pyrazine, oxazole, pyridine, thiophene, or thiazole.

In another embodiment of Formula II, $R^3$ is furan, pyridine, or thiophene;

$R^4$ is H or $C_1$-$C_4$ alkyl; and

B is a five-membered heteroaryl ring.

In another embodiment of Formula II, $R^3$ is furan, pyridine, or thiophene;

$R^4$ is H or $C_1$-$C_4$ alkyl; and

B is oxazole, thiophene, or thiazole.

In another embodiment of Formula II, $R^3$ is furan or thiophene;

$R^4$ is H or $C_1$-$C_4$ alkyl; and

B is thiophene or thiazole.

In a specific embodiment, including pharmaceutically acceptable salts thereof, Formula II is:

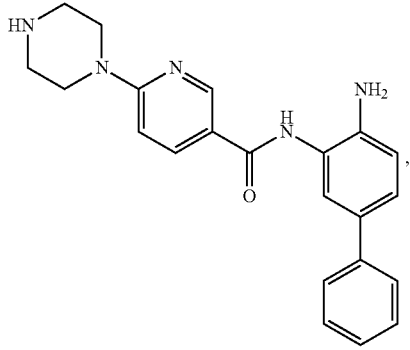

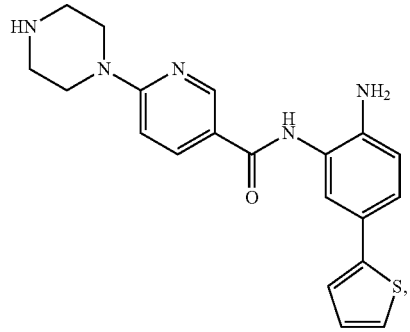

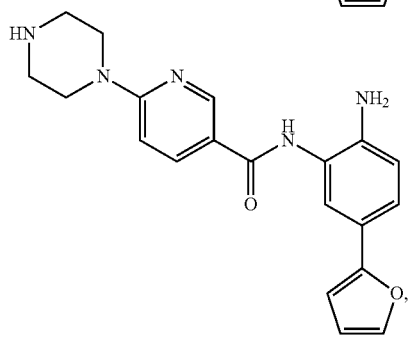

-continued
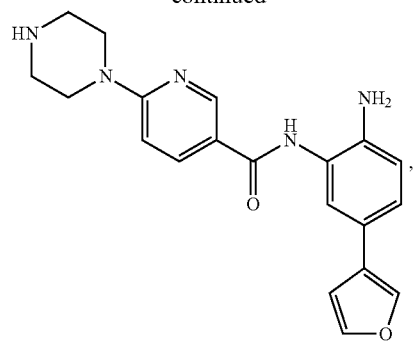
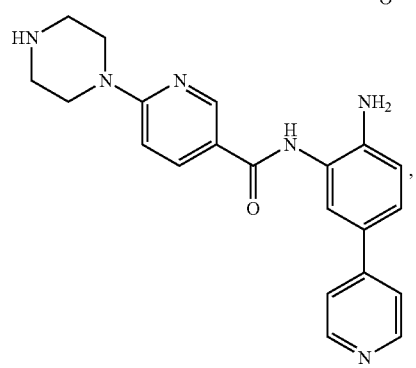
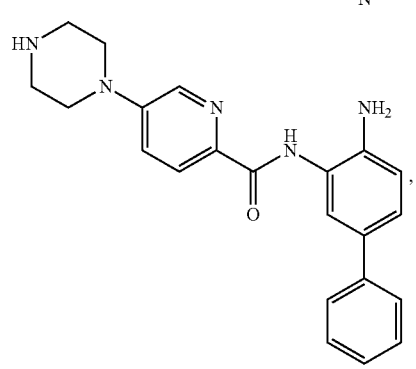
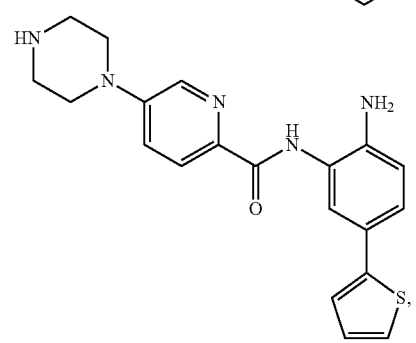
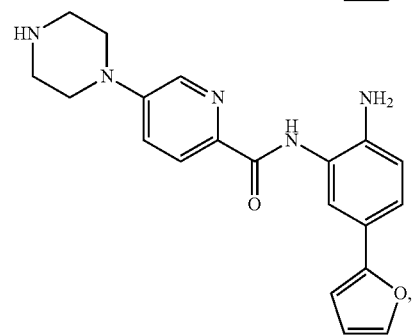
-continued
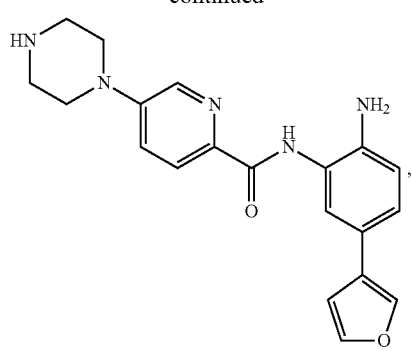
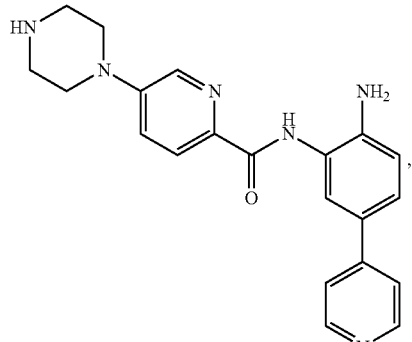
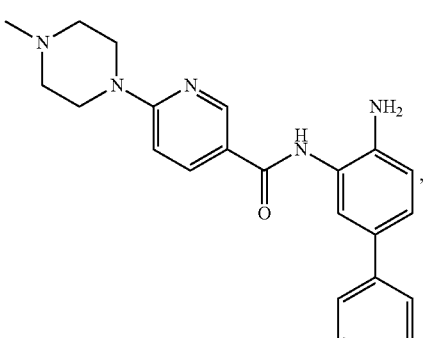
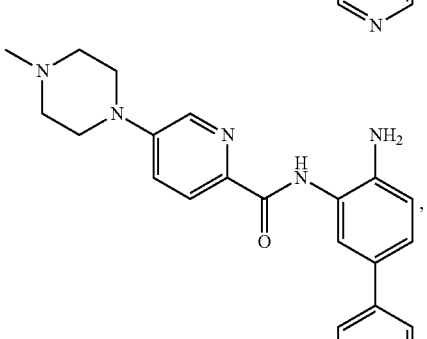
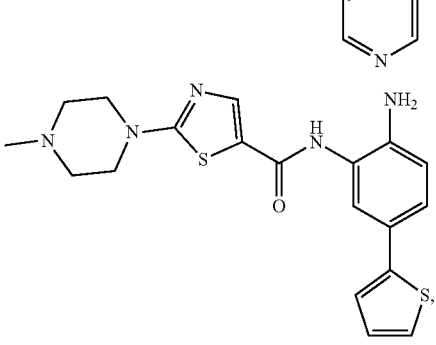

-continued
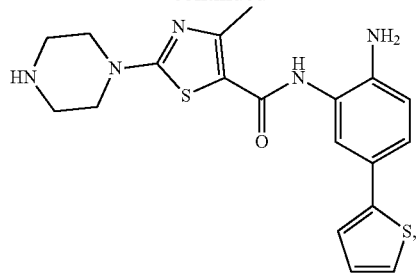
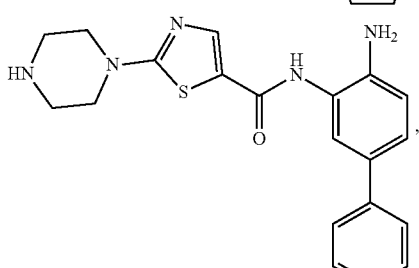
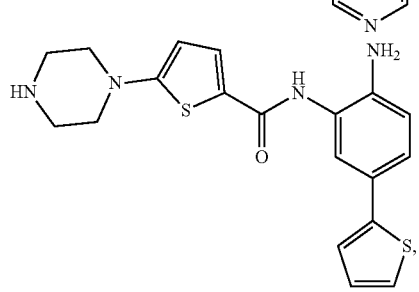
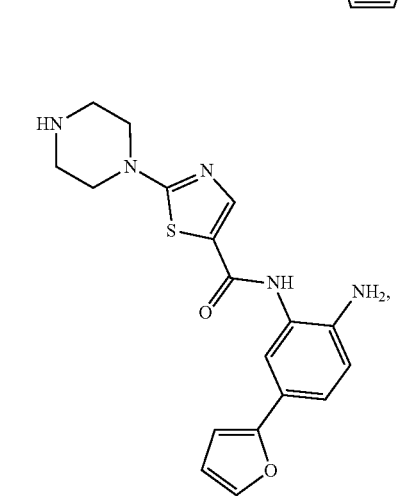
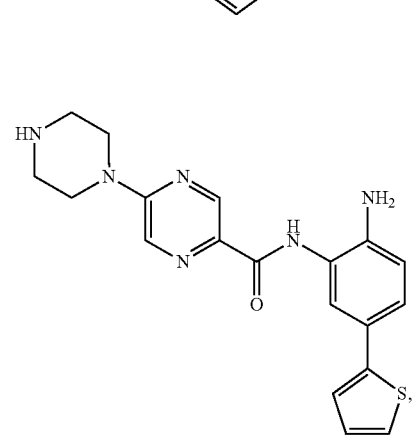
-continued
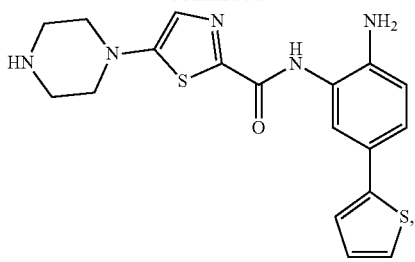
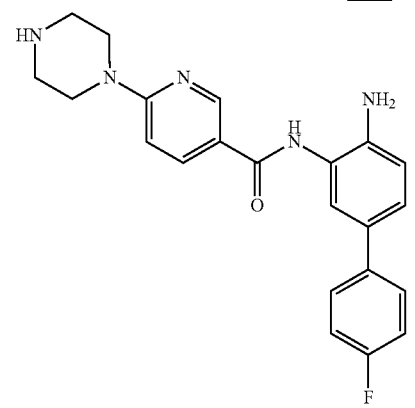
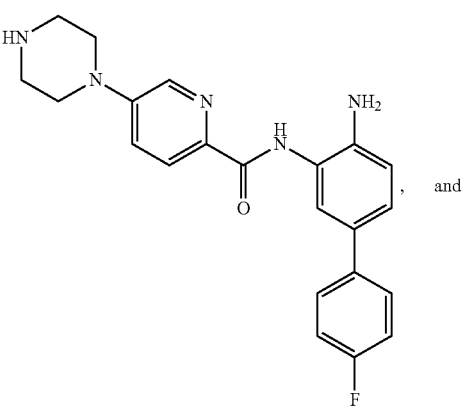, and
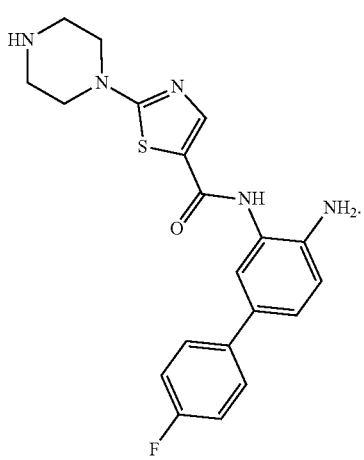

In an embodiment, the invention provides a compound of Formula III:

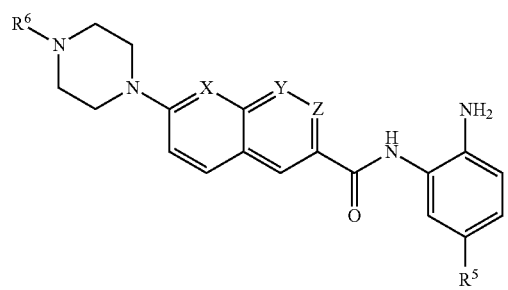

or a pharmaceutically acceptable salt thereof;
wherein
(a) X is C(H), Y is C(H), and Z is N;
R$^5$ is H or phenyl; and
R$^6$ is H; or
(b) X is C(H), Y is C(H), and Z is N;
R$^5$ is 1-furan; and
R$^6$ is C$_{1-4}$ alkyl, wherein the C$_{1-4}$ alkyl group is optionally, independently substituted one or more times with halo, —CN, —NO$_2$, —C$_1$-C$_6$ alkoxy, —C$_1$-C$_6$ alkyl, —C$_1$-C$_6$ haloalkyl, and C(O)—C$_1$-C$_6$ alkyl; or
(c) X is C(H), Y is N, and Z is C(H);
R$^5$ is H, 1-furan, 2-furan, pyridine, or thiophene; and
R$^6$ is H; or
(d) X is N, Y is C(H), and Z is C(H);
R$^5$ is H, 1-furan, 2-furan, pyridine, or phenyl, wherein phenyl is optionally substituted with halogen; and
R$^6$ is H.

In another embodiment of Formula III, X is C(H), Y is C(H), and Z is N; R$^5$ is 1-furan; and R$^6$ is CH$_3$.

In another embodiment of Formula III, X is C(H), Y is C(H), and Z is N; R$^5$ is H; and R$^6$ is H.

In a specific embodiment, including pharmaceutically acceptable salts thereof, Formula III is:

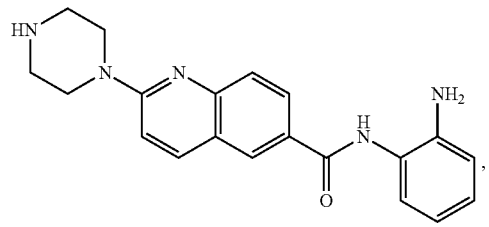

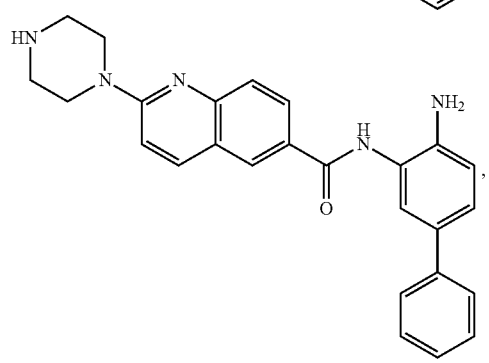

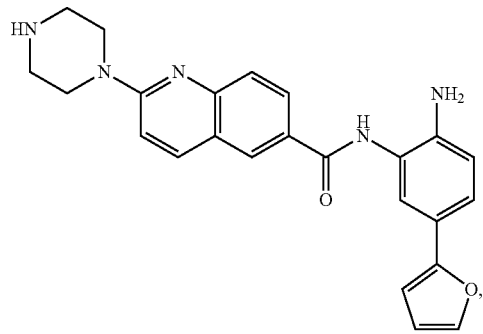

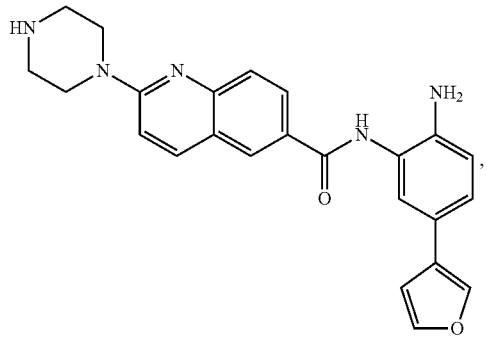

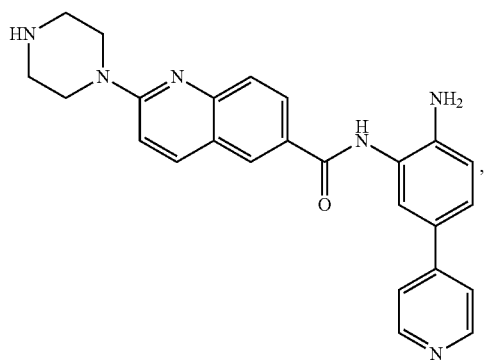

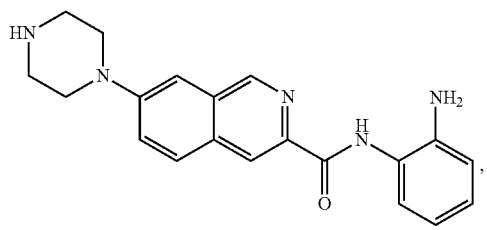

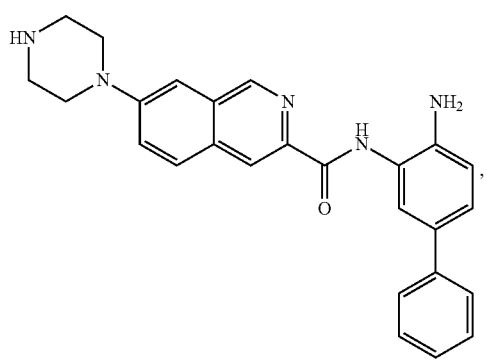

-continued
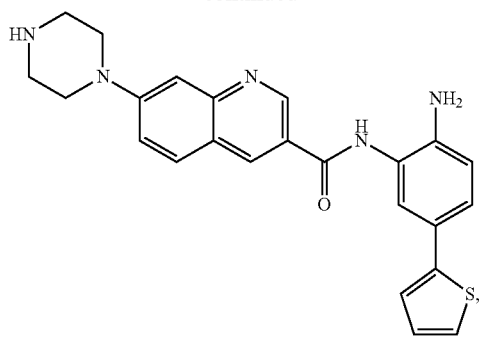
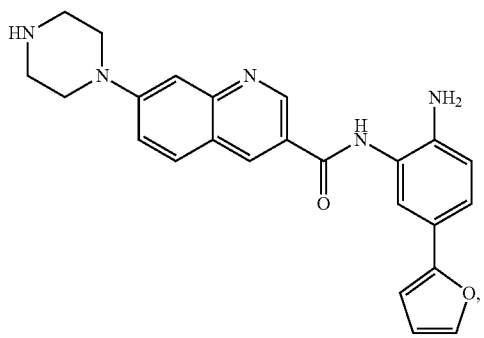
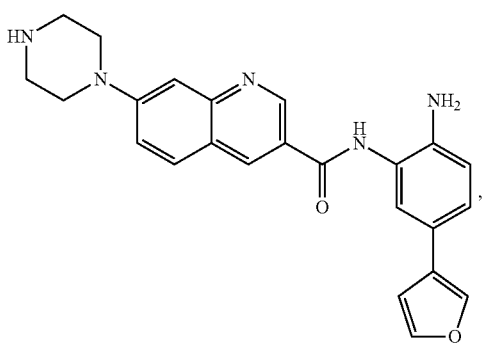
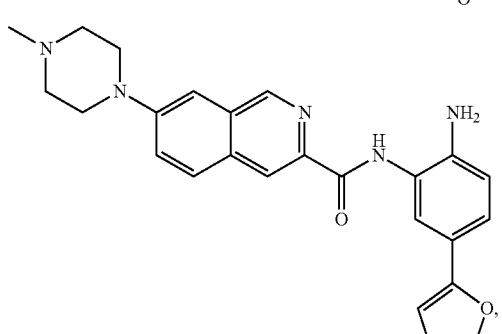
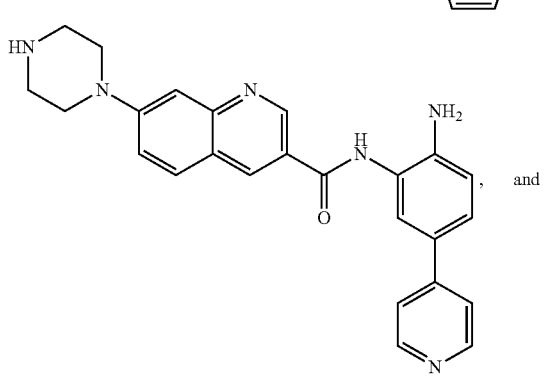
-continued
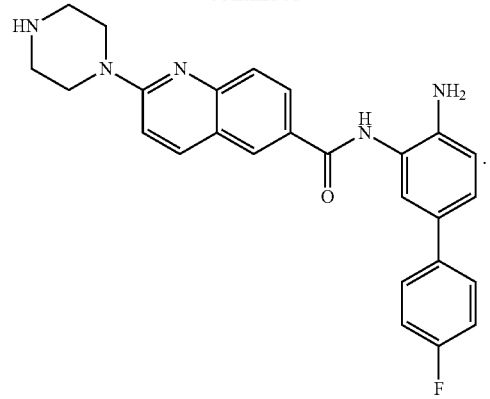
In an embodiment, the invention provides a compound of Formula IV:
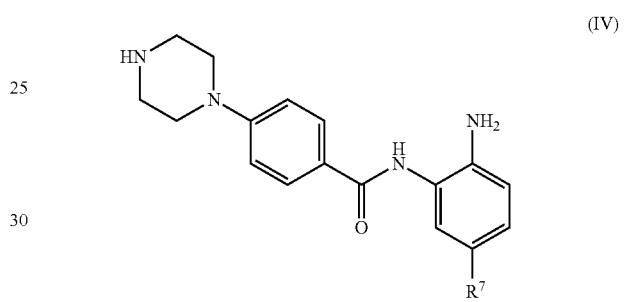
(IV)
or a pharmaceutically acceptable salt thereof;
wherein
$R^7$ is H, furan, pyridine, or thiophene.
In a specific embodiment, including pharmaceutically acceptable salts thereof, Formula IV is:
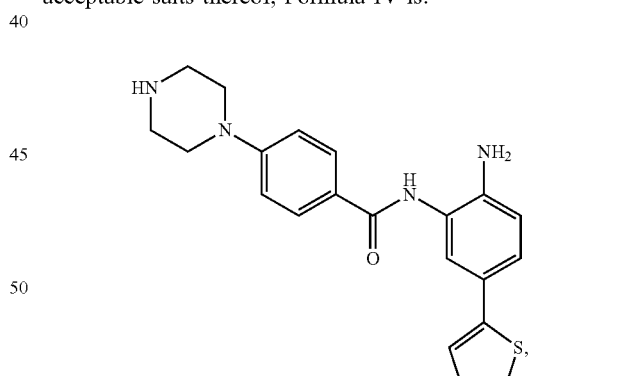

-continued

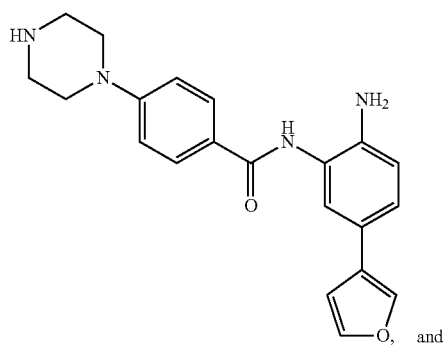

and

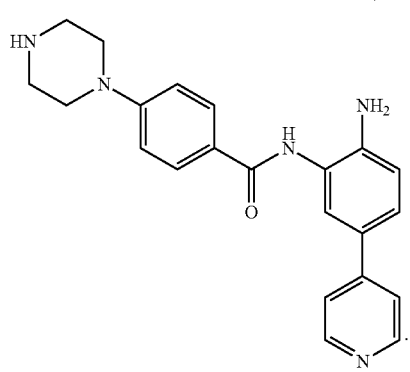

Certain embodiments of Formula I, II, III, or IV, or pharmaceutically acceptable salts thereof, are shown below in Table 1. Compounds of Formula I, II, III, or IV, or pharmaceutically acceptable salts thereof, and compounds of Table 1, or pharmaceutically acceptable salts thereof, are sometimes referred to herein as "compounds of the invention," or "compounds provided herein."

TABLE 1

| Structure | Compound No. |
|---|---|
| 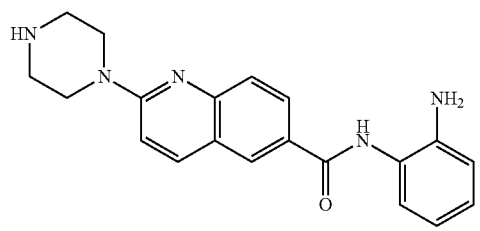 [SMILES: Nc1ccccc1NC(=O)c1ccc2nc(N3CCNCC3)ccc2c1] | 001 |
| 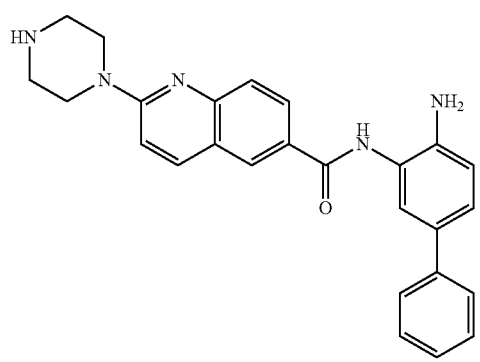 [SMILES: Nc1ccc(-c2ccccc2)cc1NC(=O)c1ccc2nc(N3CCNCC3)ccc2c1] | 002 |

TABLE 1-continued

| Structure | Compound No. |
|---|---|
| 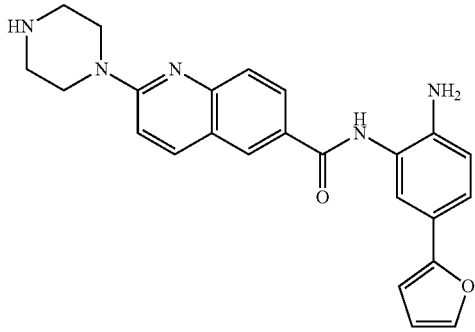 [SMILES: Nc1ccc(-c2ccco2)cc1NC(=O)c1ccc2nc(N3CCNCC3)ccc2c1] | 003 |
| 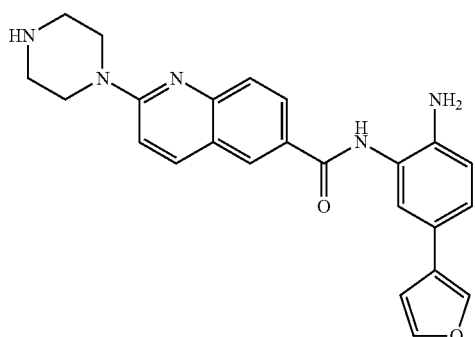 | 004 |
| 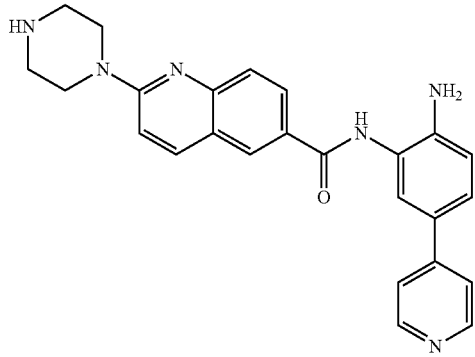 [SMILES: Nc1ccc(-c2ccncc2)cc1NC(=O)c1ccc2nc(N3CCNCC3)ccc2c1] | 005 |
| 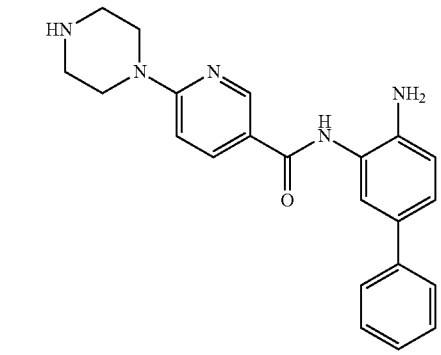 [SMILES: Nc1ccc(-c2ccccc2)cc1NC(=O)c1ccc(N2CCNCC2)nc1] | 006 |

TABLE 1-continued
| Structure | Compound No. |
|---|---|
| 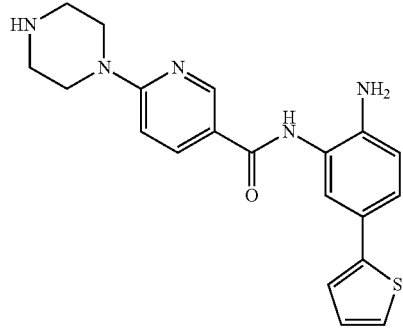 [SMILES: Nc1ccc(-c2cccs2)cc1NC(=O)c1ccc(N2CCNCC2)nc1] | 007 |
| 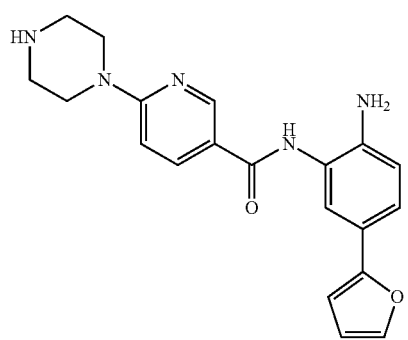 [SMILES: Nc1ccc(-c2ccco2)cc1NC(=O)c1ccc(N2CCNCC2)nc1] | 008 |
| 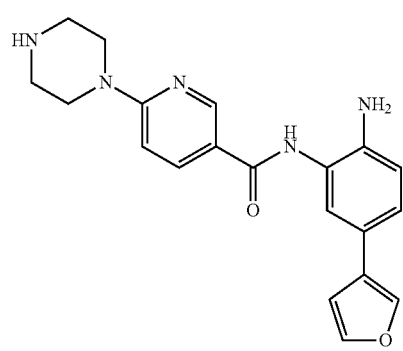 [SMILES: Nc1ccc(-c2ccoc2)cc1NC(=O)c1ccc(N2CCNCC2)nc1] | 009 |
| 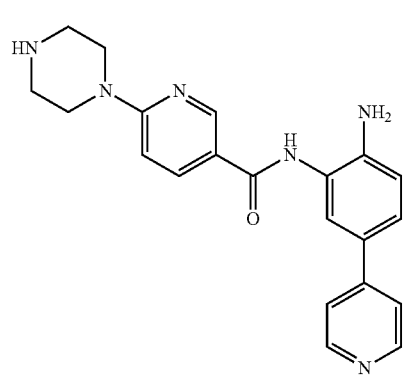 [SMILES: Nc1ccc(-c2ccncc2)cc1NC(=O)c1ccc(N2CCNCC2)nc1] | 010 |
| 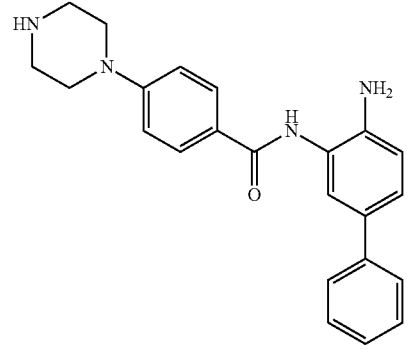 [SMILES: Nc1ccc(-c2ccccc2)cc1NC(=O)c1ccc(N2CCNCC2)cc1] | 011 |
| 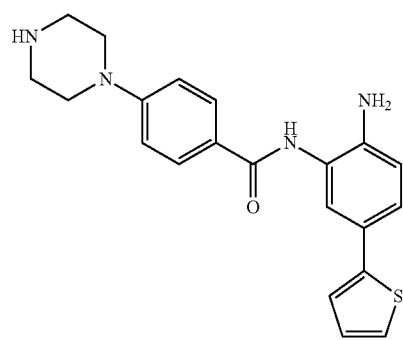 [SMILES: Nc1ccc(-c2cccs2)cc1NC(=O)c1ccc(N2CCNCC2)cc1] | 012 |
| 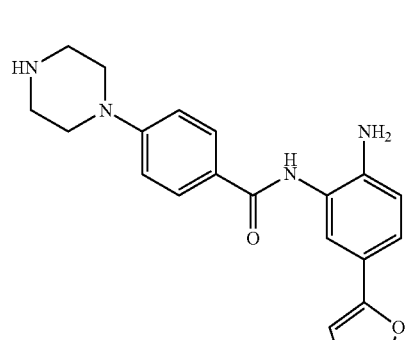 | 013 |
| 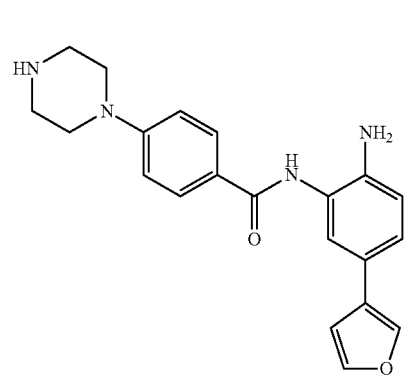 [SMILES: Nc1ccc(-c2ccoc2)cc1NC(=O)c1ccc(N2CCNCC2)cc1] | 014 |

TABLE 1-continued
| Structure | Compound No. |
|---|---|
| 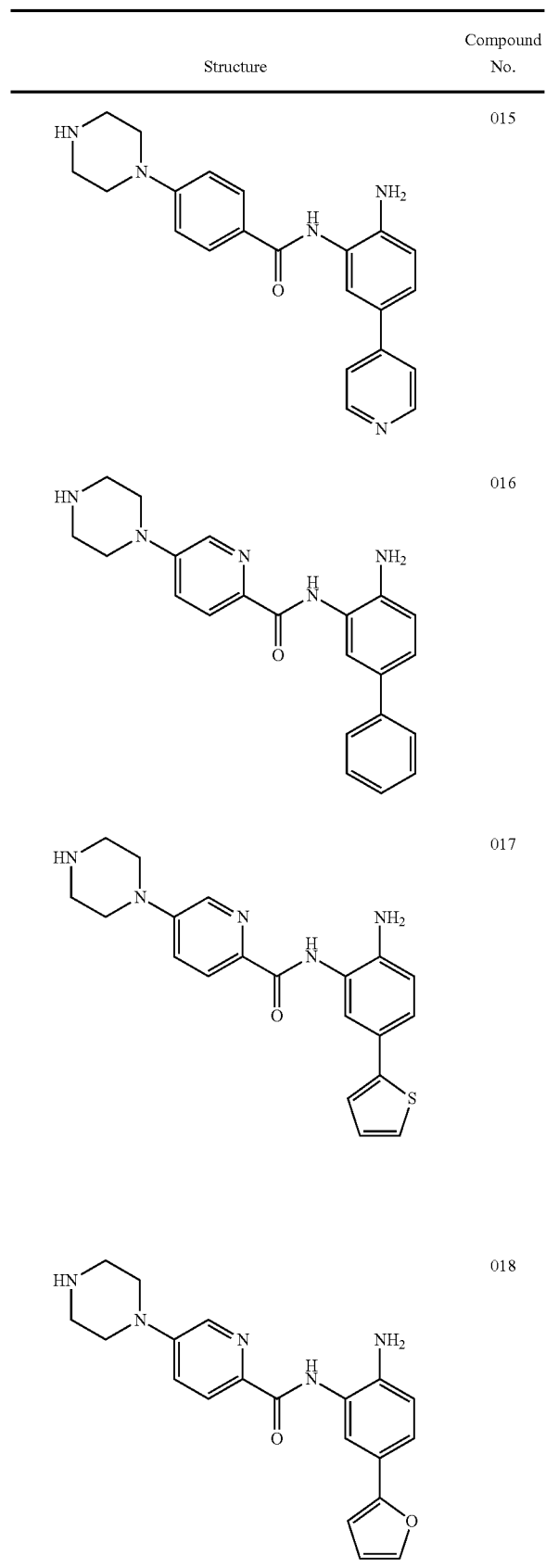 | 015 |
| 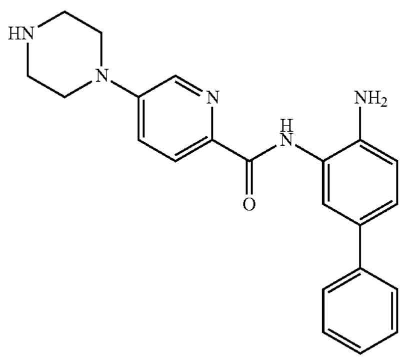 [SMILES: Nc1ccc(-c2ccccc2)cc1NC(=O)c1ccc(N2CCNCC2)cn1] | 016 |
| 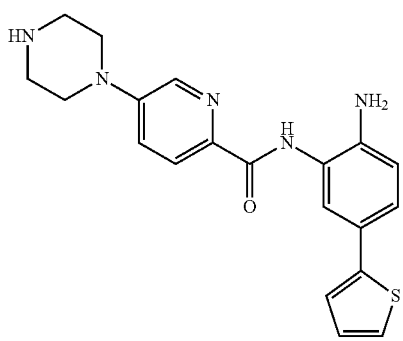 [SMILES: Nc1ccc(-c2ccco2)cc1NC(=O)c1ccc(N2CCNCC2)cn1] | 017 |
| 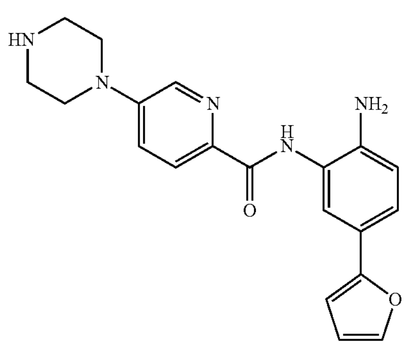 | 018 |
TABLE 1-continued
| Structure | Compound No. |
|---|---|
| 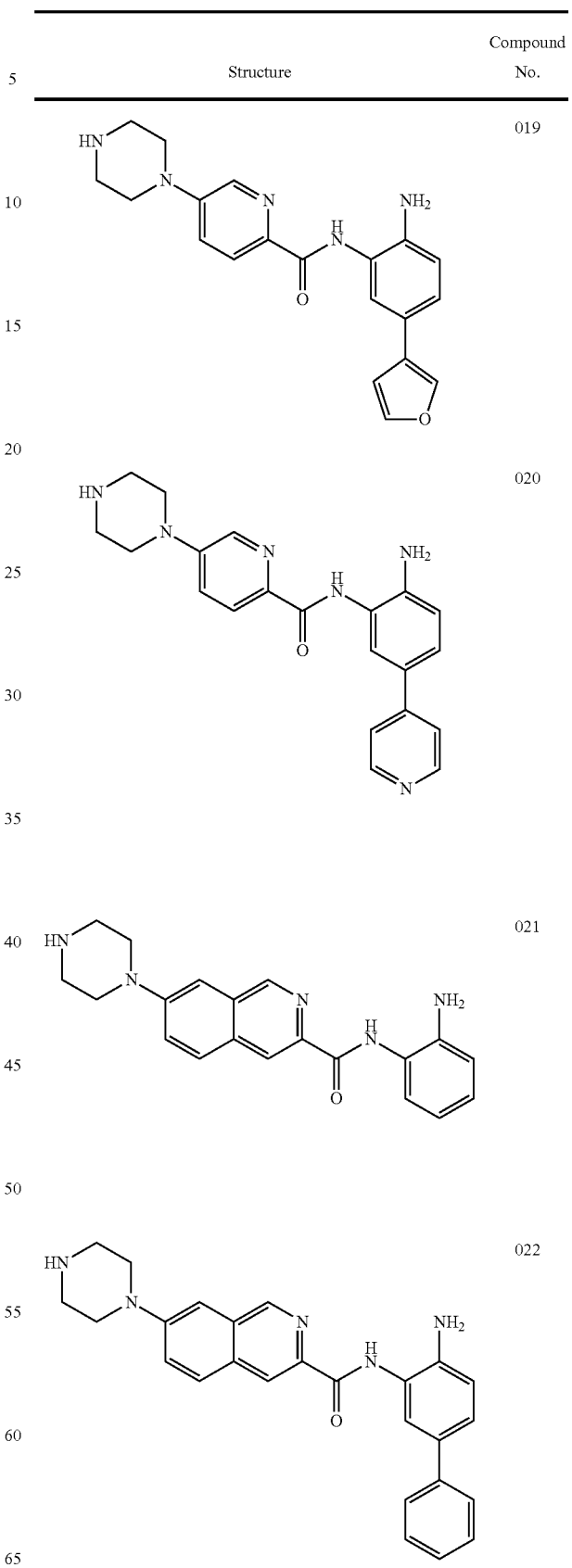 | 019 |
| 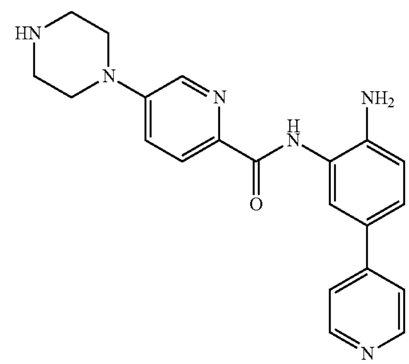 [SMILES: Nc1ccc(-c2ccncc2)cc1NC(=O)c1ccc(N2CCNCC2)cn1] | 020 |
| 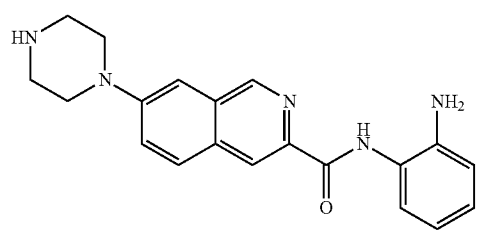 [SMILES: Nc1ccccc1NC(=O)c1cc2ccc(N3CCNCC3)cc2cn1] | 021 |
| 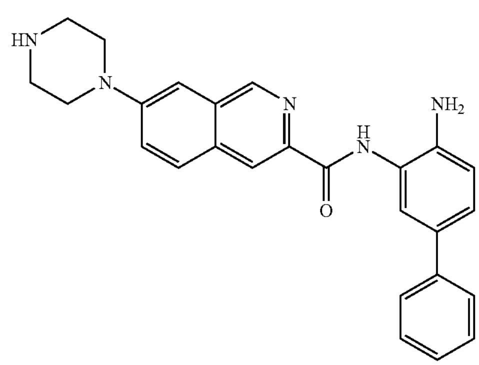 [SMILES: Nc1ccc(-c2ccccc2)cc1NC(=O)c1cc2ccc(N3CCNCC3)cc2cn1] | 022 |

TABLE 1-continued
| Structure | Compound No. |
|---|---|
| 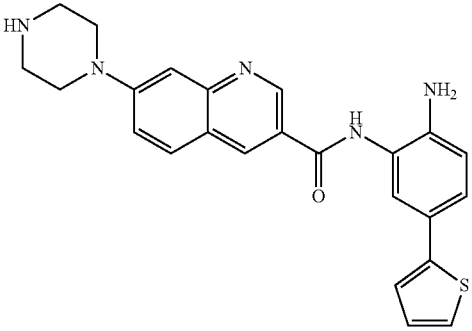 [SMILES: Nc1ccc(-c2cccs2)cc1NC(=O)c1cnc2cc(N3CCNCC3)ccc2c1] | 023 |
| 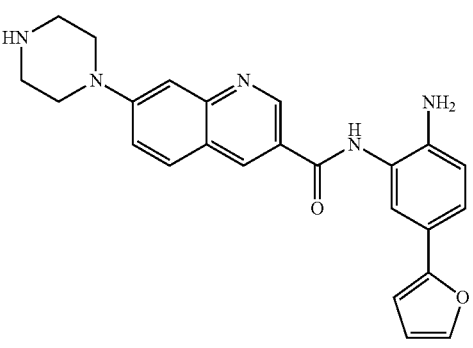 [SMILES: Nc1ccc(-c2ccco2)cc1NC(=O)c1cnc2cc(N3CCNCC3)ccc2c1] | 024 |
| 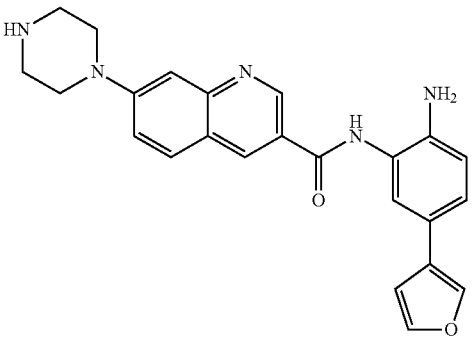 [SMILES: Nc1ccc(-c2ccoc2)cc1NC(=O)c1cnc2cc(N3CCNCC3)ccc2c1] | 025 |
| 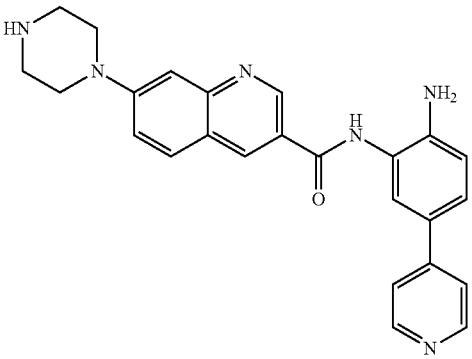 [SMILES: Nc1ccc(-c2ccncc2)cc1NC(=O)c1cnc2cc(N3CCNCC3)ccc2c1] | 026 |
| 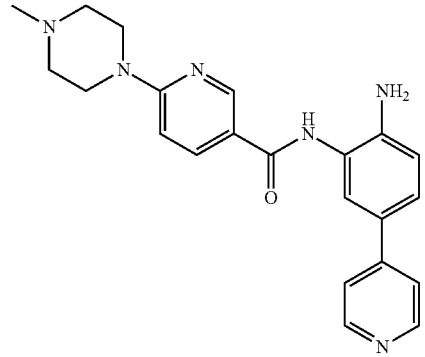 [SMILES: CN1CCN(c2ccc(C(=O)Nc3cc(-c4ccncc4)ccc3N)cn2)CC1] | 027 |
| 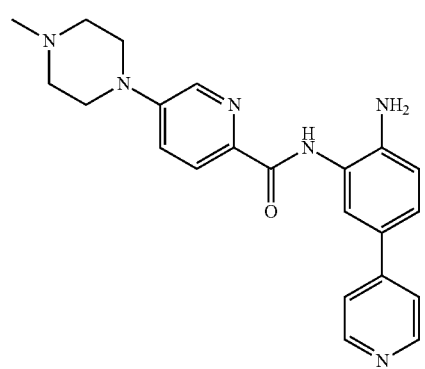 [SMILES: CN1CCN(c2ccc(C(=O)Nc3cc(-c4ccncc4)ccc3N)nc2)CC1] | 028 |
| 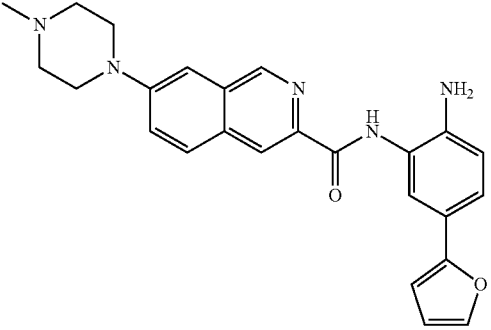 [SMILES: CN1CCN(c2ccc3cc(C(=O)Nc4cc(-c5ccco5)ccc4N)ncc3c2)CC1] | 029 |
| 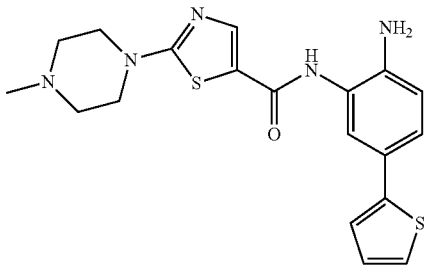 [SMILES: CN1CCN(c2ncc(C(=O)Nc3cc(-c4cccs4)ccc3N)s2)CC1] | 030 |

TABLE 1-continued
| Structure | Compound No. |
|---|---|
| 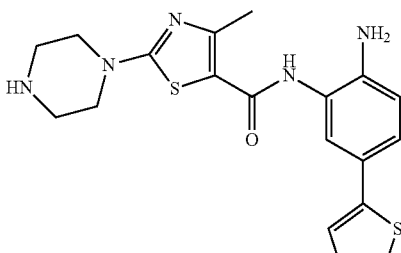 | 031 |
| 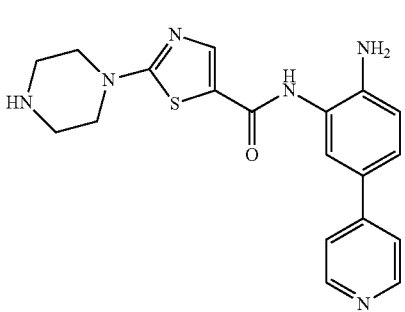 [SMILES: Nc1ccc(-c2ccncc2)cc1NC(=O)c1cnc(N2CCNCC2)s1] | 032 |
| 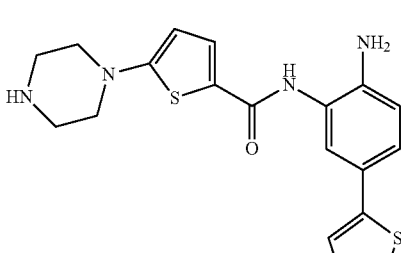 | 033 |
| 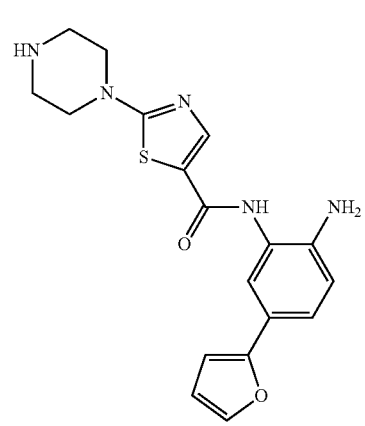 [SMILES: Nc1ccc(-c2ccco2)cc1NC(=O)c1cnc(N2CCNCC2)s1] | 034 |
| 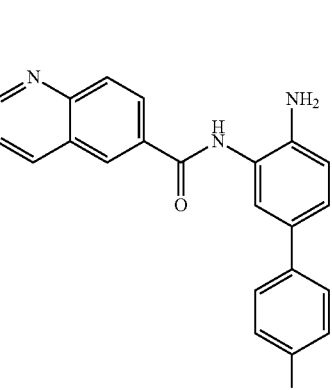 | 035 |
| 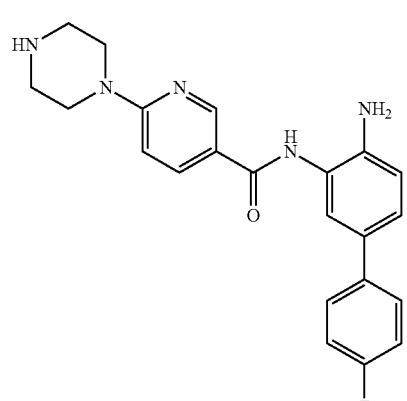 | 036 |
| 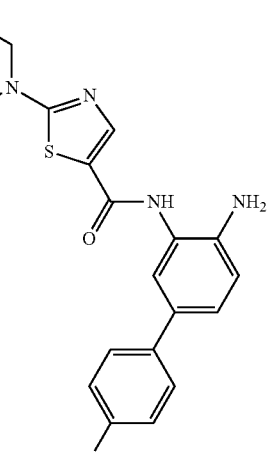 | 037 |

TABLE 1-continued
| Structure | Compound No. |
|---|---|
| 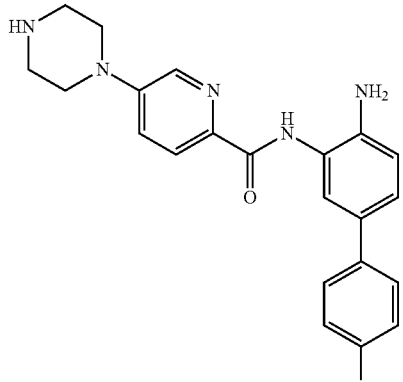 | 038 |
| 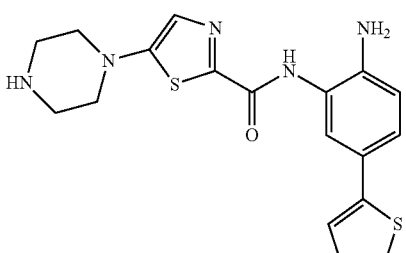 | 039 |
| 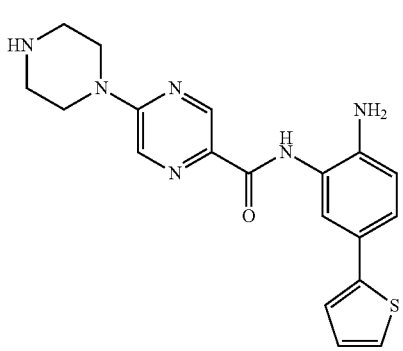 [SMILES: Nc1ccc(-c2cccs2)cc1NC(=O)c1cnc(N2CCNCC2)cn1] | 040 |
| 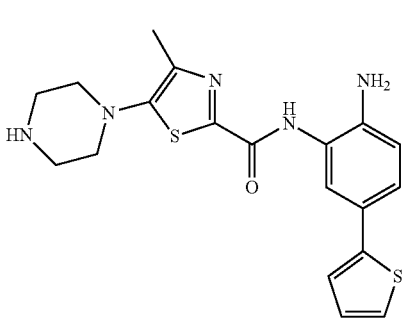 [SMILES: Cc1nc(C(=O)Nc2cc(-c3ccco3)ccc2N)sc1N1CCNCC1] | 041 |
| 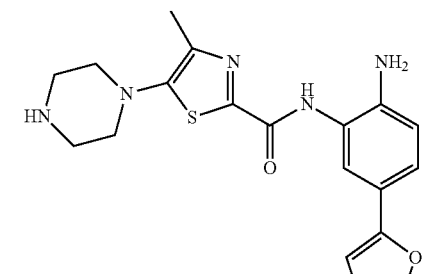 | 042 |
| 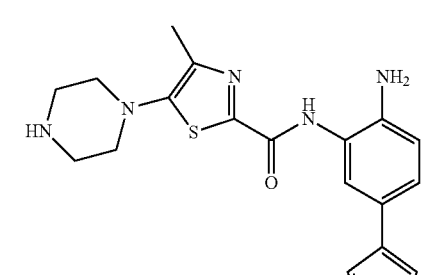 | 043 |
| 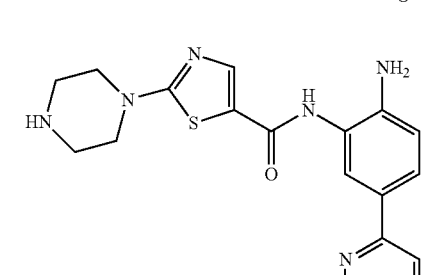 | 044 |
| 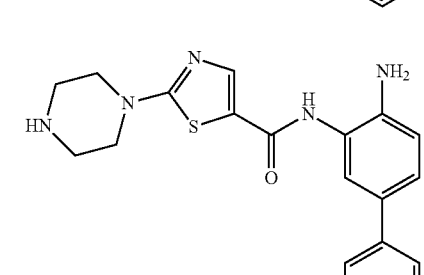 | 045 |
| 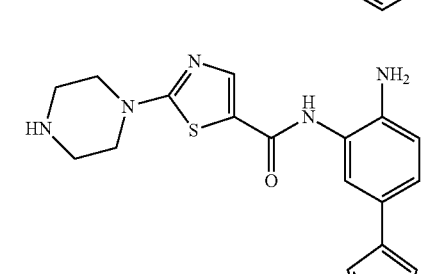 | 046 |

TABLE 1-continued

| Structure | Compound No. |
|---|---|
| 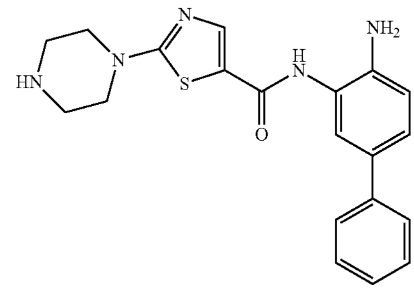 | 047 |
| 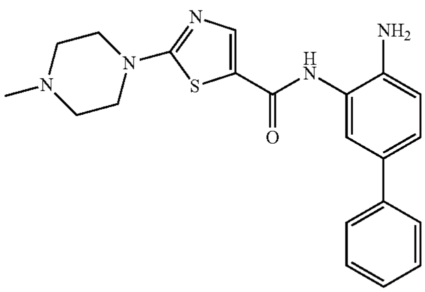 [SMILES: CN1CCN(c2ncc(C(=O)Nc3cc(-c4ccccc4)ccc3N)s2)CC1] | 048 |
| 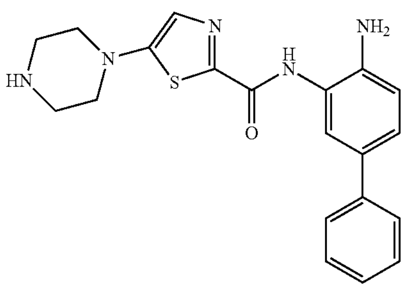 [SMILES: Nc1ccc(-c2ccccc2)cc1NC(=O)c1ncc(N2CCNCC2)s1] | 049 |
| 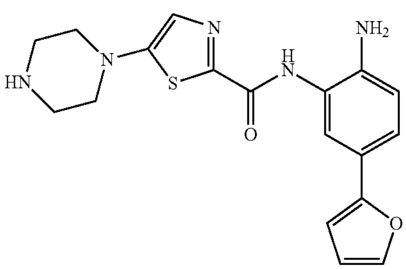 [SMILES: Nc1ccc(-c2ccco2)cc1NC(=O)c1ncc(N2CCNCC2)s1] | 050 |
| 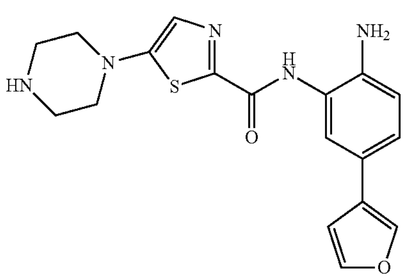 [SMILES: Nc1ccc(-c2ccoc2)cc1NC(=O)c1ncc(N2CCNCC2)s1] | 051 |
| 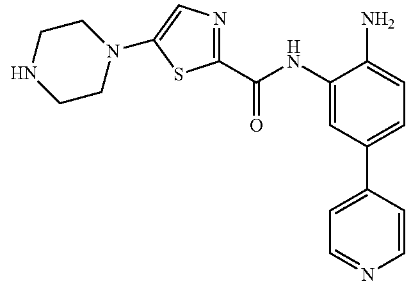 [SMILES: Nc1ccc(-c2ccncc2)cc1NC(=O)c1ncc(N2CCNCC2)s1] | 052 |
| 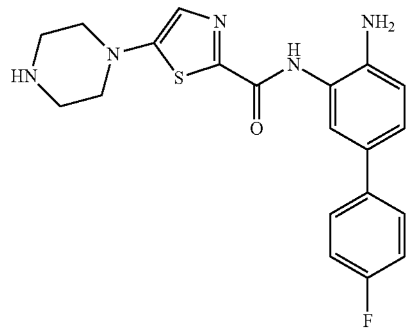 [SMILES: Nc1ccc(-c2ccc(F)cc2)cc1NC(=O)c1ncc(N2CCNCC2)s1] | 053 |
| 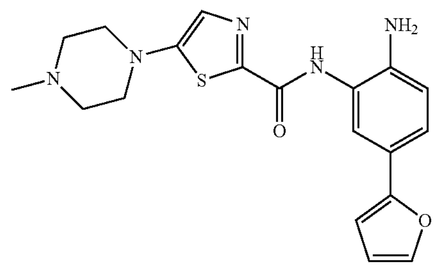 [SMILES: CN1CCN(c2cnc(C(=O)Nc3cc(-c4ccco4)ccc3N)s2)CC1] | 054 |
| 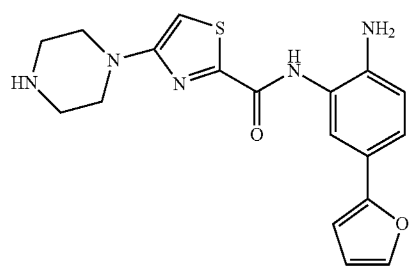 [SMILES: Nc1ccc(-c2ccco2)cc1NC(=O)c1nc(N2CCNCC2)cs1] | 055 |
| 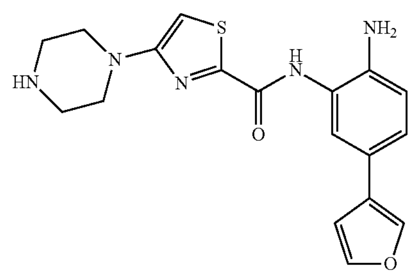 [SMILES: Nc1ccc(-c2ccoc2)cc1NC(=O)c1nc(N2CCNCC2)cs1] | 056 |

TABLE 1-continued

| Structure | Compound No. |
|---|---|
| 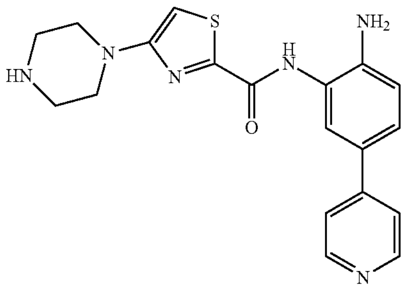 [SMILES: Nc1ccc(-c2ccncc2)cc1NC(=O)c1nc(N2CCNCC2)cs1] | 057 |
| 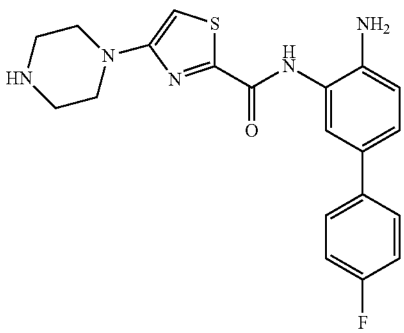 [SMILES: Nc1ccc(-c2ccc(F)cc2)cc1NC(=O)c1nc(N2CCNCC2)cs1] | 058 |
| 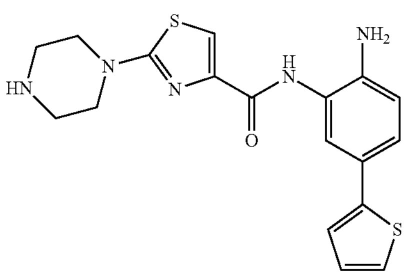 [SMILES: Nc1ccc(-c2cccs2)cc1NC(=O)c1csc(N2CCNCC2)n1] | 059 |
| 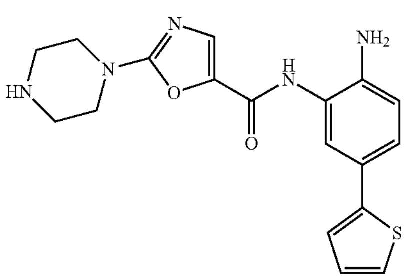 [SMILES: Nc1ccc(-c2ccco2)cc1NC(=O)c1cnc(N2CCNCC2)o1] | 060 |
| 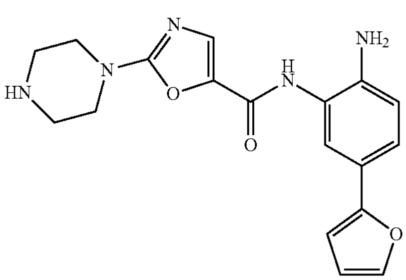 | 061 |
| | 062 |
| | 063 |
| | 064 |
| | 065 |
| | 066 |

TABLE 1-continued
| Structure | Compound No. |
|---|---|
| 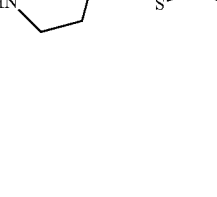 | 067 |
| 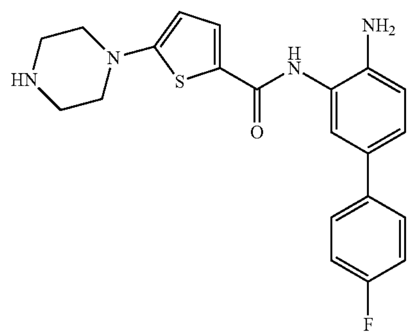 [SMILES: Nc1ccc(-c2ccc(F)cc2)cc1NC(=O)c1ccc(N2CCNCC2)s1] | 068 |
| 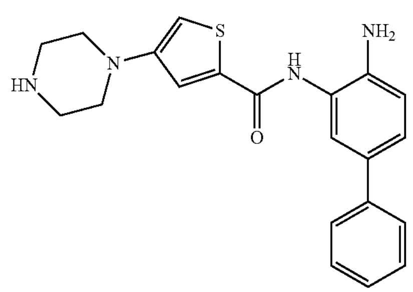 [SMILES: Nc1ccc(-c2ccccc2)cc1NC(=O)c1cc(N2CCNCC2)cs1] | 069 |
| 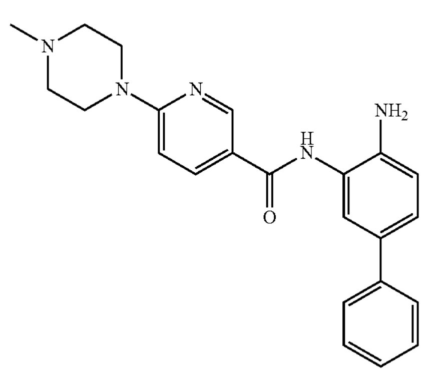 [SMILES: CN1CCN(c2ccc(C(=O)Nc3cc(-c4ccccc4)ccc3N)cn2)CC1] | 070 |
| | 071 |
| | 072 |
| | 073 |
| | 074 |

TABLE 1-continued
| Structure | Compound No. |
|---|---|
| 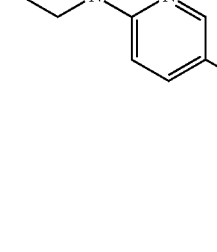 | 075 |
| 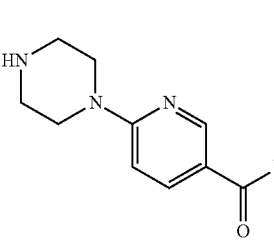 | 076 |
| 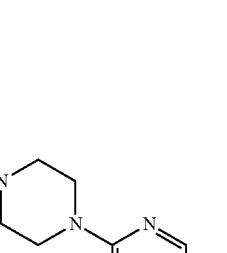 | 077 |
| 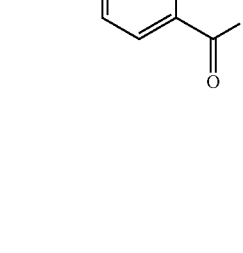 | 078 |
| 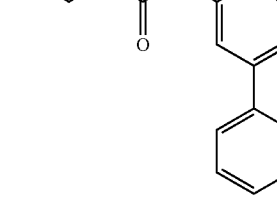 | 079 |
| 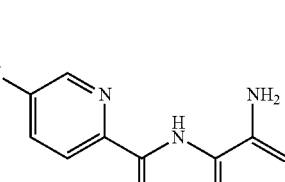 | 080 |
|  | 081 |
| 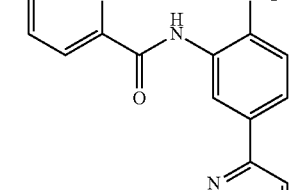 | 082 |

TABLE 1-continued

| Structure | Compound No. |
|---|---|
| (structure) | 083 |
| (structure) | 084 |
| (structure) | 085 |
| (structure) | 086 |
| (structure) | 087 |
| (structure) | 088 |
| (structure) | 089 |
| (structure) | 090 |

In one embodiment, the disclosed compounds may exist as tautomers. All tautomers are included within the scope of the compounds presented herein.

Compounds described herein also include isotopically-labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^{2}H$, $^{3}H$, $^{11}C$, $^{13}C$, $^{14}C$, $^{36}Cl$, $^{18}F$, $^{123}I$, $^{125}I$, $^{13}N$, $^{15}N$, $^{15}O$, $^{17}O$, $^{18}O$, $^{32}P$, and $^{35}S$. In one embodiment, isotopically-labeled compounds are useful in drug or substrate tissue distribution studies. In another embodiment, substitution with heavier isotopes such as deuterium affords greater metabolic stability (for example, increased in vivo half-life or reduced dosage requirements). In another embodiment, the compounds described herein include a $^{2}H$ (i.e., deuterium) isotope.

In yet another embodiment, substitution with positron emitting isotopes, such as $^{11}C$, $^{18}F$, $^{15}O$ and $^{13}N$, is useful in Positron Emission Topography (PET) studies for examining substrate receptor occupancy. Isotopically-labeled compounds are prepared by any suitable method or by processes using an appropriate isotopically-labeled reagent in place of the non-labeled reagent otherwise employed.

The specific compounds described herein, and other compounds encompassed by one or more of the Formulas described herein having different substituents are synthesized using techniques and materials described herein and as described, for example, in Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry 4$^{th}$ Ed., (Wiley 1992); Carey and Sundberg, Advanced Organic Chemistry 4th Ed., Vols. A and B (Plenum 2000, 2001), and Green and Wuts, Protective Groups in Organic Synthesis 3rd Ed., (Wiley 1999) (all of which are incorporated by reference for such disclosure). General methods for the preparation of compounds as described herein are modified by the use of appropriate reagents and conditions, for the introduction of the various moieties found in the Formulas as provided herein.

Compounds described herein are synthesized using any suitable procedures starting from compounds that are available from commercial sources, or are prepared using procedures described herein.

Methods of Treatment

The compounds of the invention can be used in a method of treating a disease or condition in a subject, said method comprising administering to the subject a compound of the invention, or a pharmaceutical composition comprising a compound of the invention.

In one aspect, the invention provides a method of selectively inhibiting HDAC1 and/or HDAC2 over other HDACs (e.g., HDAC3 and HDAC6) in a subject, comprising administering to the subject a compound of Formula I or any of the compounds of Table 1 or pharmaceutically acceptable salts thereof.

In another aspect, the invention provides a method of selectively inhibiting HDAC1 and/or HDAC2 over other HDACs (e.g., HDAC3 and HDAC6) in a subject, comprising administering to the subject a compound of Formula II, III, IV, or any of the compounds of Table 1 or pharmaceutically acceptable salts thereof.

In one embodiment, the compound of any of the formulae herein (e.g., Formula I, II, III, or IV) has a selectivity for HDAC1 and/or HDAC2 of 5 to 1000 fold over other HDACs.

In another embodiment, the compound of any of the formulae herein (e.g., Formula I, II, III, or IV) has a selectivity for HDAC1 and/or HDAC2 when tested in a HDAC enzyme assay of about 5 to 1000 fold over other HDACs.

In certain embodiments, the compound has a selectivity for HDAC1 and/or HDAC2 of 15 to 40 fold over other HDACs.

In another aspect, the invention provides a method of treating a disease mediated by HDAC1 and/or HDAC2 in a subject comprising administering to the subject a compound of Formula I or any of the compounds of Table 1.

In another aspect, the invention provides a method of treating a disease mediated by HDAC1 and/or HDAC2 in a subject comprising administering to the subject a compound of Formula II, III, IV or any of the compounds of Table 1.

In certain embodiments, the compounds are able to treat a subject suffering from or susceptible to a hemoglobinopathy. In a preferred embodiment, the compounds are able to treat sickle-cell disease or beta-thalessemia.

In another embodiment, the compounds of the invention are useful in the treatment of myelodysplastic syndromes.

In certain embodiments, the disease is cancer.

In certain embodiments, the cancer is lung cancer, colon and rectal cancer, breast cancer, prostate cancer, liver cancer, pancreatic cancer, brain cancer, kidney cancer, ovarian cancer, stomach cancer, skin cancer, bone cancer, gastric cancer, breast cancer, glioma, glioblastoma, neuroblastoma, hepatocellular carcinoma, papillary renal carcinoma, head and neck squamous cell carcinoma, leukemia, lymphomas, myelomas, retinoblastoma, cervical cancer, melanoma and/or skin cancer, bladder cancer, uterine cancer, testicular cancer, esophageal cancer, and solid tumors. In some embodiments, the cancer is lung cancer, colon cancer, breast cancer, neuroblastoma, leukemia, or lymphomas. In other embodiments, the cancer is lung cancer, colon cancer, breast cancer, neuroblastoma, leukemia, or lymphoma. In a further embodiment, the cancer is non-small cell lung cancer (NSCLC) or small cell lung cancer.

In a particular embodiment, the cancer is neuroblastoma.

In further embodiments, the cancer is a hematologic cancer, such as leukemia or lymphoma. In a certain embodiment, lymphoma is Hodgkin's lymphoma or Non-Hodgkin's lymphoma. In certain embodiments, leukemia is myeloid, lymphocytic, myelocytic, lymphoblastic, or megakaryotic leukemia.

In a particular embodiment, the leukemia is acute myelogenous leukemia and megakaryocytic leukemia.

In another aspect, provided herein is a method for treating sickle cell disease, beta thalassemia, myelodysplastic syndrome, acute myelogenous leukemia, neuroblastoma, or megakaryocytic leukemia in a subject comprising administering to the subject in need thereof a therapeutically effective amount of a compound of Formula I, a compound of Table 1, or a pharmaceutically acceptable salt thereof.

In another aspect, provided herein is a method for treating sickle cell disease, beta thalassemia, myelodysplastic syndrome, acute myelogenous leukemia, neuroblastoma, or megakaryocytic leukemia in a subject comprising administering to the subject in need thereof a therapeutically effective amount of a compound of Formula II, III, IV, a compound of Table 1, or a pharmaceutically acceptable salt thereof.

Thus, in another aspect of the invention, methods for the treatment of a disease mediated by HDAC1 and/or HDAC2 are provided comprising administering a therapeutically effective amount of a compound of Formula I, as described herein, to a subject in need thereof. In certain embodiments, the subject is identified as in need of such treatment. In certain embodiments, a method for the treatment of a diseases is provided comprising administering a therapeutically effective amount of a compound of Formula I, or a pharmaceutical composition comprising a compound of Formula I to a subject in need thereof, in such amounts and for such time as is necessary to achieve the desired result.

In certain embodiments, the method involves the administration of a therapeutically effective amount of a compound of Formula I or a pharmaceutically acceptable derivative thereof to a subject (including, but not limited to a human or animal) in need of it (including a subject identified as in need).

Thus, in a further aspect of the invention, methods for the treatment of a disease mediated by HDAC1 and/or HDAC2 are provided comprising administering a therapeutically effective amount of a compound of Formula I, as described herein, to a subject in need thereof. In certain embodiments, the subject is identified as in need of such treatment. In certain embodiments, a method for the treatment of a disease is provided comprising administering a therapeutically effective amount of a compound of Formula II, III, or IV, or a pharmaceutical composition comprising a compound of Formula II, III, or IV to a subject in need thereof, in such amounts and for such time as is necessary to achieve the desired result.

In certain embodiments, the method involves the administration of a therapeutically effective amount of a compound of Formula II, III, or IV, or a pharmaceutically acceptable derivative thereof to a subject (including, but not limited to a human or animal) in need of it (including a subject identified as in need).

Administration/Dosage/Formulations

In another aspect, provided herein is a pharmaceutical composition comprising at least one compound of the invention, together with a pharmaceutically acceptable carrier.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

In particular, the selected dosage level will depend upon a variety of factors including the activity of the particular compound employed, the time of administration, the rate of excretion of the compound, the duration of the treatment, other drugs, compounds or materials used in combination with the compound, the age, sex, weight, condition, general health and prior medical history of the patient being treated, and like factors well, known in the medical arts.

A medical doctor, e.g., physician or veterinarian, having ordinary skill in the art may readily determine and prescribe the effective amount of the pharmaceutical composition required. For example, the physician or veterinarian could begin administration of the pharmaceutical composition to dose the disclosed compound at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of the disclosed compound calculated to produce the desired therapeutic effect in association with the required pharmaceutical vehicle. The dosage unit forms of the invention are dictated by and directly dependent on (a) the unique characteristics of the disclosed compound and the particular therapeutic effect to be achieved, and (b) the limitations inherent in the art of compounding/formulating such a disclosed compound for the treatment of pain, a depressive disorder, or drug addiction in a patient.

In one embodiment, the compounds of the invention are formulated using one or more pharmaceutically acceptable excipients or carriers. In one embodiment, the pharmaceutical compositions of the invention comprise a therapeutically effective amount of a disclosed compound and a pharmaceutically acceptable carrier.

Routes of administration of any of the compositions of the invention include oral, nasal, rectal, intravaginal, parenteral, buccal, sublingual or topical. The compounds for use in the invention may be formulated for administration by any suitable route, such as for oral or parenteral, for example, transdermal, transmucosal (e.g., sublingual, lingual, (trans)buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration. In one embodiment, the preferred route of administration is oral.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

For oral application, particularly suitable are tablets, dragees, liquids, drops, suppositories, or capsules, caplets and gel caps. The compositions intended for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

For parenteral administration, the disclosed compounds may be formulated for injection or infusion, for example, intravenous, intramuscular or subcutaneous injection or infusion, or for administration in a bolus dose or continuous infusion. Suspensions, solutions or emulsions in an oily or aqueous vehicle, optionally containing other formulatory agents such as suspending, stabilizing or dispersing agents may be used.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth.

EXAMPLES

The invention is further illustrated by the following examples, which should not be construed as further limiting. The practice of the present invention will employ, unless otherwise indicated, conventional techniques of organic synthesis, cell biology, cell culture, molecular biology, transgenic biology, microbiology and immunology, which are within the skill of the art.

Abbreviations

Ac acetyl
° C. degree Celsius
dba dibenzylideneacetone
DCM dichloromethane
DIPEA N,N-Diisopropylethylamine
DMAP 4-dimethylaminopyridine
DMF dimethylformamide
DMSO dimethylsulfoxide
dppf 1,1'-bis(diphenylphosphino)ferrocene
EDCl 1-ethyl-3-[3-(dimethylamino)propyl]carbodiimid-hydrochloride
EA ethyl acetate
HATU O-(7-Azabenzotriazol-1-yl)-N,N,N',N'-tetramethyluronium Hexafluorophosphate
HOAt 1-hydroxy-7-azabenzotriazole
HOBt 1-hydroxybenzotriazole
HPLC high performance liquid chromatography
m-CPBA m-chloroperoxybenzoicacid
PE petroleum ether
Ph phenyl
Py pyridine
Ruphos 2-Dicyclohexylphosphino-2',6'-di-i-propoxy-1,1'-biphenyl
S-Phos 2-Dicyclohexylphosphino-2',6'-dimethoxybiphenyl TFA trifluoroacetic acid
THF tetrahydrofuran
TLC thin layer chromatography
Tol toluene or tolyl
Xantphos 4,5-Bis(diphenylphosphino)-9,9-dimethylxanthene Synthesis Procedures Example 1—Synthesis of Compound 001

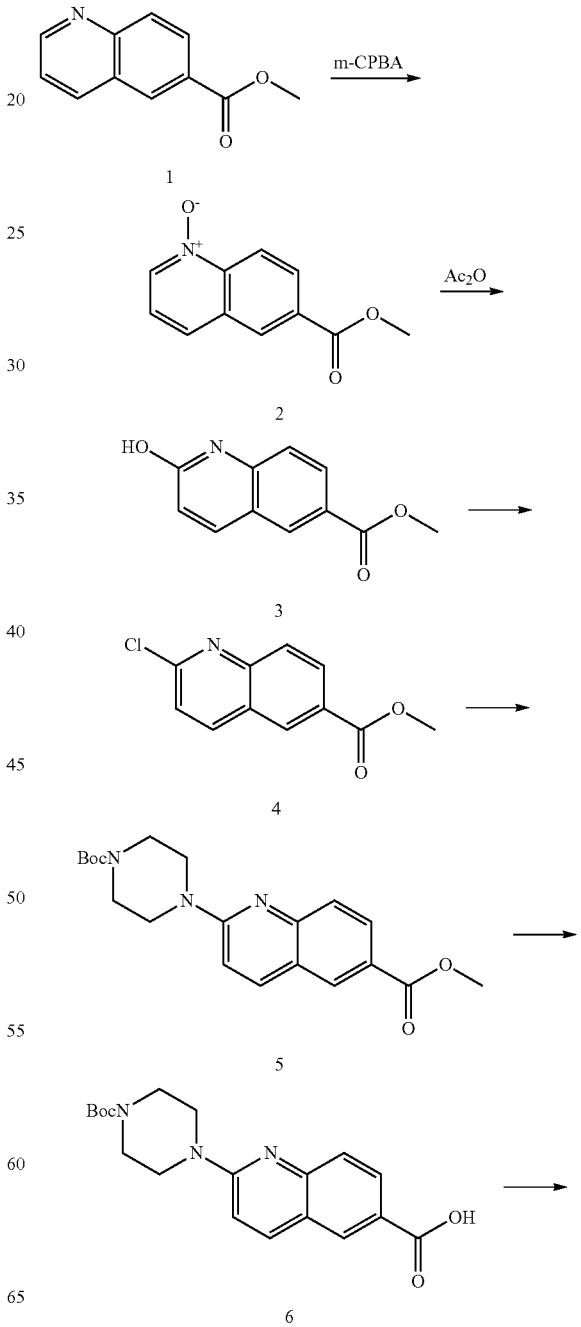

-continued

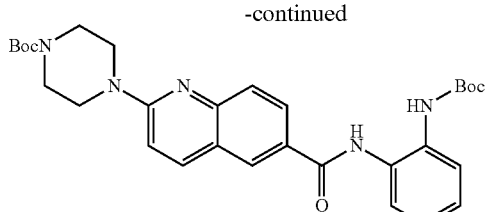

7

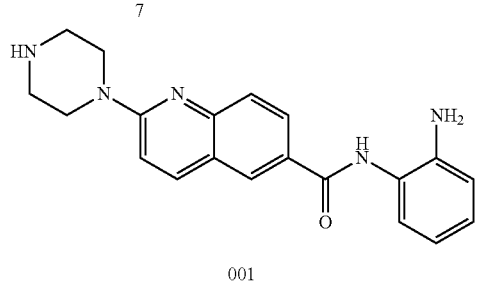

001

Step 1:

To a solution of methyl quinoline-6-carboxylate (3.6 g, 20 mmol) in DCM (60 mL) was slowly added m-CPBA (9.0 g, 40 mmol) at room temperature, the mixture was stirred at room temperature overnight. After completion, the mixture was quenched by aqueous saturated NaHCO₃, then washed with water, concentrated to get a residue which was purified by recrystallization from EtOH added DCM (200 mL), added aqueous saturated NaHCO₃ at 0° C. to PH>7. The organic layer was separated, dried, filtered to afford compound 2 as a yellow solid (4.6 g, 77%).

Step 2:

To a solution of 6-(methoxycarbonyl)quinoline 1-oxide (2.0 g, 10 mmol) in Ac₂O (50 mL), the mixture was heated at 135° C. overnight. After completion, the mixture was diluted with water, extracted with EA, washed with saturated NaHCO₃, purified on column (DCM/MeOH/NH3-H2O=250:50:1) to afford the crude. The mixture was purified by recrystallization from EA to afford compound 3 as a pale solid (1.4 g, 70%).

Step 3:

To a solution of compound methyl 2-hydroxyquinoline-6-carboxylate (10 g, 0.049 mol) and DMF (20 mL) in DCM (100 mL) was slowly added SOCl₂ (20 mL) at 0° C., the mixture was stirred at room temperature for 5 hours. TLC monitored completion, then the mixture was concentrated to get a residue, added DCM (200 mL), added aqueous Sat. NaHCO₃ at 0° C. to PH>7. The organic layer was separated, dried, filtered (flash silica gel) and concentrated to afford compound 4 (10 g, 92%) as a yellow solid.

Step 4:

A mixture of compound methyl 2-chloroquinoline-6-carboxylate (10 g, 0.045 mol), CuI (10 g, 0.53 mol), N-boc-piperazine (25 g, 0.135 mol) and K₂CO₃ (18.6 g, 0.135 mol) was stirred at 100° C. for overnight. TLC monitored completion. The mixture was added EA (300 mL), filtered (flash silica gel), concentrated to get a residue, added water (300 mL) and aqueous saturated citric acid (30 mL), stirred at room temperature for 30 minutes, filtered to obtain compound 5 (18 g, crude) as yellow solid without the further purification.

Step 5:

A mixture of compound methyl 2-(4-(tert-butoxycarbonyl)piperazin-1-yl)quinoline-6-carboxylate (18 g, crude) and 2M NaOH (50 mL) in EtOH (100 mL) and THF (100 mL) was stirred 70° C. for 4 hours. TLC monitored completion. The mixture concentrated to a residue, added water (300 mL) and aqueous saturated citric acid (40 mL), filtered to obtain compound 6 (14.5 g, 91% for two step) as a yellow solid.

Step 6:

A mixture of compound 6 (357 mg, 1 mmol), benzene-1,2-diamine (100 mg, 0.9 mmol) and 1-(3-dimethylaminopropyl)-3-ethylcarbodiimide hydrochloride (380 mg, 2 mmol) in pyridine (10 mL) was stirred at room temperature for overnight. After completed, the mixture was concentrated, poured into water (100 mL), filtered to obtain compound 7 (350 mg, crude) as a yellow solid.

Step 7:

A mixture of compound 7 (350 mg, crude) and TFA (3 mL) in DCM (3 mL) was stirred at room temperature for 1 hour. The mixture was purified by Prep-HPLC to obtain compound 001 (119 mg, 34%, 2 steps) as yellow solid. LCMS: m/z=348 (M+H)⁺. ¹H NMR (500 MHz, DMSO) δ 9.94 (s, 1H), 8.18 (dd, J=9.0, 2.0 Hz, 1H), 7.70 (d, J=8.5 Hz, 1H), 7.63 (dd, J=16.5, 1.5 Hz, 2H), 7.41 (m, 2H), 7.28-6.94 m, 4H), 4.00 (m, 4H), 3.27 (s, 4H).

Example 2—Synthesis of Compound 002

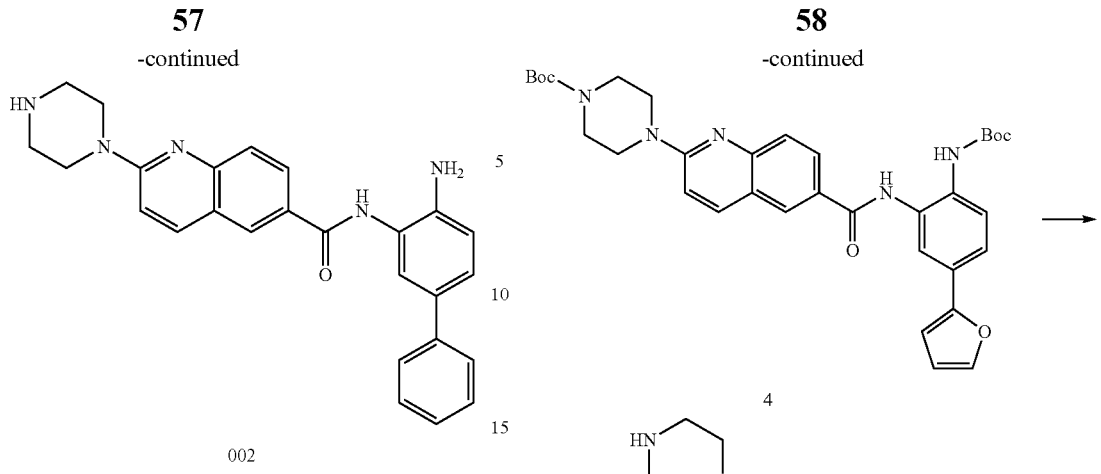

Step 1:

A mixture of compound 1 (357 mg, 1 mmol), tert-butyl (4-amino-[1,1'-biphenyl]-3-yl)carbamate (260 mg, 0.9 mmol) and 1-(3-dimethylaminopropyl)-3-ethylcarbodiimide hydrochloride (380 mg, 2 mmol) in pyridine (12 mL) was stirred at room temperature for overnight. After completed, the mixture was concentrated, poured into water (80 mL), filtered to get compound 2 (415 mg, crude) as a yellow solid.

Step 2:

A mixture of compound 2 (415 mg, crude) and TFA (4 mL) in DCM (4 mL) was stirred at room temperature for 1 hour. The mixture was purified by Prep-HPLC to obtain compound 002 (139 mg, 33%, 2 steps) as yellow solid. LCMS: m/z=424 (M+H)+. 1H NMR (500 MHz, DMSO) δ 9.94 (s, 1H), 8.99 (brs, 2H), 8.49 (d, J=1.5 Hz, 1H), 8.27 (d, J=9.5 Hz, 1H), 8.18 (dd, J=9.0, 2.0 Hz, 1H), 7.70 (d, J=8.5 Hz, 1H), 7.63 (dd, J=16.5, 1.5 Hz, 2H), 7.41 (m, 2H), 7.28-6.94 (m, 5H), 4.00 (m, 4H), 3.27 (s, 4H).

Example 3—Synthesis of Compound 003

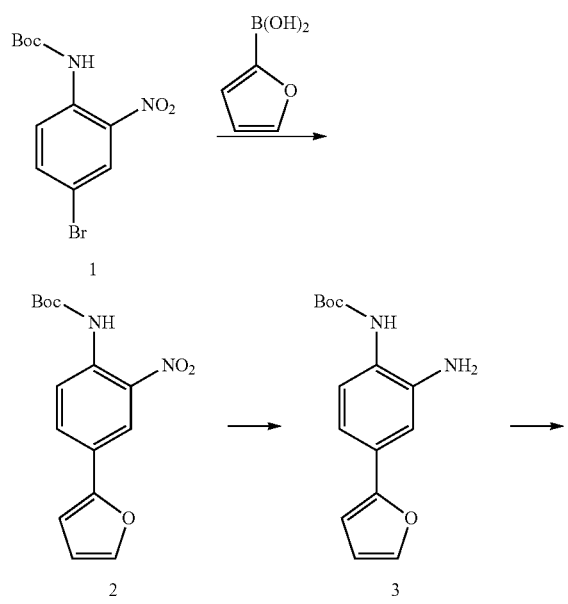

Step 1:

Under N2, a mixture of tert-butyl 4-bromo-2-nitrophenylcarbamate (1.00 g, 3.15 mmol) and furan-2-ylboronic acid (494 mg, 4.41 mmol), 1,1'-Bis(diphenylphosphino)ferrocene-palladium(II)dichloride dichloromethane complex (200 mg, 0.24 mmol) and potassium carbonate (872 mg, 6.31 mmol) in dioxane (40 mL) and water (8 mL) was heated at 90° C. for 18 hours. Then it was cooled to room temperature, and dioxane was removed in vacuo. The residue was extracted with EA and concentrated in vacuo. The residue was purified by silica gel chromatography (PE, PE/EA=50/1) to give compound 2 as a yellow solid (723 mg, 76%).

Step 2:

To a mixture of tert-butyl 4-(furan-2-yl)-2-nitrophenylcarbamate (673 mg, 2.21 mmol), FeCl3 (219 mg, 5.21 mmol) and active charcoal (200 mg) in EtOH (30 mL) was added N2H4 (4 mL). It was stirred at 60° C. for 2 h. Then it was filtrated and concentrated in vacuo. And the residue was partitioned with EA and water. The combined EA layers were concentrated in vacuo and the residue was purified by silica gel chromatography (PE/EA=5/1, DCM) to give compound 3 as a white solid (576 mg, 95%). LCMS: m/z=219.0 (M−56+H)+.

Step 3:

A mixture of 2-(4-(tert-butoxycarbonyl)piperazin-1-yl)quinoline-6-carboxylic acid (140 mg, 0.39 mmol) and HATU (140 mg, 0.43 mmol) in DMF (10 mL) was stirred at room temperature for 15 minutes. Then tert-butyl 2-amino-4-(furan-2-yl)phenylcarbamate (108 mg, 0.43 mmol) was added. It was stirred at 50° C. for 18 hours. Then it was poured into water. The mixture was extracted with EA. The combined EA layers were concentrated in vacuo and the residue was purified by prep-TLC to give the compound 4 (261 mg). LCMS: m/z=614.2 (M+H)+.

Step 4:

To a mixture of tert-butyl 3-(5-(4-methylpiperazin-1-yl)picolinamido)biphenyl-4-ylcarbamate (261 mg) in MeOH (2 mL) was added HCl/dioxane (4 mL) at 0° C. It was stirred at 0° C. to room temperature for 18 h. It was concentrated in vacuo and the residue was purified by prep-HPLC to give compound 003 as a white solid (56 mg, lot SP-0017146-043). LCMS: m/z=414.2 (M+H)+. 1H NMR (500 MHz, DMSO) δ 9.94 (s, 1H), 8.99 (brs, 2H), 8.49 (d, J=1.5 Hz, 1H), 8.27 (d, J=9.5 Hz, 1H), 8.18 (dd, J=9.0, 2.0 Hz, 1H), 7.70 (d, J=8.5 Hz, 1H), 7.63 (dd, J=16.5, 1.5 Hz, 2H), 7.41 (m, 2H), 6.94 (d, J=8.5 Hz, 1H), 6.68 (d, J=3.2 Hz, 1H), 6.53 (m, 1H), 4.00 (m, 4H), 3.27 (s, 4H).

Example 4—Synthesis of Compound 004

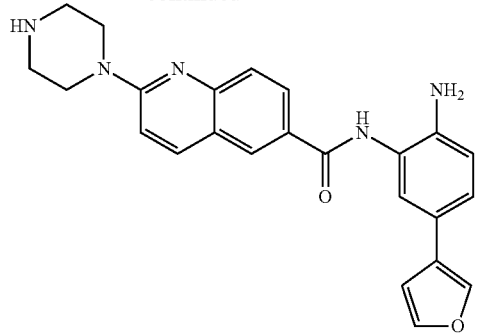

004

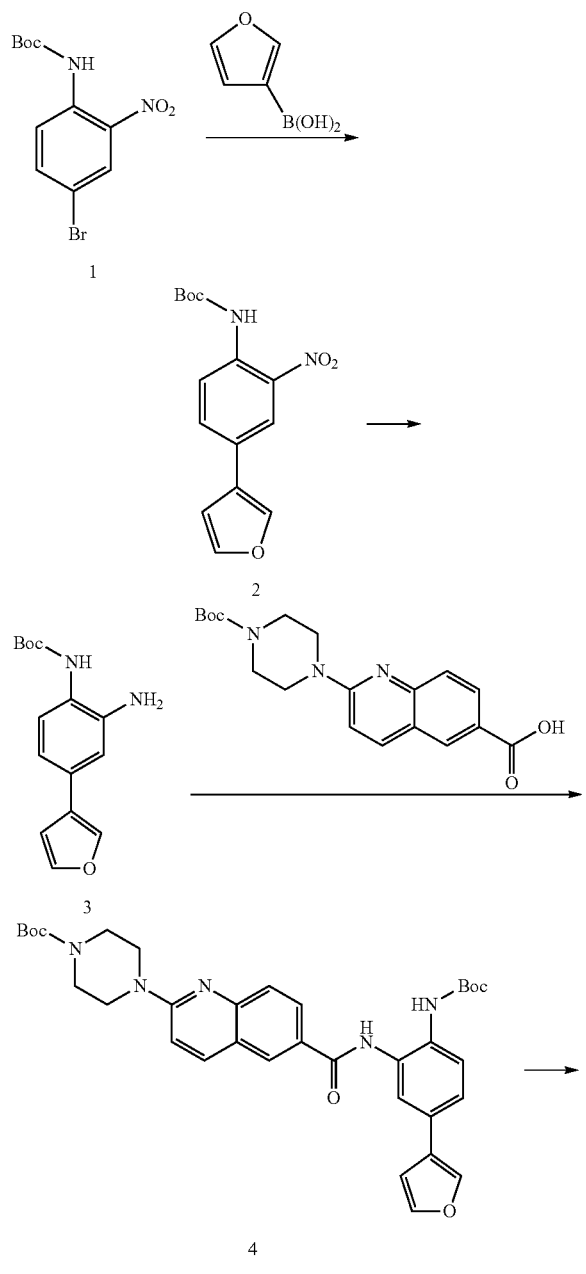

Step 1:

To a solution of compound 1 (3.16 g, 10 mmol) in dioxane (20 mL) was added furan-3-ylboronic acid (1.45 g, 13 mmol), K3PO4 (4.23 g, 20 mmol) and Pd[P(C6H5)3]4 (700 mg, 0.7 mmol). The mixture was stirred at 90° C. for overnight. After completed, water was added and the mixture was extracted with EA (2×150 mL), the organic layer was purified by silica column chromatography (PE/EA 2/1) to afford compound 2 (2.2 g, 72%) as a yellow oil.

Step 2:

To a solution of compound 2 (200 mg, 0.65 mmol) in EA (10 mL) was added Pd/C (20 mg). The reaction mixture was stirred under H2 for 5 hour at room temperature. After completion, the mixture was filtrated, extracted with EA (2×50 mL) to afford compound 3 (180 mg, 100%) as a yellow solid.

Step 3:

A mixture of compound 3 (180 mg, 0.66 mmol), 2-(4-(tert-butoxycarbonyl)piperazin-1-yl)quinoline-6-carboxylic acid (260 mg, 0.73 mmol), and EDCl (835 mg, 4.4 mmol) in pyridine (5 mL) was stirred at room temperature for overnight, TLC monitored. Put into water and extracted with EA (2×100 mL), the organic layer was separated, dried, and purified by prep-TLC (PE/EA 2/1) to afford compound 4 (250 mg, 62%) as an off-white solid.

Step 4:

To a solution of compound 4 (250 mg, 0.4 mmol) in DCM (5 mL) was added TFA (2 mL), the mixture was stirred at room temperature for 2 hours. After completed, the resulting mixture was concentrated and alkalified with (aqueous) NaHCO3 to pH=8. The precipitate was collected and washed by water to afford compound 004 as a white powder (100 mg, 59%). LCMS: m/z=414 (M+H)+. 1H NMR (400 MHz, DMSO) δ 9.77 (s, 1H), 8.41 (d, J=1.7 Hz, 1H), 8.11 (dd, J=11.3, 5.4 Hz, 2H), 7.97 (s, 1H), 7.67 (t, J=1.6 Hz, 1H), 7.59 (d, J=8.8 Hz, 1H), 7.42 (d, J=1.8 Hz, 1H), 7.33-7.22 (m, 2H), 6.81 (d, J=8.2 Hz, 2H), 5.01 (s, 2H), 3.74-3.63 (m, 4H), 2.88-2.73 (m, 4H).

Example 5—Synthesis of Compound 005

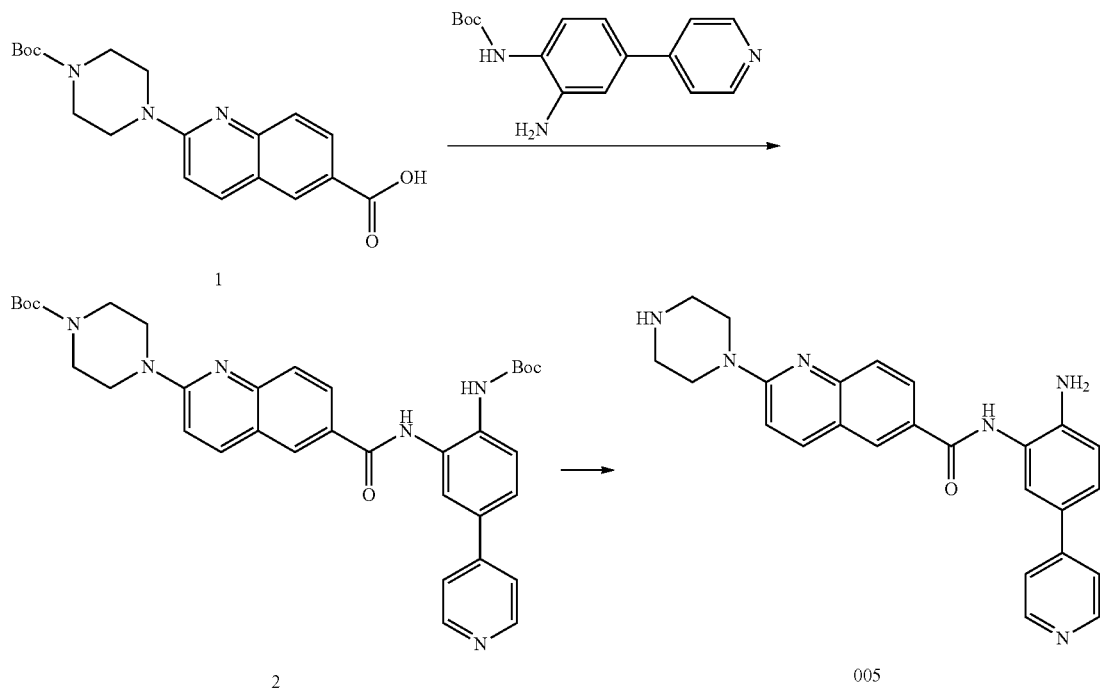

Step 1:

2-(4-(tert-butoxycarbonyl) piperazin-1-yl) quinoline-6-carboxylic acid (108 mg, 0.3 mmol), tert-butyl 2-amino-4-(pyridin-4-yl) phenylcarbamate (86 mg, 0.3 mmol) and EDCl (173 mg, 0.9 mmol) were added into pyridine (3 ml). The mixture was stirred for overnight at room temperature. When the reaction finished, it was extracted by EA and washed by $NaHCO_3$ and saturated brine. Then the EA layer was concentrated to afford compound 2 (200 mg, crude).

Step 2:

Tert-butyl 4-(6-(2-(tert-butoxycarbonylamino)-5-(pyridin-4-yl) phenylcarbamoyl) quinolin-2-yl) piperazine-1-carboxylate (260 mg, crude) was added into DCM (2 ml). Then TFA (2 ml) was added. The mixture was stirred at room temperature for 1 hour. It was purified by Prep-HPLC (base method). Compound 005 was obtained as a white solid (90 mg, 51% yield, lot SP-0017467-057). LCMS: m/z=425.2 (M+H)$^+$. $^1$H NMR (400 MHz, DMSO) δ 9.79 (s, 1H), 8.52 (d, J=6.1 Hz, 2H), 8.41 (s, 1H), 8.18-8.05 (m, 2H), 7.72 (d, J=2.0 Hz, 1H), 7.60 (d, J=6.4 Hz, 3H), 7.52 (dd, J=8.4, 2.1 Hz, 1H), 7.30 (d, J=9.3 Hz, 1H), 6.90 (d, J=8.4 Hz, 1H), 5.41 (s, 2H), 3.68 (d, J=4.7 Hz, 4H), 2.88-2.74 (m, 4H).

Example 6—Synthesis of Compound 006

-continued

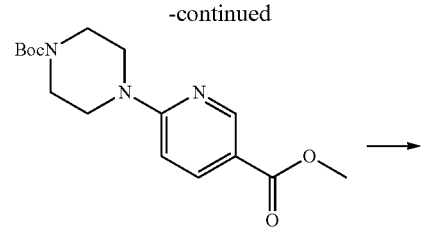

2

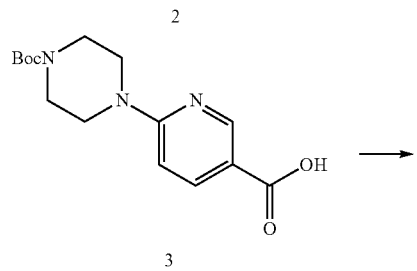

3

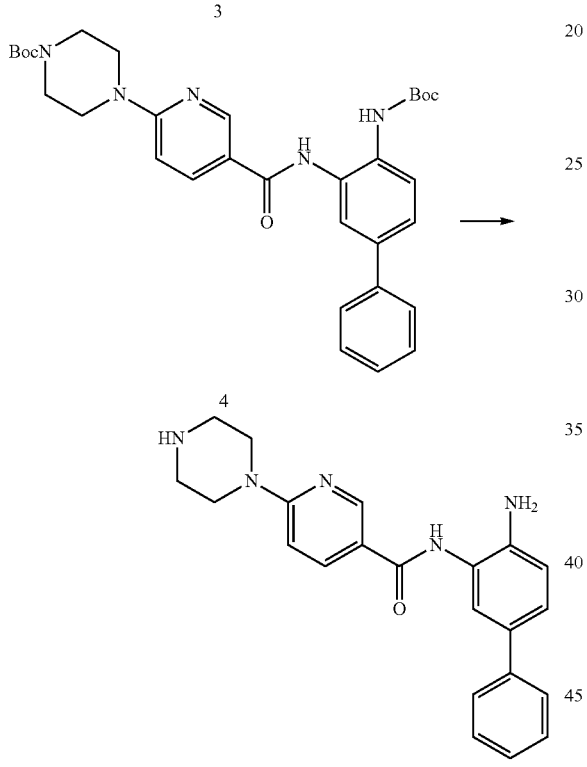

Step 1:

A mixture of methyl 6-chloronicotinate (1.7 g, 10 mmol), tert-butyl piperazine-1-carboxylate (5.58 g, 30 mmol), DIPEA (6.45 g, 50 mmol) in 1,4-dioxane (30 mL) was stirred at 95° C. under $N_2$ atmosphere for overnight. The mixture was cool and EA (100 mL) and water (100 mL) were added, stirred for 30 min, the organic layer was separated, dried, concentrated to get a residue, which was washed by PE (100 mL) to obtain compound 2 (2.9 g, 91%) as a light yellow solid.

Step 2:

A mixture of compound 2 (3.2 g, 10 mmol) and 2M NaOH (50 mL) in THF (50 ml) and EtOH (50 mL) was stirred at 60° C. for 3 h. The mixture was concentrated to obtain a residue, HCl (2 M) was added to adjust pH 7, filtered to give compound 3 as a white solid (3.0 g, 97%)

Step 3:

A mixture of compound 3 (307 mg, 1 mmol), tert-butyl 3-aminobiphenyl-4-ylcarbamate (256 mg, 0.9 mmol) and 1-(3-dimethylaminopropyl)-3-ethylcarbodiimide hydrochloride (573 mg, 3 mmol) in pyridine (15 mL) was stirred at room temperature for overnight. The mixture was poured into water (100 mL), filtered to get compound 4 (470 mg, 82%) as a yellow solid.

Step 4:

A mixture of compound 4 (286 mg, 0.5 mmol) and TFA (3 mL) in DCM (3 mL) was stirred at room temperature for 1 h. The mixture was purified by Prep-HPLC to obtain compound 006 (84 mg, 45%) as a yellow solid. LCMS: m/z=374 (M+H)$^+$. $^1$H NMR (400 MHz, DMSO) δ 9.62 (s, 1H), 8.85 (s, 2H), 8.81 (s, 1H), 8.20 (d, J=8.9 Hz, 1H), 7.55 (d, J=7.7 Hz, 2H), 7.50 (s, 1H), 7.39 (t, J=7.7 Hz, 2H), 7.33 (dd, J=8.3, 1.9 Hz, 1H), 7.24 (t, J=7.3 Hz, 1H), 7.02 (d, J=9.1 Hz, 1H), 6.87 (d, J=8.3 Hz, 1H), 5.11 (s, 2H), 3.90-3.78 (m, 4H), 3.22 (d, J=4.9 Hz, 4H).

Example 7—Synthesis of Compound 007

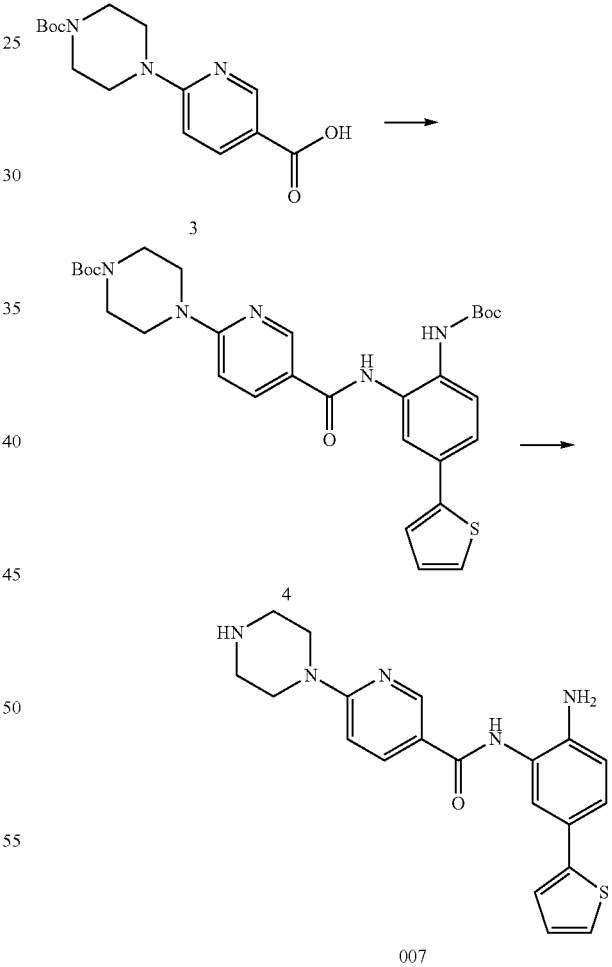

Step 1:

A mixture of compound 3 (307 mg, 1 mmol), tert-butyl 2-amino-4-(thiophen-2-yl)phenylcarbamate (261 mg, 0.9 mmol) and 1-(3-dimethylaminopropyl)-3-ethylcarbodiimide hydrochloride (573 mg, 3 mmol) in pyridine (15 mL) was stirred at room temperature for overnight. The mixture was poured into water (100 mL), filtered to obtain compound 4 (463 mg, 80%) as a yellow solid.

Step 2:

A mixture of compound 4 (290 mg, 0.5 mmol) and TFA (3 mL) in DCM (3 mL) was stirred at room temperature for 1 hour. The mixture was purified by Prep-HPLC to obtain compound 007 (95 mg, 50%) as a yellow solid. LCMS: m/z=380 (M+H)+. 1H NMR (400 MHz, DMSO) δ 9.62 (s, 1H), 8.90 (s, 2H), 8.81 (s, 1H), 8.19 (d, J=7.2 Hz, 1H), 7.45 (s, 1H), 7.36 (d, J=5.0 Hz, 1H), 7.31 (d, J=8.4 Hz, 1H), 7.25 (d, J=3.4 Hz, 1H), 7.09-6.98 (m, 2H), 6.81 (d, J=8.3 Hz, 1H), 5.20 (s, 2H), 3.86 (s, 4H), 3.22 (s, 4H).

Example 8—Synthesis of Compound 008

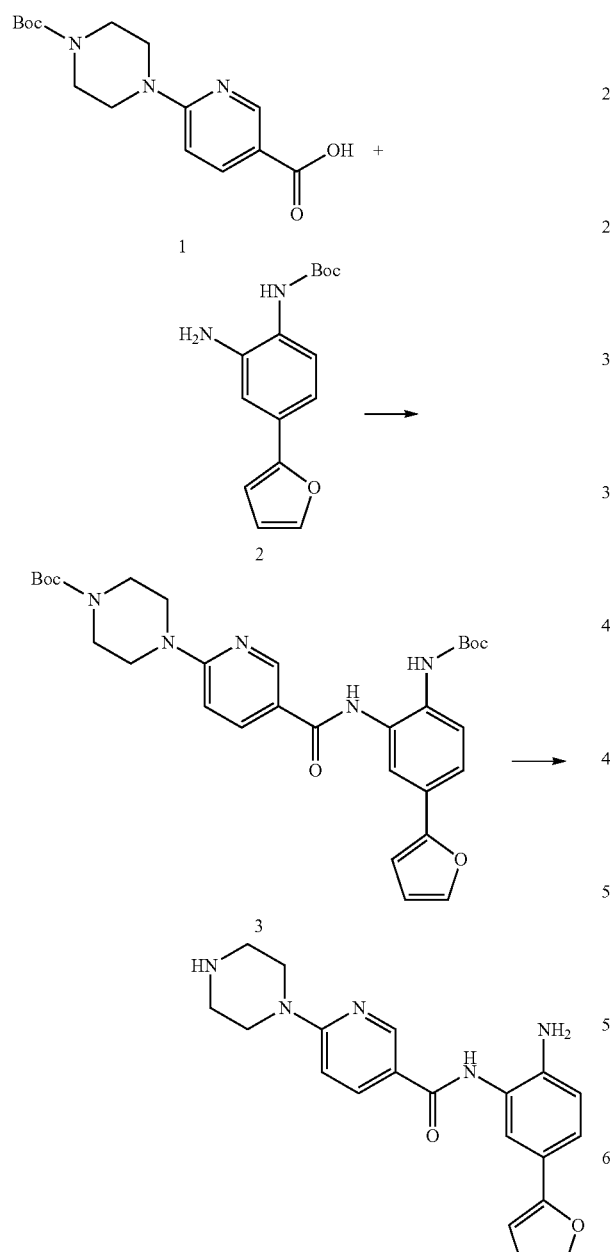

Step 1:

To a solution of compound 1 (175 mg, 0.57 mmol) in pyridine (4 ml) was added tert-butyl (2-amino-4-(furan-2-yl)phenyl)carbamate (156 mg, 0.57 mmol) and EDCl (218 mg). The mixture was stirred at room temperature for overnight. The solution was evaporated off and washed with HCl (1N), extracted by EA (20 ml×3), washed with water, brine, purified by prep-TLC (PE/EA=1/1) to afford compound 3 as a white solid (128 mg, 40%).

Step 2:

To a solution of compound 3 (124 mg, 0.22 mmol) in DCM (3 ml) was added TFA (1 ml).

The mixture was stirred at room temperature for overnight. The solution was concentrated, the pH adjusted to >7, filtered, and washed with water to afford compound 008 as a yellow solid (77 mg, 97.4%). 1H NMR (400 MHz, DMSO) δ 9.50 (s, 1H), 8.75 (d, J=2.3 Hz, 1H), 8.08 (dd, J=9.0, 2.4 Hz, 1H), 7.60 (d, J=1.2 Hz, 1H), 7.51 (d, J=1.8 Hz, 1H), 7.31 (dd, J=8.4, 2.0 Hz, 1H), 6.86 (d, J=9.1 Hz, 1H), 6.80 (d, J=8.4 Hz, 1H), 6.60 (d, J=3.3 Hz, 1H), 6.50 (dd, J=3.2, 1.8 Hz, 1H), 5.14 (s, 2H), 3.58-3.50 (m, 4H), 2.81-2.72 (m, 4H). LCMS: m/z=364.2 (M+H)+

Example 9—Synthesis of Compound 009

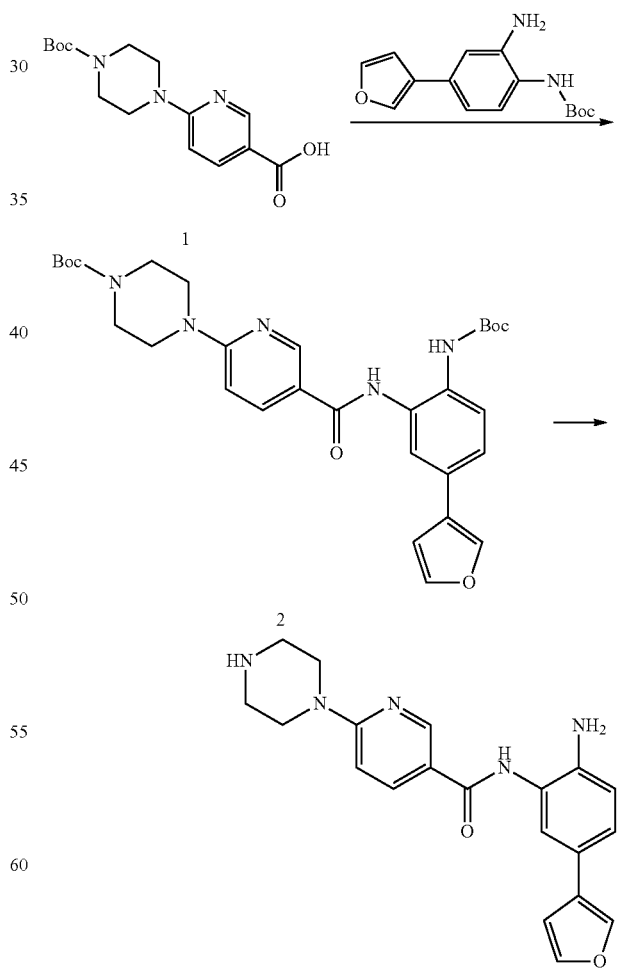

Step 1:

6-(4-(tert-butoxycarbonyl) piperazin-1-yl) nicotinic acid (92 mg, 0.3 mmol), tert-butyl 2-amino-4-(furan-3-yl) phenylcarbamate (82 mg, 0.3 mmol) and EDCl (173 mg, 0.9 mmol) were added into pyridine (3 ml). The mixture was stirred at room temperature for overnight. The crude compound 2 was prepared for next step (200 mg, crude).

Step 2:

Tert-butyl 4-(5-(2-(tert-butoxycarbonylamino)-5-(furan-3-yl) phenylcarbamoyl) pyridin-2-yl) piperazine-1-carboxylate (180 mg, crude) was added into DCM (2 ml). Then TFA (2 ml) was added. The mixture was stirred at room temperature for 6 hours. When the reaction finished, the solid was filtered and washed by Et$_2$O. A White solid was afforded compound 009 (76 mg, 66% yield, lot SP-0017467-083). LCMS: m/z=364.2 (M+H)$^+$. $^1$H NMR (400 MHz, DMSO) δ 9.52 (s, 1H), 8.75 (s, 1H), 8.08 (d, J=8.4 Hz, 1H), 7.97 (s, 1H), 7.66 (s, 1H), 7.37 (s, 1H), 7.23 (d, J=8.1 Hz, 1H), 7.04-6.67 (m, 3H), 4.97 (s, 2H), 3.56 (s, 4H), 2.79 (s, 4H).

Example 10—Synthesis of Compound 010

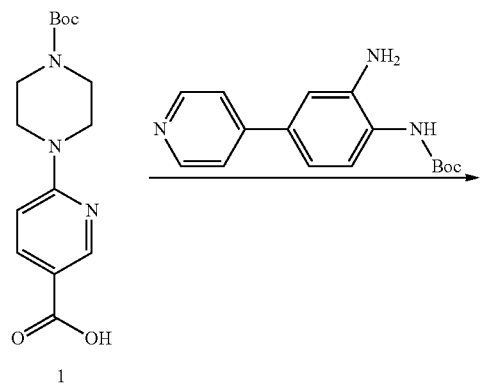

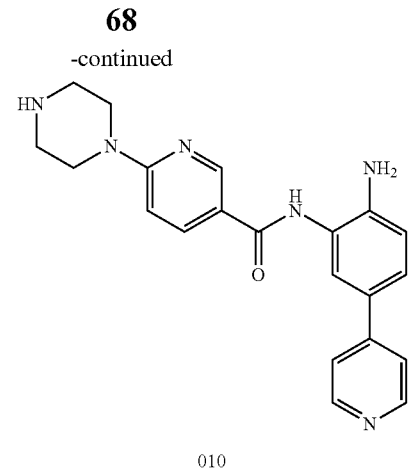

010

Step 1:

6-(4-(tert-butoxycarbonyl) piperazin-1-yl) nicotinic acid (92 mg, 0.3 mmol), tert-butyl 2-amino-4-(pyridin-4-yl) phenylcarbamate (86 mg, 0.3 mmol) and EDCl (173 mg, 0.9 mmol) were added into pyridine (3 ml). The mixture was stirred for overnight at room temperature. When the reaction finished, it was extracted by EA and washed by citric acid, NaHCO$_3$ and saturated brine. Then the EA layer was concentrated to afford compound 2 as a grey solid (150 mg, 85% yield).

Step 2:

Tert-butyl 4-(5-(2-(tert-butoxycarbonylamino)-5-(pyridin-4-yl) phenylcarbamoyl) pyridin-2-yl) piperazine-1-carboxylate (150 mg, crude) was added into DCM (2 ml). Then TFA (2 ml) was added. The mixture was stirred at room temperature for 1 hour. It was purified by Prep-HPLC (base method). Compound 010 was obtained as a light yellow solid (60 mg, 61% yield, lot SP-0017467-049). LCMS: m/z=375.1 (M+H)$^+$. $^1$H NMR (400 MHz, DMSO) δ 9.52 (s, 1H), 8.76 (d, J=2.3 Hz, 1H), 8.51 (dd, J=4.6, 1.5 Hz, 2H), 8.09 (dd, J=9.0, 2.4 Hz, 1H), 7.67 (d, J=2.1 Hz, 1H), 7.58 (dd, J=4.7, 1.6 Hz, 2H), 7.50 (dd, J=8.4, 2.2 Hz, 1H), 6.88 (dd, J=8.8, 2.5 Hz, 2H), 5.36 (s, 2H), 3.62-0.48 (m, 4H), 2.84-.73 (m, 4H).

Example 11—Synthesis of Compound 011

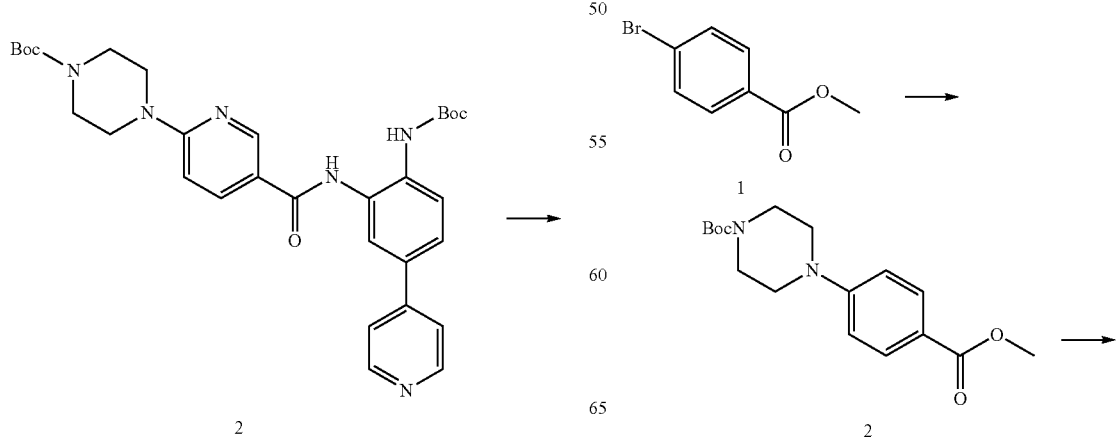

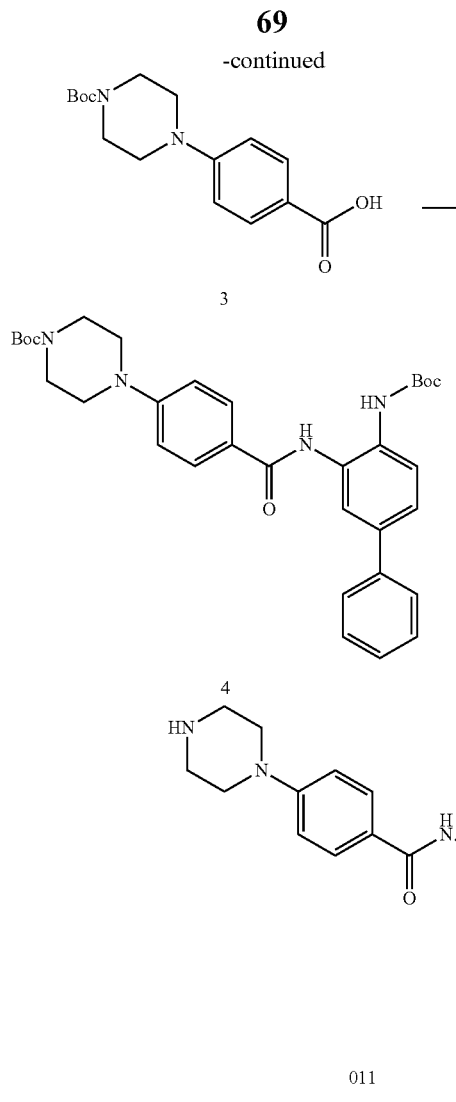

Step 4:

A mixture of compound 4 (286 mg, 0.5 mmol) and TFA (3 mL) in DCM (3 mL) was stirred at room temperature for 1 h. The mixture was purified by Prep-HPLC to obtain compound 011 (112 mg, 60%) as a yellow solid. LCMS: m/z=373 (M+H)+. 1H NMR (400 MHz, DMSO) δ 9.54 (s, 1H), 7.91 (d, J=8.7 Hz, 2H), 7.54 (dd, J=17.4, 4.6 Hz, 3H), 7.40 (t, J=7.6 Hz, 2H), 7.32 (dd, J=8.3, 1.8 Hz, 1H), 7.25 (t, J=7.3 Hz, 1H), 7.00 (d, J=8.8 Hz, 2H), 6.87 (d, J=8.3 Hz, 1H), 5.06 (s, 2H), 3.25-3.13 (m, 4H), 2.92-2.78 (m, 4H).

Example 12—Synthesis of Compound 012

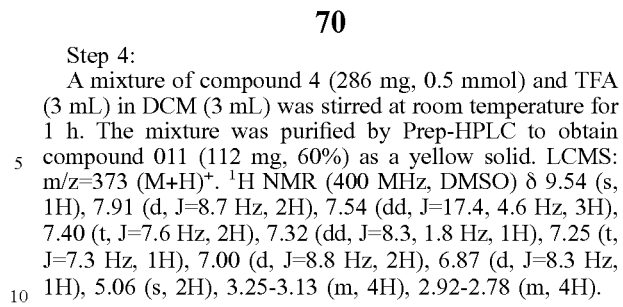

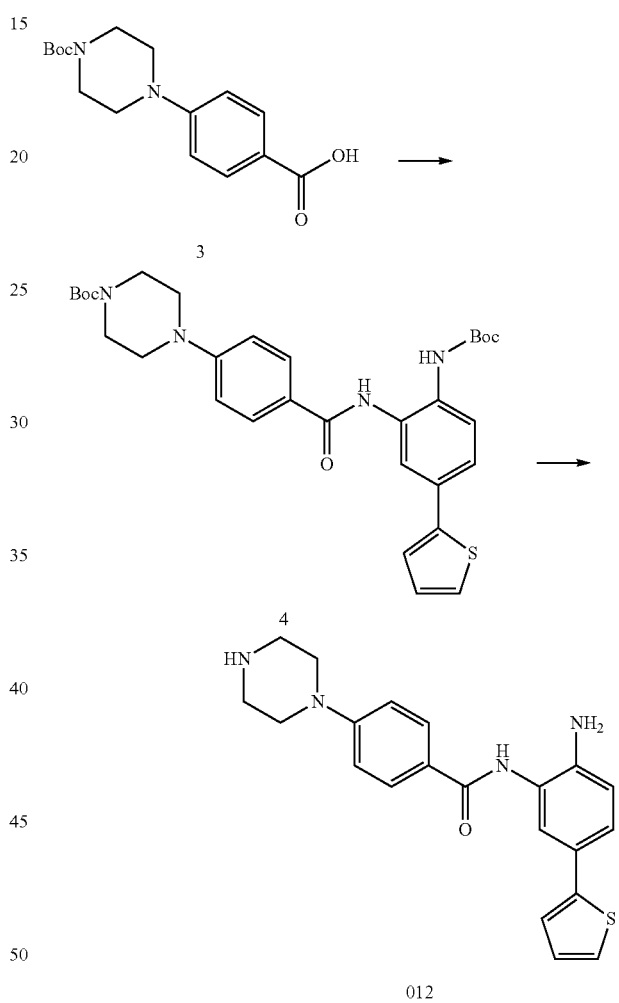

Step 1:

A mixture of methyl 4-bromobenzoate (2.15 g, 10 mmol), tert-butyl piperazine-1-carboxylate (5.58 g, 30 mmol), Pd2(dba)3 (915 mg, 1 mmol), Xantphos (478 mg, 1 mmol) and Cs2CO3 (9.75 g, 30 mmol, 3 eq) in toluene (30 mL) was stirred at 95° C. under N2 atmosphere for overnight. The mixture was cool and added EA (100 mL), filtered, concentrated to obtain a residue, which was washed by PE (100 mL) to obtain compound 2 (2.88 g, 90%) as a light yellow solid.

Step 2:

A mixture of compound 2 (3.2 g, 10 mmol) and 2M NaOH (50 mL) in THF (50 ml) and EtOH (50 mL) was stirred at 60° C. for 3 hours. The mixture was concentrated to obtain a residue, HCl (2 M) was added to adjust pH to 7, filtered to give compound 3 as a white solid (3.0 g, 100%).

Step 3:

A mixture of compound 3 (306 mg, 1 mmol), tert-butyl 3-aminobiphenyl-4-ylcarbamate (256 mg, 0.9 mmol) and 1-(3-dimethylaminopropyl)-3-ethylcarbodiimide hydrochloride (573 mg, 3 mmol) in pyridine (15 mL) was stirred at room temperature for overnight. The mixture was poured into water (100 mL) then filtered to obtain compound 4 (438 mg, 85%) as a yellow solid.

Step 1:

A mixture of compound 3 (306 mg, 1 mmol), tert-butyl 2-amino-4-(thiophen-2-yl)phenylcarbamate (260 mg, 0.9 mmol) and 1-(3-dimethylaminopropyl)-3-ethylcarbodiimide hydrochloride (573 mg, 3 mmol) in pyridine (15 mL) was stirred at room temperature for overnight. The mixture was poured into water (100 mL), filtered to obtain compound 4 (442 mg, 85%) as a yellow solid.

Step 2:

A mixture of compound 4 (289 mg, 0.5 mmol) and TFA (3 mL) in DCM (3 mL) was stirred at room temperature for 1 hour. The mixture was purified by Prep-HPLC to obtain compound 012 (113 mg, 60%) as a yellow solid. LCMS: m/z=379 (M+H)+. 1H NMR (400 MHz, DMSO) δ 9.51 (s, 1H), 7.89 (d, J=8.9 Hz, 2H), 7.46 (d, J=2.0 Hz, 1H), 7.36 (dd, J=5.1, 0.8 Hz, 1H), 7.32-7.20 (m, 2H), 7.05 (dd, J=5.0, 3.6 Hz, 1H), 6.99 (d, J=8.9 Hz, 2H), 6.81 (d, J=8.3 Hz, 1H), 5.10 (s, 2H), 3.24-3.15 (m, 4H), 2.89-2.77 (m, 4H).

Example 13—Synthesis of Compound 013

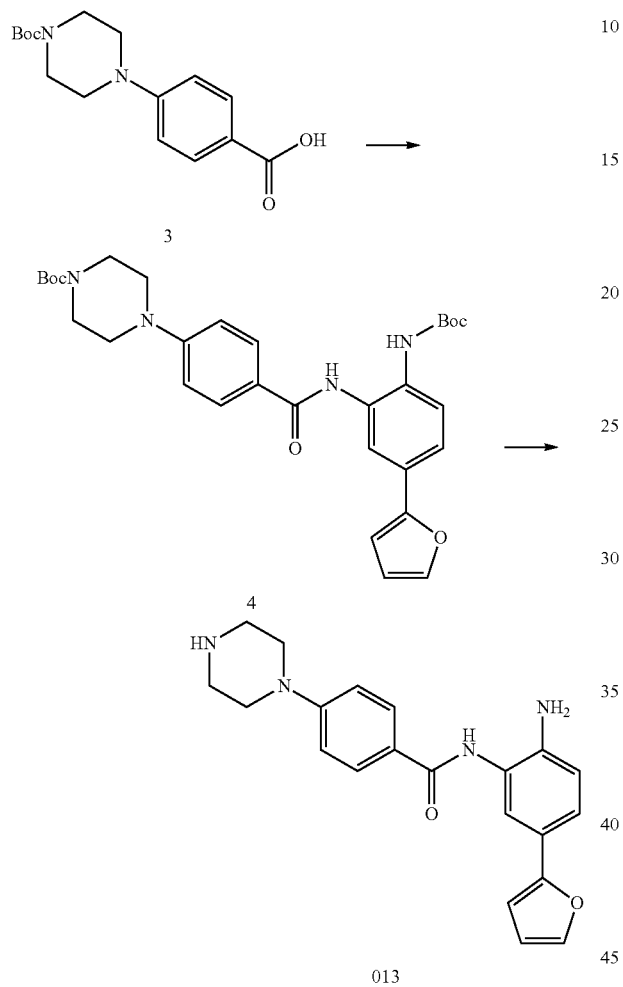

Example 14—Synthesis of Compound 014

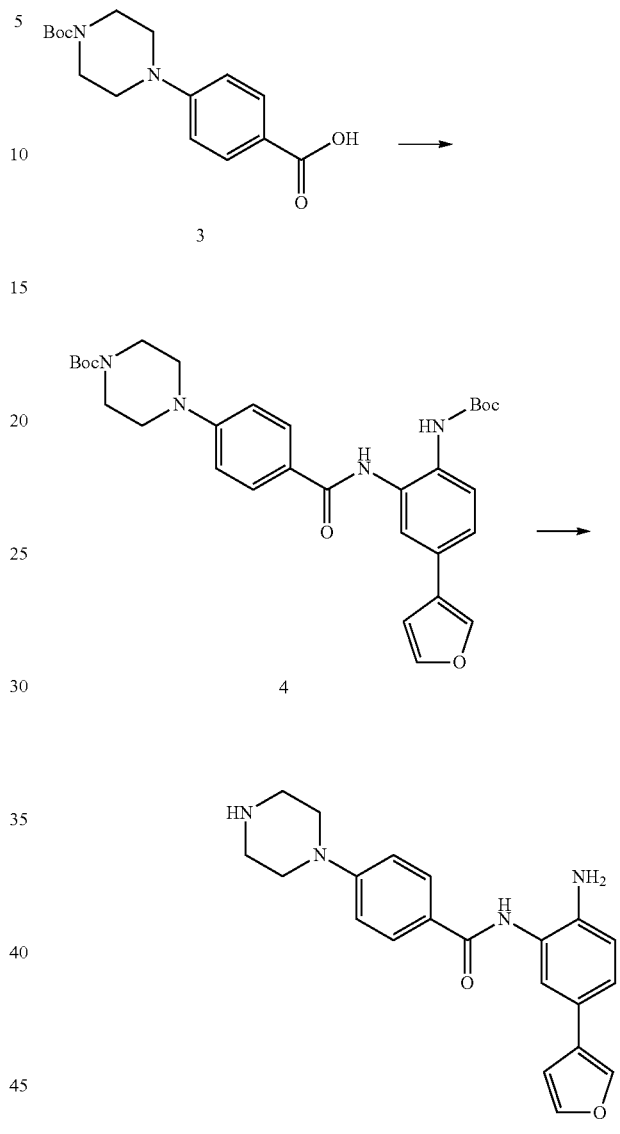

Step 1:

A mixture of compound 3 (306 mg, 1 mmol), tert-butyl 2-amino-4-(furan-2-yl)phenylcarbamate (247 mg, 0.9 mmol) and 1-(3-dimethylaminopropyl)-3-ethylcarbodiimide hydrochloride (573 mg, 3 mmol) in pyridine (15 mL) was stirred at room temperature for overnight. The mixture was poured into water (100 mL), filtered to obtain compound 4 (410 mg, 81%) as a yellow solid.

Step 2:

A mixture of compound 4 (281 mg, 0.5 mmol) and TFA (3 mL) in DCM (3 mL) was stirred at room temperature for 1 hour. The mixture was purified by Prep-HPLC to obtain compound 013 (107 mg, 59%) as a yellow solid. LCMS: m/z=363 (M+H)$^+$. $^1$H NMR (400 MHz, DMSO) δ 9.49 (s, 1H), 7.89 (d, J=8.7 Hz, 2H), 7.61 (s, 1H), 7.51 (d, J=1.4 Hz, 1H), 7.32 (d, J=8.3 Hz, 1H), 6.99 (d, J=8.7 Hz, 2H), 6.81 (d, J=8.3 Hz, 1H), 6.61 (d, J=3.1 Hz, 1H), 6.51 (d, J=1.7 Hz, 1H), 5.10 (s, 2H), 3.20 (s, 4H), 2.84 (s, 4H).

Step 1:

A mixture of compound 3 (306 mg, 1 mmol), tert-butyl 2-amino-4-(furan-3-yl)-phenylcarbamate (246 mg, 0.9 mmol) and 1-(3-dimethylaminopropyl)-3-ethylcarbodiimide hydrochloride (573 mg, 3 mmol) in pyridine (15 mL) was stirred at room temperature for overnight. The mixture was poured into water (100 mL), filtered to obtain compound 4 (420 mg, 83%) as a yellow solid.

Step 2:

A mixture of compound 4 (281 mg, 0.5 mmol) and TFA (3 mL) in DCM (3 mL) was stirred at room temperature for 1 hour. The mixture was purified by Prep-HPLC to obtain compound 014 (100 mg, 55%) as a yellow solid. LCMS: m/z=363 (M+H)$^+$. $^1$H NMR (400 MHz, DMSO) δ 9.50 (s, 1H), 7.96 (s, 1H), 7.89 (d, J=8.7 Hz, 2H), 7.66 (s, 1H), 7.37

(s, 1H), 7.23 (d, J=8.2 Hz, 1H), 6.98 (d, J=8.8 Hz, 2H), 6.86-6.73 (m, 2H), 4.92 (s, 2H), 3.19 (d, J=4.8 Hz, 4H), 2.84 (d, J=4.6 Hz, 4H).

Example 15—Synthesis of Compound 015

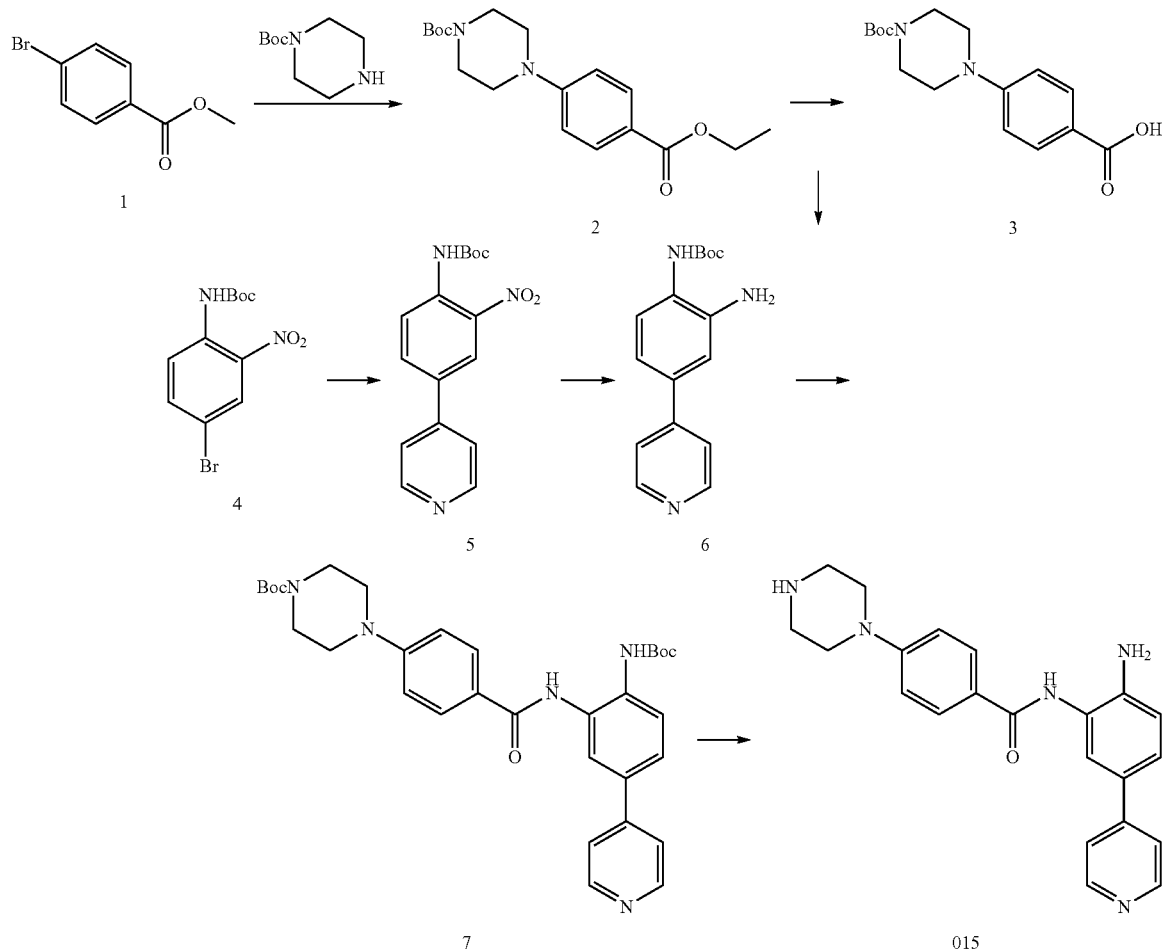

Step 1:

To a solution of compound 1 (500 mg, 2.32 mmol) in toluene (20 ml) was added tert-butyl piperazine-1-carboxylate (1.3 g, 3.0 eq.), Pd$_2$(dba)$_3$ (213 mg, 0.1 eq.), Ruphos (108 mg, 0.1 eq.) and Cs$_2$CO$_3$ (2.273 g, 3.0 eq.) at 95° C. overnight under N$_2$ atmosphere. It was filtered through celite and concentrated. It was extracted by EA (2×80 ml). Then it was washed by Et$_2$O. Compound 2 was obtained as a yellow solid (623 mg, 84%).

Step 2:

To a solution of compound 2 (623 mg, 1.94 mmol) in THF (8 ml) was added 2N NaOH (5 ml) and EtOH (2 ml) at 60° C. overnight. It was concentrated and neutralized by dilute HCl. After filtration, a white solid compound 3 (550 mg, 92%) was obtained.

Step 3:

To a solution of compound 4 (3.17 g, 10 mmol) in dioxane (30 ml) and H2O (6 ml) was added pyridin-4-ylboronic acid (1.6 g, 1.3 eq.), K2CO3 (2.763 g, 2.0 eq.), Pd[PPh3]4 (808 mg, 0.07 eq.) at 90° C. overnight under N$_2$ atmosphere. It was filtered with silica gel. It was extracted by EA (2×150 ml) and purified by column chromatography (PE:EA=4:1). A Yellow solid compound 5 (2.127 g, 67%) was obtained.

Step 4:

To a solution of compound 5 (1.5 g, 4.76 mmol) in EtOH (15 ml) was added FeCl$_3$ (154 mg, 0.2 eq.), C (1.5 g) at 60° C. N$_2$H$_4$H$_2$O (2.77 ml, 12.0 eq.) was dropped slowly. It was reacted for 3 hours. It was filtered through celite and concentrated. It was washed by H$_2$O. A brown solid compound 6 (895 mg, 66%) was obtained.

Step 5:

A mixture of compound 3 (100 mg, 0.33 mmol), compound 6 (131 mg, 1.4 eq.) and EDCl (250 mg, 4.0 eq.) in pyridine (5 ml) were stirred at room temperature overnight. It was concentrated and extracted with EA (2×70 ml), washed by brine (2×60 ml). It was purified by prep-TLC (PE:EA=1:2). Compound 7 (126 mg, Yield: 67%) was obtained as a white solid.

Step 6:

To a solution of compound 7 (126 mg, 0.22 mmol) in DCM (3 ml) was added TFA (0.5 ml) at room temperature. The reaction was stirred for 2 hours. Then it was concentrated. It was purified by prep-HPLC. Compound 015 was obtained as a white solid (26 mg, 32%). LCMS: m/z=374 (M+H)$^+$ $^1$H NMR (500 MHz, DMSO) δ 10.10 (s, 1H), 9.34 (s, 1H), 8.96 (s, 1H), 8.89 (s, 2H), 8.06 (d, J=9.2 Hz, 1H), 8.01 (s, 1H), 7.69 (t, J=1.6 Hz, 1H), 7.65 (dd, J=9.3, 2.2 Hz, 1H), 7.46 (s, 1H), 7.40 (d, J=1.9 Hz, 1H), 7.33 (dd, J=8.3, 2.0 Hz, 1H), 6.90 (d, J=8.3 Hz, 1H), 6.84 (s, 1H), 3.70-3.66 (m, 4H), 3.32 (s, 4H).

Example 16—Synthesis of Compound 016

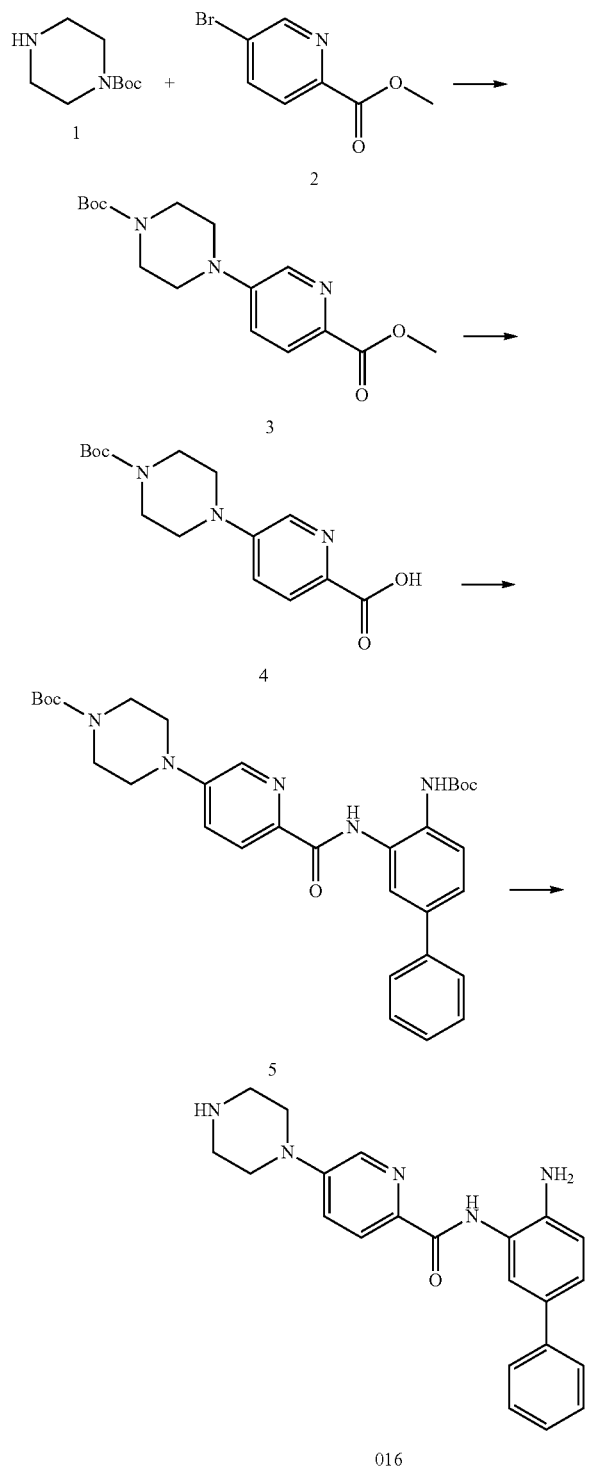

Step 1:
Under $N_2$, a mixture of tert-butyl piperazine-1-carboxylate (1.04 g, 5.55 mmol) and methyl 5-bromopicolinate (1.00 g, 4.63 mmol), tris(dibenzylideneacetone)dipalladium (212 mg, 0.23 mmol), S-Phos (384 mg, 0.94 mmol) and potassium phosphate (1.38 g, 6.48 mmol) in toluene (20 mL) was heated at 100° C. for 3 days. Then it was cooled to room temperature and filtrated. The filtrate was concentrated in vacuo. And the residue was purified by silica gel chromatography to give compound 3 as a yellow solid (837 mg, 56%).

Step 2:
A mixture of tert-butyl 4-(6-(methoxycarbonyl)pyridin-3-yl)piperazine-1-carboxylate (837 mg, 2.60 mmol) and LiOH (219 mg, 5.21 mmol) in THF (12 mL), water (6 mL) and MeOH (3 mL) was stirred at 0° C. to room temperature until completion. Then it was concentrated in vacuo to give a crude Li salt of compound 4. LCMS: m/z=308.1 (M+H)+.

Step 3:
A mixture of lithium 5-(4-(tert-butoxycarbonyl)piperazin-1-yl)picolinate (1.30 mmol) and HATU (545 mg, 1.43 mmol) in DMF (4 mL) was stirred at room temperature for 30 minutes. Then tert-butyl 3-aminobiphenyl-4-ylcarbamate (407 mg, 1.43 mmol) was added. It was stirred at room temperature for 2 h. Then it was poured into water. The resulting solid was collected by filtration and dried in vacuo to give the crude compound 5. LCMS: m/z=574.2 (M+H)+.

Step 4:
To a mixture of tert-butyl 3-(5-(4-methylpiperazin-1-yl)picolinamido)biphenyl-4-ylcarbamate (1.30 mmol) in MeOH (4 mL) was added HCl/dioxane (8 mL) at 0° C. It was stirred at 0° C. to room temperature for 18 hours. It was concentrated in vacuo and the residue was purified by Prep-HPLC to give compound 016 as a white solid (73 mg, yield: 15%, lot SP-0017146-033). LCMS: m/z=374.1 (M+H)+. ¹H NMR (500 MHz, DMSO) δ 9.88 (s, 1H), 8.37 (d, J=3.0 Hz, 1H), 7.95 (d, J=8.5 Hz, 1H), 7.90 (d, J=2.5 Hz, 1H), 7.56 (d, J=7.4 Hz, 2H), 7.45 (dd, J=8.8, 2.8 Hz, 1H), 7.40 (t, J=7.7 Hz, 2H), 7.28-7.24 (m, 2H), 6.91 (d, J=8.0 Hz, 1H), 5.03 (s, 2H), 3.28 (m, 4H), 2.85 (m, 4H).

Example 17—Synthesis of Compound 017

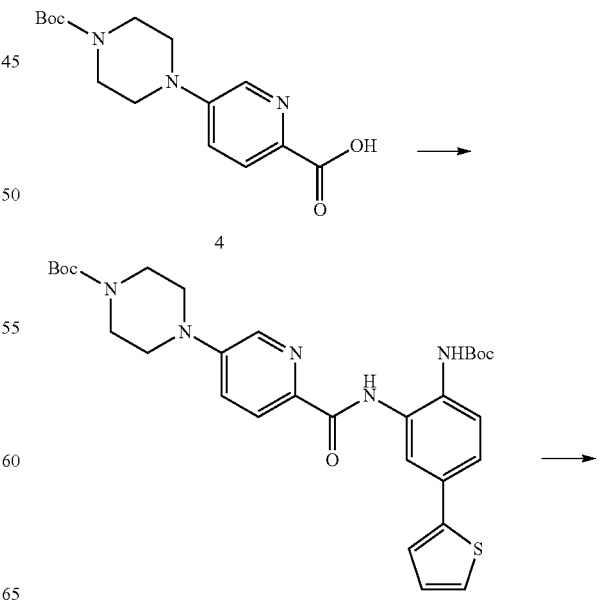

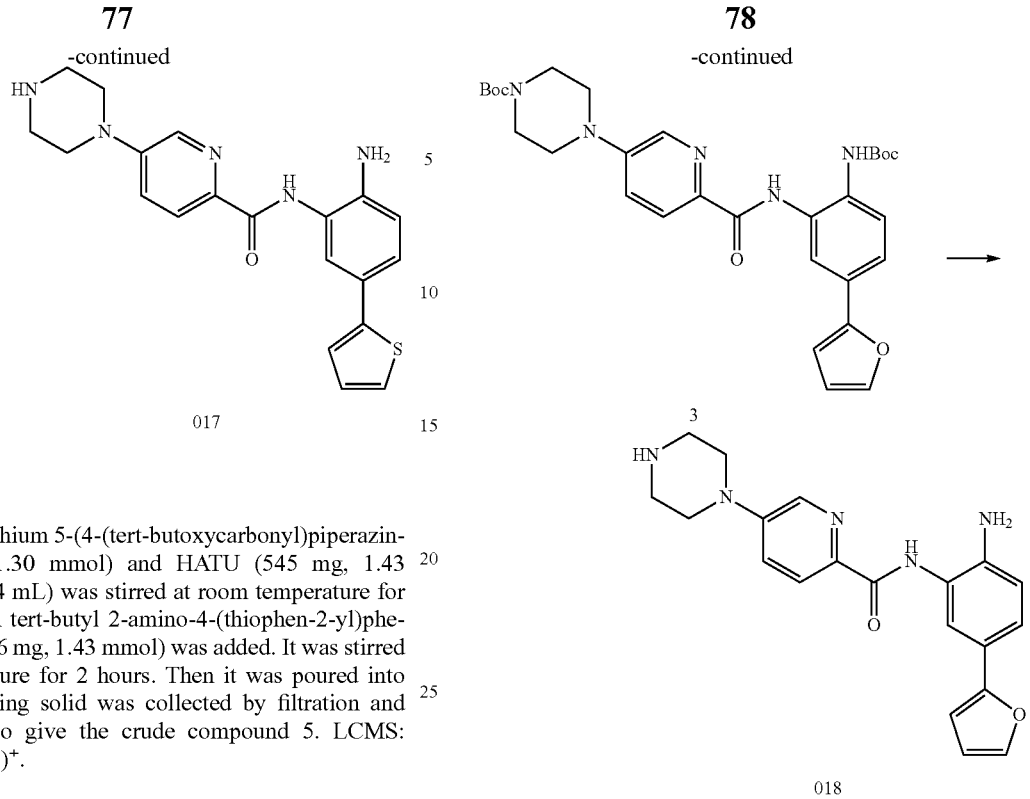

Step 1:

A mixture of lithium 5-(4-(tert-butoxycarbonyl)piperazin-1-yl)picolinate (1.30 mmol) and HATU (545 mg, 1.43 mmol) in DMF (4 mL) was stirred at room temperature for 30 minutes. Then tert-butyl 2-amino-4-(thiophen-2-yl)phenylcarbamate (416 mg, 1.43 mmol) was added. It was stirred at room temperature for 2 hours. Then it was poured into water. The resulting solid was collected by filtration and dried in vacuo to give the crude compound 5. LCMS: m/z=580.2 (M+H)+.

Step 2:

To a mixture of tert-butyl 3-(5-(4-methylpiperazin-1-yl)picolinamido)biphenyl-4-ylcarbamate (1.30 mmol) in MeOH (4 mL) was added HCl/dioxane (8 mL) at 0° C. It was stirred at 0° C. to room temperature for 18 hours. It was concentrated in vacuo and the residue was purified by Prep-HPLC to give compound 017 as a white solid (75 mg, yield: 15%, lot SP-0017146-032). LCMS: m/z=380.1 (M+H)+. 1H NMR (500 MHz, DMSO) δ 9.86 (s, 1H), 8.37 (d, J=3.0 Hz, 1H), 7.95 (d, J=8.5 Hz, 1H), 7.88 (d, J=2.0 Hz, 1H), 7.45 (dd, J=8.5, 3.0 Hz, 1H), 7.37 (d, J=5.5 Hz, 1H), 7.25 (m, 2H), 7.06 (dd, J=5.0, 4.0 Hz, 1H), 6.85 (d, J=8.5 Hz, 1H), 5.08 (s, 2H), 3.28 (m, 4H), 2.85 (m, 4H).

Example 18—Synthesis of Compound 018

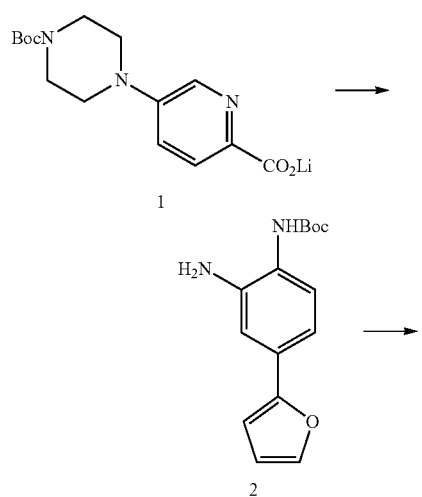

Step 1:

A mixture of lithium 5-(4-(tert-butoxycarbonyl)piperazin-1-yl)picolinate (200 mg, 0.56 mmol) and HATU (214 mg, 0.56 mmol) in DMF (2 mL) was stirred at room temperature for 15 minutes. Tert-butyl 2-amino-4-(furan-2-yl)phenylcarbamate (86 mg, 0.31 mmol) was added. It was stirred at room temperature for 18 hours. Water was added. The resulting solid was collected by filtration and dried in vacuo to give crude compound 3 as an off-white solid (170 mg, 97%).

Step 2:

At 0° C., to a solution of tert-butyl 4-(6-(2-(tert-butoxycarbonylamino)-5-(furan-2-yl) phenylcarbamoyl)pyridin-3-yl)piperazine-1-carboxylate (170 mg, 0.30 mmol) in DCM (2 mL) was added TFA (1 mL). It was stirred at 0° C. for 2 h and then concentrated in vacuo. The residue was purified by Prep-HPLC to obtain compound 018 as a yellow solid (53 mg, 47%, two steps, lot SP-0017146-122). LCMS: m/z=364.1 (M+H)+. 1H NMR (400 MHz, DMSO) δ 9.83 (s, 1H), 8.37 (d, J=2.8 Hz, 1H), 7.95 (d, J=8.8 Hz, 1H), 7.91 (d, J=1.2 Hz, 1H), 7.62 (d, J=1.6 Hz, 1H), 7.45 (dd, J=8.8, 2.8 Hz, 1H), 7.29 (dd, J=8.4, 2.0 Hz, 1H), 6.85 (d, J=8.4 Hz, 1H), 6.61 (d, J=3.2 Hz, 1H), 6.52 (m, 1H), 5.09 (s, 2H), 3.28 (m, 4H), 2.85 (m, 4H).

Example 19—Synthesis of Compound 019

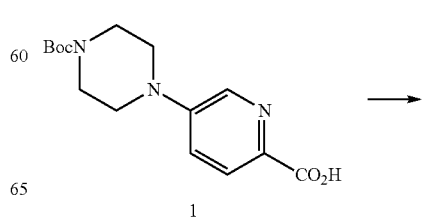

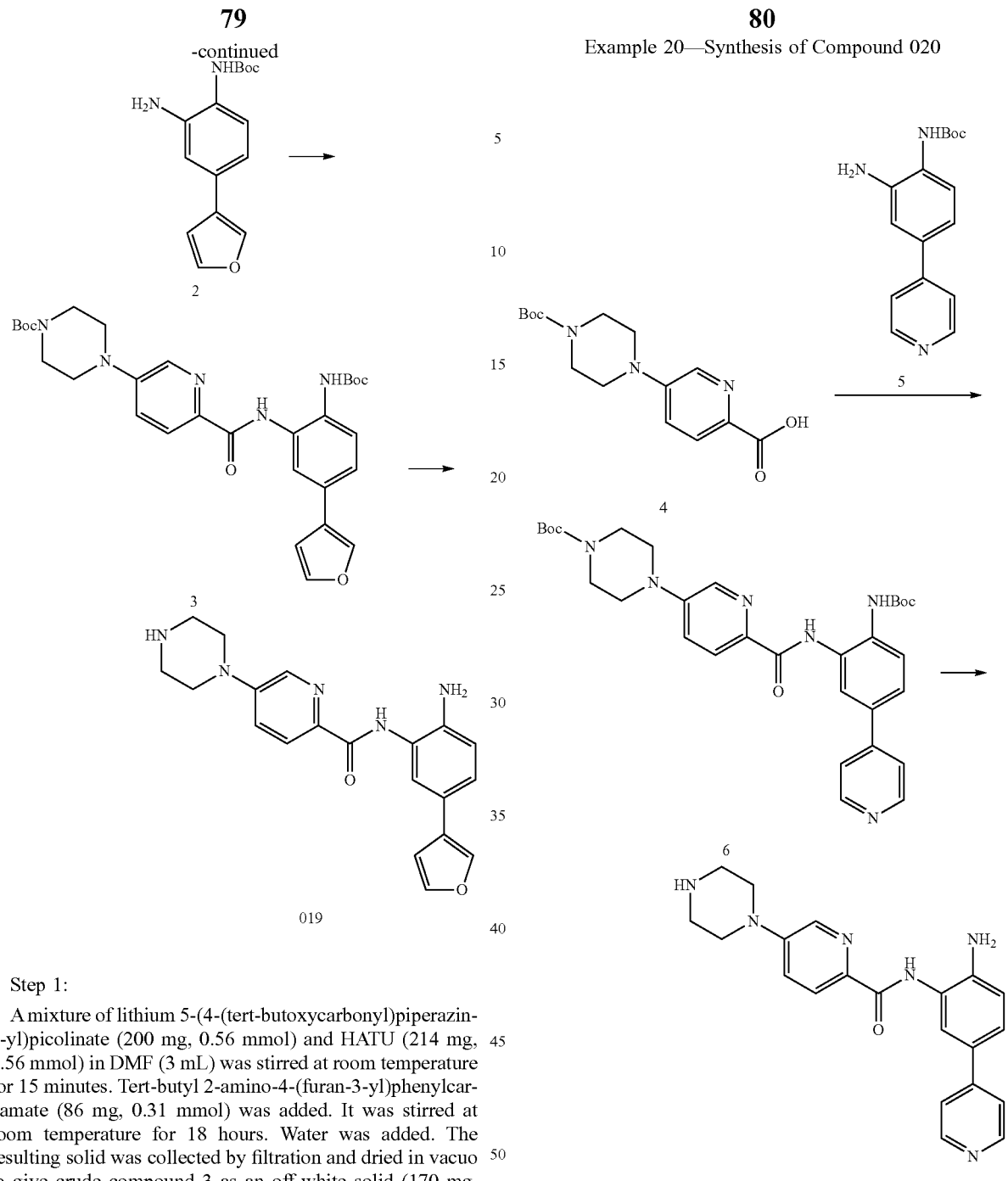

Example 20—Synthesis of Compound 020

Step 1:

A mixture of lithium 5-(4-(tert-butoxycarbonyl)piperazin-1-yl)picolinate (200 mg, 0.56 mmol) and HATU (214 mg, 0.56 mmol) in DMF (3 mL) was stirred at room temperature for 15 minutes. Tert-butyl 2-amino-4-(furan-3-yl)phenylcarbamate (86 mg, 0.31 mmol) was added. It was stirred at room temperature for 18 hours. Water was added. The resulting solid was collected by filtration and dried in vacuo to give crude compound 3 as an off-white solid (170 mg, 97%).

Step 2:

At 0° C., to a solution of tert-butyl 4-(6-(2-(tert-butoxycarbonylamino)-5-(furan-3-yl) phenylcarbamoyl)pyridin-3-yl)piperazine-1-carboxylate (170 mg, 0.30 mmol) in DCM (1.5 mL) was added TFA (1 mL). It was stirred at 0° C. for 2 hours. Then it was concentrated in vacuo. The residue was purified by prep-HPLC to obtain compound 019 as a yellow solid (67 mg, yield: 59%, two steps, lot SP-0017146-120). LCMS: m/z=364.1 (M+H)+. 1H NMR (400 MHz, DMSO) δ 9.83 (s, 1H), 8.36 (d, J=2.8 Hz, 1H), 7.96 (s, 1H), 7.95 (d, J=8.8 Hz, 1H), 7.74 (d, J=2.0 Hz, 1H), 7.67 (m, 1H), 7.44 (dd, J=8.8, 2.8 Hz, 1H), 7.19 (dd, J=8.0, 2.0 Hz, 1H), 6.83 (d, J=8.0 Hz, 1H), 6.80 (d, J=0.8 Hz, 1H), 4.93 (s, 2H), 3.28 (m, 4H), 2.85 (m, 4H).

Step 1:

A mixture of compound 4 (224 mg, 0.63 mmol) and HATU (240 mg, 0.63 mmol) in DMF (5 mL) was stirred at room temperature for 15 minutes. Then compound 5 (100 mg, 0.35 mmol) was added. It was stirred at room temperature for 18 hours. Then it was poured into water. The mixture was collected by filtration and dried in vacuo to give the compound 6. LCMS: m/z=575.3 (M+H)+.

Step 2:

To a mixture of compound 6 (0.36 mmol) in MeOH (1 mL) was added HCl/dioxane (2.5 mL) at 0° C. It was stirred at 0° C. to room temperature for 18 hours. Then it was concentrated in vacuo and the residue was purified by prep-HPLC to give compound 020 as a light yellow solid (79 mg, free amine, yield: 33%, two steps, lot SP-0017146-109). LCMS: m/z=375.2 (M+H)+. 1H NMR (400 MHz, DMSO) δ 9.87 (s, 1H), 8.52 (m, 2H), 8.37 (d, J=2.8 Hz, 1H), 7.99 (d, J=2.4 Hz, 1H), 7.95 (d, J=8.8 Hz, 1H), 7.58 (m, 2H), 7.45 (m, 2H), 6.92 (d, J=8.0 Hz, 1H), 5.30 (s, 2H), 3.28 (m, 4H), 2.85 (m, 4H).

Example 21—Synthesis of Compound 021

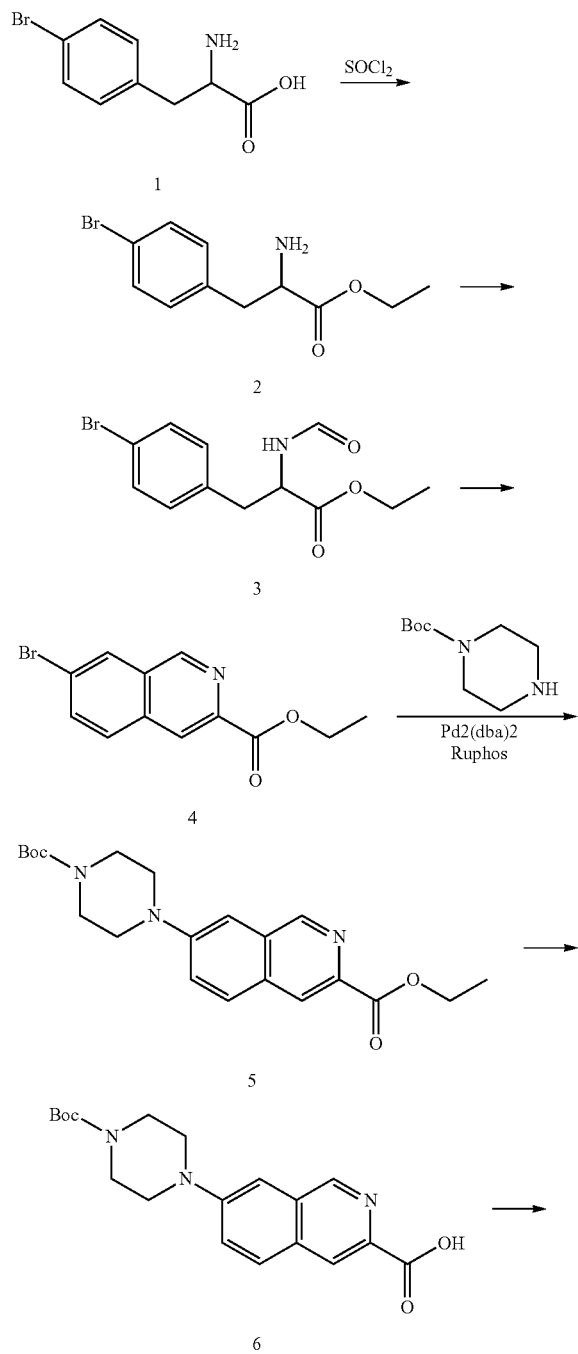

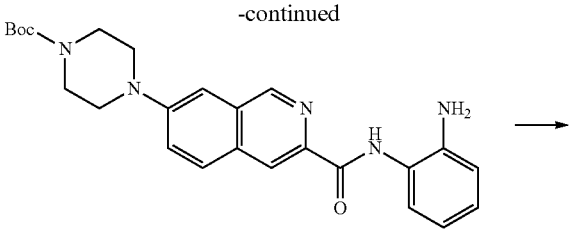

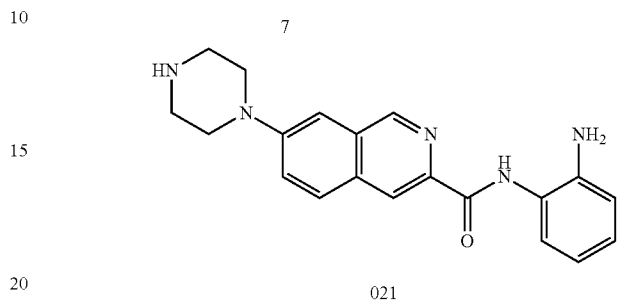

Step 1:

To 2-amino-3-(4-bromophenyl)propanoic acid (50 g, 0.2 mol) in ethanol (1 L) was added dropwise SOCl$_2$ (30 ml) at 0° C. After addition was completed, the mixture was refluxed for overnight. The reaction was stopped, the mixture was evaporated to dryness, to the residue was added EA (500 ml) and saturated aqueous NaHCO$_3$ (500 ml). The organic layer was separated out, the water was extracted with EA (200 ml), the combined organic layer was washed with brine and dried with Na$_2$SO$_4$, evaporated to dryness and the residue was used in next step without further purification. 45 g of compound 2 as a yellow solid was obtained. Yield: 81%. LCMS: 99% UV-214, [M+H]:272

Step 2:

To a flask containing ethyl 2-amino-3-(4-bromophenyl) propanoate (45 g, 166 mmol) in CH$_3$CN (500 ml) was added HCOONH$_4$ (95 g, 1.5 mol) at room temperature, followed by stirring at 90° C. overnight. After the solvent was evaporated, to the residue was added water (1 L) and then extracted by EA (300 ml×3). The combined organic layer was washed with brine, dried by anhydrous Na$_2$SO$_4$, and concentrated in vacuo. The resulting residue was purified by silica gel chromatography (Elution:From PE/EA=4:1 to 3:1) to afford ethyl 3-(4-bromophenyl)-2-formamidopropanoate as a red solid (39 g, yield: 80%). LCMS: 92% UV-214, [M+H]: 300

Step 3:

To a mixture of ethyl-3-(4-bromophenyl)-2-formamidopropanoate (39 g, 130 mmol) in DCM (500 mL) was added (COCl)$_2$ (18 g, 143 mmol). The reaction mixture was stirred at room temperature for 30 minutes. Then the reaction solution was cooled to 0° C. and FeCl$_3$ (26 g, 163 mmol) was added into the solution, followed by stirring at room temperature overnight. After the solution was extracted by CH$_2$Cl$_2$, the combined organic layers were concentrated in vacuo to afford a black oil. The oil was dissolved in the EtOH (300 ml), and concentrated H$_2$SO$_4$ was added into the solution and refluxed at 80° C. overnight. The solution was poured into saturated NaHCO$_3$ and extracted by EA. After drying with anhydrous Na$_2$SO$_4$, the solution was concentrated in vacuo, and the residue was purified by silica gel chromatography (PE/EA=8:1 to 5:1) to afford ethyl 7-bromoisoquinoline-3-carboxylate as a yellow solid (5.2 g, yield: 15 percent). LCMS: 95% UV-214, [M+H]: 280

Step 4:

A mixture of compound 4 (5.2 g, 18.6 mmol), tert-butyl piperazine-1-carboxylate (4.2 g, 22.4 mmol), Pd$_2$(dba)$_3$ (920 mg, 1 mmol), RuPhos (950 mg, 2 mmol) and Cs$_2$CO$_3$ (12 g, 37 mmol) in dioxane (150 mL) was stirred at 100° C. under N$_2$ atmosphere for 4 hours. The mixture was cooled, filtered, and concentrated to obtain a residue, which was purified by combiflash (Elution, PE:EA=40%) to afford compound 5 (4.5 g, 63%) as a yellow solid. LCMS: 98% UV-214, [M+H]: 386

Step 5:

A solution of compound 5 (4.5 g, 11.7 mmol) in MeOH (50 mL) and THF (50 ml) was added the aqueous of NaOH (2.4 g, 58.5 mmol) in water 30 ml and stirred at 60° C. for 3 hours. The mixture was concentrated to obtain a residue, to the residue was added water (100 mL), and then adjusted pH to about 6 using HCl (0.5N) carefully, yellow solid was separated out, the mixture was filtered, the solid was washed by water (50 ml) and dried to give compound 6 as a yellow solid (3.5 g, yield: 83%). LCMS: 98.9% UV-214, [M+H]: 358

Step 6:

A mixture of compound 6 (357 mg, 1 mmol), benzene-1,2-diamine (100 mg, 0.9 mmol) and 1-(3-dimethylaminopropyl)-3-ethylcarbodiimide hydrochloride (380 mg, 2 mmol) in pyridine (10 mL) was stirred at room temperature for overnight. After completed, the mixture was concentrated, poured into water (100 mL), filtered to obtain compound 7 (328 mg, crude) as a yellow solid.

Step 7:

A mixture of compound 7 (328 mg, crude) and TFA (3 mL) in DCM (3 mL) was stirred at room temperature for 1 hour. The mixture was purified by Prep-HPLC to obtain compound 021 (101 mg, 29%, 2 steps) as a yellow solid. LCMS: m/z=348 (M+H)$^+$. $^1$HNMR (500 MHz, DMSO): 3.501 (t, 4H), 3.88 (t, 4H), 7.45 (t, 1H), 7.53 (t, 2H), 7.61 (d, 1H), 8.146 (dd, 1H), 8.34 (d, 1H), 9.17 (s, 1H), 9.57 (s, 1H).

Example 22—Synthesis of Compound 022

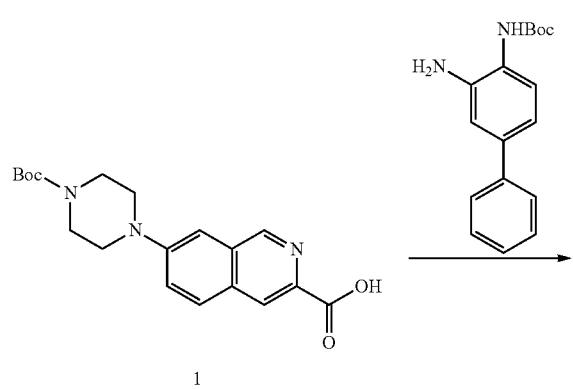

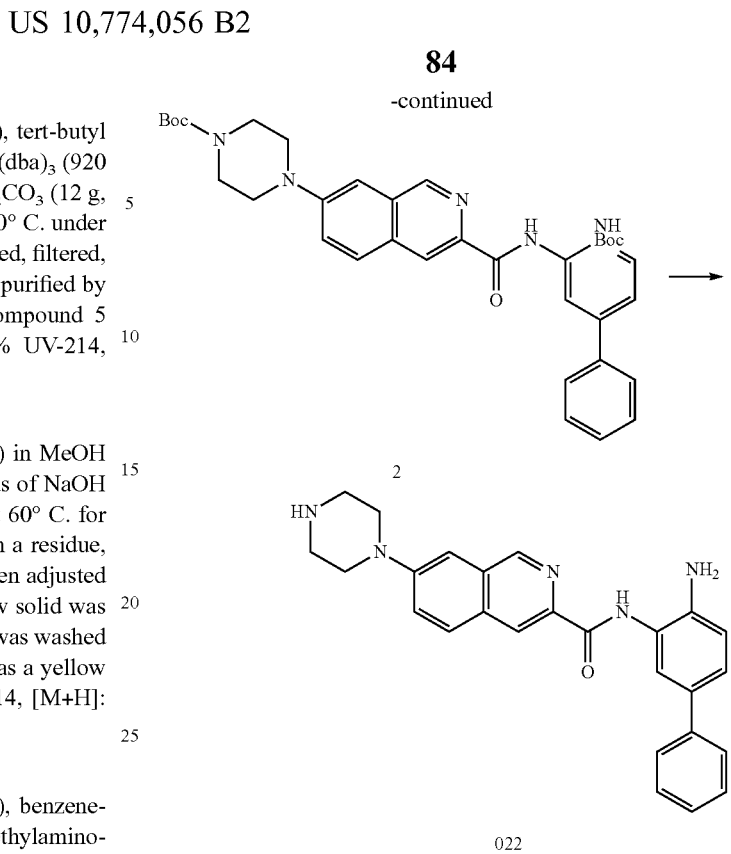

Step 1:

A mixture of compound 1 (1.5 g, 4.2 mmol), tert-butyl 3-aminobiphenyl-4-ylcarbamate (1.43 g, 5 mmol), HATU (2.4 g, 6.3 mmol), DIPEA (1.1 g, 8.4 mmol) in DCM (100 ml) was stirred at room temperature for 1 hour. The mixture was evaporated to be dry, the residue was purified by silica gel column chromatography (DCM:MeOH=20:1) to give compound 2 as a yellow solid (1.6 g, Yield: 62%). LCMS: 97% UV-214, [M+H]: 624

Step 2:

To a solution of compound 2 (1.6 g, 2.57 mmol) in DCM (100 ml) was added 4N HCl in dioxane (30 ml), the mixture was stirred at room temperature for 2 h, the reaction was stopped, the mixture was filtered, the solid was washed by ether (20 ml) and dried to give compound 022 (1.29 g, HCl salt, yield: 83%) as a yellow solid. LCMS: 100% UV-214, [M+H]: 424. $^1$HNMR (500 MHz, MeOD): 3.506 (t, 4H), 3.881 (t, 4H), 7.453 (t, 1H), 7.527 (t, 2H), 7.671 (d, 1H), 7.737 (d, 2H), 7.811 (dd, 1H), 7.924 (m, 2H), 8.146 (dd, 1H), 8.343 (d, 1H), 9.171 (s, 1H), 9.574 (s, 1H).

Example 23—Synthesis of Compound 023

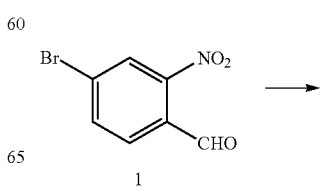

-continued

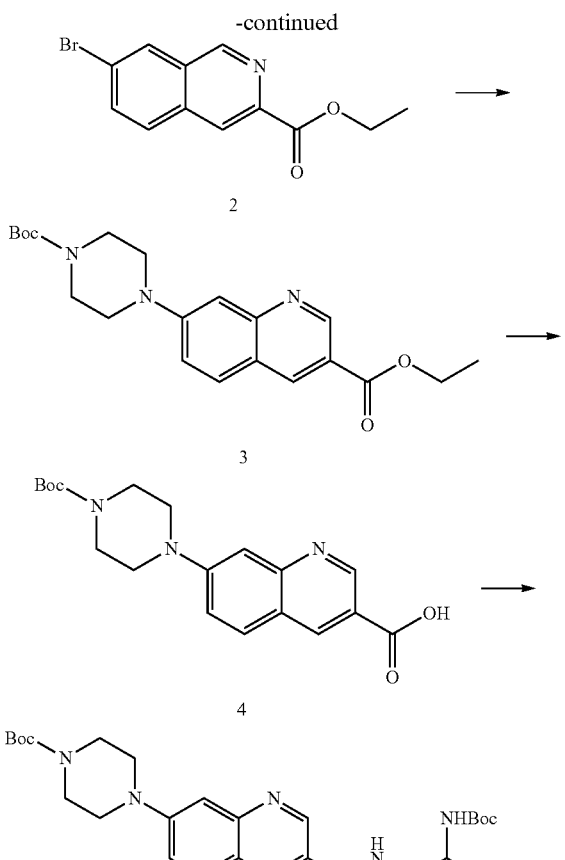

Step 2:
A mixture of compound 2 (560 mg, 2 mmol), N-boc-piperazine (1.3 g, 7 mmol), Pd$_2$(dba)$_3$ (200 mg, 0.2 mmol), Ruphos (200 mg, 0.4 mmol), Cs$_2$CO$_3$ (1.4 g, 7.3 mmol) in toluene (20 mL) using microwave (80° C. 10 min, 110° C. 30 min, 145° C. 60 min). TLC monitored completion. The mixture was added EA (30 mL), and H$_2$O (30 mL). Filtered off through diatomite. The organic layer was separated, washed, dried, filtered and concentrated to obtain compound 3. Washed with PE to obtain purified compound 3 (620 mg, ~100%) as a yellow solid.

Step 3:
A mixture of compound 3 (600 mg, 1.56 mol) and 2M NaOH (5 ml) in MeOH (10 ml) and THF (10 ml) was stirred 70° C. for 4 hours. TLC monitored completion. The mixture concentrated to a residue, added water (30 mL) and citric acid to adjust to PH=4-5, extracted with EA. The organic layer was separated, washed, dried, filtered and concentrated to obtain compound 4 (500 mg, 89.2%).

Step 4:
To a solution of compound 4 (107 mg, 0.30 mmol), tert-butyl (2-amino-4-(thiophen-2-yl)phenyl)carbamate (70 mg, 0.3 mmol) in 10 ml DMF was added HOAT (81.6 mg, 0.6 mmol), EDCl (114.6 mg, 0.6 mmol), DIPEA (193.5 mg, 1.5 mmol). The mixture was stirred at 60° C. for overnight. LCMS monitored completion, added water (10 ml) extracted with EA. The organic layer was separated, washed, dried, filtered and concentrated to obtain crude product. Purified by Prep-TLC to obtain compound 5 (95 mg, 56%)

Step 5:
A mixture of compound 5 (95 mg, 0.16 mmol) and 2 ml TFA in 5 ml DCM was stirred room temperature for 2 hours, LCMS monitored completion. Evaporated to get the crude product and purified by Prep-HPLC to obtain compound 023 (20 mg, 34.2%). LCMS: m/z=430 (M+H)$^+$. $^1$H NMR (400 MHz, MeOD) δ 9.29 (s, 1H), 8.86 (s, 1H), 7.99 (d, J=9.2 Hz, 1H), 7.62-7.59 (m, 2H), 7.47-7.44 (m, 2H), 7.40 (s, 1H), 7.28 (d, J=8.4 Hz, 1H), 7.19 (d, J=3.6 Hz, 1H), 7.09 (m, 1H), 3.72 (m, 4H), 3.45 (m, 4H)

Example 24—Synthesis of Compound 024

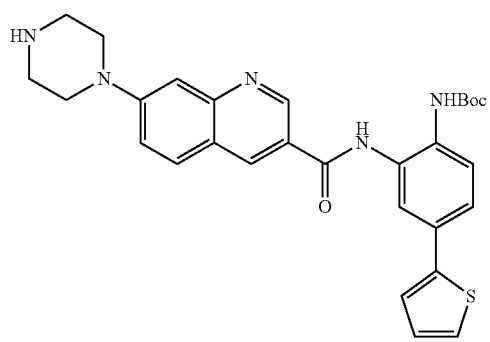

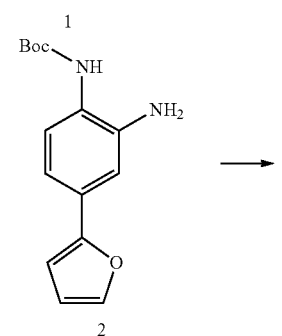

Step 1:
To a solution of compound 1 (20 g, 0.087 mol) and ethyl 3,3-diethoxypropionate (33 g, 0.17 mol) in EtOH (500 mL) was added SnCl$_2$-2H2O (87 g, 0.39 mol), the mixture was stirred at 90° C. for 12 hours. TLC monitored completion. After cooled, evaporated to obtain the crude product. Then put into EA (600 mL), H$_2$O (300 mL), Na$_2$CO$_3$ (32 g) and stirred for 1 hour. The organic layer was separated, dried, filtered and concentrated to obtain compound 2 (15 g, 92%) as a yellow solid.

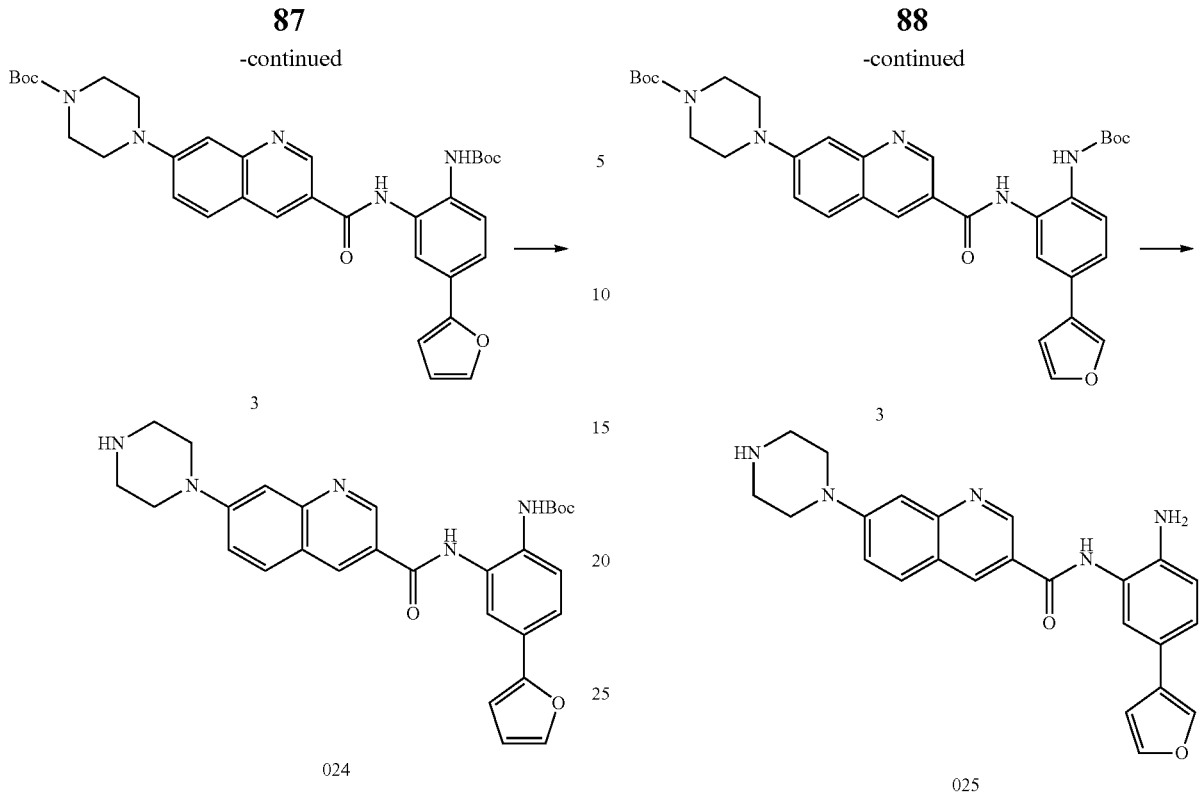

Step 1:

A mixture of 7-(4-(tert-butoxycarbonyl)piperazin-1-yl)quinoline-3-carboxylic acid (139 mg, 0.39 mmol) and EDCl (151 mg, 0.79 mmol) in pyridine (6 mL) was stirred at room temperature for 20 minutes. Then tert-butyl 2-amino-4-(furan-2-yl)phenylcarbamate (107 mg, 0.39 mmol) was added. It was stirred at room temperature for 16 hours. Then it was concentrated in vacuo. The residue was purified by prep-TLC to give compound 3 (143 mg, 48%) as an oil. LCMS: m/z=614.3 (M+H)+.

Step 2:

To a mixture of tert-butyl 4-(3-(2-(tert-butoxycarbonylamino)-5-(furan-2-yl)phenyl-carbamoyl)quinolin-7-yl)piperazine-1-carboxylate (143 mg, 0.23 mmol) in DCM (1 mL) was added TFA (1 mL) at 0° C. It was stirred at 0° C. to room temperature for 18 hours. It was concentrated in vacuo and the residue was purified by prep-HPLC to give compound 024 as a grey solid (37 mg, TFA salt, lot SP-0017146-056). LCMS: m/z=414.2 (M+H)+. ¹H NMR (400 MHz, MeOD) δ 9.29 (s, 1H), 8.86 (s, 1H), 7.99 (d, J=9.2 Hz, 1H), 7.62-7.59 (m, 2H), 7.47-7.44 (m, 2H), 7.40 (s, 1H), 6.96 (d, J=8.4 Hz, 1H), 6.56 (d, J=3.6 Hz, 1H), 6.47 (m, 1H), 3.72 (m, 4H), 3.45 (m, 4H).

Example 25—Synthesis of Compound 025

Step 1:

A mixture of compound 3 (178 mg, 0.5 mmol), tert-butyl (2-amino-4-(furan-3-yl)phenyl)carbamate (123 mg, 0.45 mmol), and EDCl (573 mg, 3 mmol) in pyridine (5 mL) was stirred at room temperature for overnight and monitored by TLC. After pouring into water and extracting with EA (2×100 mL), the organic layer was separated, dried, and purified by prep-TLC (PE/EA 1/1) to afford compound 4 (140 mg, 51%) as an off-white solid.

Step 2:

To a solution of compound 4 (140 mg, 0.23 mmol) in DCM (5 mL) was added TFA (2 mL), the mixture was stirred at room temperature for 2 hours. After completed, the resulting mixture was concentrated and alkalified with (aqueous) NaHCO₃ to pH=8. The precipitate was collected and washed by water to afford compound 025 as an off-white solid (19 mg, 14%). LCMS: m/z=364.2 (M+H)+. ¹H NMR (500 MHz, DMSO) δ 10.10 (s, 1H), 9.34 (s, 1H), 8.96 (s, 1H), 8.89 (s, 2H), 8.06 (d, J=9.2 Hz, 1H), 8.01 (s, 1H), 7.69 (t, J=1.6 Hz, 1H), 7.65 (dd, J=9.3, 2.2 Hz, 1H), 7.46 (s, 1H), 7.40 (d, J=1.9 Hz, 1H), 7.33 (dd, J=8.3, 2.0 Hz, 1H), 6.90 (d, J=8.3 Hz, 1H), 6.84 (s, 1H), 3.70-3.66 (m, 4H), 3.32 (s, 4H).

Example 26—Synthesis of Compound 026

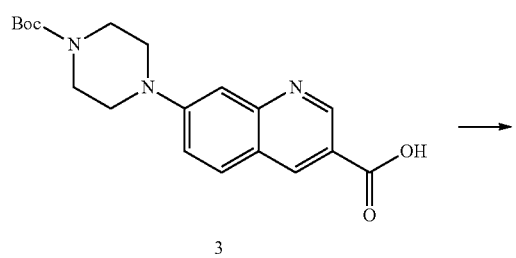

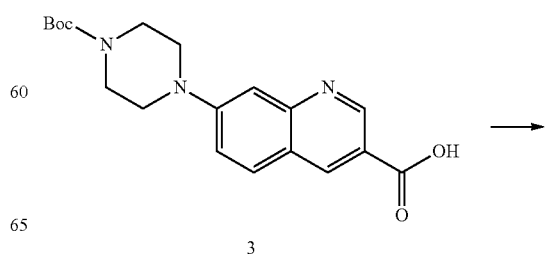

89

-continued

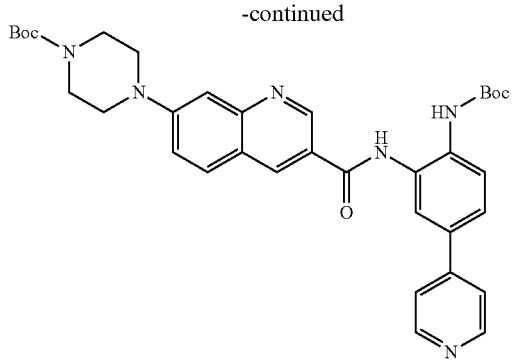

4

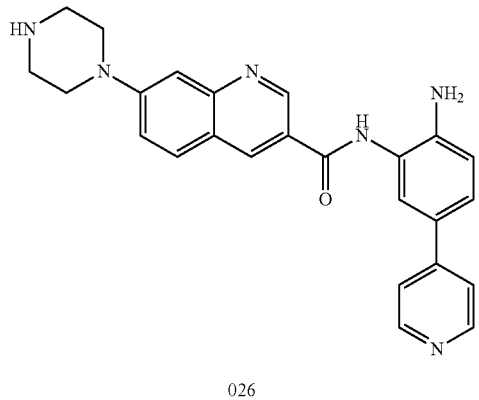

026

Step 1:

A mixture of compound 3 (357 mg, 1 mmol), tert-butyl (2-amino-4-(pyridin-4-yl)phenyl)carbamate (260 mg, 0.9 mmol), and EDCl (381 mg, 2 mmol) in pyridine (5 mL) was stirred at room temperature for overnight and monitored by TLC. Poured into water and extracted with EA (2×100 mL), the organic layer was separated, dried, and purified by prep-TLC (PE/EA 1/1) to afford compound 4 (240 mg, 39%) as an off-white solid.

Step 2:

To a solution of compound 4 (240 mg, 0.23 mmol) in DCM (5 mL) was added TFA (2 mL), the mixture was stirred at room temperature for 2 hours. After completion, the resulting mixture was concentrated and made alkaline with (aqueous) NaHCO₃ to pH=8. The precipitate was collected and washed by water to afford compound 026 as an off-white solid (100 mg, 62%). LCMS: m/z=425 (M+H)⁺. ¹H NMR (500 MHz, DMSO) δ 9.909 (s, 1H), 9.28 (s, 1H), 8.79 (s, 1H), 8.52 (s, 1H), 7.92-7.90 (d, J=8 Hz, 1H), 7.74 (s, 1H), 7.61-7.53 (m, 4H), 7.26 (s, 1H), 6.92-6.90 (d, J=8 Hz, 1H), 5.48 (s, 2H), 2.90 (m, 4H), 2.51 (s, 4H).

90

Example 27—Synthesis of Compound 027

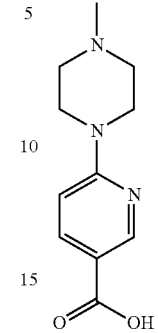

1

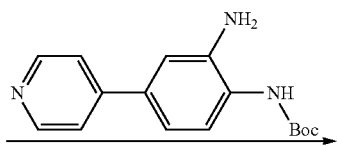

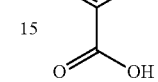

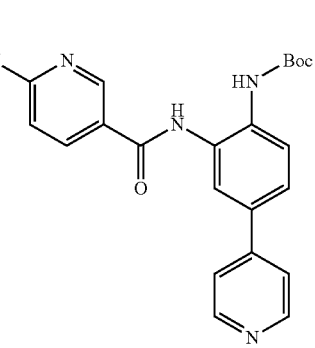

2

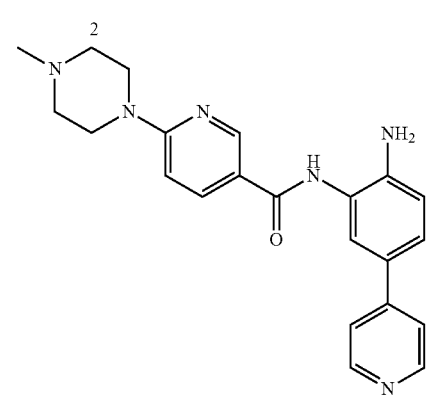

027

Step 1:

6-(4-methylpiperazin-1-yl)nicotinic acid (132 mg, 0.6 mmol), tert-butyl 2-amino-4-(pyridin-4-yl) phenylcarbamate (172 mg, 0.6 mmol) and EDCl (346 mg, 1.8 mmol) were added into pyridine (5 ml). The mixture was stirred for overnight at room temperature. When the reaction finished, it was extracted by EA and washed by citric acid, NaHCO₃ and saturated brine. Then the organic layer was concentrated to afford compound 2 (300 mg, crude).

Step 2:

Tert-butyl 2-(6-(4-methylpiperazin-1-yl) nicotinamido)-4-(pyridin-4-yl) phenylcarbamate (300 mg, crude) was added into DCM (2 ml). Then TFA (2 ml) was added. The mixture was stirred at room temperature for 1 hours. It was purified by Prep-HPLC (base method). Compound 027 was obtained as a yellow solid (40 mg, 13% yield, lot SP-0017467-055). LCMS: m/z=389.2 (M+H)⁺. ¹H NMR (400 MHz, DMSO) δ 9.53 (s, 1H), 8.76 (d, J=2.3 Hz, 1H), 8.53-8.45 (m, 2H), 8.10 (dd, J=9.0, 2.5 Hz, 1H), 7.67 (d, J=2.1 Hz, 1H), 7.58 (d, J=6.2 Hz, 2H), 7.50 (dd, J=8.4, 2.2 Hz, 1H), 6.90 (dd, J=13.9, 8.7 Hz, 2H), 5.36 (s, 2H), 3.67-3.58 (m, 4H), 2.43-2.35 (m, 4H), 2.22 (s, 3H).

Example 28—Synthesis of Compound 028

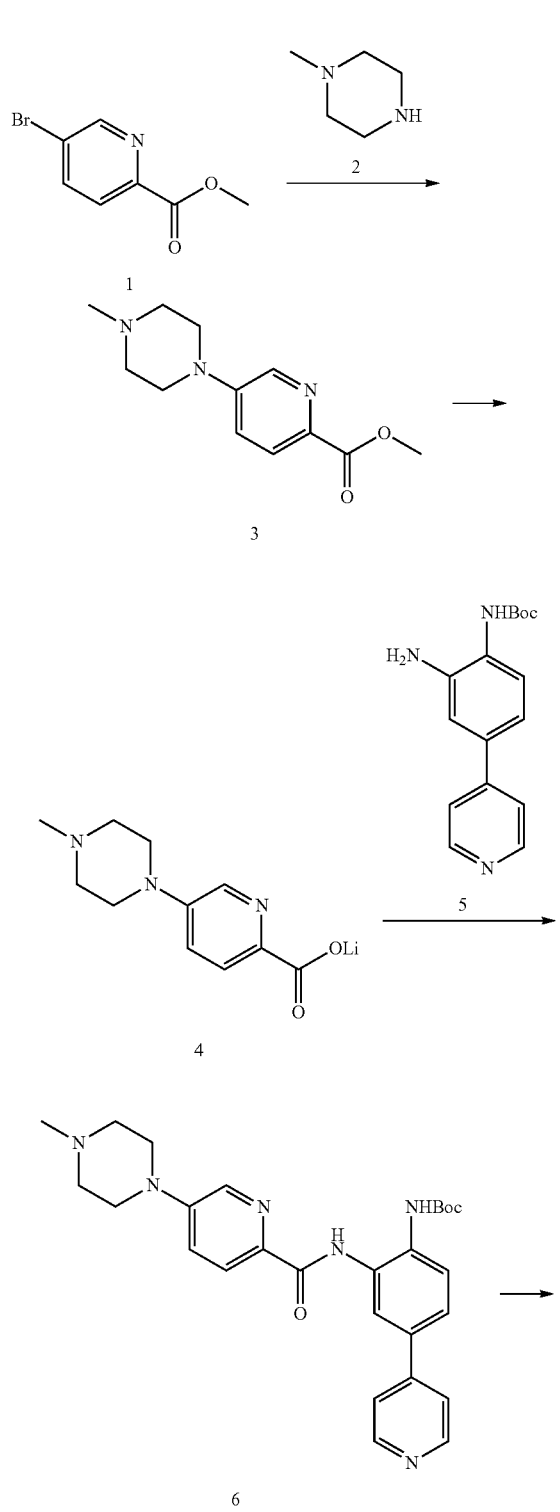

Step 1:

Under $N_2$, a mixture 1-methylpiperazine (232 mg, 2.31 mmol) and methyl 5-bromopicolinate (500 mg, 2.31 mmol), tris(dibenzylideneacetone)dipalladium (53 mg, 0.058 mmol), Ru-Phos (108 mg, 0.23 mmol) and cesium carbonate (2.26 g, 6.94 mmol) in toluene (20 mL) was heated at 100° C. for 18 hours. Then it was cooled to room temperature and filtrated. The filtrate was concentrated in vacuo. And the residue was washed with PE-EA to give compound 3 as a white solid (528 mg, 100%).

Step 2:

At 0° C., to a mixture of methyl 5-(4-methylpiperazin-1-yl)picolinate (528 mg, 2.24 mmol) and LiOH (188 mg, 4.49 mmol) in THF (6 mL), MeOH (1 mL) and water (3 mL). It was stirred at 0° C. to room temperature for 18 hours. Then it was concentrated in vacuo to give crude compound 4 as a Li salt (294 mg). LCMS: m/z=222.1 (M+H)+.

Step 3:

A mixture of compound 4 (143 mg, 0.63 mmol) and HATU (240 mg, 0.63 mmol) in DMF (10 mL) was stirred at room temperature for 10 minutes. Then compound 5 (100 mg, 0.35 mmol) was added. It was stirred at room temperature for 18 hours. Then it was poured into water. The resulting solid was collected by filtration and dried in vacuo to give the crude compound 6 (150 mg). LCMS: m/z=489.3 (M+H)+.

Step 4:

To a mixture of compound 6 (0.36 mmol) in MeOH (1 mL) was added HCl/dioxane (4 M, 2 mL) at 0° C. It was stirred at 0° C. to room temperature for 18 hours. Then it was concentrated in vacuo and the residue was purified by Prep-HPLC to give compound 028 as a yellow solid (59 mg, free amine, yield: 24%, two steps, lot SP-0017146-108). LCMS: m/z=389.3 (M+H)+. 1 H NMR (400 MHz, DMSO) δ 9.88 (s, 1H), 8.52 (m, 2H), 8.39 (d, J=2.4 Hz, 1H), 7.99 (d, J=2.0 Hz, 1H), 7.96 (d, J=9.2 Hz, 1H), 7.58 (m, 2H), 7.47 (m, 2H), 6.92 (d, J=8.0 Hz, 1H), 5.30 (s, 2H), 3.38 (m, 4H), 2.47 (m, 4H).

Example 29—Synthesis of Compound 029

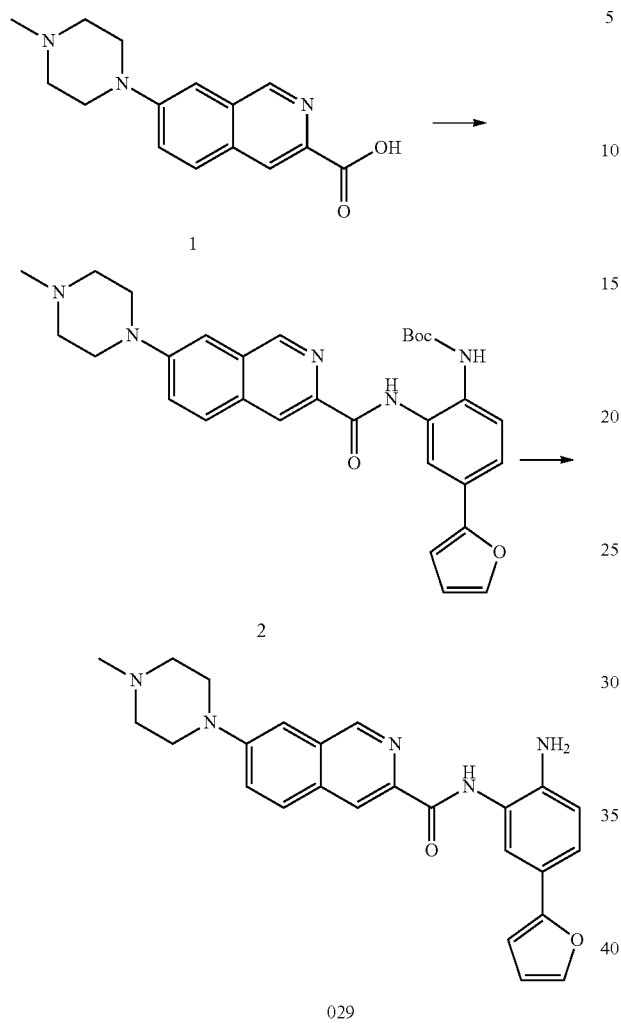

Step 1:

A mixture of compound 1 (100 mg, 0.37 mmol), tert-butyl 2-amino-4-(furan-2-yl)phenylcarbamate (151 mg, 1.5 eq.) and EDCl (550 mg, 7.0 eq.) in pyridine (5 ml) were stirred at 25° C. overnight. It was concentrated and extracted with EA (2×50 ml), washed by brine (2×60 ml). It was purified by prep-TLC (PE:EA=1:3). Compound 2 (150 mg, Yield: 39%) was obtained as a yellow oil.

Step 2:

To a solution of compound 2 (150 mg, 0.28 mmol) in DCM (2 ml) was added TFA (0.5 ml) at room temperature. The reaction was stirred for 2 hours. Then it was concentrated. Compound 029 was obtained as a yellow solid (33 mg, 27%). LCMS: m/z=428 (M+H)$^+$. $^1$H NMR (400 MHz, MeOD) δ 9.17 (s, 1H), 8.50 (s, 1H), 7.99 (d, J=9.1 Hz, 1H), 7.90 (d, J=1.8 Hz, 1H), 7.75-7.68 (m, 1H), 7.49 (s, 2H), 7.43 (dd, J=8.3, 1.9 Hz, 1H), 6.97 (d, J=8.4 Hz, 1H), 6.59 (d, J=3.3 Hz, 1H), 6.48 (dd, J=3.2, 1.8 Hz, 1H), 3.62 (s, 4H), 3.19 (s, 4H), 2.78 (s, 3H).

Example 30—Synthesis of Compound 030

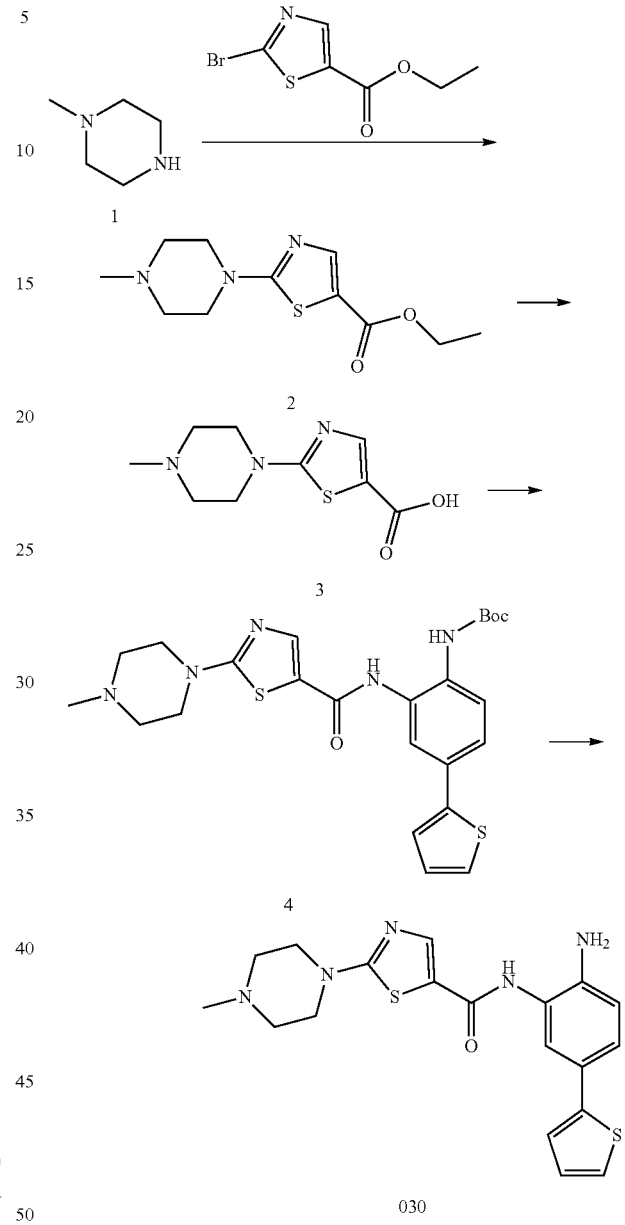

Step 1:

To a solution of compound 1 (432 mg, 4.6 mmol) and ethyl 2-bromothiazole-5-carboxylate (1 g, 4.2 mmol), Et$_3$N (1.27 g, 12.6 mmol) in DMF (20 ml) was stirred at 90° C. for overnight. The solvent was evaporated off and extracted by EA (20 ml×2), washed with water, brine, concentrated in vacuo to afford compound 2 as a yellow solid (1.2 g, crude).

Step 2:

To a solution of compound 2 (1.2 g, 4.7 mmol) NaOH (2.5 ml, 2M) in EtOH (10 ml) was stirred at 60° C. for 2 hours. The solvent was evaporated off, adjusted to pH<7, concentrated to afford compound 3 (2.0 g, containing some NaCl).

Step 3:

To a solution of compound 3 (454 mg, 2 mmol) tert-butyl (2-amino-4-(thiophen-2-yl)phenyl)carbamate (290 mg, 1 mmol) EDCl (382 mg, 2 mmol) in pyridine (10 ml). The mixture was stirred at room temperature for overnight. The solvent was evaporated off, extracted by EA (15 ml×2) and washed with water to afford compound 4 as a white solid (210 mg, crude).

Step 4:

To a solution of compound 4 (210 mg, 0.42 mmol) in DCM (5 ml) was added TFA (2 ml). The mixture was stirred room temperature for 2 hours. The solvent was evaporated off, adjusted to pH<7 and filtered to afford compound 030 as a white solid (58 mg, 34%). LCMS: m/z=500 (M+H)+ 1H NMR (500 MHz, DMSO) δ 9.53 (s, 1H), 8.04 (s, 1H), 7.32-7.23 (m, 4H), 6.80 (s, 1H), 6.79-6.76 (d, J=8 Hz, 1H), 5.13 (s, 2H), 3.505-3.485 (s, 4H), 2.42-2.41 (s, 4H), 2.227 (s, 3H).

Example 31—Synthesis of Compound 031

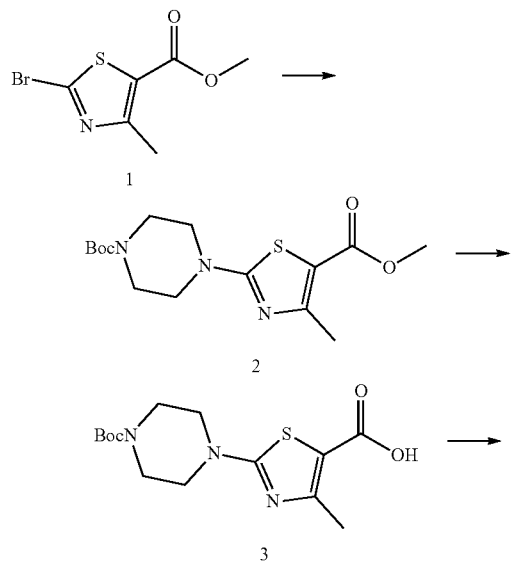

Step 1:

A mixture of methyl 2-bromo-4-methylthiazole-5-carboxylate (472 mg, 2 mmol), tert-butyl piperazine-1-carboxylate (1.12 g, 6 mmol), DIPEA (1.29 g, 10 mmol) in 1,4-dioxane (30 mL) was stirred at 95° C. under N2 atmosphere for overnight. The mixture was cool and added EA (100 mL) and water (100 mL), stirred for 30 min, the organic layer was separated, dried, concentrated to get a residue, which was washed by PE (100 mL) to obtain compound 2 (477 g, 70%) as a light yellow solid.

Step 2:

A mixture of compound 2 (341 mg, 1 mmol) and 2M NaOH (5 mL) in THF (5 ml) and EtOH (5 mL) was stirred at 60° C. for 3 h The mixture was concentrated to get a residue, HCl (2 M) was added to adjust pH 7, filtered to give compound 3 as a white solid (298 mg, 91%).

Step 3:

A mixture of compound 3 (307 mg, 1 mmol), tert-butyl 2-amino-4-(thiophen-2-yl)phenylcarbamate (290 mg, 1 mmol), HOAT (136 mg, 1 mmol), 1-(3-dimethylaminopropyl)-3-ethylcarbodiimide hydrochloride (573 mg, 3 mmol) and DMAP (244 mg, 2 mmol) in DMF (5 mL) was stirred at 55° C. for overnight. The mixture was poured into water (100 mL), filtered to get a residue which was purified by Prep-TLC to obtain compound 4 (90 mg, 15%) as a yellow solid.

Step 4:

A mixture of compound 4 (90 mg, 0.15 mmol) and TFA (3 mL) in DCM (3 mL) was stirred at room temperature for 1 hour. The mixture was purified by Prep-HPLC to obtain compound 031 (34 mg, 57%) as a yellow solid. LCMS: m/z=400 (M+H)+. 1H NMR (500 MHz, DMSO) δ 8.95 (s, 1H), 8.21 (s, 1H), 7.45 (s, 1H), 7.37 (m, 1H), 7.27 (m, 2H), 7.06 (m, 1H), 6.80 (m, 1H), 5.06 (s, 2H), 3.43 (s, 4H), 2.85 (s, 4H).

Example 32—Synthesis of Compound 032

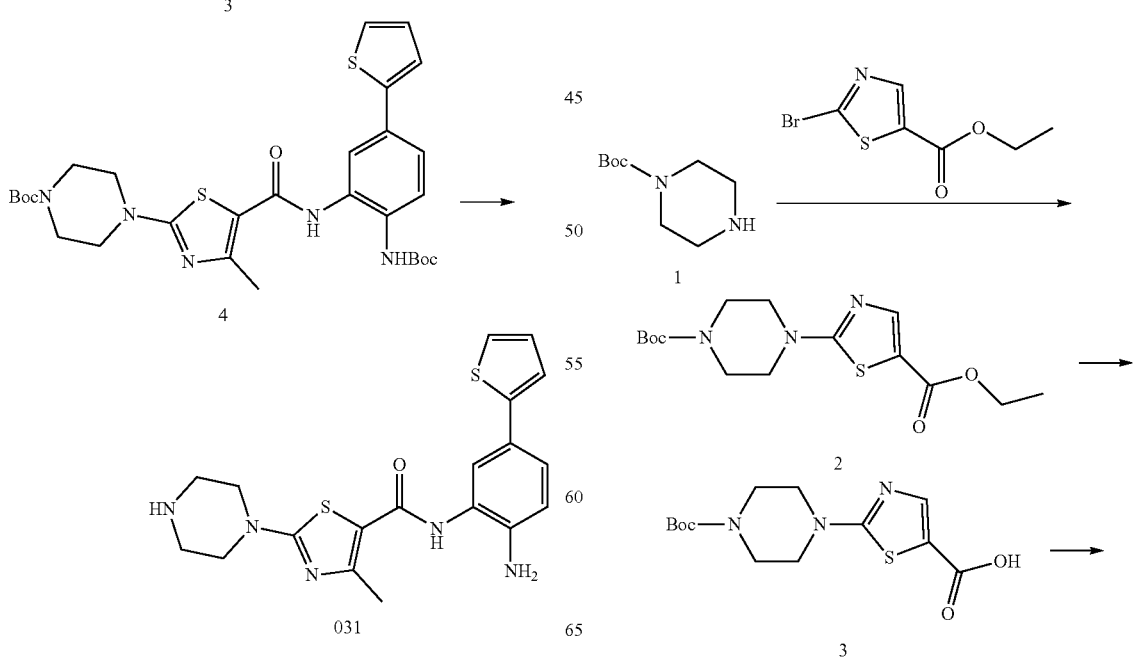

-continued

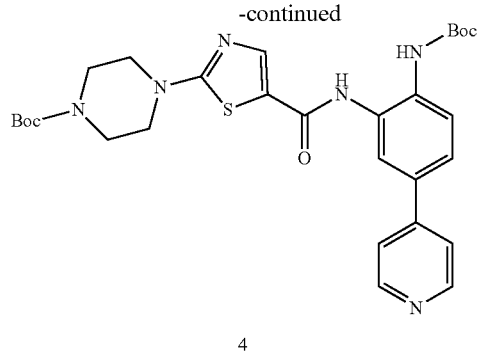

4

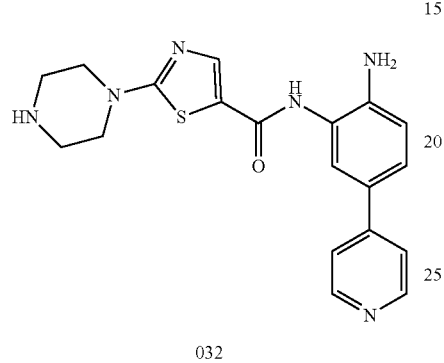

032

Step 1:

To a solution of compound 1 (860 mg, 4.6 mmol) and ethyl 2-bromothiazole-5-carboxylate (1 g, 4.2 mmol), Et₃N (1.27 g, 12.6 mmol) in DMF (20 ml) was stirred at 90° C. for overnight. The solvent was evaporated off and extracted by EA (20 ml×2), washed with water, brine, concentrated in vacuo to afford compound 2 as a yellow solid (1.8 g, crude).

Step 2:

To a solution of compound 2 (500 mg, 1.46 mmol) NaOH (2 ml, 2M) in EtOH (10 ml) was stirred at 60° C. for 2 hours. The solvent was evaporated off, adjusted to pH<7, filtered and washed with water to afford compound 3 as a white solid (394 mg, 86.1%).

Step 3:

To a solution of compound 3 (95 mg, 0.3 mmol) tert-butyl (2-amino-4-(pyridin-4-yl)phenyl)carbamate (86 mg, 0.3 mmol) EDCl (172 mg, 0.9 mmol) in pyridine (4 ml). The mixture was stirred at room temperature for overnight. The solvent was evaporated off, extracted by EA (15 ml×2) and washed with water to afford compound 4 as a white solid (220 mg, crude).

Step 4:

To a solution of compound 4 (200 mg, 0.37 mmol) in DCM (2 ml) was added TFA (1 ml). The mixture was stirred room temperature for 2 hours. The solvent was evaporated off, adjusted to pH<7 and filtered to afford compound 032 as a white solid (68 mg, 34%). ¹H NMR (400 MHz, DMSO) δ 9.54 (s, 1H), 8.50 (d, J=6.0 Hz, 2H), 8.06 (s, 1H), 7.62 (s, 1H), 7.58 (d, J=6.1 Hz, 2H), 7.49 (d, J=8.3 Hz, 1H), 6.87 (d, J=8.4 Hz, 1H), 5.36 (s, 2H), 3.45-3.38 (m, 4H), 2.79 (s, 4H). LCMS: m/z=382 (M+H)⁺

Example 33—Synthesis of Compound 033

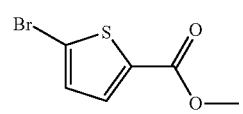

1

[structure]

2

[structure]

3

[structure]

4

[structure]

033

Step 1:

Methyl 5-bromothiophene-2-carboxylate (663 mg, 3 mmol), tert-butyl piperazine-1-carboxylate (1.674 g, 9 mmol), Pd₂(dba)₃ (275 mg, 0.3 mmol), RuPhos (140 mg, 0.3 mg) and Cs₂CO₃ (2.934 g, 9 mmol) were added into toluene (15 ml). The mixture was stirred at 95° C. for overnight. It was purified by column chromatography. Compound 2 was obtained as a green solid (660 mg, 56% yield).

Step 2:

Tert-butyl 4-(5-(methoxycarbonyl) thiophen-2-yl) piperazine-1-carboxylate (640 mg, 1.96 mmol) and NaOH (2 mol/L, 4 ml) were added into EtOH (4 ml) and THF (4 ml). The mixture was stirred at 60° C. for 3 hours. The pH was adjusted to 6-7 and it was filtered and washed by Et₂O. Compound 3 was obtained as a green solid (600 mg, 87% yield).

Step 3:

5-(4-(tert-butoxycarbonyl) piperazin-1-yl) thiophene-2-carboxylic acid (94 mg, 0.3 mmol), tert-butyl 2-amino-4-(thiophen-2-yl) phenylcarbamate (87 mg, 0.3 mmol) and EDCl (173 mg, 0.9 mmol) were added into pyridine (3 ml). The mixture was stirred at room temperature for overnight. A crude compound 4 (200 mg) was used for next step.

Step 4:

Tert-butyl 4-(5-(2-(tert-butoxycarbonylamino)-5-(thiophen-2-yl) phenylcarbamoyl) thiophen-2-yl) piperazine-1-carboxylate (180 mg, 0.32 mmol) was added into DCM (2 ml). Then TFA (2 ml) was added. The mixture was stirred at room temperature for 2 hours. When the reaction finished, the pH was adjusted to 8-9. It was extracted by EA and washed by brine, HCl. Compound 033 was afforded as HCl salt (49 mg, 42% yield, lot SP-0017467-087). LCMS: m/z=385.1 (M+H)⁺. ¹H NMR (400 MHz, DMSO) δ 10.23 (s, 1H), 9.40 (s, 2H), 8.04 (d, J=3.8 Hz, 1H), 7.72 (s, 1H), 7.51 (dd, J=22.9, 10.9 Hz, 3H), 7.29 (d, J=8.2 Hz, 1H), 7.13 (s, 1H), 6.38 (d, J=3.9 Hz, 1H)⁺. ¹H NMR (400 MHz, D2O) δ 7.55 (dd, J=11.5, 6.6 Hz, 2H), 7.45 (s, 1H), 7.39-7.31 (m, 2H), 7.28 (d, J=8.2 Hz, 1H), 7.04 (s, 1H), 6.24 (d, J=4.4 Hz, 1H), 3.46 (d, J=5.3 Hz, 4H), 3.35-3.20 (m, 4H).

Example 34—Synthesis of Compound 034

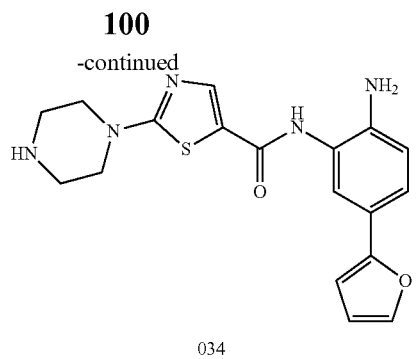

Step 1:

To a solution of compound 1 (130 mg, 0.41 mmol) and tert-butyl (2-amino-4-(furan-2-yl)phenyl)carbamate (118 mg, 0.41 mmol) in pyridine (2 ml) was added EDCl (237 mg, 1.23 mmol). The mixture was stirred at room temperature for overnight. After completed, the solvent was evaporated off and extracted by EA (20 ml×2), washed with water, brine, purified by prep-TLC (PE/EA=1/1) to afford compound 2 as a white solid (135 mg, 56%).

Step 2:

To a solution of compound 2 (120 mg, 0.2 mmol) in DCM (2 ml) was added TFA (1 ml). The mixture was stirred at room temperature for 2 hours. The solvent was evaporated off, adjusted to pH 7-8 and purified by prep-HPLC to afford compound 034 as a white solid (28 mg, 31.8%). ¹H NMR (400 MHz, DMSO) δ 9.53 (s, 1H), 8.30 (s, 1H), 8.05 (s, 1H), 7.60 (s, 1H), 7.45 (d, J=1.7 Hz, 1H), 7.31 (dd, J=8.3, 1.8 Hz, 1H), 6.79 (d, J=8.3 Hz, 1H), 6.61 (d, J=3.3 Hz, 1H), 6.52-6.48 (m, 1H), 5.14 (s, 2H), 3.43 (s, 4H), 2.82 (s, 4H). LCMS: m/z=370 (M+H)⁺

Example 35—Synthesis of Compound 035

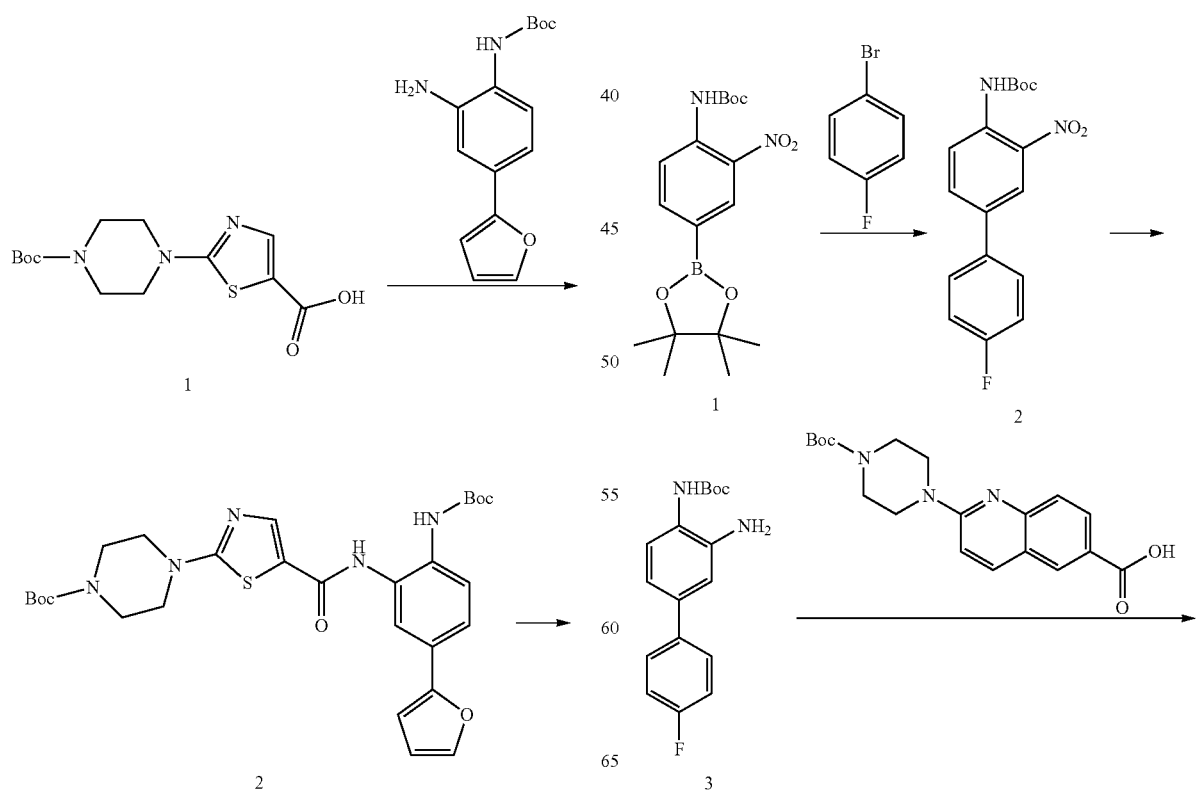

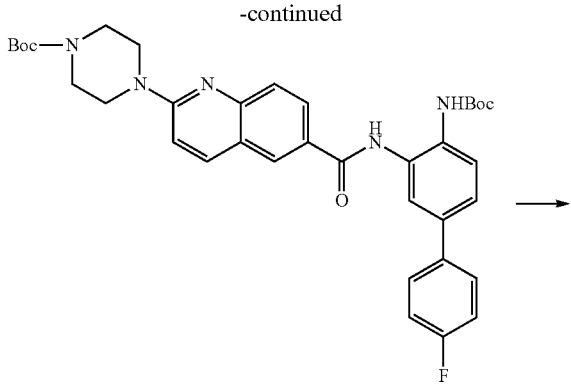

4

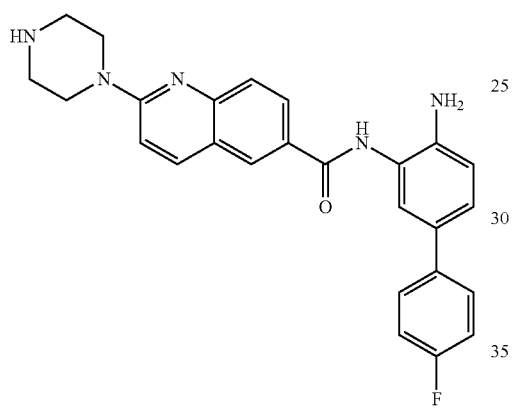

035

Step 1:

To a solution of tert-butyl 2-nitro-4-(4,4,5,5-tetramethyl-1,3,2-dioxaborolan-2-yl) phenylcarbamate (1.0 g, 2.75 mmol) and 1-bromo-4-fluorobenzene (480 mg, 2.750 mmol) in Dioxane (6 ml) and H₂O (3 ml) was added K₂CO₃ (560 mg, 5.50 mmol) and Pd(PPh₃)₄ (160 mg, 0.14 mmol). The mixture was stirred at 100° C. under N₂ for overnight. The mixture was directly purified on a column with (PE/EA=20/1) to afford compound 2 as a yellow solid (820 mg, 90%).

Step 2:

To a solution of tert-butyl 4'-fluoro-3-nitrobiphenyl-4-ylcarbamate (800 mg, 2.41 mmol) and FeCl₃ (80 mg, 0.48 mmol) in EtOH (12 ml) was added C (800 mg, 63.41 mmol) and drop wise N₂H₄H₂O (5 ml). The mixture was stirred at 60° C. for 2 hours. The mixture was extracted with H₂O (3×100 ml). The combined organic layers were washed with brine (50 ml), dried over Na₂SO₄ and concentrated in vacuo to afford compound 3 as a white solid (600 mg, 80%).

Step 3:

To a solution of tert-butyl 3-amino-4'-fluorobiphenyl-4-ylcarbamate (115 mg, 0.38 mmol) and 2-(4-(tert-butoxycarbonyl)piperazin-1-yl)quinoline-6-carboxylic acid (151 mg, 0.38 mmol) in pyridine (2.5 ml) was added EDCl (226 mg, 1.08 mmol). The mixture was stirred at room temperature for overnight. The aqueous layer was extracted with H₂O (3×100 ml). The combined organic layers were washed with brine (50 ml), dried over Na₂SO₄ and concentrated in vacuo to afford compound 4 as a white solid (200 mg, 100%).

Step 4:

To a solution of tert-butyl 4-(6-(4-(tert-butoxycarbonylamino)-4'-fluorobiphenyl-3-ylcarbamoyl)quinolin-2-yl)piperazine-1-carboxylate (200 mg, 0.31 mmol) in DCM (2 ml) at 0° C. was added TFA (2 ml) drop-wise. And the resulted was stirred at room temperature for 2 hours. The residue was purified by Prep-HPLC (0.1% NH₄HCO₃/water-acetonitrile to afford compound 035 as a white solid (64 mg, 47%). ¹H NMR (400 MHz, DMSO) δ 9.77 (s, 1H), 8.40 (d, J=1.9 Hz, 1H), 8.11 (dd, J=13.3, 5.6 Hz, 2H), 7.62-7.55 (m, 3H), 7.53 (d, J=2.0 Hz, 1H), 7.34-7.26 (m, 2H), 7.22 (t, J=8.9 Hz, 2H), 6.87 (d, J=8.4 Hz, 1H), 5.13 (s, 2H), 3.81-3.53 (m, 4H), 2.78 (dd, J=33.1, 28.1 Hz, 4H). LCMS: m/z=442.3 (M+H)⁺.

Example 36—Synthesis of Compound 036

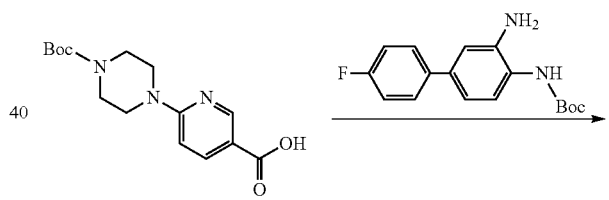

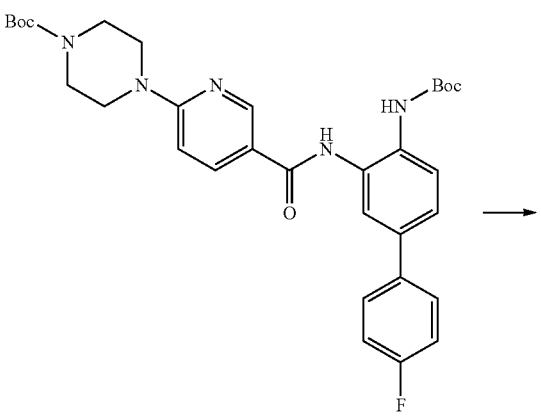

2

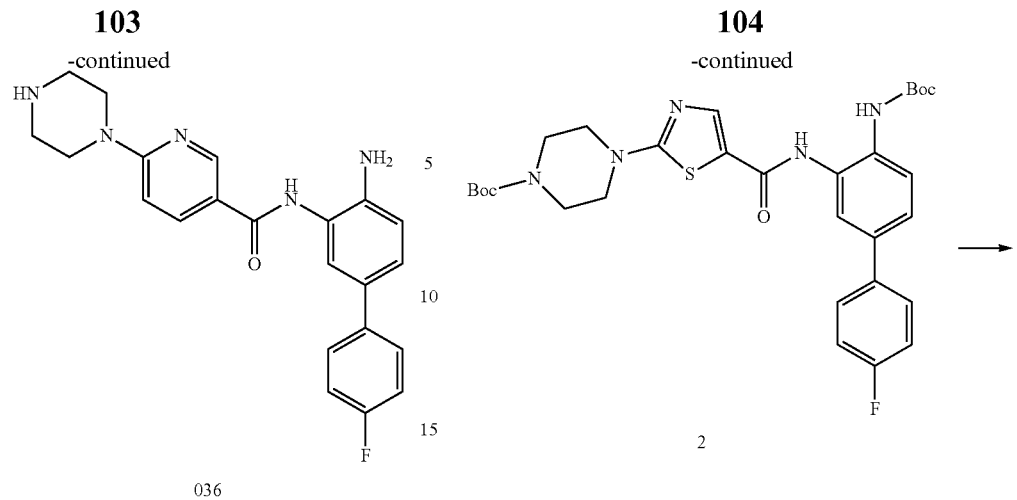

Step 1:

6-(4-(tert-butoxycarbonyl) piperazin-1-yl) nicotinic acid (144 mg, 0.47 mmol), tert-butyl 3-amino-4'-fluorobiphenyl-4-ylcarbamate (100 mg, 0.33 mmol), HATU (357 mg, 0.94 mmol) and DIPEA (0.25 ml, 1.41 mmol) were added into THF (5 ml). The mixture was stirred for 2 days at room temperature. When the reaction finished, it was extracted by EA and washed by brine. It was purified by column chromatography (PE/EA=2:1). A White solid was afforded as compound 2 (100 mg, 51% yield).

Step 2:

Tert-butyl 4-(5-(4-(tert-butoxycarbonylamino)-4'-fluoro-biphenyl-3-ylcarbamoyl) pyridin-2-yl) piperazine-1-carboxylate (100 mg, 0.17 mmol) was dissolved in DCM (0.5 ml). Then TFA (2 ml) was added. The mixture was stirred for 2 hours. When the reaction finished, the pH was adjusted to 10. And it was extracted by EA. The organic layer was concentrated and washed by Et$_2$O. A white solid was afforded as compound 036 (52 mg, 79% yield, lot SP-0017467-103). LCMS: m/z=392.2 (M+H)$^+$. $^1$H NMR (400 MHz, DMSO) δ 9.51 (s, 1H), 8.75 (s, 1H), 8.09 (s, 1H), 7.53 (d, J=36.6 Hz, 3H), 7.25 (d, J=25.7 Hz, 3H), 6.86 (s, 2H), 5.09 (s, 2H), 3.55 (s, 4H), 2.77 (s, 4H).

Example 37—Synthesis of Compound 037

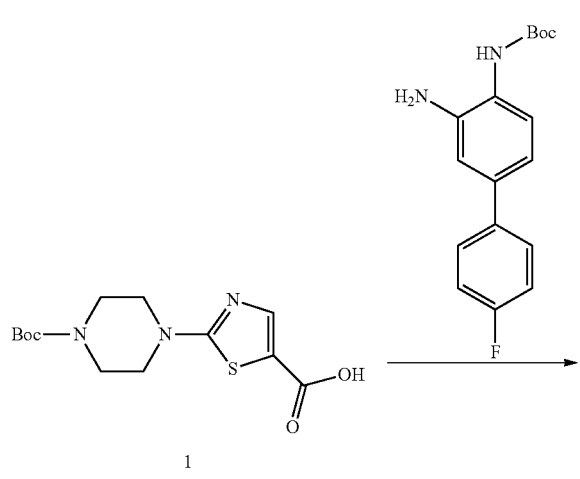

Step 1:

To a solution of compound 1 (200 mg, 0.66 mmol) and tert-butyl (3-amino-4'-fluoro-[1,1'-biphenyl]-4-yl)carbamate (100 mg, 0.33 mmol) EDCl (189 mg, 0.99 mmol) in pyridine (2 ml) was stirred at room temperature for overnight. The solvent was evaporated off and extracted by EA (20 ml×2), then it was washed with HCl (1N, 10 ml), water and brine, concentrated in vacuo to afford compound 2 as a yellow solid (165 mg, 83.7%).

Step 2:

To a solution of compound 2 (165 mg, 0.27 mmol) in DCM (1 ml) was added TFA (1 ml).

The mixture was stirred room temperature for 2 hours. The solvent was evaporated off, adjusted to pH 7-8 and washed with Et$_2$O (10 ml) to afford compound 037 as a yellow solid (101 mg, 92.6%). $^1$H NMR (400 MHz, MeOD) δ 7.99 (s, 1H), 7.60-7.54 (m, 2H), 7.41 (d, J=2.1 Hz, 1H), 7.34 (dd, J=8.3, 2.2 Hz, 1H), 7.12 (t, J=8.8 Hz, 2H), 6.98-6.94 (m, 1H), 3.59-3.53 (m, 4H), 2.99-2.93 (m, 4H). LCMS: m/z=398 (M+H)$^+$ Example 38—Synthesis of Compound 038

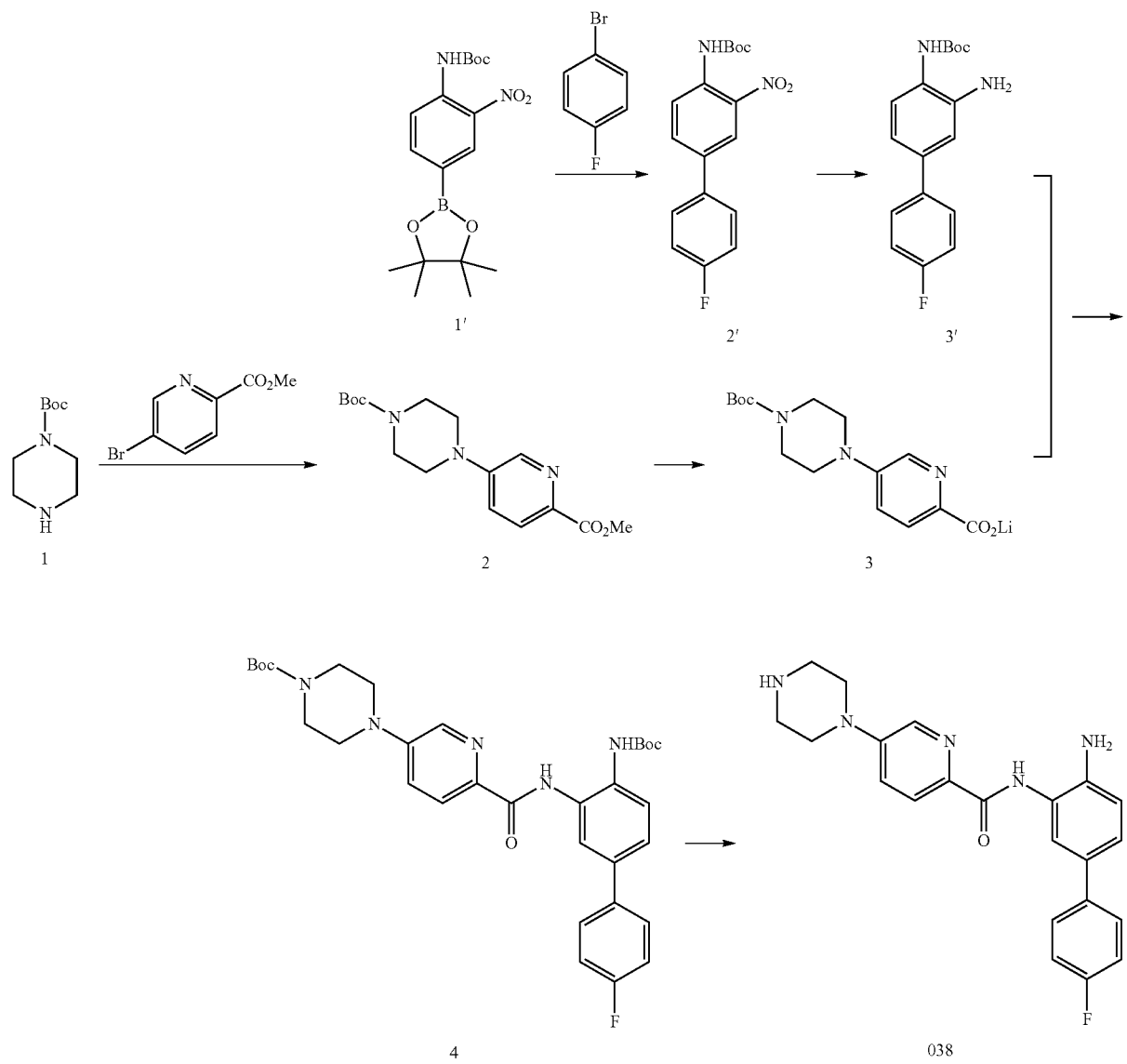

Step 1:

Under N$_2$, a mixture of tert-butyl piperazine-1-carboxylate (448 mg, 2.41 mmol), methyl 5-bromopicolinate (520 mg, 2.41 mmol), Ruphos (109 mg, 0.24 mmol), Pd$_2$(dba)$_3$ (55 mg, 0.06 mmol) and Cs$_2$CO$_3$ (2.35 g, 7.23 mmol) in toluene (20 ml) was heated at 100° C. for overnight. Then it was cooled to room temperature and filtered. The residue was concentrated in vacuum to afford a yellow solid (750 mg, 96%).

Step 2:

A mixture of tert-butyl 4-(6-(methoxycarbonyl)pyridin-3-yl)piperazine-1-carboxylate (750 mg, 4.67 mmol) and LiOH (200 mg, 4.67 mmol) in MeOH (1 ml), THF (6 ml) and water (3 ml) was stirred at 0° C. for overnight. The reaction mixture was concentrated in vacuum. Then it was washed by EA and concentrated in vacuum to afford a yellow solid (800 mg, 100%).

Step 3:

To a solution of tert-butyl 2-nitro-4-(4,4,5,5-tetramethyl-1,3,2-dioxaborolan-2-yl) phenylcarbamate (1.5 g, 4.12 mmol) and 1-bromo-4-fluorobenzene (717 mg, 4.12 mmol) in Dioxane (10 ml) and H$_2$O (5 ml) was added K$_2$CO$_3$ (824 mg, 8.24 mmol) and Pd(pph$_3$)$_4$ (238 mg, 0.21 mmol). The mixture was stirred at 100° C. under N$_2$ for overnight. The mixture was directly purified on a column with (PE/EA=20/1) to afford yellow solid (1.26 g, 91%).

Step 4:

To a solution of tert-butyl 4'-fluoro-3-nitrobiphenyl-4-ylcarbamate (1.1 g, 3.31 mmol) and FeCl$_3$ (98 mg, 0.60 mmol) in EtOH (10 ml) was added activate carbon (1.1 g, 87.05 mmol) and drop wise N$_2$H$_4$—H$_2$O (5 ml). The mixture was stirred at 60° C. for 2 h. The mixture was extracted with H$_2$O (3×100 ml). The combined organic layers were washed with brine (50 ml), dried over Na$_2$SO$_4$ and concentrated in vacuum to afford a white solid (1 g, 100%).

Step 5:

To a solution of lithium 5-(4-(tert-butoxycarbonyl)piperazin-1-yl)picolinate (800 mg, 2.61 mmol) and HATU (992 mg, 2.61 mmol) in DMF (10 ml) was stirred at room temperature for 15 minutes. Tert-butyl 3-amino-4'-fluorobiphenyl-4-ylcarbamate (438 mg, 1.45 mmol) was added. The mixture was stirred at room temperature for overnight. The aqueous layer was extracted with H$_2$O (3×200 ml). The combined organic layers were washed with brine (50 ml), dried over Na$_2$SO$_4$, filtered and concentrated in vacuum. The residue was purified by preparative TLC (silica gel, GF254 10-40 u, 25×25 cm) with petroleum ether/EtOAc (2:1) to afford a white solid (120 mg, 14%).

Step 6:

To a solution of tert-butyl 4-(6-(4-(tert-butoxycarbonylamino)-4'-fluorobiphenyl-3-ylcarbamoyl) pyridin-3-yl) piperazine-1-carboxylate (120 mg, 0.20 mmol) in DCM (1.5 ml) at 0° C. was added TFA (1.5 ml) drop wise. And the resulted was stirred at room temperature for 2 hours. The residue mixture was concentrated in vacuum. The residue was purified by Prep-HPLC. The white solid was re-crystallized from water, dried by lyophilization to afford compound 038 as a white solid (47 mg, 59%). LCMS: m/z=392.2 (M+H)$^+$ $^1$H NMR (400 MHz, DMSO) δ 9.87 (s, 1H), 8.38 (d, J=2.8 Hz, 1H), 8.20 (s, 1H), 7.96 (d, J=8.8 Hz, 1H), 7.84 (d, J=2.1 Hz, 1H), 7.55 (dt, J=22.5, 12.9 Hz, 2H), 7.47 (dd, J=8.9, 2.8 Hz, 1H), 7.31-7.14 (m, 3H), 6.88 (d, J=8.3 Hz, 1H), 5.02 (s, 2H), 3.41-3.35 (m, 4H), 3.02-2.95 (m, 4H).

Example 39—Synthesis of Compound 039

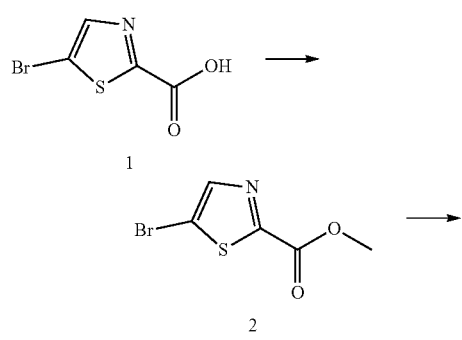

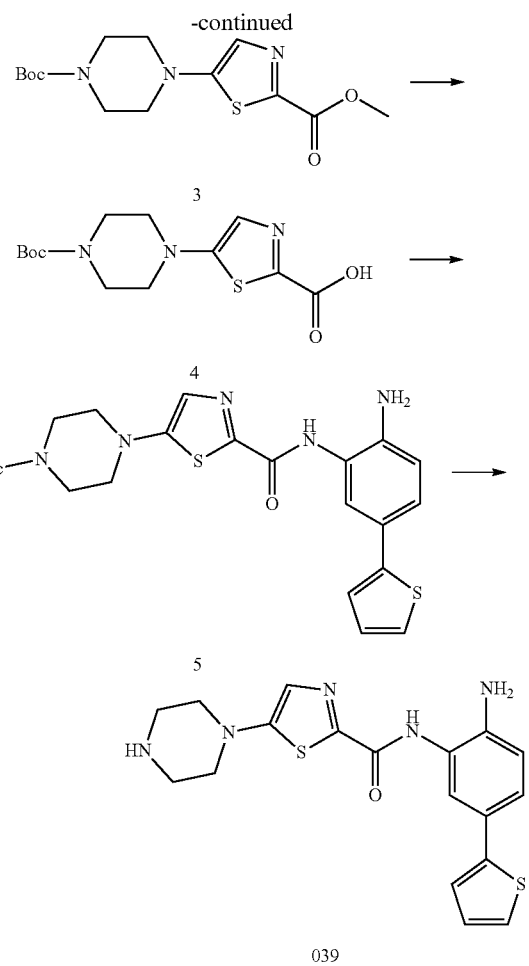

Step 1:

To a solution of 5-bromothiazole-2-carboxylic acid (957 mg, 4.58 mmol) in DCM (20 ml) was added oxalyl chloride (0.49 ml), containing a catalytic amount of DMF (0.11 ml) at room temperature and resulting reaction mixture was stirred at room temperature for 0.5 hours. Then MeOH (8 ml) was added to the solution and the reaction mixture was stirred for addition 2 hours. The reaction mixture was a saturated aqueous solution of NaHCO$_3$ (50 ml) and extracted with DCM (2×50 ml), the combined organic layer was washed with water and brine (50 ml), dried over Na$_2$SO$_4$ and concentrated in vacuum to afford a white solid (900 mg, 90%).

Step 2:

Under N$_2$, a mixture of tert-butyl piperazine-1-carboxylate (750 mg, 4.04 mmol), methyl 5-bromothiazole-2-carboxylate (900 mg, 4.04 mmol), Brettphos (215 mg, 0.40 mmol), Pd$_2$(dba)$_3$ (370 mg, 0.40 mmol) and Cs$_2$CO$_3$ (3.95 g, 12.1 mmol) in toluene (20 ml) was heated at 100° C. for overnight. The residue was purified by preparative TLC (silica gel, GF 254 10-40 u, 25×25 cm) with petroleum ether/EtOAc (5:6) to afford a yellow solid (210 mg, 15.9%).

Step 3:

To a solution of methyl 5-(4-(tert-butoxycarbonyl) piperazin-1-yl) thiazole-2-carboxylate (210 mg, 0.64 mmol) and LiOH (81 mg, 1.92 mmol) in MeOH (1 ml), THF (3 ml) and H$_2$O (1.5 ml) was stirred at 0° C. for 5 h. The reaction mixture was concentrated in vacuum to afford a yellow solid (200 mg, 100%).

Step 4:

To a solution of lithium 5-(4-(tert-butoxycarbonyl)piperazin-1-yl)thiazole-2-carboxylate (60 mg, 0.19 mmol) and HATU (73 mg, 0.19 mmol) in DMF (1.5 ml) was stirred at room temperature for 15 min. tert-butyl 2-amino-4-(thiophen-2-yl)phenylcarbamate (31 mg, 0.11 mmol) was added. The mixture was stirred at room temperature for overnight. The residue was purified by preparative TLC (silica gel, GF254 10-40 u, 25×25 cm) with petroleum ether/EtOAc (2:1) to afford a yellow solid (50 mg, 45%).

Step 5:

To a solution of tert-butyl 4-(2-(2-(tert-butoxycarbonylamino)-5-(thiophen-2-yl) phenylcarbamoyl) thiazol-5-yl) piperazine-1-carboxylate (50 mg, 0.09 mmol) in DCM (1 ml) at 0° C. was added TFA (1 ml) drop wise. The resulting mixture was stirred at room temperature for 2 h. The reaction mixture was concentrated in vacuum. The pH was adjusted to around 7 by progressively adding NaOH (5 ml). The mixture was filtered to afford compound 039 as a yellow solid. (31 mg, 94%) LCMS: m/z=386.1 (M+H)$^+$ $^1$H NMR (400 MHz, DMSO) δ 9.70 (s, 1H), 7.61 (d, J=1.9 Hz, 1H), 7.37 (d, J=5.0 Hz, 1H), 7.25 (dd, J=10.1, 7.1 Hz, 3H), 7.09-7.01 (m, 1H), 6.82 (d, J=8.3 Hz, 1H), 5.14 (s, 2H), 3.21-3.12 (m, 4H), 2.90-2.80 (m, 4H), 1.24 (s, 1H).

Example 40—Synthesis of Compound 040

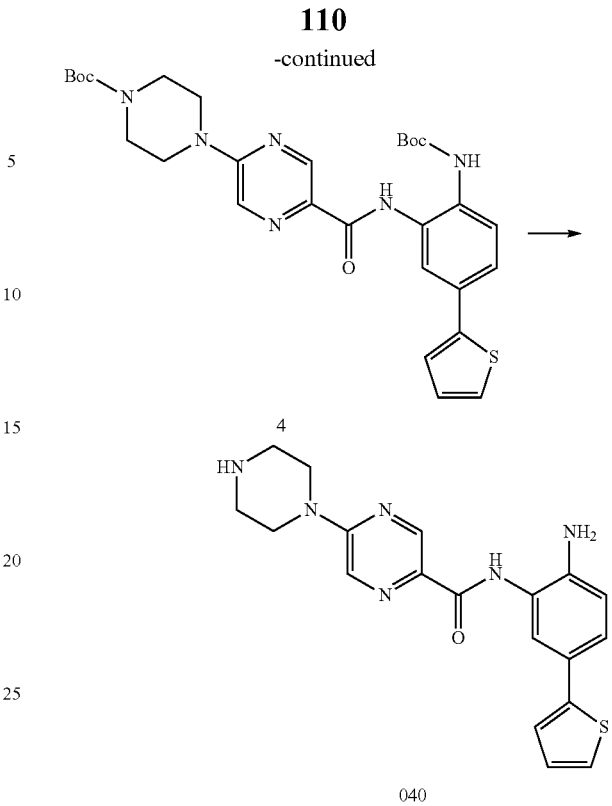

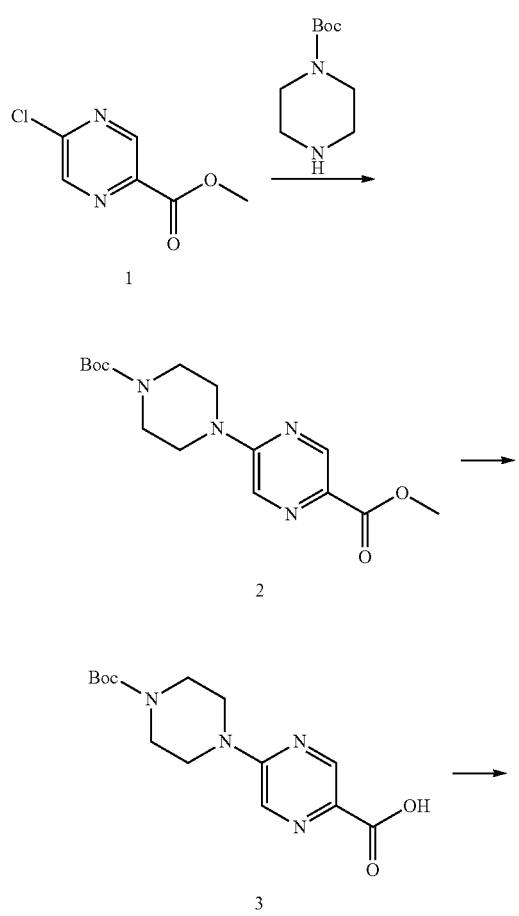

Step 1:

Tert-butyl piperazine-1-carboxylate (3.72 g, 20 mmol), methyl 5-chloropyrazine-2-carboxylate (1.72 g, 10 mmol) and DIPEA (2.02 g, 20 mmol) were added into 1,4-dioxane (15 ml). The mixture was stirred for overnight at 100° C. When the reaction finished, it was extracted by EA and washed by brine. It was purified by flash column chromatography (EA, 100%) to afford the yellow solid as product (6 g, crude).

Step 2:

Methyl 5-(4-(tert-butoxycarbonyl) piperazin-1-yl) pyrazine-2-carboxylate (2 g, crude) was added into a solution of EtOH (5 ml), THF (5 ml) and NaOH (2 N, 5 ml). The mixture was stirred at 60° C. for 2 h. When the reaction finished, the pH was adjusted to 1 and it was extracted by EA, concentrated to afford the pink solid. (300 mg, 15% yield, 2 steps).

Step 3:

5-(4-(tert-butoxycarbonyl) piperazin-1-yl) pyrazine-2-carboxylic acid (200 mg, 0.65 mmol), tert-butyl 2-amino-4-(thiophen-2-yl) phenylcarbamate (157 mg, 0.54 mmol) and EDCl (311 mg, 1.62 mmol) were added into Py (5 ml). The mixture was stirred at room temperature for overnight. When the reaction finished, it was concentrated and washed with Et2O. The yellow solid was collected as product (310 mg, 65% yield).

Step 4:

Tert-butyl 4-(5-(2-(tert-butoxycarbonylamino)-5-(thiophen-2-yl) phenylcarbamoyl) pyrazin-2-yl) piperazine-1-carboxylate (300 mg, 0.52 mmol) was dissolved into DCM (2 ml). Then TFA (2 ml) was added. The mixture was stirred at room temperature for 2 h. When the reaction finished, it was adjusted to pH=10 and extracted by EA. It was concentrated and washed by Et$_2$O to afford compound 040 as a yellow solid product (140 mg, 69% yield, Lots SP-0017467-141). LCMS: m/z=381.2 (M+H)$^+$. $^1$H NMR (400 MHz, DMSO) δ 9.68 (s, 1H), 8.72 (s, 1H), 8.34 (s, 1H), 7.79 (s, 1H), 7.37 (d, J=4.7 Hz, 1H), 7.26 (d, J=8.7 Hz, 2H), 7.06 (s, 1H), 6.84 (d, J=8.1 Hz, 1H), 5.10 (s, 2H), 3.68 (s, 4H), 2.83 (s, 4H).

Example 41—Synthesis of Compound 041

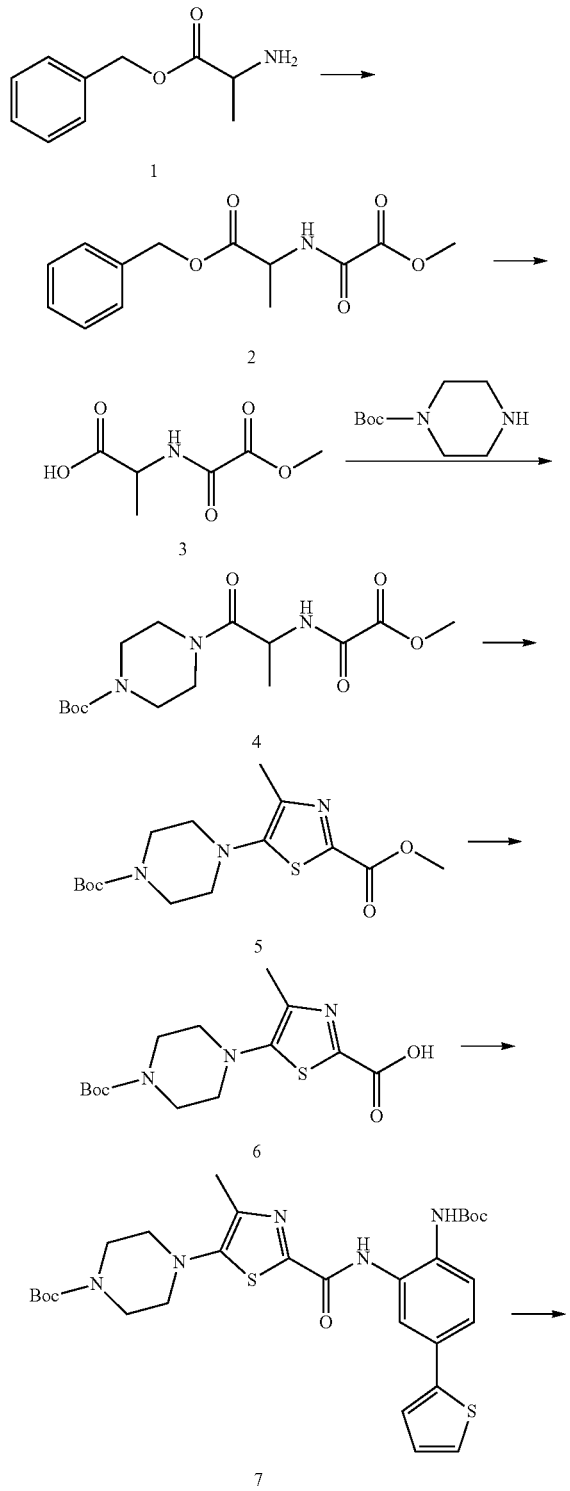

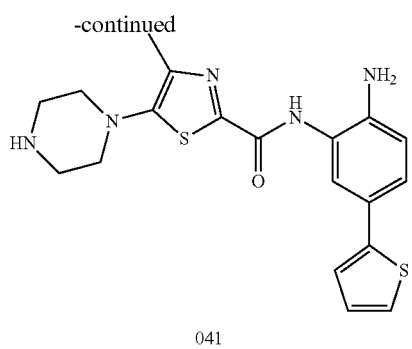

041

Step 1:
To a solution of benzyl 2-aminopropanoate (10 g, 46.52 mmol), methyl 2-chloro-2-oxoacetate (6.4 g, 51.16 mmol) and TEA (14 g, 139.56 mmol) in DCM (200 ml) was stirred at room temperature for 2 h. The mixture was directly purified on column chromatograph on silica gel (200-300 mesh, eluting with petroleum ether/EtOAc=4:1) to afford yellow oil (8.7 g, 70.7%).

Step 2:
Under $H_2$, a mixture of benzyl 2-(2-methoxy-2-oxoacetamido)propanoate (8.7 g, 32.8 mmol), Pd/C (400 mg, 3.8 mmol) was stirred at room temperature for overnight. The residue mixture was concentrated in vacuum to afford colorless oil (5.5 g, 96%).

Step 3:
To a solution of tert-butyl piperazine-1-carboxylate (6.5 g, 34.57 mmol) and 2-(2-methoxy-2-oxoacetamido)propanoic acid (5.5 g, 31.43 mmol) in Py (100 ml) was added EDCl (12 g, 62.86 mmol). The mixture was stirred at room temperature for overnight. The mixture was directly purified on column chromatograph on silica gel (200-300 mesh, eluting with petroleum/DCM/EtOAc=10:10:1) to afford yellow solid (5.1 g, 48%).

Step 4:
Under a nitrogen atmosphere, a mixture of tert-butyl 4-(2-(2-methoxy-2-oxoacetamido)propanoyl)piperazine-1-carboxylate (750 mg, 2.19 mmol) and LR (750 mg, 2.62 mmol) in toluene (15 mL) was stirred at 100° C. for 3 h. The residue was purified by preparative TLC (silica gel, GF 254 10-40 u, 25×25 cm) with petroleum ether/EtOAc (1:1) to afford a yellow solid (300 mg, 40%).

Step 5:
To a solution of methyl 5-(4-(tert-butoxycarbonyl)piperazin-1-yl)-4-methylthiazole-2-carboxylate (300 mg, 0.88 mmol) and LiOH (55 mg, 1.32 mmol) in MeOH (1 ml), THF (3 ml) and $H_2O$ (1.5 ml) was stirred at 0° C. for 5 h. The reaction mixture was concentrated in vacuum to afford a yellow solid (290 mg, 100%).

Step 6:
To a solution of 5-(4-(tert-butoxycarbonyl)piperazin-1-yl)-4-methylthiazole-2-carboxylic acid (200 mg, 0.62 mmol) and HATU (233 mg, 0.62 mmol) in DMF (5 ml) was stirred at room temperature for 15 min. Tert-butyl 2-amino-4-(thiophen-2-yl)phenylcarbamate (99 mg, 0.35 mmol) was added. The mixture was stirred at room temperature for overnight. The residue was purified by preparative TLC (silica gel, GF254 10-40 u, 25×25 cm) with petroleum ether/EtOAc (3:1) to afford a yellow solid (183 mg, 87%).

Step 7:
To a solution of tert-butyl 4-(2-(2-(tert-butoxycarbonylamino)-5-(thiophen-2-yl)phenylcarbamoyl)-4-methylthiazol-5-yl)piperazine-1-carboxylate (183 mg, 0.31 mmol) in DCM (1.5 ml) at 0° C. was added TFA (1.5 ml) dropwise. And the resulted was stirred at room temperature for 2 h. The reaction mixture was concentrated in vacuum. The pH was adjusted to around 7 by progressively adding NaHCO$_3$ (~5 ml). The mixture was filtered and the filtrate was concentrated to afford a yellow solid compound 041 (114 mg, 92%). LCMS: m/z=400.2 (M+H)$^+$. $^1$H NMR (400 MHz, DMSO) δ 9.89 (s, 1H), 7.55 (d, J=1.8 Hz, 1H), 7.37 (d, J=5.0 Hz, 1H), 7.29 (dd, J=8.3, 1.9 Hz, 1H), 7.23 (d, J=3.3 Hz, 1H), 7.10-7.01 (m, 1H), 6.82 (d, J=8.4 Hz, 1H), 5.16 (s, 2H), 3.19 (d, J=4.6 Hz, 4H), 3.06 (s, 4H), 2.37 (s, 3H).

Example 42—Synthesis of Compound 042 azol-5-yl)piperazine-1-carboxylate (113 mg, 0.19 mmol) in DCM (2 ml) at 0° C. was added TFA (2 ml) dropwise. And the reaction mixture was stirred at room temperature for 2 h. The reaction mixture was concentrated in vacuum. The residue was purified by Prep-HPLC to afford a yellow solid compound 042 (52 mg, 71.5%). LCMS: m/z=384.2 (M+H)$^+$. $^1$H NMR (400 MHz, DMSO) δ 7.61 (s, 2H), 7.32 (d, J=7.8 Hz, 1H), 6.82 (d, J=8.3 Hz, 1H), 6.60 (s, 1H), 6.51 (s, 1H), 5.15 (s, 2H), 2.85 (s, 7H), 2.35 (s, 4H).

Example 43—Synthesis of Compound 043

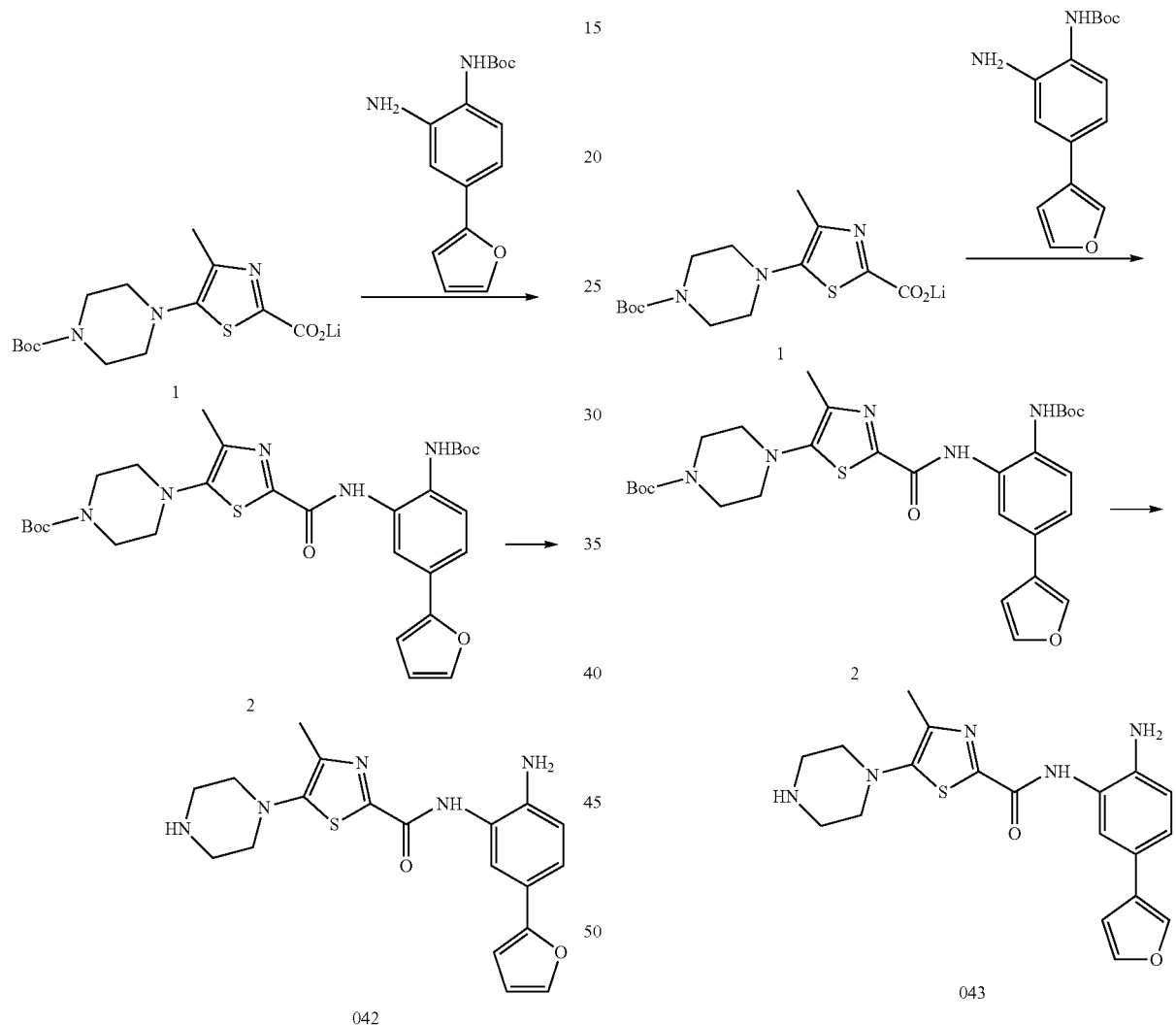

Step 1:
To a solution of lithium 5-(4-(tert-butoxycarbonyl)piperazin-1-yl)-4-methylthiazole-2-carboxylate (100 mg, 0.31 mmol) and HATU (116 mg, 0.31 mmol) in DMF (4 ml) was stirred at room temperature for 15 min. Tert-butyl 2-amino-4-(furan-2-yl)phenylcarbamate (47 mg, 0.17 mmol) was added. The mixture was stirred at room temperature for overnight. The residue was added water (5 mL) and the precipitate was afforded as a yellow solid (113 mg, 100%).
Step 2:
To a solution of tert-butyl 4-(2-(2-(tert-butoxycarbonylamino)-5-(furan-2-yl)phenylcarbamoyl)-4-methylthi- Step 1:
To a solution of 5 lithium 5-(4-(tert-butoxycarbonyl)piperazin-1-yl)-4-methylthiazole-2-carboxylate (100 mg, 0.31 mmol) and HATU (116 mg, 0.31 mmol) in DMF (4 ml) was stirred at room temperature for 15 min. Tert-butyl 2-amino-4-(furan-3-yl)phenylcarbamate (47 mg, 0.17 mmol) was added. The mixture was stirred at room temperature for overnight. The residue was added water (5 mL) and the precipitate was afforded as a yellow solid (73 mg, 73%).
Step 2:
To a solution of tert-butyl 4-(2-(2-(tert-butoxycarbonylamino)-5-(furan-3-yl)phenylcarbamoyl)-4-methylthiazol-5-yl)piperazine-1-carboxylate (73 mg, 0.13 mmol) in DCM (2 ml) at 0° C. was added TFA (2 ml) dropwise. The mixture was stirred at room temperature for 2 h. The reaction mixture was concentrated in vacuum. The residue was purified by Prep-HPLC to afford a yellow solid (45 mg, 93.8%). LCMS: m/z=384.3 (M+H)$^+$. $^1$H NMR (400 MHz, DMSO) δ 9.85 (s, 1H), 8.15 (d, J=19.5 Hz, 1H), 7.95 (s, 1H), 7.67 (s, 1H), 7.46 (s, 1H), 7.24 (d, J=8.0 Hz, 1H), 6.80 (d, J=5.4 Hz, 2H), 5.00 (s, 2H), 3.13 (s, 4H), 3.02 (s, 4H), 2.37 (s, 3H).

Example 44—Synthesis of Compound 044

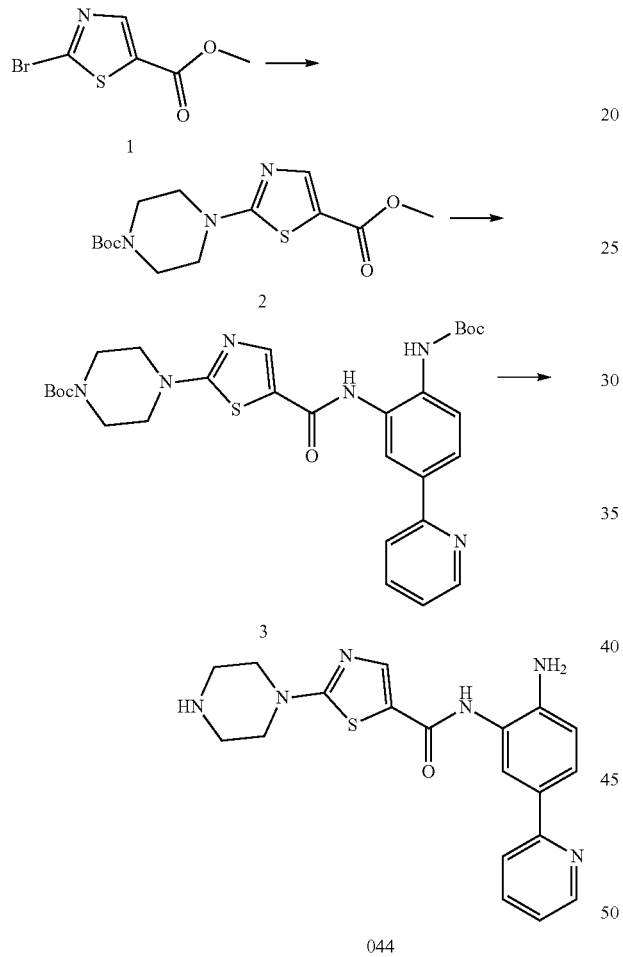

Step 1:

A mixture of methyl 2-bromothiazole-5-carboxylate (2.22 g, 10 mmol), tert-butyl piperazine-1-carboxylate (3.72 g, 20 mmol) and DIPEA (3.87 g, 30 mmol) in 1,4-dioxane (20 mL) was stirred at 100° C. for overnight. The mixture was concentrated to get a residue, which was purified by silica gel to get desired compound (2.94 g, 90%).

Step 2:

A mixture of methyl 2-(4-(tert-butoxycarbonyl)piperazin-1-yl)thiazole-5-carboxylate (327 mg, 1 mmol) and LiOH (126 mg, 3 mmol) in MeOH (20 mL) was stirred at 60° C. for 3 h. The mixture was concentrated to get a residue, which was added tert-butyl 2-amino-4-(pyridin-2-yl)phenylcarbamate (285 mg, 1 mmol), EDCl (573 mg, 3 mmol) and Py (10 mL). The mixture was stirred at room temperature for overnight. The mixture was poured into water (50 mL), filtered to get desired compound (435 mg, 75%).

Step 3:

To a solution of tert-butyl 4-(5-(2-(tert-butoxycarbonylamino)-5-(pyridin-2-yl)phenylcarbamoyl)thiazol-2-yl)piperazine-1-carboxylate (290 mg, 0.5 mmol) in DCM (5 mL) was added TFA (2.5 mL), stirred for 1 h. The mixture was concentrated to get a residue, which was purified by Prep-HPLC to afford compound 044 (124 mg, 65%). LCMS: m/z=381.2 (M+H)$^+$. $^1$H NMR (400 MHz, DMSO) δ 9.63 (s, 1H), 8.54 (d, J=4.7 Hz, 1H), 8.07 (s, 1H), 7.91 (s, 1H), 7.80-7.69 (m, 3H), 7.18 (t, J=6.5 Hz, 1H), 6.83 (d, J=8.5 Hz, 1H), 5.28 (s, 2H), 3.44-3.38 (m, 4H), 2.82-2.75 (m, 4H).

Example 45—Synthesis of Compound 045

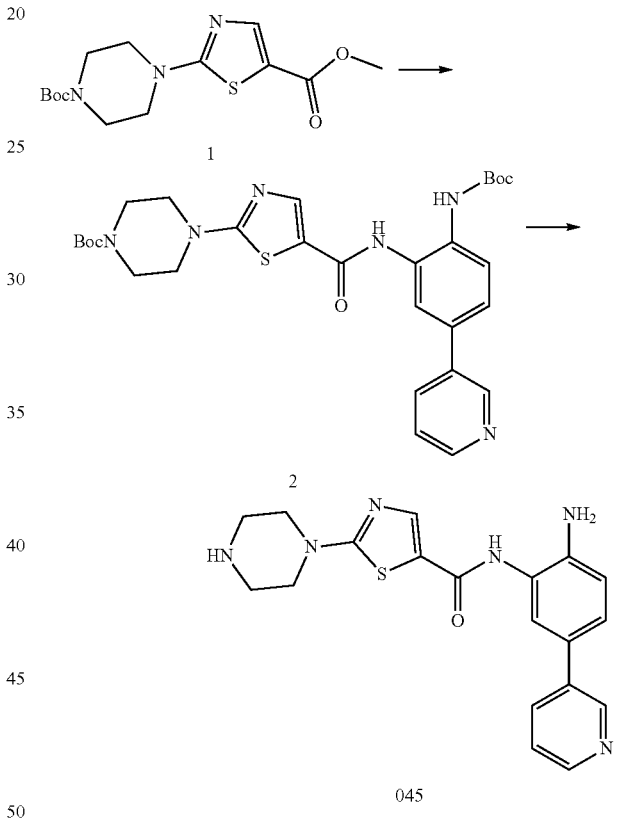

Step 1:

A mixture of methyl 2-(4-(tert-butoxycarbonyl)piperazin-1-yl)thiazole-5-carboxylate (327 mg, 1 mmol) and LiOH (126 mg, 3 mmol) in MeOH (20 mL) was stirred at 60° C. for 3 h. The mixture was concentrated to get a residue, which was added tert-butyl 2-amino-4-(pyridin-3-yl)phenylcarbamate (285 mg, 1 mmol), EDCl (573 mg, 3 mmol) and Py (10 mL). The mixture was stirred at room temperature for overnight. The mixture was poured into water (50 mL), filtered to afford desired compound (435 mg, 75%).

Step 2:

To a solution of tert-butyl 4-(5-(2-(tert-butoxycarbonylamino)-5-(pyridin-3-yl)phenylcarbamoyl)thiazol-2-yl)piperazine-1-carboxylate (290 mg, 0.5 mmol) in DCM (5 mL) was added TFA (2.5 mL), stirred for 1 h. The mixture was concentrated to get a residue, which was purified by Prep-HPLC to afford compound 045 (124 mg, 65%). LCMS: m/z=381.2 (M+H)+. 1H NMR (400 MHz, DMSO) δ 9.53 (s, 1H), 8.79 (s, 1H), 8.44 (d, J=4.4 Hz, 1H), 8.05 (s, 1H), 7.94 (d, J=8.0 Hz, 1H), 7.50 (d, J=1.8 Hz, 1H), 7.39 (td, J=8.3, 3.4 Hz, 2H), 6.88 (d, J=8.3 Hz, 1H), 5.19 (s, 2H), 3.45-3.37 (m, 4H), 2.79 (s, 4H).

Example 46—Synthesis of Compound 046

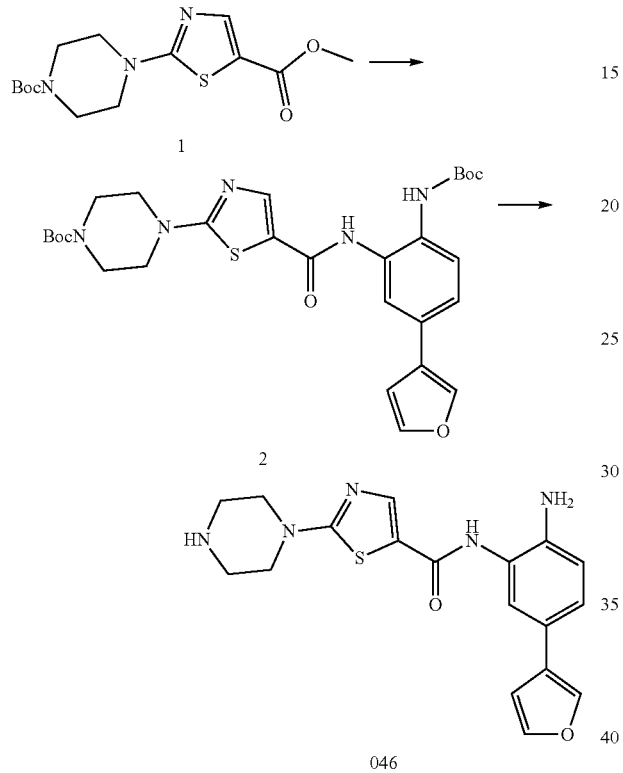

Example 47—Synthesis of Compound 047

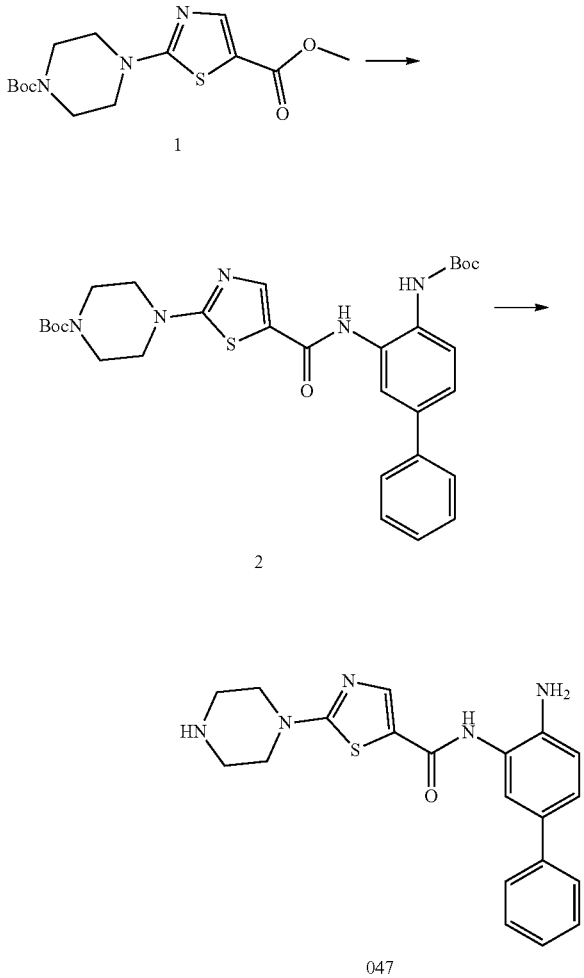

Step 1:

A mixture of methyl 2-(4-(tert-butoxycarbonyl)piperazin-1-yl)thiazole-5-carboxylate (327 mg, 1 mmol) and LiOH (126 mg, 3 mmol) in MeOH (20 mL) was stirred at 60° C. for 3 h. The mixture was concentrated to get a residue, which was added tert-butyl 2-amino-4-(furan-3-yl)phenylcarbamate (274 mg, 1 mmol), EDCl (573 mg, 3 mmol) and Py (10 mL). The mixture was stirred at room temperature for overnight. The mixture was poured into water (50 mL), filtered to afford desired compound (398 mg, 70%).

Step 2:

To a solution of tert-butyl 4-(5-(2-(tert-butoxycarbonylamino)-5-(furan-3-yl)phenylcarbamoyl)thiazol-2-yl)piperazine-1-carboxylate (285 mg, 0.5 mmol) in DCM (5 mL) was added TFA (2.5 mL), stirred for 1 h. The mixture was concentrated to get a residue, which was purified by Prep-HPLC to afford compound 046 (120 mg, 65%) LCMS: m/z=370.4 (M+H)+. 1H NMR (400 MHz, DMSO) δ 9.57 (s, 2H), 8.05 (s, 2H), 7.97 (s, 2H), 7.66 (s, 2H), 7.32 (s, 2H), 7.22 (d, J=7.8 Hz, 2H), 6.81 (s, 2H), 6.77 (d, J=8.2 Hz, 2H), 3.44 (s, 4H), 2.89 (s, 4H).

Step 1:

A mixture of methyl 2-(4-(tert-butoxycarbonyl)piperazin-1-yl)thiazole-5-carboxylate (327 mg, 1 mmol) and LiOH (126 mg, 3 mmol) in MeOH (20 mL) was stirred at 60° C. for 3 h. The mixture was concentrated to get a residue, which was added tert-butyl 3-aminobiphenyl-4-ylcarbamate (284 mg, 1 mmol), EDCl (573 mg, 3 mmol) and Py (10 mL). The mixture was stirred at room temperature for overnight. The mixture was poured into water (50 mL), filtered to afford desired compound (405 mg, 70%).

Step 2:

To a solution of tert-butyl 4-(5-(4-(tert-butoxycarbonylamino)biphenyl-3-ylcarbamoyl)thiazol-2-yl)piperazine-1-carboxylate (290 mg, 0.5 mmol) in DCM (5 mL) was added TFA (2.5 mL), stirred for 1 h. The mixture was concentrated to get a residue, which was purified by Prep-HPLC to afford compound 047 (133 mg, 70%). LCMS: m/z=380.1 (M+H)+. 1H NMR (400 MHz, DMSO) δ 9.53 (s, 1H), 8.79 (s, 1H), 8.44 (d, J=4.4 Hz, 1H), 8.34 (m, 1H), 8.05 (s, 1H), 7.94 (d, J=8.0 Hz, 1H), 7.50 (d, J=1.8 Hz, 1H), 7.39 (td, J=8.3, 3.4 Hz, 2H), 6.88 (d, J=8.3 Hz, 1H), 5.19 (s, 2H), 3.45-3.37 (m, 4H), 2.79 (s, 4H).

Example 48—Synthesis of Compound 048

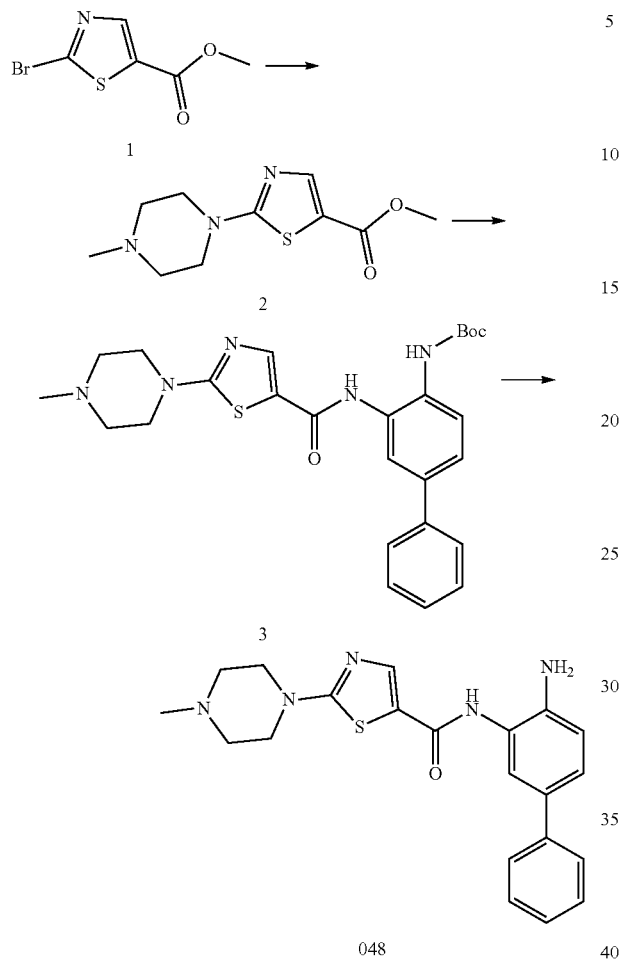

Step 1:
A mixture of methyl 2-bromothiazole-5-carboxylate (2.22 g, 10 mmol), tert-butyl piperazine-1-carboxylate (2.00 g, 20 mmol) and DIPEA (3.87 g, 30 mmol) in 1,4-dioxane (20 mL) was stirred at 100° C. for overnight. The mixture was concentrated to get a residue, which was purified by silica gel to afford desired compound (2.17 g, 90%)

Step 2:
A mixture of methyl 2-(4-methylpiperazin-1-yl)thiazole-5-carboxylate (241 mg, 1 mmol) and LiOH (126 mg, 3 mmol) in MeOH (20 mL) was stirred at 60° C. for 3 h. The mixture was concentrated to get a residue, which was added tert-butyl 3-aminobiphenyl-4-ylcarbamate (284 mg, 1 mmol), EDCl (573 mg, 3 mmol) and Py (10 mL). The mixture was stirred at room temperature for overnight. The mixture was poured into water (50 mL), filtered to get desired compound (371 mg, 75%)

Step 3:
To a solution of tert-butyl 3-(2-(4-methylpiperazin-1-yl)thiazole-5-carboxamido)biphenyl-4-ylcarbamate (247 mg, 0.5 mmol) in DCM (5 mL) was added TFA (2.5 mL), stirred for 1 h. The mixture was concentrated to get a residue, which was purified by Prep-HPLC to afford compound 048 (138 mg, 70%). LCMS: m/z=394.2 (M+H)$^+$. $^1$H NMR (400 MHz, DMSO) δ 9.53 (s, 1H), 8.79 (s, 1H), 8.44 (d, J=4.4 Hz, 1H), 8.34 (m, 1H), 8.05 (s, 1H), 7.94 (d, J=8.0 Hz, 1H), 7.50 (d, J=1.8 Hz, 1H), 7.39 (td, J=8.3, 3.4 Hz, 2H), 6.88 (d, J=8.3 Hz, 1H), 5.19 (s, 2H), 3.45-3.37 (m, 4H), 2.79 (s, 4H), 2.32 (s, 3H).

Example 49—Synthesis of Compound 049

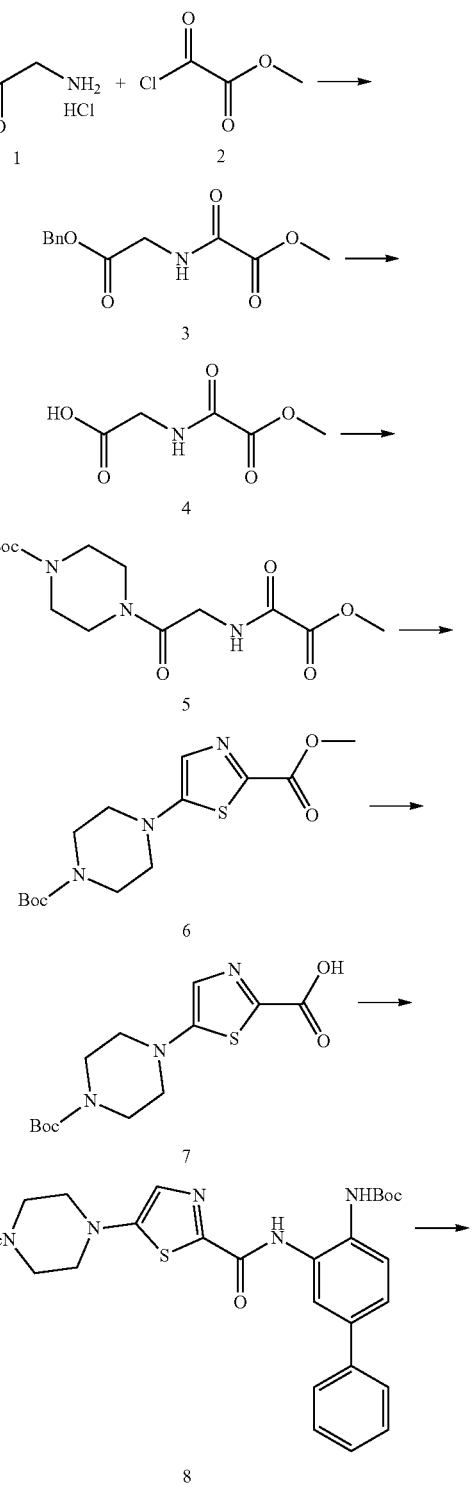

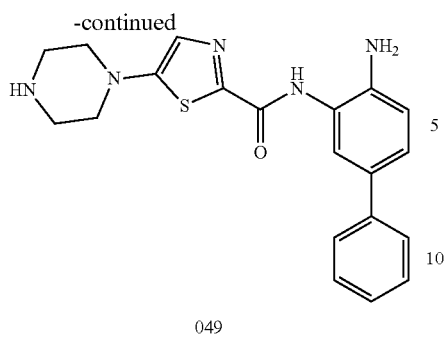

049

Step 1:

At 0° C., to a mixture of benzyl 2-aminoacetate hydrochloride (5.00 g, 24.80 mmol), and pyridine (6.0 mL, 74.39 mmol) in DCM (100 mL) was added methyl 2-chloro-2-oxoacetate (2.51 mL, 27.28 mmol). It was stirred at 0° C. to room temperature for 18 h. Then it was washed with water and concentrated in vacuo. The residue was washed with EA-PE to give crude compound (4.73 g).

Step 2:

Under $H_2$, a mixture of methyl 2-(2-(benzyloxy)-2-oxoethylamino)-2-oxoacetate (8.55 g, 34.03 mmol) and Pd/C (10%, 700 mg) in MeOH (150 mL) was stirred at room temperature for 18 h. After filtering, the filtrate was concentrated in vacuo to give compound as a white solid (5.54 g, yield: 100%).

Step 3:

A mixture of tert-2-(2-methoxy-2-oxoacetamido)acetic acid (4.38 g, 27.19 mmol), EDCl (5.73 g, 29.91 mmol) and HOBT (4.04 g, 29.91 mmol) in DMF (100 mL) was stirred at room temperature for 15 mins. Then DIEA (18 mL, 108.76 mmol) and tert-butyl piperazine-1-carboxylate (5.57 g, 29.91 mmol) was added. It was stirred at room temperature for 18 h. The resulting precipitate was filtered to give the compound (1.80 g, yield: 20%) as a white solid.

Step 4:

Under N2, a mixture of tert-butyl 4-(2-(2-methoxy-2-oxoacetamido)acetyl)piperazine-1-carboxylate (100 mg, 0.30 mmol), phosphorus pentasulfide (100 mg, 0.23 mmol) in pyridine (10 mL) was stirred at 100° C. for 4 h. It was cooled to room temperature and concentrated in vacuo. The residue was purified by prep-TLC to give compound as a light yellow solid (47 mg, yield: 47%).

Step 5:

At 0° C., a mixture of methyl 5-(4-(tert-butoxycarbonyl)piperazin-1-yl)thiazole-2-carboxylate 128 mg, 0.39 mmol) and LiOH (33 mg, 0.78 mmol) in THF (6 ml) MeOH (1 mL) and water (2 mL) was stirred at 0° C. to room temperature for 2 h. It was concentrated in vacuo to give crude compound as a Li salt.

Step 6:

A mixture of above Li salt (0.39 mmol) and HATU (164 mg, 0.43 mol) in DMF (4 mL) was stirred at room temperature for 15 mins. Tert-butyl 3-aminobiphenyl-4-ylcarbamate (122 mg, 0.43 mmol) was added. It was stirred at room temperature for 18 h. Water was added. The precipitate was collected by filtration to give crude compound as a brown solid.

Step 7:

At 0° C., to a solution of above tert-butyl 4-(2-(4-(tert-butoxycarbonylamino)biphenyl-3-ylcarbamoyl)thiazol-5-yl)piperazine-1-carboxylate (0.39 mmol) in DCM (2 mL) was added TFA (2 mL). It was stirred at 0° C. for 2 h. Then it was concentrated in vacuo. The residue was purified by Prep-HPLC to compound 049 as a yellow solid (51.3 mg, yield: 36%, three steps). LCMS: m/z=380.2 (M+H)+. $^1$H NMR (400 MHz, DMSO) δ 9.73 (s, 1H), 7.64 (s, 1H), 7.54 (d, J=7.7 Hz, 2H), 7.39 (t, J=7.6 Hz, 2H), 7.28 (dd, J=15.2, 6.8 Hz, 3H), 6.87 (d, J=8.3 Hz, 1H), 5.09 (s, 2H), 3.15 (s, 4H), 2.84 (s, 4H).

Example 50—Synthesis of Compound 050

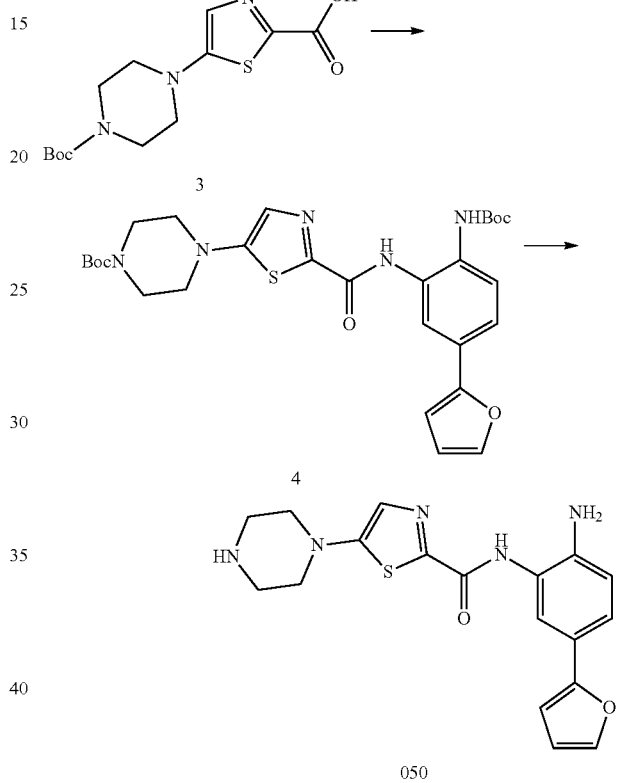

050

Step 1:

A mixture of above Li salt (0.39 mmol) and HATU (164 mg, 0.43 mol) in DMF (4 mL) was stirred at room temperature for 15 mins. Tert-butyl 2-amino-4-(furan-2-yl)phenylcarbamate (118 mg, 0.43 mmol) was added. It was stirred at room temperature for 18 h. Water was added. The precipitate was collected by filtration to give crude compound as a brown solid.

Step 2:

At 0° C., to a solution of above tert-butyl 4-(2-(2-(tert-butoxycarbonylamino)-5-(furan-2-yl)phenylcarbamoyl)thiazol-5-yl)piperazine-1-carboxylate (0.39 mmol) in DCM (2 mL) was added TFA (2 mL). It was stirred at 0° C. for 2 h. Then it was concentrated in vacuo. The residue was purified by Prep-HPLC to compound 050 as a yellow solid (51.3 mg, yield: 36%, three steps). LCMS: m/z=370.0 (M+H)+. $^1$H NMR (400 MHz, DMSO) δ 9.67 (s, 1H), 7.65 (d, J=2.0 Hz, 1H), 7.61 (s, 1H), 7.30 (dd, J=8.4, 2.0 Hz, 1H), 7.25 (s, 1H), 6.81 (d, J=8.0 Hz, 1H), 6.61 (d, J=2.8 Hz, 1H), 6.51 (m, 1H), 5.14 (s, 2H), 3.16 (m, 4H), 2.84 (m, 4H).

Example 51—Synthesis of Compound 051

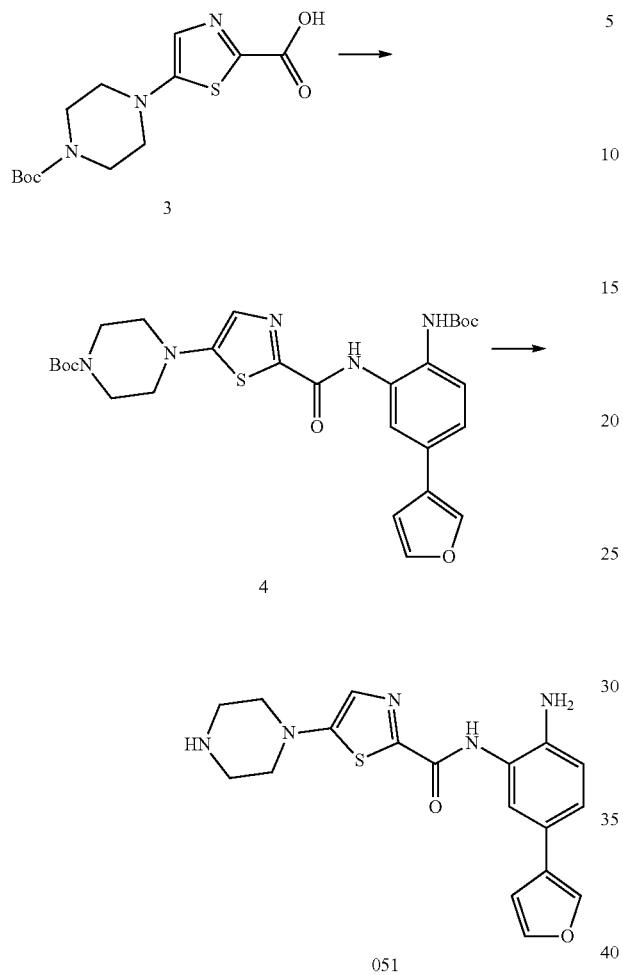

Step 1:

A mixture of above Li salt (0.42 mmol) and HATU (175 mg, 0.46 mol) in DMF (4 mL) was stirred at room temperature for 15 mins. Tert-butyl 2-amino-4-(furan-3-yl)phenylcarbamate (126 mg, 0.46 mmol) was added. It was stirred at room temperature for 4 h. Water was added. The precipitate was collected by filtration. It was purified by prep-TLC to give compound (158 mg, yield: 64%) as a light yellow solid.

Step 2:

At 0° C., to a solution of tert-butyl 4-(2-(2-(tert-butoxycarbonylamino)-5-(furan-3-yl) phenylcarbamoyl)thiazol-5-yl)piperazine-1-carboxylate (153 mg, 0.27 mmol) in DCM (2 mL) was added TFA (2 mL). It was stirred at 0° C. for 2 h. Then it was concentrated in vacuo. The residue was neutralized with aqueous saturated $NaHCO_3$ to pH8. The resulting solid was collected and dried in vacuo to compound 051 as a light yellow solid (31.7 mg, yield: 32%). LCMS: m/z=369.9 (M+H)+. $^1$H NMR (400 MHz, DMSO) δ 9.67 (s, 1H), 7.96 (s, 1H), 7.67 (m, 1H), 7.51 (d, J=1.6 Hz, 1H), 7.24 (s, 1H), 7.22 (dd, J=8.4, 2.0 Hz, 1H), 6.80 (m, 2H), 4.97 (s, 2H), 3.16 (m, 4H), 2.84 (m, 4H).

Example 52—Synthesis of Compound 052

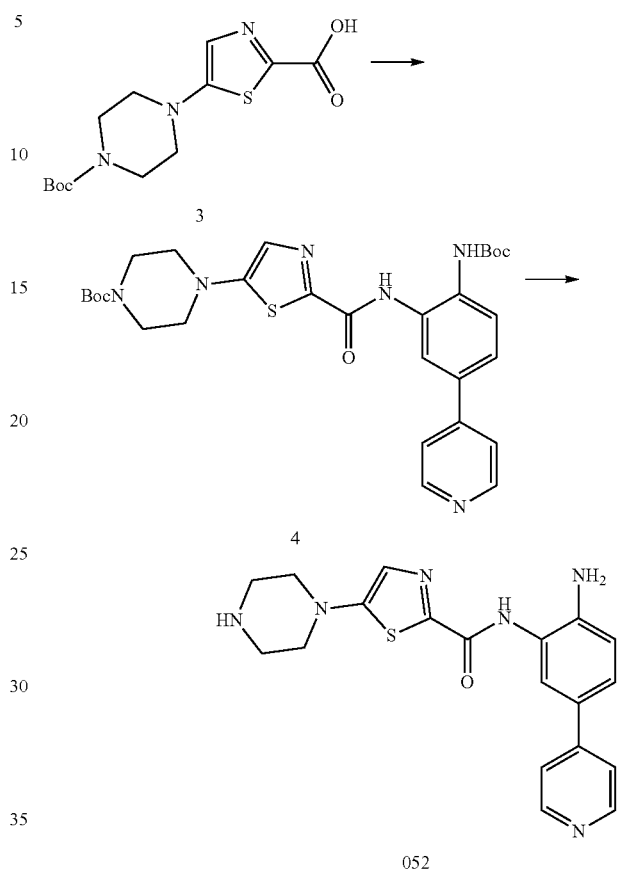

Step 1:

A mixture of 5-(4-(tert-butoxycarbonyl)piperazin-1-yl) thiazole-2-carboxylic acid (120 mg, 0.38 mmol), tert-butyl 2-amino-4-(pyridin-4-yl)phenylcarbamate (120 mg, 0.42 mmol) and EDCl (147 mg, 0.77 mmol) in pyridine (6 mL) was stirred at room temperature for 18 h. Then it was concentrated in vacuo and the residue was washed with water and purified by prep-TLC to give compound (140 mg, 63%) as a yellow solid.

Step 2:

At 0° C., to a solution of tert-butyl 4-(2-(2-(tert-butoxycarbonylamino)-5-(pyridine-4-yl)phenylcarbamoyl)thiazol-5-yl)piperazine-1-carboxylate (140 mg, 0.24 mmol) in DCM (2 mL) was added TFA (2 mL). It was stirred at 0° C. for 2 h. Then it was concentrated in vacuo. The residue was neutralized with aqueous saturated $NaHCO_3$ to pH8. The resulting solid was collected and dried in vacuo to compound 052 as a light yellow solid (77.1 mg, yield: 84%). LCMS: m/z=381.1 (M+H)+. $^1$H NMR (400 MHz, DMSO) δ 9.76 (s, 1H), 8.51 (dd, J=4.6, 1.5 Hz, 2H), 7.77 (d, J=2.1 Hz, 1H), 7.57 (dd, J=4.7, 1.6 Hz, 2H), 7.48 (dd, J=8.4, 2.2 Hz, 1H), 7.25 (s, 1H), 6.89 (d, J=8.4 Hz, 1H), 5.36 (s, 2H), 3.18-3.12 (m, 4H), 2.89-2.79 (m, 4H).

Example 53—Synthesis of Compound 053

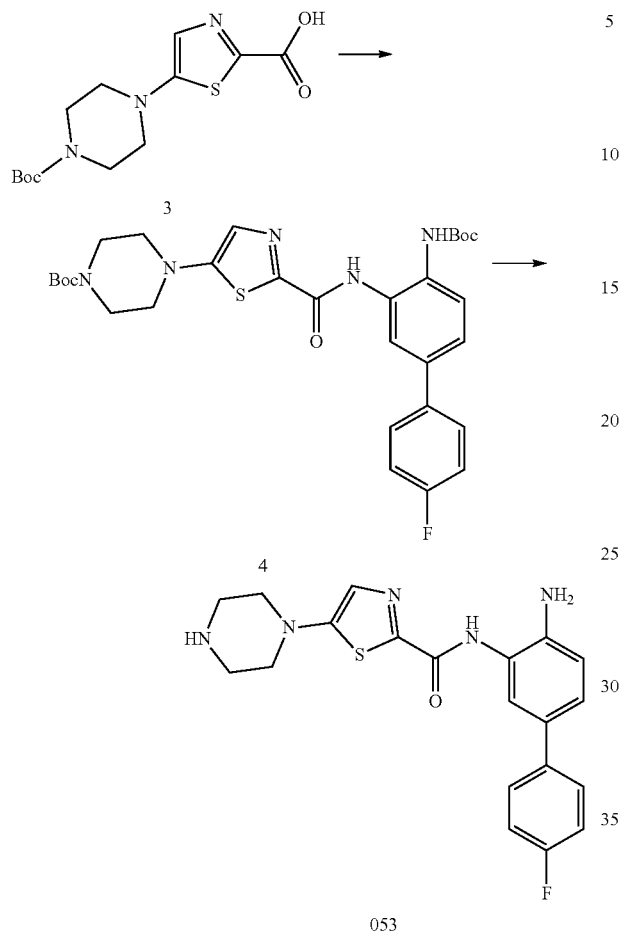

Step 1:

A mixture of 5-(4-(tert-butoxycarbonyl)piperazin-1-yl) thiazole-2-carboxylic acid (60 mg, 0.19 mmol), tert-butyl 3-amino-4'-fluorobiphenyl-4-ylcarbamate (64 mg, 0.21 mmol) and EDCl (73 mg, 0.38 mmol) in pyridine (6 mL) was stirred at room temperature for 18 h. Then it was concentrated in vacuo and the residue was washed with water and purified by prep-TLC to give compound (140 mg, 63%) as a white solid.

Step 2:

At 0° C., to a solution of tert-butyl 4-(2-(4-(tert-butoxycarbonylamino)-4'-fluorobiphenyl-3-ylcarbamoyl)thiazol-5-yl)piperazine-1-carboxylate (140 mg, 0.23 mmol) in DCM (2 mL) was added TFA (2 mL). It was stirred at 0° C. for 4 h. Then it was concentrated in vacuo. The residue was neutralized with aqueous saturated $NaHCO_3$ to pH8. The resulting solid was collected and dried in vacuo to compound 53 as a light yellow solid (17.0 mg, yield: 18%). LCMS: m/z=398.2 $(M+H)^+$. $^1H$ NMR (400 MHz, DMSO) δ 9.72 (s, 1H), 7.69-7.50 (m, 3H), 7.34-7.16 (m, 4H), 6.86 (d, J=8.3 Hz, 1H), 5.09 (s, 2H), 3.21-3.09 (m, 4H), 2.90-2.77 (m, 4H).

Example 54—Synthesis of Compound 054

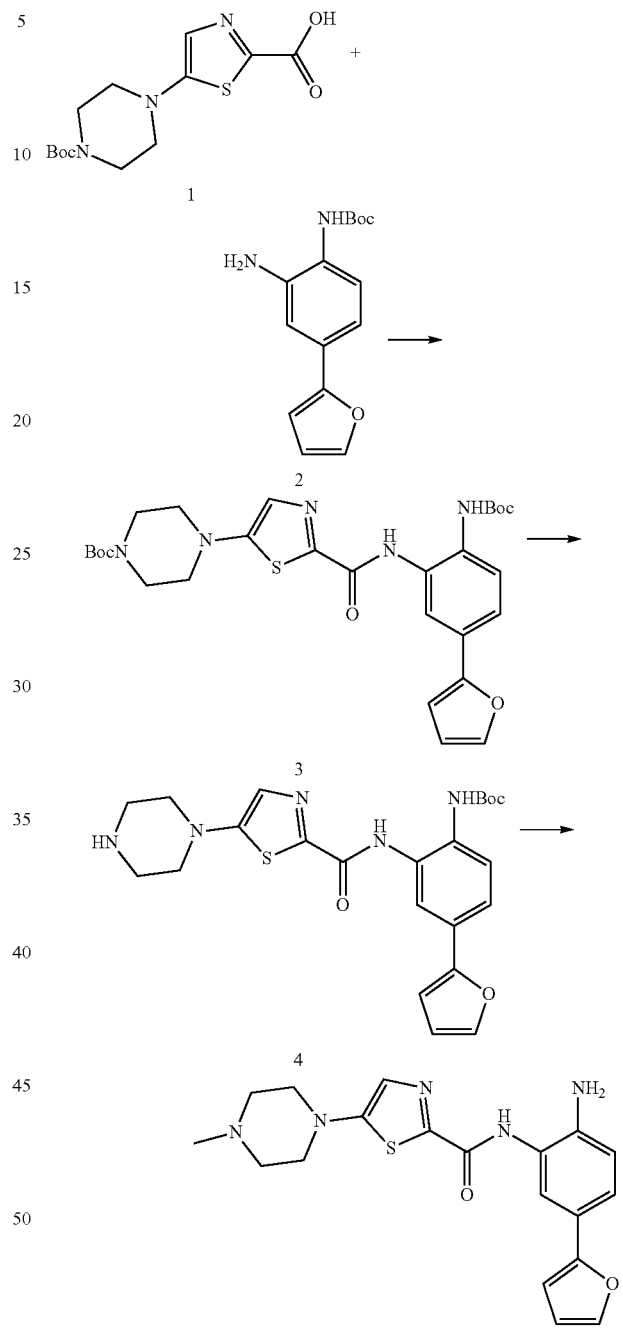

Step 1:

A mixture of 5-(4-(tert-butoxycarbonyl)piperazin-1-yl) thiazole-2-carboxylic acid (153 mg, 0.49 mmol) and HATU (204 mg, 0.54 mmol) in DMF (2 mL) was stirred at room temperature for 15 mins. Then DIEA (188 mg, 1.46 mmol) and tert-butyl 2-amino-4-(furan-2-yl)phenylcarbamate (147 mg, 0.54 mmol) were added. It was stirred at room temperature for 1 h. Then water was added. The resulting solid was collected by filtration and dried in vacuo to give compound.

Step 2:

To a mixture of above tert-butyl 4-(2-(2-(tert-butoxycarbonylamino)-5-(furan-2-yl)phenyl carbamoyl)thiazol-5-yl)piperazine-1-carboxylate in DCM (2 mL) was added TFA (2 mL) at 0° C. It was stirred at 0° C. to room temperature for 2 h. It was concentrated in vacuo and the residue was washed with aqueous saturated NaHCO₃ solution to give product (160 mg) as a white solid.

Step 3:

It was stirred at 0° C. to give a complete reaction. It was concentrated in vacuo and the residue was purified by Prep-HPLC to give compound 054 as a yellow solid. LCMS: m/z=384.1 (M+H)⁺. ¹H NMR (400 MHz, DMSO) δ 9.67 (s, 1H), 7.63 (d, J=17.9 Hz, 2H), 7.30 (d, J=6.8 Hz, 1H), 7.26 (s, 1H), 6.82 (d, J=8.7 Hz, 1H), 6.60 (d, J=3.3 Hz, 1H), 6.51 (s, 1H), 5.13 (s, 2H), 3.28-3.23 (m, 4H), 2.46 (d, J=5.1 Hz, 4H), 2.23 (s, 3H).

Example 55—Synthesis of Compound 055

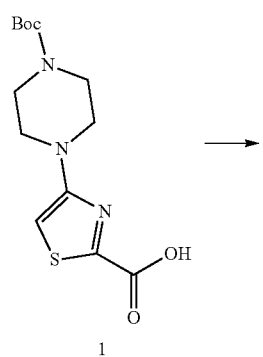

1

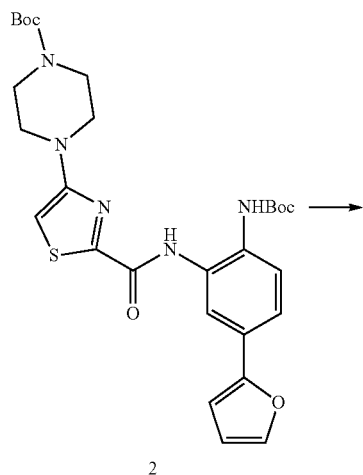

2

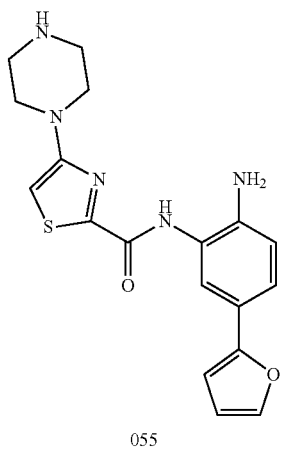

055

Step 1:

A mixture of 4-(4-(tert-butoxycarbonyl) piperazin-1-yl) thiazole-2-carboxylic acid (48 mg, 0.15 mmol), tert-butyl 2-amino-4-(furan-2-yl) phenylcarbamate (42 mg, 0.15 mmol) and EDCl (88 mg, 0.46 mmol) in Py (3 ml) was stirred at room temperature for overnight. It was purified by column chromatography (DCM:EA=5:1). Light yellow solid was afforded (50 mg, 57% yield).

Step 2:

To a solution of tert-butyl 4-(2-(2-(tert-butoxycarbonylamino)-5-(furan-2-yl) phenylcarbamoyl) thiazol-4-yl) piperazine-1-carboxylate (50 mg, 0.09 mmol) in DCM (3 ml) was added HCl/1,4-dioxane (1 ml). The mixture was stirred at room temperature for 2 h. It was concentrated and washed by Et₂O. Yellow solid was afforded as compound 055. (16 mg, HCl salt, lot SP-0017550-050). LCMS: m/z=370.1 (M+H)⁺. ¹H NMR (400 MHz, DMSO) δ 10.23 (s, 1H), 9.24 (s, 2H), 7.70 (t, J=13.0 Hz, 2H), 7.50 (d, J=8.0 Hz, 1H), 7.13 (s, 1H), 6.88 (d, J=14.2 Hz, 1H), 6.77 (d, J=28.9 Hz, 1H), 6.57 (d, J=1.8 Hz, 1H), 3.63 (s, 4H), 3.24 (s, 4H).

Example 56—Synthesis of Compound 056

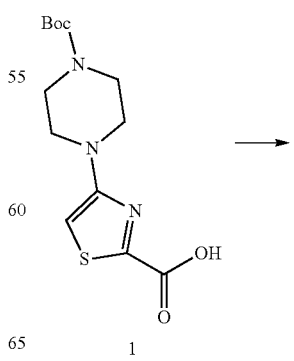

1

-continued

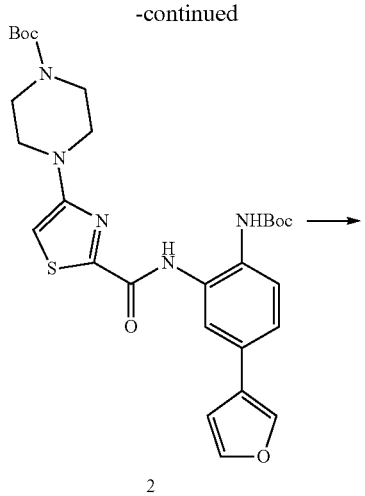

2

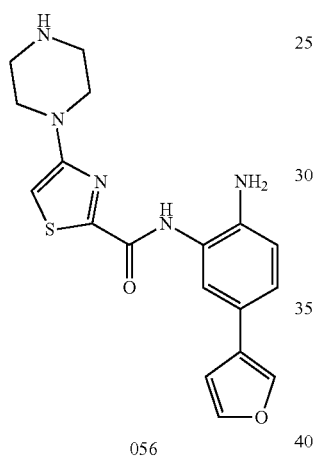

056

Step 1:

A mixture of 4-(4-(tert-butoxycarbonyl) piperazin-1-yl) thiazole-2-carboxylic acid (59 mg, 0.19 mmol), tert-butyl 2-amino-4-(furan-3-yl) phenylcarbamate (52 mg, 0.19 mmol) and EDCl (109 mg, 0.57 mmol) in Py (3 ml) was stirred at room temperature for overnight. It was purified by column chromatography (DCM:EA=5:1). Light yellow solid was afforded (25 mg, 23% yield).

Step 2:

To a solution of tert-butyl 4-(2-(2-(tert-butoxycarbonylamino)-5-(furan-3-yl) phenylcarbamoyl) thiazol-4-yl) piperazine-1-carboxylate (25 mg, 0.04 mmol) in DCM (2 ml) was added TFA (1 ml). The mixture was stirred at room temperature for 2 h. It was concentrated and washed by Et$_2$O. Yellow solid was afforded as Compound 056. (20 mg, TFA salt, lot SP-0018270-093). LCMS: m/z=370.1 (M+H)$^+$. $^1$H NMR (400 MHz, DMSO) δ 9.64 (s, 1H), 9.37 (s, 2H), 8.28 (s, 1H), 7.87-7.76 (m, 2H), 7.60 (dd, J=8.4, 1.7 Hz, 1H), 7.48 (s, 1H), 6.93 (s, 1H), 6.87-6.78 (m, 1H), 4.39 (s, 2H), 3.93 (d, J=57.2 Hz, 4H), 3.58 (s, 1H), 3.27 (s, 3H).

Example 57—Synthesis of Compound 057

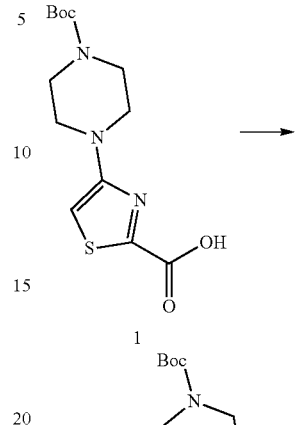

1

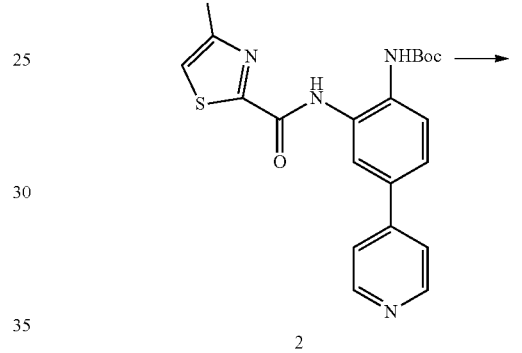

057

Step 1:

A mixture of 4-(4-(tert-butoxycarbonyl) piperazin-1-yl) thiazole-2-carboxylic acid (45 mg, 0.14 mmol), tert-butyl 2-amino-4-(pyridin-4-yl) phenylcarbamate (83 mg, 0.14 mmol) and EDCl (83 mg, 0.43 mmol) in Py (3 ml) was stirred at room temperature for overnight. It was purified by column chromatography (DCM:EA=1:1). Green solid was afforded (40 mg, 48% yield).

Step 2:

To a solution of tert-butyl 4-(2-(2-(tert-butoxycarbonylamino)-5-(pyridin-4-yl) phenylcarbamoyl) thiazol-4-yl) piperazine-1-carboxylate (40 mg, 0.07 mmol) in DCM (2 ml) was added HCl/1,4-dioxane (1 ml). The mixture was stirred at room temperature for 2 h. It was concentrated and washed by Et$_2$O. Yellow solid was afforded as compound 057. (20 mg, HCl salt, lot SP-0017550-067). LCMS: m/z=381.0 (M+H)$^+$. $^1$H NMR (400 MHz, DMSO) δ 10.02 (s, 1H), 9.48 (s, 2H), 8.71 (d, J=6.4 Hz, 2H), 8.19 (d, J=6.5 Hz, 2H), 7.97 (d, J=1.9 Hz, 1H), 7.87-7.79 (m, 1H), 6.94 (d, J=8.6 Hz, 1H), 6.88 (s, 1H), 3.63 (s, 4H), 3.23 (s, 4H).

Example 58—Synthesis of Compound 058

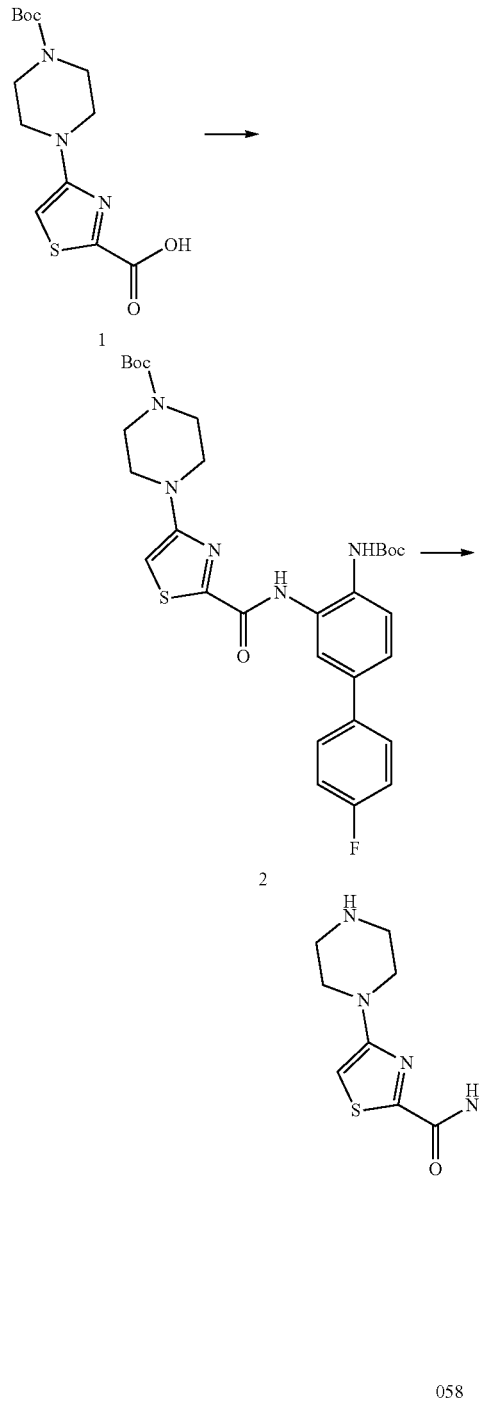

Step 1:

A mixture of 4-(4-(tert-butoxycarbonyl) piperazin-1-yl) thiazole-2-carboxylic acid (45 mg, 0.14 mmol), tert-butyl 3-amino-4'-fluorobiphenyl-4-ylcarbamate (86 mg, 0.14 mmol) and EDCl (83 mg, 0.43 mmol) in Py (3 ml) was stirred at room temperature for overnight. It was extracted by EA and purified by column chromatography (DCM:EA=5:1). Yellow solid was afforded (30 mg, 35% yield).

Step 2:

To a solution of tert-butyl 4-(2-(4-(tert-butoxycarbonylamino)-4'-fluorobiphenyl-3-ylcarbamoyl) thiazol-4-yl) piperazine-1-carboxylate (30 mg, 0.05 mmol) in DCM (2 ml) was added HCl/1,4-dioxane (1 ml). The mixture was stirred at room temperature for 2 h. It was concentrated and washed by Et$_2$O. Yellow solid was afforded as compound 058. (22 mg, HCl salt, lot SP-0017550-058). LCMS: m/z=398.1 (M+H)$^+$. $^1$H NMR (400 MHz, DMSO) δ 10.37 (s, 1H), 9.30 (s, 2H), 7.71 (d, J=31.3 Hz, 3H), 7.51 (s, 1H), 7.29 (t, J=8.8 Hz, 3H), 6.91 (s, 1H), 3.60 (d, J=30.0 Hz, 4H), 3.24 (s, 4H).

Example 59—Synthesis of Compound 059

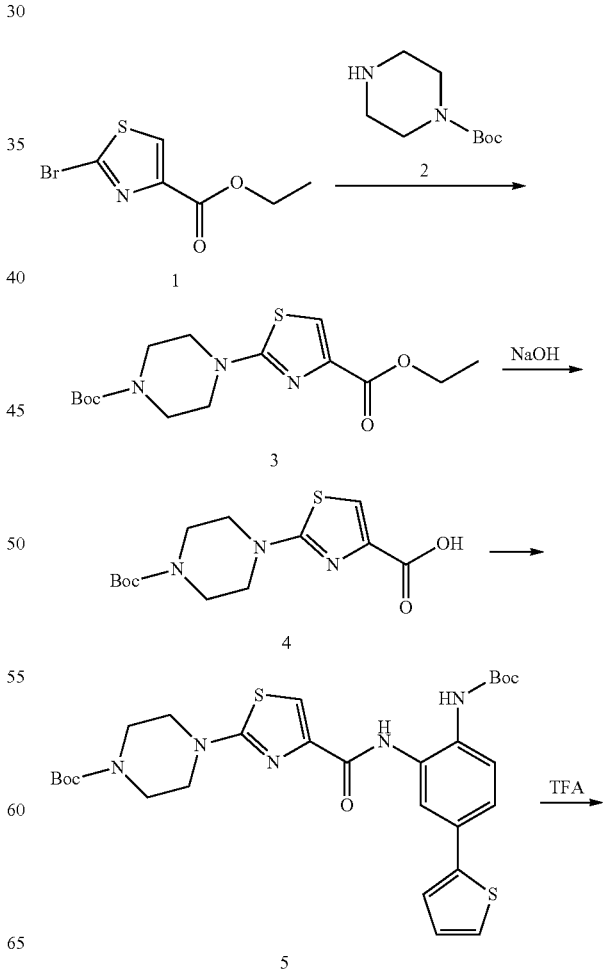

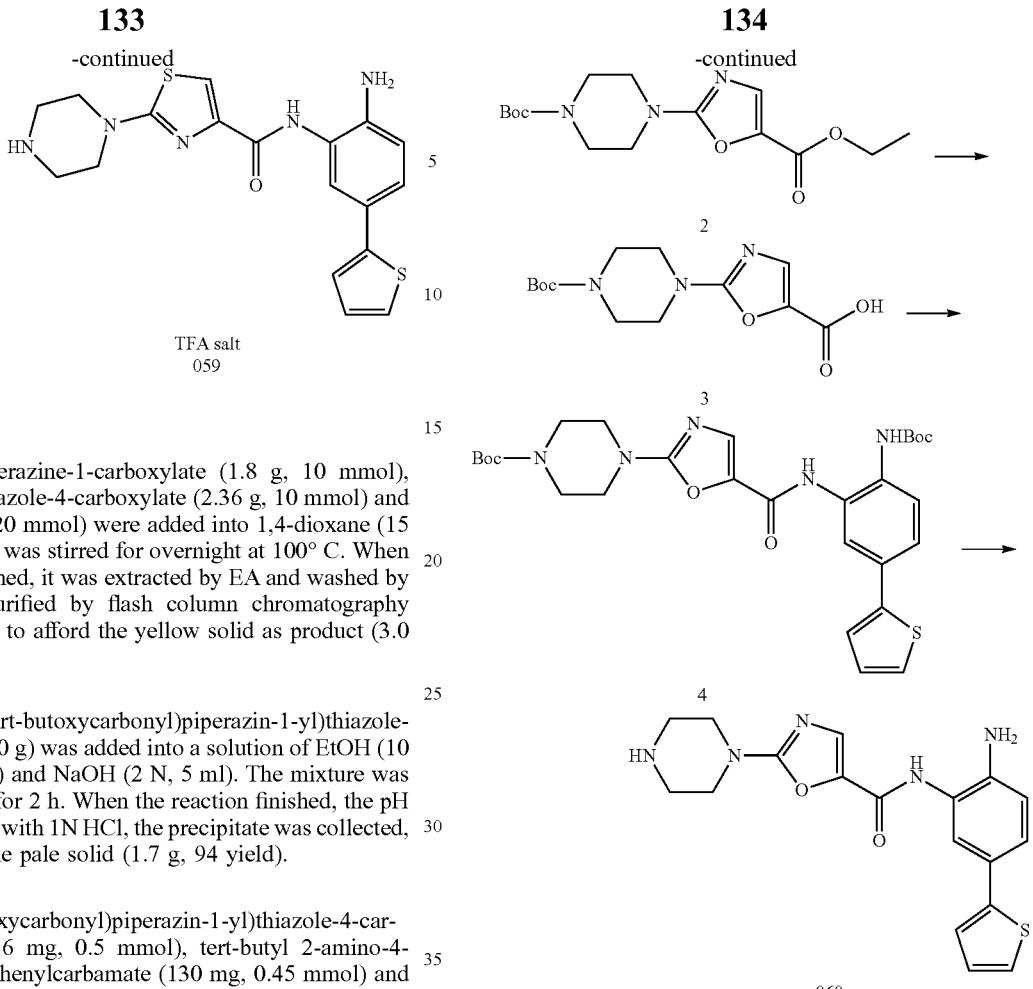

Step 1:

Tert-butyl piperazine-1-carboxylate (1.8 g, 10 mmol), ethyl 2-bromothiazole-4-carboxylate (2.36 g, 10 mmol) and DIPEA (2.02 g, 20 mmol) were added into 1,4-dioxane (15 ml). The mixture was stirred for overnight at 100° C. When the reaction finished, it was extracted by EA and washed by brine. It was purified by flash column chromatography (PE/EA=5:1-3:1) to afford the yellow solid as product (3.0 g, 88%).

Step 2:

Ethyl 2-(4-(tert-butoxycarbonyl)piperazin-1-yl)thiazole-4-carboxylate (2.0 g) was added into a solution of EtOH (10 ml), THF (10 ml) and NaOH (2 N, 5 ml). The mixture was stirred at 60° C. for 2 h. When the reaction finished, the pH was adjusted to 1 with 1N HCl, the precipitate was collected, dried to afford the pale solid (1.7 g, 94 yield).

Step 3:

2-(4-(tert-butoxycarbonyl)piperazin-1-yl)thiazole-4-carboxylic acid (156 mg, 0.5 mmol), tert-butyl 2-amino-4-(thiophen-2-yl) phenylcarbamate (130 mg, 0.45 mmol) and EDCl (191 mg, 1 mmol) were added into Py (5 ml). The mixture was stirred at room temperature for overnight. When the reaction finished, it was concentrated and water was added. The yellow solid was collected as product (210 mg, 80% yield).

Step 4:

Tert-butyl 4-(4-(2-(tert-butoxycarbonylamino)-5-(thiophen-2-yl)phenylcarbamoyl)thiazol-2-yl)piperazine-1-carboxylate (210 mg, 0.36 mmol) was dissolved into DCM (5 ml). Then TFA (1 ml) was added. The mixture was stirred at room temperature for 2 h. When the reaction finished, it was concentrated and ether was added to afford compound 059 as a yellow solid product (150 mg, TFA salt, Lots SP-008851-024). LCMS: m/z=386.5 (M+H)+. 1H NMR (400 MHz, DMSO) δ 9.72 (s, 1H), 8.47 (s, 1H), 7.70 (J=8.0 Hz, 1H), 7.54 (s, 1H), 7.40 (d, J=8.0 Hz, 1H), 7.13 (m, 3H), 6.99 (dd, J=8.8 Hz, 1H), 6.67 (d, J=8.8 Hz, 1H), 3.43 (m, 4H), 2.81 (m, 4H).

Example 60—Synthesis of Compound 060

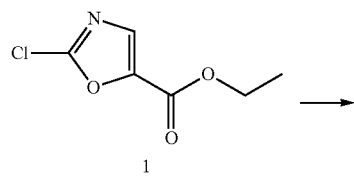

Step 1:

Tert-butyl piperazine-1-carboxylate (744 mg, 4 mmol), ethyl 2-chlorooxazole-5-carboxylate (700 mg, 4 mmol) and DIPEA (1032 mg, 8 mmol) were added into 1,4-dioxane (15 ml). The mixture was stirred for 2 h at 100° C. When the reaction finished, it was cooled and water was added. The precipitate was collected to afford the yellow solid as product (1.45 g, crude).

Step 2:

Ethyl 2-(4-(tert-butoxycarbonyl)piperazin-1-yl)oxazole-5-carboxylate (1.45 g, crude) was added into a solution of EtOH (5 ml), THF (5 ml) and NaOH (2 N, 5 ml). The mixture was stirred at 60° C. for 2 h. When the reaction finished, the pH was adjusted to 1. The solid was collected to afford the pale solid. (1.3 g, 91% yield, 2 steps).

Step 3:

2-(4-(tert-butoxycarbonyl)piperazin-1-yl)oxazole-5-carboxylic acid (300 mg, 1 mmol), tert-butyl 2-amino-4-(thiophen-2-yl) phenylcarbamate (261 mg, 0.9 mmol) and EDCl (382 mg, 2 mmol) were added into Py (8 ml). The mixture was stirred at room temperature for overnight. When the reaction finished, it was concentrated and washed with water. The pale yellow solid was collected as product (600 mg, 100% yield).

Step 4:

Tert-butyl 4-(5-(2-(tert-butoxycarbonylamino)-5-(thiophen-2-yl)phenylcarbamoyl)oxazol-2-yl)piperazine-1-carboxylate (362 mg, crude) was dissolved into DCM (5 ml). Then TFA (2 ml) was added. The mixture was stirred at room temperature for 2 h. When the reaction finished, it was adjusted to pH=10 and extracted by EA. It was concentrated and washed by 5 ml EA to afford pure compound 060 as a white solid product (78 mg, 38% yield, Lots SP-0017054-174). LCMS: m/z=369.4 (M+H)⁺. ¹H NMR (400 MHz, DMSO) δ 9.42 (s, 1H), 7.62 (s, 1H), 7.44-7.33 (m, 2H), 7.27 (dd, J=19.5, 5.6 Hz, 2H), 7.12-6.98 (m, 1H), 6.80 (d, J=8.4 Hz, 1H), 5.14 (s, 2H), 5.14 (s, 2H), 3.48 (s, 4H), 3.48 (s, 4H), 2.78 (s, 4H).

Example 61—Synthesis of Compound 061

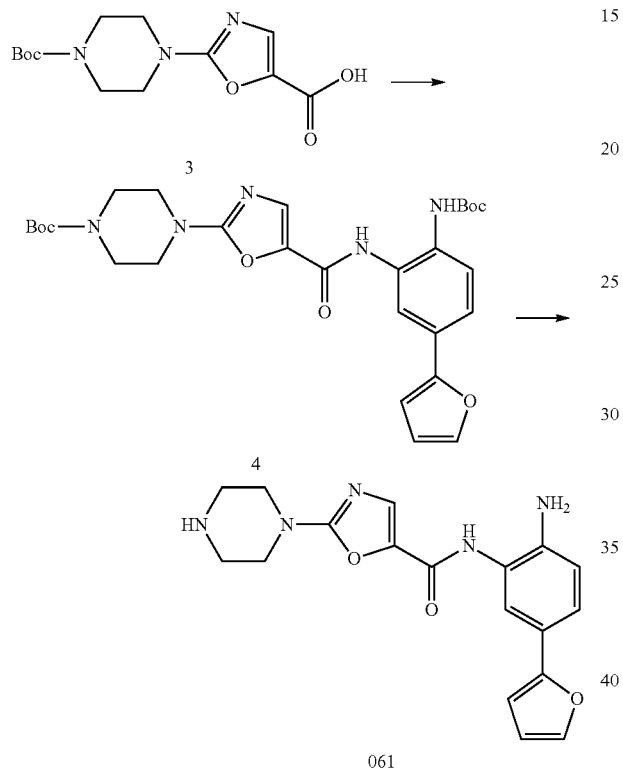

Step 1:
2-(4-(tert-butoxycarbonyl)piperazin-1-yl)oxazole-5-carboxylic acid (205 mg, 0.69 mmol), tert-butyl 2-amino-4-(furan-2-yl)phenylcarbamate (170 mg, 0.621 mmol) and EDCl (267 mg, 1.4 mmol) were added into Py (8 ml). The mixture was stirred at room temperature for overnight. When the reaction finished, it was concentrated and washed with water. The pale yellow solid was collected as product (360 mg, 100% yield).

Step 2:
Tert-butyl 4-(5-(2-(tert-butoxycarbonylamino)-5-(furan-2-yl)phenylcarbamoyl)oxazol-2-yl)piperazine-1-carboxylate (360 mg, crude) was dissolved into DCM (5 ml). Then TFA (2 ml) was added. The mixture was stirred at room temperature for 2 h. When the reaction finished, it was adjusted to pH=10 and extracted with EA. It was concentrated and washed with 5 ml EA to afford pure compound 061 as a white solid product (109 mg, 53% yield, Lots SP-0017054-180). LCMS: m/z=354.4 (M+H)⁺. ¹H NMR (400 MHz, DMSO) δ 9.45 (s, 1H), 7.74-7.54 (m, 2H), 7.45 (d, J=1.9 Hz, 1H), 7.32 (dd, J=8.3, 2.0 Hz, 1H), 6.80 (d, J=8.4 Hz, 1H), 6.61 (d, J=3.3 Hz, 1H), 6.49 (dt, J=22.4, 11.2 Hz, 1H), 5.11 (d, J=30.3 Hz, 2H), 3.55-3.43 (m, 4H), 2.87-2.71 (m, 4H).

Example 62—Synthesis of Compound 062

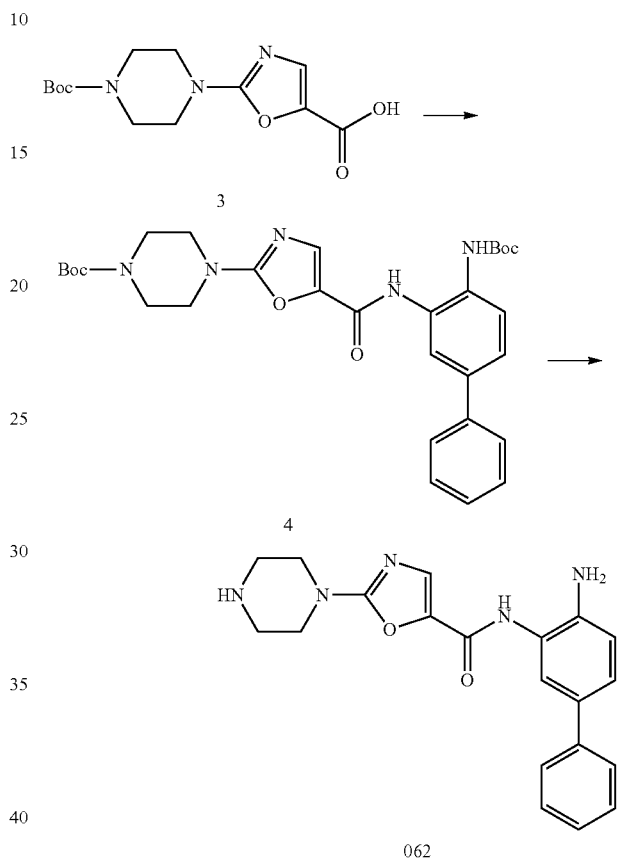

Step 1:
2-(4-(tert-butoxycarbonyl)piperazin-1-yl)oxazole-5-carboxylic acid (205 mg, 0.69 mmol), tert-butyl 3-aminobiphenyl-4-ylcarbamate (176 mg, 0.62 mmol) and EDCl (267 mg, 1.4 mmol) were added into Py (8 ml). The mixture was stirred at room temperature for overnight. When the reaction finished, it was concentrated and washed with water. The pale yellow solid was collected as product (893 mg, crude).

Step 2:
Tert-butyl 4-(5-(4-(tert-butoxycarbonylamino)biphenyl-3-ylcarbamoyl)oxazol-2-yl)piperazine-1-carboxylate (362 mg, crude) was dissolved into DCM (5 ml). Then TFA (2 ml) was added. The mixture was stirred at room temperature for 2 h. When the reaction finished, it was adjusted to pH=10 and extracted with EA. It was concentrated and washed with 5 ml EA to afford pure compound 062 as a white solid product (170 mg, 68% yield, Lots SP-0017054-177). LCMS: m/z=364.4 (M+H)⁺. ¹H NMR (400 MHz, DMSO) δ 9.45 (s, 1H), 7.70-7.16 (m, 9H), 6.86 (d, J=8.1 Hz, 1H), 5.09 (s, 2H), 3.46 (d, J=28.8 Hz, 4H), 2.79 (s, 4H).

Example 63—Synthesis of Compound 063

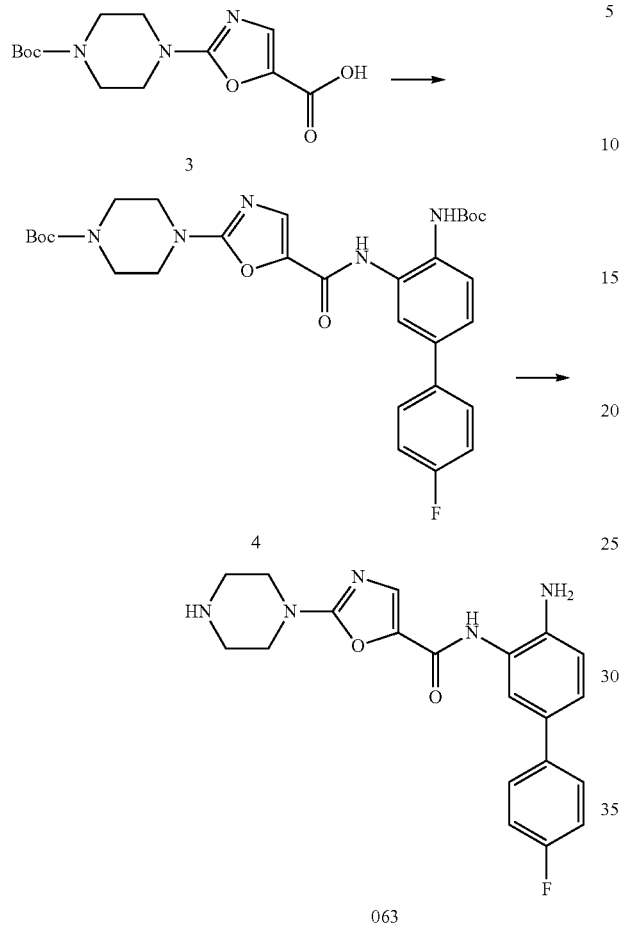

Step 1:

2-(4-(tert-butoxycarbonyl)piperazin-1-yl)oxazole-5-carboxylic acid (155 mg, 0.52 mmol), tert-butyl 3-amino-4'-fluorobiphenyl-4-ylcarbamate (141 mg, 0.47 mmol) and HATU (300 mg, 0.78 mmol), DIPEA (134 mg, 1.04 mmol) were added into THF (8 ml). The mixture was stirred at room temperature for overnight. When the reaction finished, it was purified on silica gel column to afford the product (202 mg, 96%).

Step 2:

Tert-butyl 4-(5-(4-(tert-butoxycarbonylamino)-4'-fluorobiphenyl-3-ylcarbamoyl)oxazol-2-yl)piperazine-1-carboxylate (202 mg, 0.35 mmol) was dissolved into DCM (5 ml). Then TFA (2 ml) was added. The mixture was stirred at room temperature for 2 h. When the reaction finished, it was adjusted to pH=10 and extracted with EA to afford pure compound 063 as a white solid product (123 mg, 92% yield, Lots SP-0017054-188). LCMS: m/z=382.4 (M+H)+. 1H NMR (400 MHz, DMSO) δ 9.45 (s, 1H), 7.64 (s, 1H), 7.57 (dd, J=8.6, 5.5 Hz, 2H), 7.42 (d, J=1.7 Hz, 1H), 7.29 (dd, J=8.3, 2.0 Hz, 1H), 7.21 (t, J=8.8 Hz, 2H), 6.85 (d, J=8.3 Hz, 1H), 5.09 (s, 2H), 3.53-3.43 (m, 4H), 2.86-2.73 (m, 4H).

Example 64—Synthesis of Compound 064

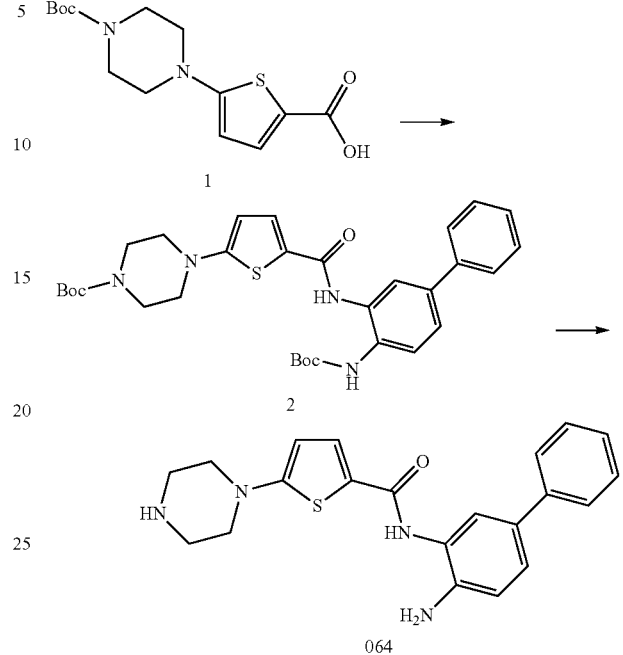

Step 1:

A mixture of 5-(4-(tert-butoxycarbonyl) piperazin-1-yl) thiophene-2-carboxylic acid (94 mg, 0.3 mmol), tert-butyl 3-aminobiphenyl-4-ylcarbamate (85 mg, 0.3 mmol) and EDCl (173 mg, 0.9 mmol) in Py (3 ml) was stirred at room temperature for overnight. It was extracted with EA and purified by column chromatography (PE:EA=2:1). Green solid was afforded (140 mg, 61%).

Step 2:

To a solution of tert-butyl 4-(5-(4-(tert-butoxycarbonylamino)biphenyl-3-ylcarbamoyl)thiophen-2-yl)piperazine-1-carboxylate (120 mg, 0.21 mmol) in DCM (2 ml) was added TFA (2 ml). The mixture was stirred at room temperature for 2 h. It was concentrated and washed with Et$_2$O. Yellow solid was afforded as compound 064. (130 mg, TFA salt, lot SP-0017550-024). LCMS: m/z=379.1 (M+H)+. 1H NMR (400 MHz, DMSO) δ 9.64 (s, 1H), 8.91 (s, 2H), 7.80 (d, J=4.2 Hz, 1H), 7.56 (d, J=7.3 Hz, 2H), 7.49 (d, J=1.9 Hz, 1H), 7.44-7.33 (m, 3H), 7.27 (t, J=7.4 Hz, 1H), 6.94 (d, J=8.3 Hz, 1H), 6.36 (d, J=4.2 Hz, 1H), 3.42 (d, J=5.7 Hz, 4H), 3.28 (s, 4H).

Example 65—Synthesis of Compound 065

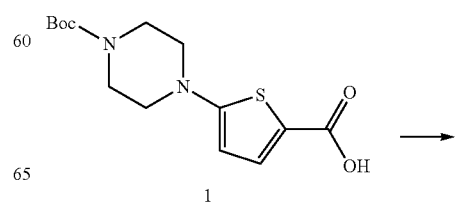

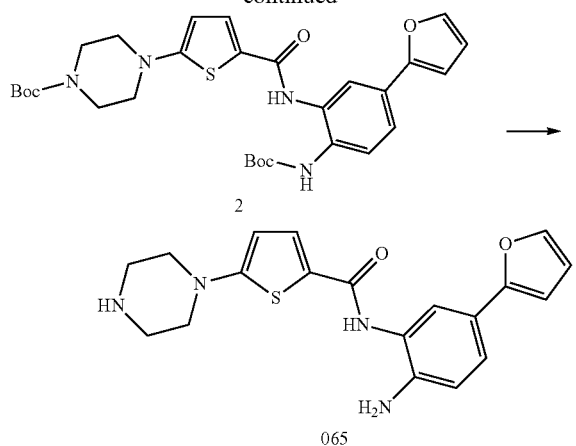

Step 1:

A mixture of 5-(4-(tert-butoxycarbonyl) piperazin-1-yl) thiophene-2-carboxylic acid (66 mg, 0.2 mmol), tert-butyl 2-amino-4-(furan-2-yl) phenylcarbamate (58 mg, 0.2 mmol) and EDCl (121 mg, 0.6 mmol) in Py (2 ml) was stirred at room temperature for overnight. It was extracted with EA and purified by column chromatography (PE:EA=2:1). White solid was afforded (50 mg, 42%).

Step 2:

To a solution of tert-butyl 4-(5-(2-(tert-butoxycarbonylamino)-5-(furan-2-yl) phenylcarbamoyl) thiophen-2-yl) piperazine-1-carboxylate (50 mg, 0.09 mmol) in DCM (2 ml) was added TFA (1 ml). The mixture was stirred at room temperature for 2 h. It was concentrated and washed with Et₂O. White solid was afforded as compound 065. (60 mg, TFA salt, lot SP-0017550-034). LCMS: m/z=369.1 (M+H)⁺. ¹H NMR (400 MHz, DMSO) δ 9.51 (s, 1H), 8.94 (s, 2H), 7.77 (d, J=4.2 Hz, 1H), 7.61 (s, 1H), 7.47 (d, J=1.9 Hz, 1H), 7.32 (dd, J=8.3, 1.9 Hz, 1H), 6.81 (d, J=8.4 Hz, 1H), 6.61 (d, J=3.2 Hz, 1H), 6.51 (dd, J=3.2, 1.8 Hz, 1H), 6.35 (d, J=4.2 Hz, 1H), 3.42 (d, J=5.4 Hz, 4H), 3.27 (s, 4H).

Example 66—Synthesis of Compound 066

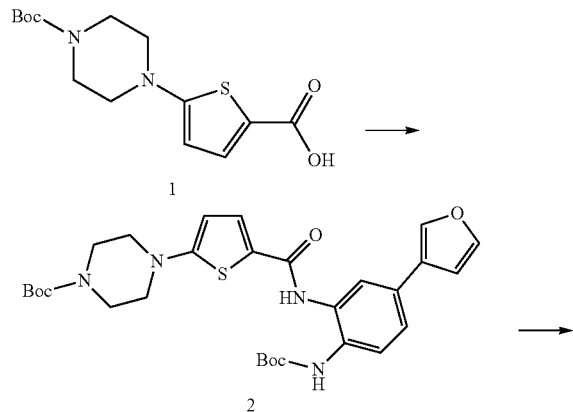

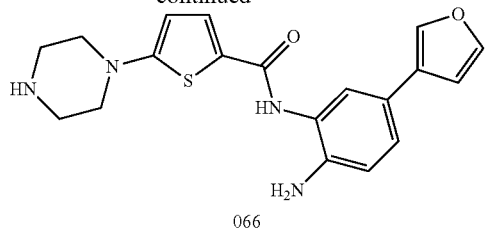

Step 1:

A mixture of 5-(4-(tert-butoxycarbonyl) piperazin-1-yl) thiophene-2-carboxylic acid (78 mg, 0.25 mmol), tert-butyl 2-amino-4-(furan-3-yl) phenylcarbamate (69 mg, 0.25 mmol) and EDCl (144 mg, 0.75 mmol) in Py (2 ml) was stirred at room temperature for overnight. It was extracted with EA and purified by column chromatography (PE:EA=2:1). White solid was afforded (110 mg, 77%).

Step 2:

To a solution of tert-butyl 4-(5-(2-(tert-butoxycarbonylamino)-5-(furan-3-yl) phenylcarbamoyl) thiophen-2-yl) piperazine-1-carboxylate (110 mg, 0.19 mmol) in DCM (2 ml) was added TFA (1 ml). The mixture was stirred at room temperature for 2 h. It was concentrated and washed with Et₂O. White solid was afforded as compound 066. (110 mg, TFA salt, lot SP-0017550-031). LCMS: m/z=369.1 (M+H)⁺. ¹H NMR (400 MHz, DMSO) δ 9.63 (s, 1H), 8.89 (s, 2H), 8.00 (s, 1H), 7.78 (d, J=4.1 Hz, 1H), 7.68 (t, J=1.6 Hz, 1H), 7.37 (d, J=1.8 Hz, 1H), 7.28 (d, J=8.3 Hz, 1H), 6.92-6.78 (m, 2H), 6.35 (d, J=4.3 Hz, 1H), 3.41 (d, J=5.2 Hz, 4H), 3.28 (s, 4H).

Example 67—Synthesis of Compound 067

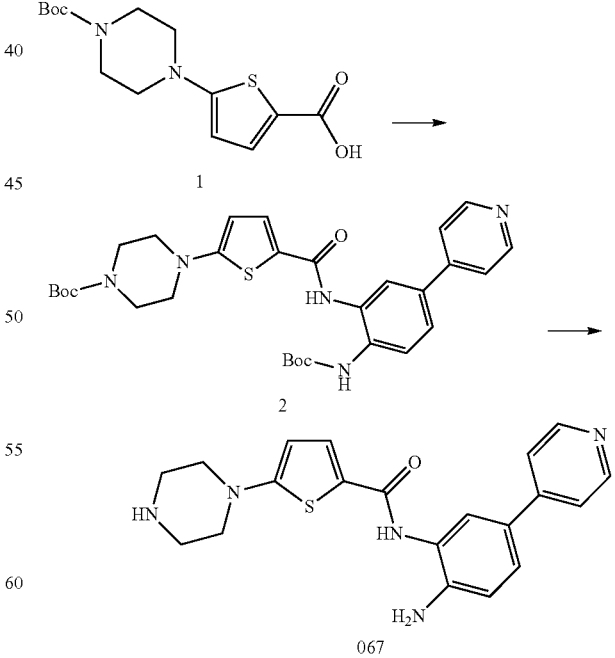

Step 1:

A mixture of 5-(4-(tert-butoxycarbonyl) piperazin-1-yl) thiophene-2-carboxylic acid (66 mg, 0.21 mmol), tert-butyl 2-amino-4-(pyridin-4-yl)phenylcarbamate (60 mg, 0.21 mmol) and EDCl (121 mg, 0.63 mmol) in Py (3 ml) was stirred at room temperature for overnight. It was extracted with EA and concentrated for next step (100 mg, crude).

Step 2:

To a solution of tert-butyl 4-(5-(2-(tert-butoxycarbonylamino)-5-(pyridin-4-yl) phenylcarbamoyl) thiophen-2-yl) piperazine-1-carboxylate (100 mg, 0.17 mmol) in DCM (2 ml) was added TFA (1 ml). The mixture was stirred at room temperature for 2 h. It was concentrated and purified by prep-HPLC (base method). White solid was afforded as compound 067. (30 mg, 65% yield, lot SP-0017550-039). LCMS: m/z=380.1 (M+H)⁺. ¹H NMR (400 MHz, DMSO) δ 9.40 (s, 1H), 8.50 (t, J=8.5 Hz, 2H), 7.75 (d, J=4.2 Hz, 1H), 7.63 (d, J=2.0 Hz, 1H), 7.58 (d, J=6.1 Hz, 2H), 7.48 (dd, J=8.3, 2.0 Hz, 1H), 6.88 (d, J=8.4 Hz, 1H), 6.19 (t, J=6.6 Hz, 1H), 5.32 (s, 2H), 3.15-3.07 (m, 4H), 2.87-2.77 (m, 4H).

Example 68—Synthesis of Compound 068

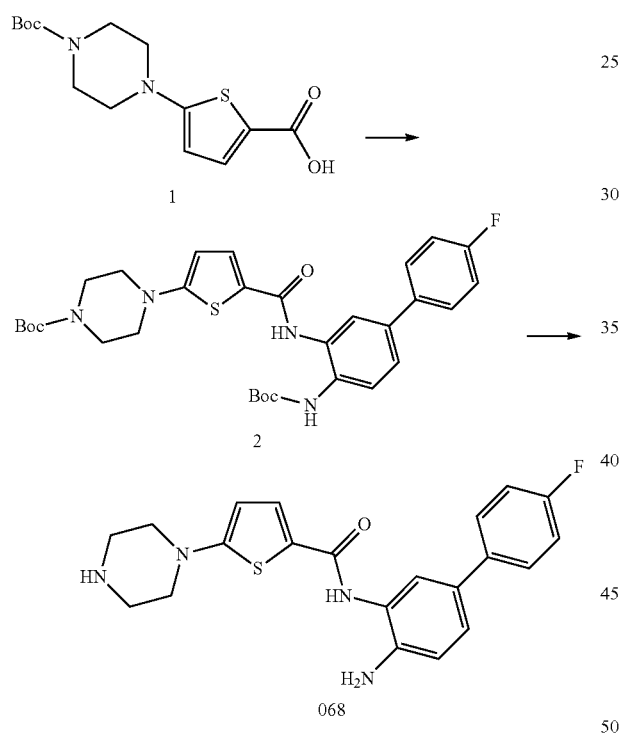

Step 1:

A mixture of 5-(4-(tert-butoxycarbonyl) piperazin-1-yl) thiophene-2-carboxylic acid (70 mg, 0.22 mmol), tert-butyl 3-amino-4'-fluorobiphenyl-4-ylcarbamate (68 mg, 0.22 mmol) and EDCl (129 mg, 0.67 mmol) in Py (3 ml) was stirred at room temperature for overnight. It was extracted with EA and purified by column chromatography (PE: EA=2:1). White solid was afforded (120 mg, 87% yield).

Step 2:

To a solution of tert-butyl 4-(5-(4-(tert-butoxycarbonylamino)-4'-fluorobiphenyl-3-ylcarbamoyl) thiophen-2-yl) piperazine-1-carboxylate (120 mg, 0.2 mmol) in DCM (4 ml) was added TFA (2 ml). The mixture was stirred at room temperature for 2 h. It was concentrated and washed with Et₂O. White solid was afforded as compound 068. (84 mg, TFA salt, lot SP-0017550-044). LCMS: m/z=397.1 (M+H)⁺.

¹H NMR (400 MHz, DMSO) δ 9.58 (s, 1H), 9.06 (s, 2H), 7.79 (d, J=4.0 Hz, 1H), 7.58 (dd, J=8.4, 5.5 Hz, 2H), 7.45 (s, 1H), 7.30 (d, J=6.6 Hz, 1H), 7.22 (t, J=8.8 Hz, 2H), 6.89 (d, J=8.3 Hz, 1H), 6.35 (d, J=4.1 Hz, 1H), 3.42 (d, J=4.9 Hz, 4H), 3.27 (s, 4H).

Example 69—Synthesis of Compound 069

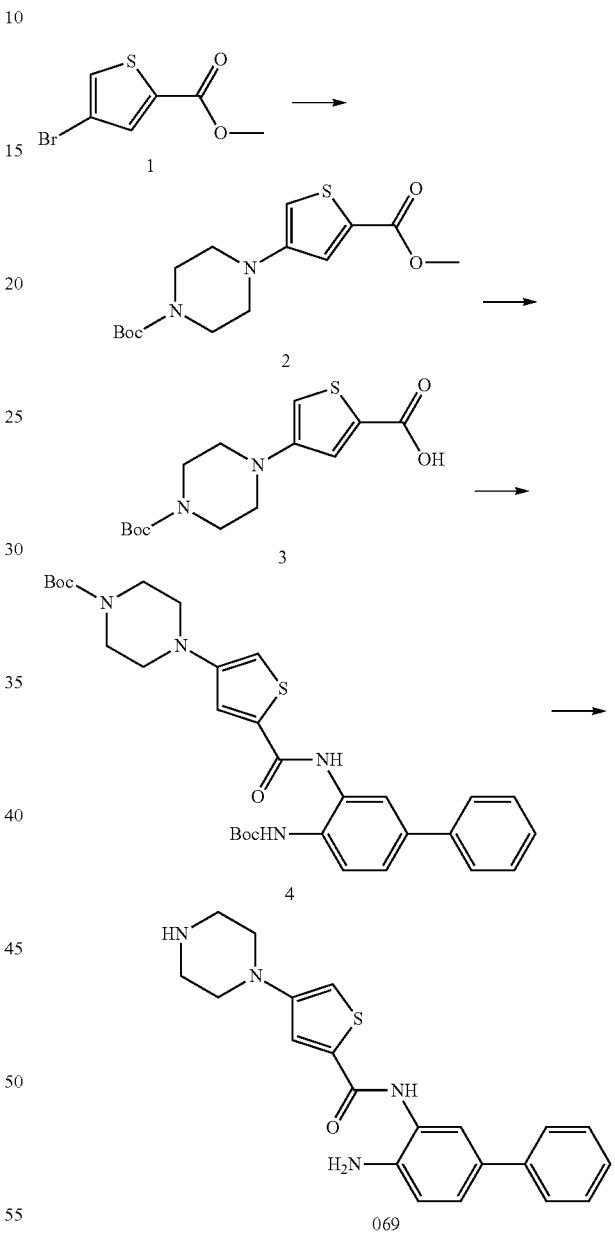

Step 1:

A mixture of methyl 4-bromothiophene-2-carboxylate (220 mg, 1 mmol), tert-butyl piperazine-1-carboxylate (372 mg, 2 mmol), Pd₂(dba)₃ (92 mg, 0.1 mmol), RuPhos (47 mg, 0.1 mmol) and Cs₂CO₃ (652 mg, 2 mmol) in PhMe (10 ml) was stirred at 95° C. for overnight under N₂ atmosphere. It was extracted with EA and purified by column chromatography (PE:EA=5:1). Yellow solid was afforded (360 mg, 92%).

Step 2:

To a solution of tert-butyl 4-(5-(methoxycarbonyl) thiophen-3-yl) piperazine-1-carboxylate (60 mg, 0.18 mmol) and LiOH H₂O (16 mg, 0.37 mmol) were added into MeOH (5 ml). The mixture was stirred at 60° C. for overnight. It was concentrated for next step (60 mg, crude).

Step 3:

A mixture of 4-(4-(tert-butoxycarbonyl) piperazin-1-yl) thiophene-2-carboxylic acid (60 mg, 0.19 mmol), tert-butyl 3-aminobiphenyl-4-ylcarbamate (55 mg, 0.19 mmol), EDCl (110 mg, 0.58 mmol) in Py (3 ml). The mixture was stirred at room temperature for overnight. It was extracted with EA and purified by column chromatography (PE:EA=2:1). Yellow solid was afforded (90 mg, 81%).

Step 4:

To a solution of tert-butyl 4-(5-(4-(tert-butoxycarbonylamino) biphenyl-3-ylcarbamoyl) thiophen-3-yl) piperazine-1-carboxylate (90 mg, 0.16 mmol) in DCM (2 ml) was added TFA (1 ml) dropwise. The mixture was stirred at room temperature for 2 h. It was concentrated and washed with Et₂O. Grey solid was afforded as compound 069 (67 mg, TFA salt, lot SP-0017550-084). LCMS: m/z=379.1 (M+H)⁺. ¹H NMR (400 MHz, DMSO) δ 9.78 (s, 1H), 8.84 (s, 2H), 7.91 (s, 1H), 7.56 (d, J=7.3 Hz, 2H), 7.50 (d, J=2.0 Hz, 1H), 7.45-7.33 (m, 3H), 7.26 (t, J=7.3 Hz, 1H), 6.93 (d, J=8.3 Hz, 1H), 6.86 (d, J=1.5 Hz, 1H), 3.29 (s, 8H).

Example 70—Synthesis of Compound 070

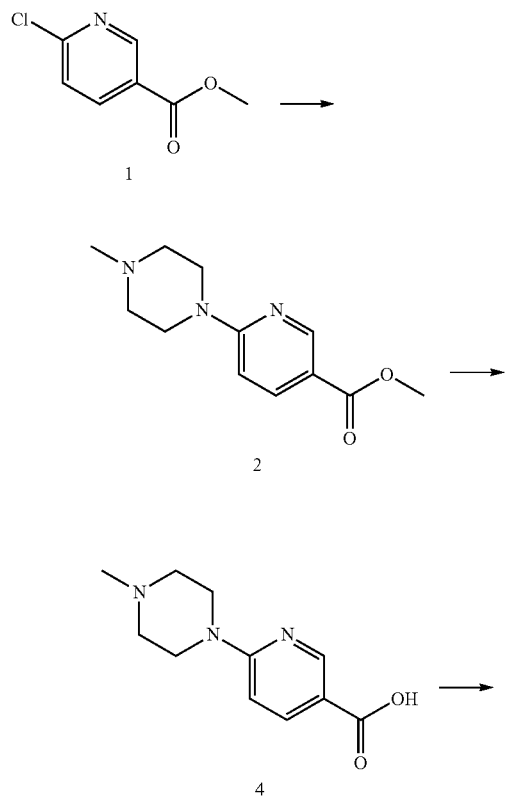

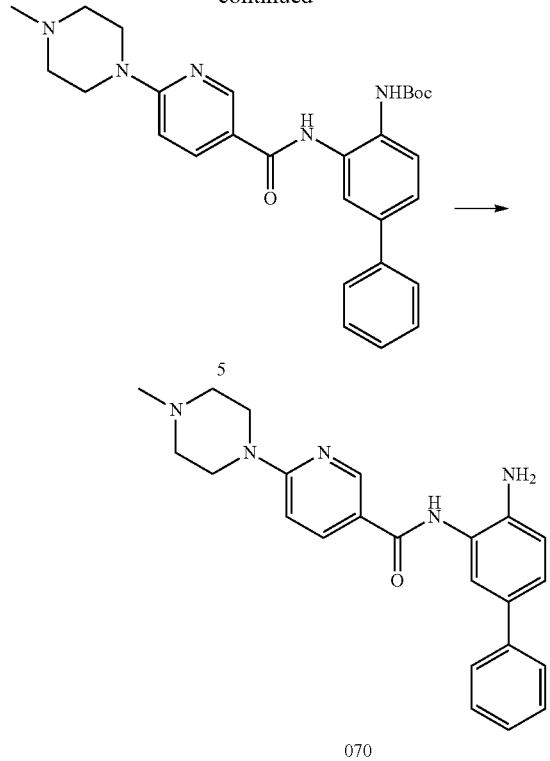

Step 1:

A mixture of methyl 6-chloronicotinate (500 mg, 2.92 mmol), 1-methylpiperazine (900 mg, 9 mmol), DIPEA (774 mg, 6 mmol) in 1,4-dioxane (15 mL) was stirred at 100° C. under N₂ atmosphere for overnight. The mixture was cool and EA (50 mL) and water (40 mL) were added, stirred for 30 min, the organic layer was separated, dried, concentrated to get a residue, which was washed with PE (30 mL) to afford as yellow solid (650 mg, 88%).

Step 2:

To a solution of methyl 6-(4-methylpiperazin-1-yl)nicotinate (650 mg, 2.76 mmol) in THF (10 ml) and EtOH (10 mL) was added 2M NaOH (1.5 mL, 3.04 mmol, 1.1 eq). The mixture was stirred at 60° C. for 3 h. When the reaction finished, it was concentrated to remove solvent, HCl (2 M) was added to adjust pH 5-7, concentrated to afford crude compound as a white solid (1.0 g, crude, contained some NaCl).

Step 3:

A mixture of 6-(4-methylpiperazin-1-yl)nicotinic acid (150 mg, crude), tert-butyl 3-aminobiphenyl-4-ylcarbamate (173 mg, 0.6 mmol) and EDCl (260 mg, 1.35 mmol) in pyridine (10 mL) was stirred at room temperature for overnight. The mixture was poured into water (20 mL), filtered to afford desired compound (300 mg, 89%) as a yellow solid.

Step 4:

A mixture of tert-butyl 3-(6-(4-methylpiperazin-1-yl) nicotinamido)biphenyl-4-ylcarbamate (300 mg, 0.616 mmol) and TFA (2 mL) in DCM (5 mL) was stirred at room temperature for 2 h.

The mixture was purified by Prep-HPLC to obtain compound 070 (70 mg, 27%, Lots SP-0016945-112) as a white solid. LCMS: m/z=388.5 (M+H)⁺. ¹H NMR (400 MHz, DMSO) δ 9.53 (s, 1H), 8.76 (s, 1H), 8.10 (d, J=8.7 Hz, 1H), 7.59-7.48 (m, 3H), 7.32 (ddd, J=35.3, 14.6, 7.2 Hz, 4H), 6.89 (dd, J=21.5, 8.6 Hz, 2H), 5.09 (s, 2H), 3.63 (s, 4H), 2.40 (s, 4H).

Example 71—Synthesis of Compound 071

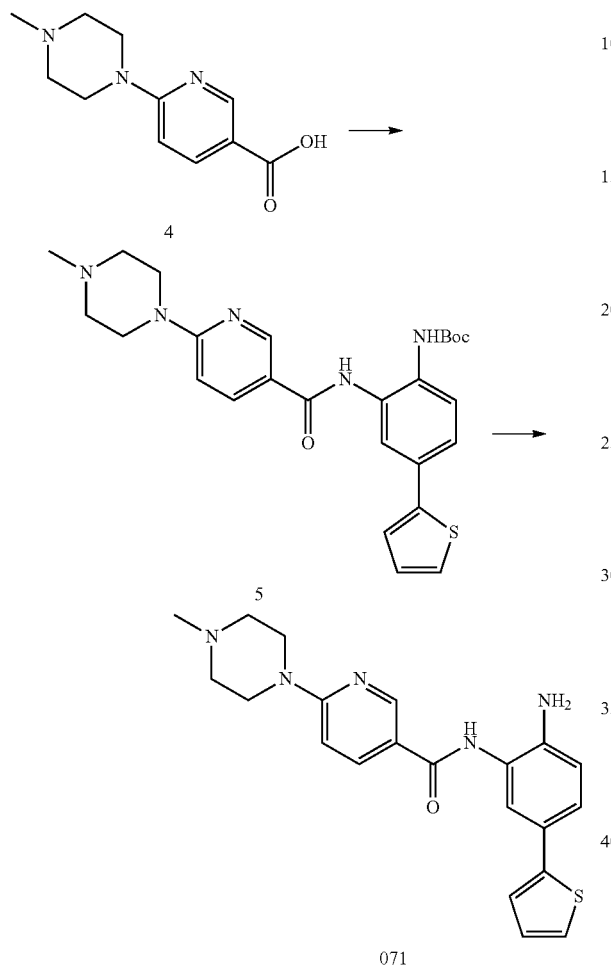

Step 1:

A mixture of 6-(4-methylpiperazin-1-yl)nicotinic acid (150 mg, crude), tert-butyl 2-amino-4-(thiophen-2-yl)phenylcarbamate (174 mg, 0.6 mmol) and EDCl (260 mg, 1.35 mmol) in pyridine (10 mL) was stirred at room temperature for overnight. The mixture was poured into water (20 mL), filtered to afford desired compound (280 mg, 84%) as a yellow solid.

Step 2:

A mixture of compound 4 (280 mg, 0.5 mmol) and TFA (3 mL) in DCM (3 mL) was stirred at room temperature for 1 h. The mixture was purified by Prep-HPLC to obtain compound 071 (170 mg, 65%, lot SP-0016945-116) as a yellow solid. LCMS: m/z=394.5 (M+H)+. 1H NMR (400 MHz, DMSO) δ 9.72 (d, J=12.1 Hz, 1H), 8.81 (t, J=3.6 Hz, 1H), 8.20 (dd, J=9.0, 2.2 Hz, 1H), 7.49 (d, J=1.8 Hz, 2H), 7.35 (ddd, J=24.5, 18.3, 4.2 Hz, 4H), 7.07 (dd, J=8.8, 4.9 Hz, 2H), 6.91 (d, J=8.4 Hz, 1H), 4.58 (d, J=13.3 Hz, 2H), 3.54 (d, J=11.4 Hz, 2H), 3.20 (dd, J=40.8, 28.4 Hz, 5H), 2.86 (s, 3H).

Example 72—Synthesis of Compound 072

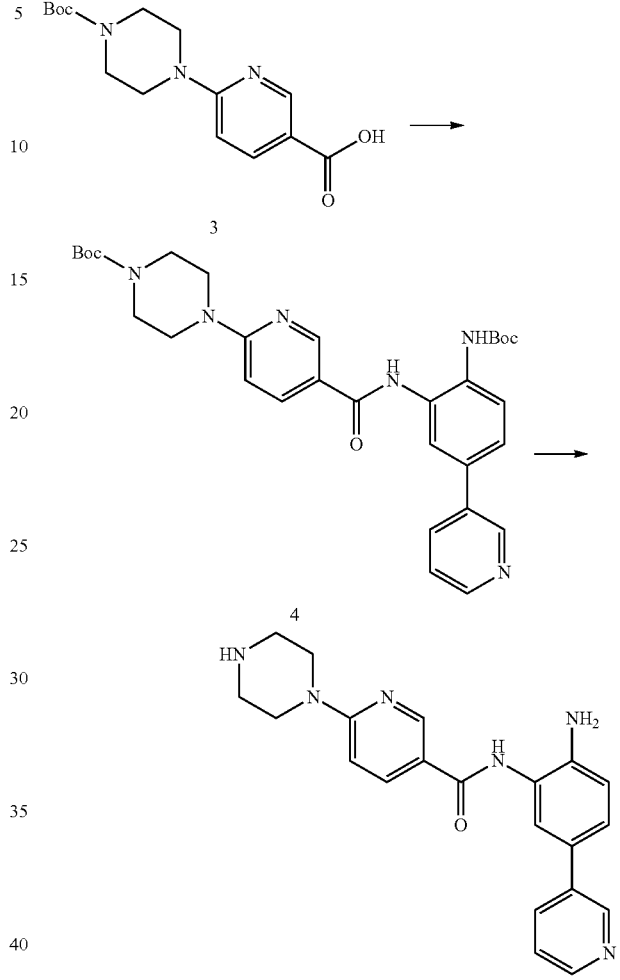

Step 1:

To a solution of 6-(4-(tert-butoxycarbonyl) piperazin-1-yl) nicotinic acid (123.7 mg, 0.40 mmol) and tert-butyl 2-amino-4-(pyridin-3-yl) phenylcarbamate (1, 3, 2-dioxaborolane) (114.5 mg, 0.40 mmol) in Py (2.5 ml) was added EDCl (230 mg, 1.20 mmol). The mixture was stirred at room temperature for overnight. The residue was purified by preparative TLC (silica gel, GF254 10-40 u, 25×25 cm) with PE/EA (2:1) to afford a yellow solid (165 mg, 72%).

Step 2:

To a solution of tert-butyl 4-(5-(2-(tert-butoxycarbonylamino)-5-(pyridin-3-yl) phenylcarbamoyl) pyridin-2-yl) piperazine-1-carboxylate (165 mg, 0.29 mmol) in DCM (5 ml) at 0° C. was added TFA (2 ml) drop wise. And the resulted was stirred at room temperature for 2 h. The ice water was added to the resulting mixture and neutralized with saturated NaOH (3 ml) solution. The mixture was filtered through a Celite pad and the filtrate was concentrated to afford compound 072 as a red solid (40 mg, 39%). LCMS: m/z=375.1 (M+H)+ 1H NMR (400 MHz, DMSO) δ 9.53 (s, 1H), 8.82-8.70 (m, 2H), 8.43 (d, J=4.0 Hz, 1H), 8.08 (d, J=9.1 Hz, 1H), 7.93 (d, J=8.2 Hz, 1H), 7.54 (d, J=1.9 Hz, 1H), 7.39 (dd, J=10.1, 6.6 Hz, 2H), 6.87 (dd, J=8.6, 5.7 Hz, 2H), 5.19 (s, 2H), 3.54 (s, 4H), 2.76 (s, 4H).

Example 73—Synthesis of Compound 073

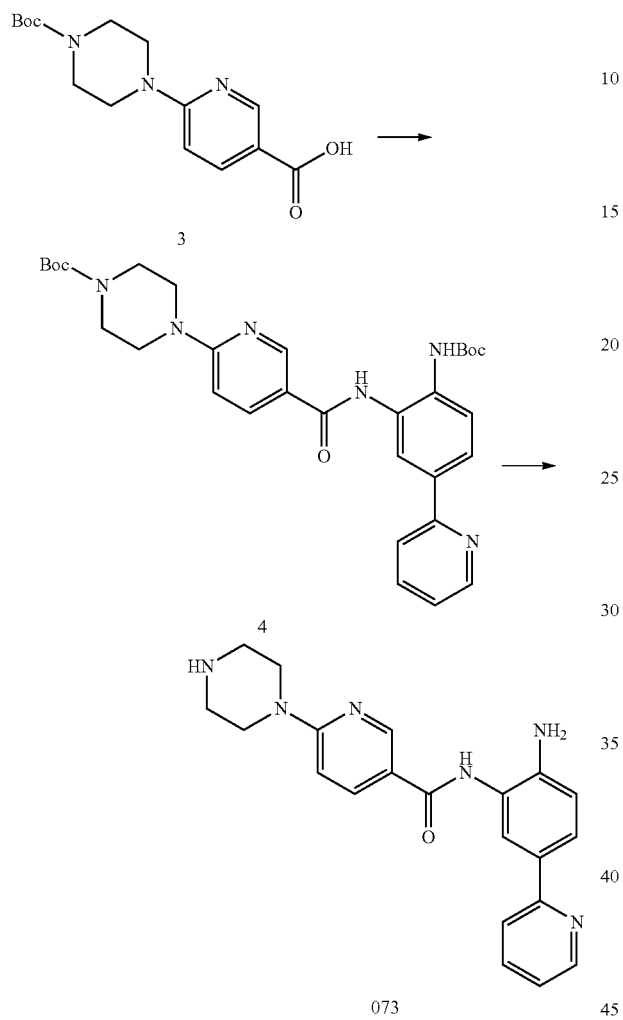

Step 1:

To a solution of tert-butyl 2-amino-4-(pyridin-2-yl)phenylcarbamate (148.5 mg, 0.52 mmol) and 6-(4-(tert-butoxycarbonyl)piperazin-1-yl)nicotinic acid (160.7 mg, 0.52 mmol) in Py (2.5 ml) was added EDCl (299 mg, 1.56 mmol). The mixture was stirred at room temperature overnight. The aqueous layer was extracted with EA (2×100 ml). The combined organic layers were washed with brine (50 ml), dried over Na$_2$SO4 and concentrated in vacuum to afford a white solid. (240 mg, 100%)

Step 2:

To a solution of tert-butyl 4-(5-(2-(tert-butoxycarbonylamino)-5-(pyridin-2-yl) phenylcarbamoyl) pyridin-2-yl) piperazine-1-carboxylate (240 mg, 0.42 mmol) in DCM (5 ml) at 0° C. was added TFA (2 ml) drop wise. And the resulting mixture was stirred at room temperature for 2 h. The residue was purified by Prep-HPLC to afford compound 073 as a white solid (97 mg, 62%). LCMS: m/z=375.2 (M+H)$^+$ 1H NMR (400 MHz, DMSO) δ 9.54 (s, 1H), 8.76 (d, J=2.4 Hz, 1H), 8.54 (d, J=4.6 Hz, 1H), 8.09 (dd, J=9.0, 2.4

Hz, 1H), 7.95 (d, J=2.0 Hz, 1H), 7.85-7.63 (m, 3H), 7.28-7.10 (m, 1H), 6.92-6.75 (m, 2H), 5.26 (s, 2H), 3.65-3.46 (m, 4H), 2.75 (dd, J=27.3, 22.3 Hz, 4H).

Example 74—Synthesis of Compound 074

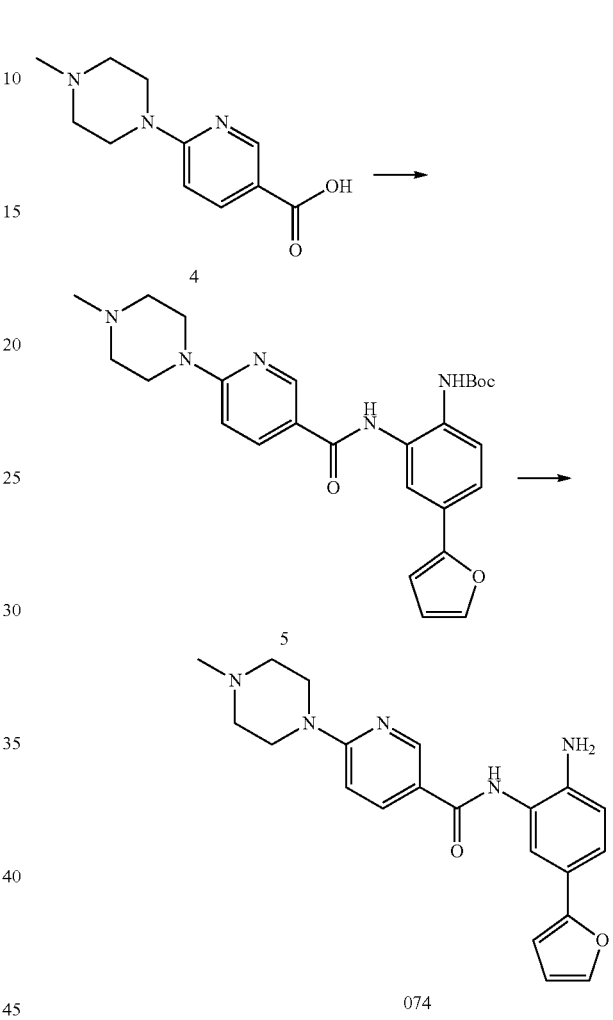

Step 1:

A mixture of 6-(4-methylpiperazin-1-yl)nicotinic acid (100 mg, 0.45 mmol), tert-butyl 2-amino-4-(furan-2-yl)phenylcarbamate (124 mg, 0.45 mmol) and EDCl (191 mg, 1 mmol) in pyridine (5 mL) was stirred at room temperature for overnight. The mixture was poured into water (20 mL) and extracted with EA to afford crude (270 mg, crude).

Step 2:

A mixture of compound tert-butyl 4-(furan-2-yl)-2-(6-(4-methylpiperazin-1-yl)nicotinamido)phenylcarbamate (270 mg, crude) and TFA (3 mL) in DCM (3 mL) was stirred at room temperature for 1 h. The mixture was purified by Prep-HPLC to obtain compound 074 (92 mg, 45%, lot SP-0018110-104) as a yellow solid. LCMS: m/z=378.5 (M+H)$^+$. $^1$H NMR (400 MHz, DMSO) δ 9.51 (s, 1H), 8.76 (s, 1H), 8.09 (d, J=7.3 Hz, 1H), 7.58 (d, J=21.9 Hz, 1H), 7.51 (s, 1H), 7.32 (d, J=8.0 Hz, 1H), 6.84 (dt, J=30.4, 15.5 Hz, 2H), 6.55 (dd, J=49.8, 11.4 Hz, 2H), 5.15 (s, 2H), 3.63 (s, 4H), 2.44-2.34 (m, 4H), 2.22 (s, 3H).

Example 75—Synthesis of Compound 075

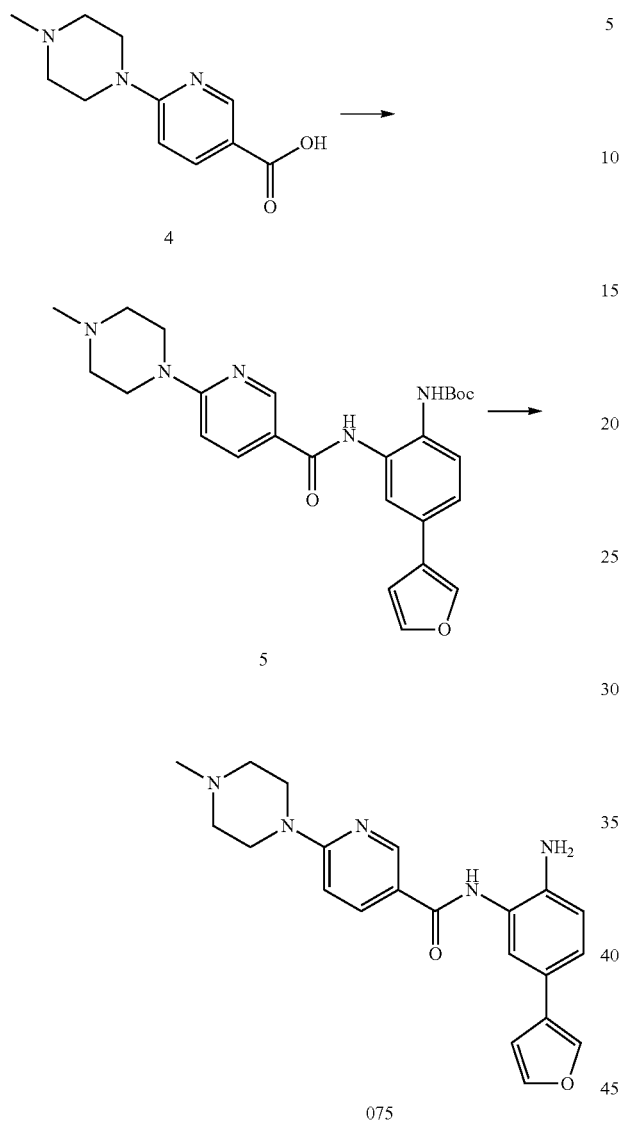

Step 1:

A mixture of 6-(4-methylpiperazin-1-yl)nicotinic acid (50 mg, 0.226 mmol), tert-butyl 2-amino-4-(furan-3-yl)phenylcarbamate (62 mg, 0.226 mmol) and EDCl (95 mg, 0.5 mmol) in pyridine (5 mL) was stirred at room temperature for overnight. The mixture was poured into water (20 mL) and extracted with EA to afford crude (170 mg, crude).

Step 2:

A mixture of compound tert-butyl 4-(furan-3-yl)-2-(6-(4-methylpiperazin-1-yl)nicotinamido)phenylcarbamate (170 mg, crude) and TFA (3 mL) in DCM (3 mL) was stirred at room temperature for 1 h. The mixture was purified by Prep-HPLC to obtain compound 075 (63 mg, 61.7%, lot SP-0018110-108) as a yellow solid. LCMS: m/z=378.5 (M+H)$^+$. $^1$H NMR (400 MHz, DMSO) δ 9.53 (s, 1H), 8.75 (s, 1H), 8.10 (d, J=8.8 Hz, 1H), 7.96 (s, 1H), 7.66 (s, 1H), 7.36 (s, 1H), 7.23 (d, J=8.3 Hz, 1H), 6.97-6.71 (m, 3H), 4.97 (s, 2H), 3.62 (s, 4H), 2.43-2.35 (m, 4H), 2.22 (s, 3H).

Example 76—Synthesis of Compound 076

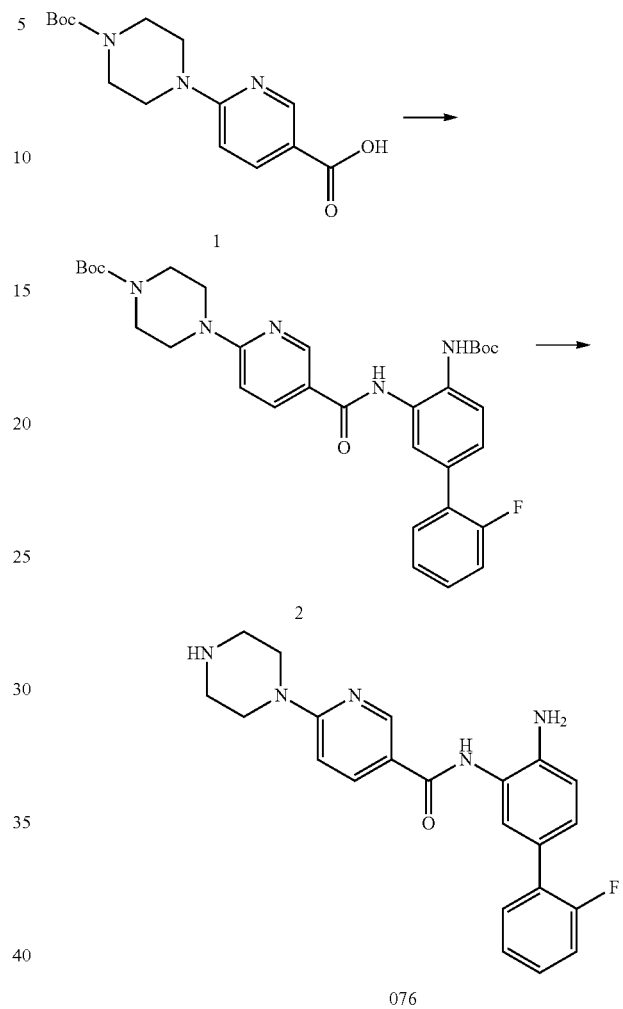

Step 1:

A mixture of 6-(4-(tert-butoxycarbonyl)piperazin-1-yl) nicotinic acid (184 mg, 0.6 mmol), tert-butyl 3-amino-2'-fluorobiphenyl-4-ylcarbamate (180 mg, 0.54 mmol) and EDCl (229 mg, 1.2 mmol) in pyridine (10 mL) was stirred at room temperature for overnight. The mixture was poured into water (20 mL) and extracted with EA, then purified by preparative TLC (PE/EA=2:1) to afford desired compound (210 mg, 66%) as a pale solid.

Step 2:

A mixture of compound tert-butyl 4-(5-(4-(tert-butoxycarbonylamino)-2'-fluorobiphenyl-3-ylcarbamoyl)pyridin-2-yl)piperazine-1-carboxylate (200 mg, 0.33 mmol) and TFA (2 mL) in DCM (5 mL) was stirred at room temperature for 1 h. The mixture was concentrated, ether was added, basified with saturated NaHCO$_3$, the solid was collected to obtain compound 076 (54 mg, 88%, lot SP-0018110-116) as a yellow solid. LCMS: m/z=392.4 (M+H)$^+$. $^1$H NMR (400 MHz, DMSO) δ 9.52 (s, 1H), 8.75 (d, J=1.8 Hz, 1H), 8.08 (d, J=7.1 Hz, 1H), 7.54-7.12 (m, 7H), 6.96-6.71 (m, 2H), 5.16 (s, 2H), 3.57 (dd, J=20.8, 16.4 Hz, 4H), 2.87-2.70 (m, 4H).

Example 77—Synthesis of Compound 077

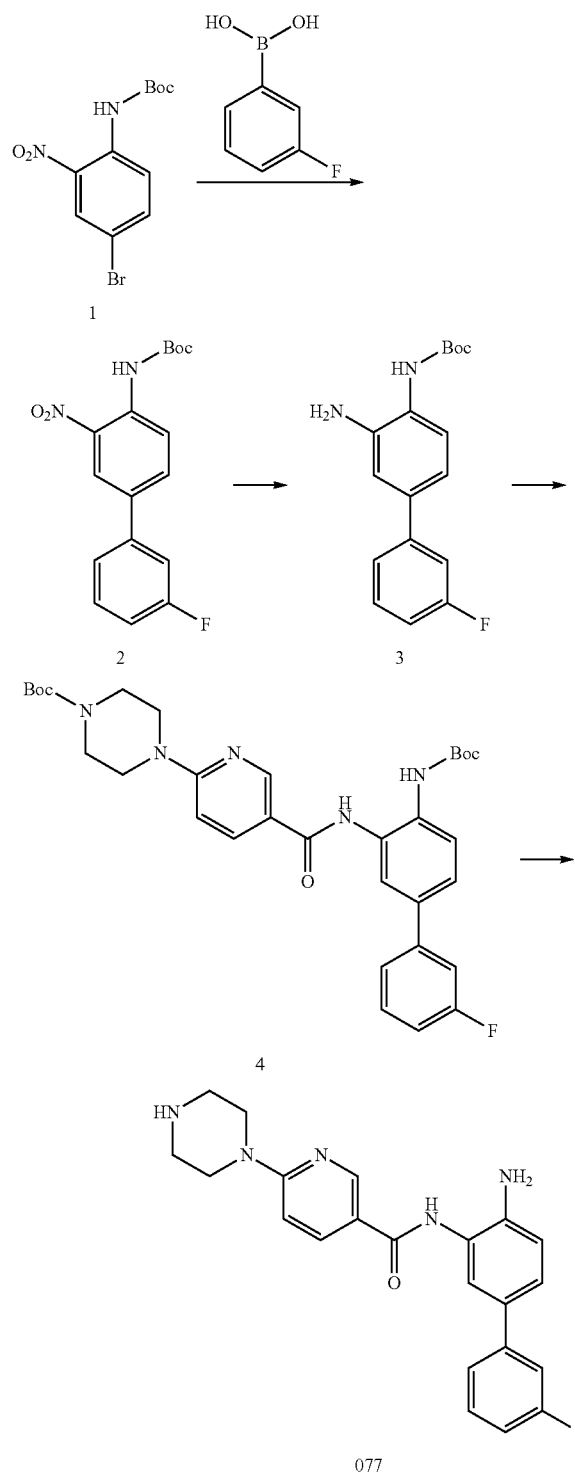

Step 1:

The title compound tert-butyl 3'-fluoro-3-nitrobiphenyl-4-ylcarbamate was synthesized following the same procedures as described in Example 3.

Step 2:

A mixture of 6-(4-(tert-butoxycarbonyl)piperazin-1-yl)nicotinic acid (100 mg, 0.3 mmol), tert-butyl 3'-fluoro-3-nitrobiphenyl-4-ylcarbamate (90 mg, 0.27 mmol) and EDCl (115 mg, 0.6 mmol) in pyridine (8 mL) was stirred at room temperature for overnight. The mixture was poured into water (20 mL) and extracted with EA, then purified by preparative TLC (PE/EA=2:1) to afford desired compound (98 mg, 50%) as a pale solid.

Step 3:

A mixture of compound tert-butyl 4-(5-(4-(tert-butoxycarbonylamino)-3'-fluorobiphenyl-3-ylcarbamoyl)pyridin-2-yl)piperazine-1-carboxylate (98 mg, 0.166 mmol) and TFA (2 mL) in DCM (5 mL) was stirred at room temperature for 1 h. The mixture was concentrated, ether was added, basified with saturated NaHCO$_3$, the solid was collected to obtain compound 077 (110 mg, 83%, lot SP-0017467-135) as a pale yellow solid. LCMS: m/z=392.4 (M+H)$^+$. $^1$H NMR (400 MHz, DMSO) δ 9.57 (s, 1H), 8.75 (s, 1H), 7.55 (s, 1H), 7.39 (dd, J=24.0, 7.5 Hz, 5H), 7.05 (s, 1H), 6.93-6.80 (m, 3H), 5.20 (s, 3H), 3.55 (s, 4H), 2.77 (s, 4H).

Example 78—Synthesis of Compound 078

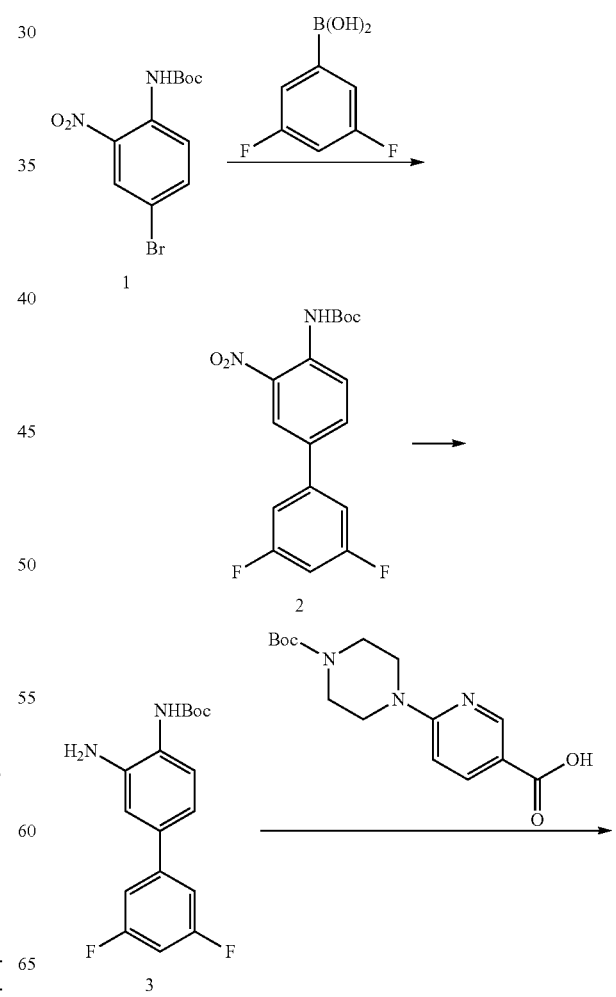

-continued

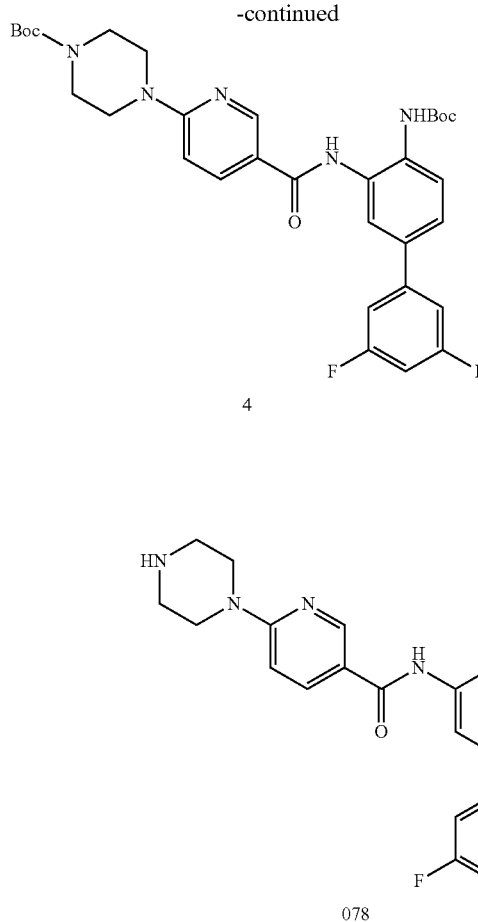

Step 1:

The title compound tert-butyl 3-amino-3',5'-difluorobiphenyl-4-ylcarbamate was synthesized following the same procedures as described in Example 3.

Step 2:

A mixture of 6-(4-(tert-butoxycarbonyl)piperazin-1-yl) nicotinic acid (307 mg, 1 mmol), tert-butyl 3-amino-3',5'-difluorobiphenyl-4-ylcarbamate (288 mg, 0.9 mmol) and EDCl (382 mg, 2 mmol) in pyridine (10 mL) was stirred at room temperature for overnight. The mixture was poured into water (20 mL) and extracted with EA, then purified by preparative TLC (PE/EA=2:1) to afford desired compound (360 mg, 59%) as a pale solid.

Step 3:

A mixture of compound tert-butyl 4-(5-(4-(tert-butoxycarbonylamino)-3',5'-difluorobiphenyl-3-ylcarbamoyl)pyridin-2-yl)piperazine-1-carboxylate (360 mg, 0.59 mmol) and TFA (3 mL) in DCM (10 mL) was stirred at room temperature for 1 h. The mixture was concentrated, basified with saturated NaHCO₃, then extracted with EA, concentrated to afford the crude, washed with 5 ml EA to obtain compound 078 (50 mg, 21%, lot SP-0018270-024) as a yellow solid. LCMS: m/z=410.5 (M+H)⁺. ¹H NMR (400 MHz, DMSO) δ 9.51 (s, 1H), 8.76 (s, 1H), 8.09 (d, J=7.1 Hz, 1H), 7.72-6.67 (m, 7H), 5.28 (s, 2H), 3.55 (s, 4H), 2.77 (s, 4H).

Example 79—Synthesis of Compound 079

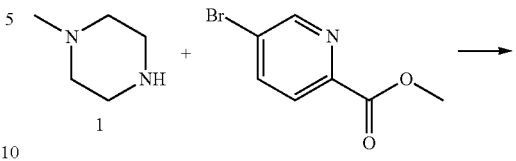

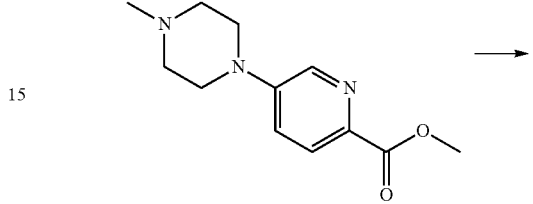

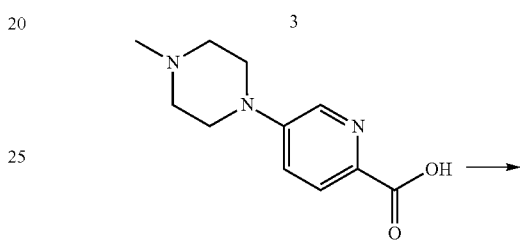

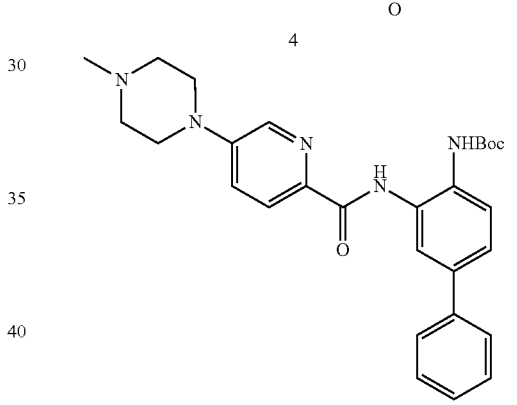

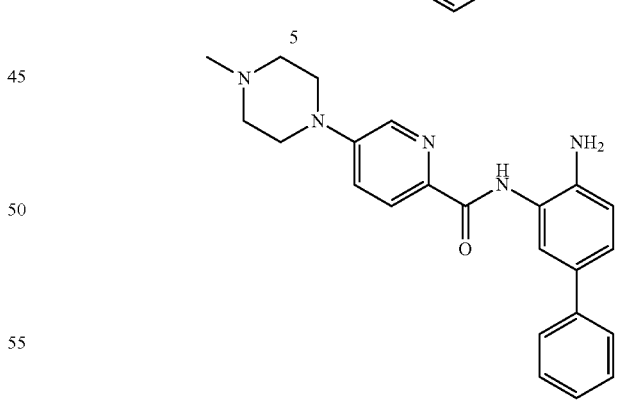

Step 1:

The title compound 5-(4-methylpiperazin-1-yl)picolinic acid (lithium salt) was synthesized following the same procedures as described in Example 28.

Step 2:

A mixture of lithium 5-(4-methylpiperazin-1-yl)picolinate (0.60 mmol) and HATU (252 mg, 0.66 mmol) in DMF (6 mL) was stirred at room temperature for 20 min. Then tert-butyl 3-aminobiphenyl-4-ylcarbamate (180 mg, 0.63 mmol) was added. It was stirred at room temperature for 2 h. Then it was poured into water. The resulting solid was collected by filtration and dried in vacuo to afford desired compound.

Step 3:

To a mixture of tert-butyl 3-(5-(4-methylpiperazin-1-yl) picolinamido) biphenyl-4-ylcarbamate (0.60 mmol) in MeOH (2 mL) was added HCl/dioxane (4 mL) at 0° C. It was stirred at 0° C. to ambient temperature for 18 h. It was concentrated in vacuo and the residue was purified by Prep-HPLC to give product as a white solid as compound 079 (117 mg, yield: 50%, three steps, lot: SP-0017146-021). LCMS: m/z=388.2 (M+H)+. $^1$H NMR (500 MHz, DMSO) δ 9.89 (s, 1H), 8.40 (d, J=2.8 Hz, 1H), 7.96 (d, J=8.8 Hz, 1H), 7.89 (d, J=2.1 Hz, 1H), 7.56 (d, J=7.3 Hz, 2H), 7.48 (dd, J=8.9, 2.9 Hz, 1H), 7.40 (t, J=7.7 Hz, 2H), 7.30-7.21 (m, 2H), 6.91 (d, J=8.3 Hz, 1H), 5.04 (s, 2H), 3.40-3.36 (m, 4H), 2.49-2.45 (m, 4H), 2.24 (s, 3H).

Example 80—Synthesis of Compound 080 tert-butyl 2-amino-4-(thiophen-2-yl)phenylcarbamate (192 mg, 0.66 mmol) was added. It was stirred at room temperature for 2 h. Then it was poured into water. The resulting solid was collected by filtration and dried in vacuo to give crude compound.

Step 2:

To a mixture of tert-butyl 3-(5-(4-methylpiperazin-1-yl) picolinamido) biphenyl-4-ylcarbamate (0.60 mmol) in MeOH (4 mL) was added HCl/dioxane (4 mL) at 0° C. It was stirred at 0° C. to ambient temperature for 18 h. It was concentrated in vacuo and the residue was purified by prep-HPLC to give compound 080 as a white solid (87 mg, yield: 29%, three steps, lot SP-0017146-020). LCMS: m/z=394.2 (M+H)+. $^1$H NMR (500 MHz, DMSO) δ 9.87 (s, 1H), 8.39 (d, J=2.8 Hz, 1H), 7.96 (d, J=8.8 Hz, 1H), 7.87 (d, J=2.1 Hz, 1H), 7.47 (dd, J=8.9, 2.8 Hz, 1H), 7.37 (d, J=4.4 Hz, 1H), 7.31-7.19 (m, 2H), 7.06 (dd, J=5.0, 3.6 Hz, 1H), 6.85 (d, J=8.3 Hz, 1H), 5.08 (s, 2H), 3.40-3.35 (m, 4H), 2.49-2.45 (m, 4H), 2.24 (s, 3H).

Example 81—Synthesis of Compound 081

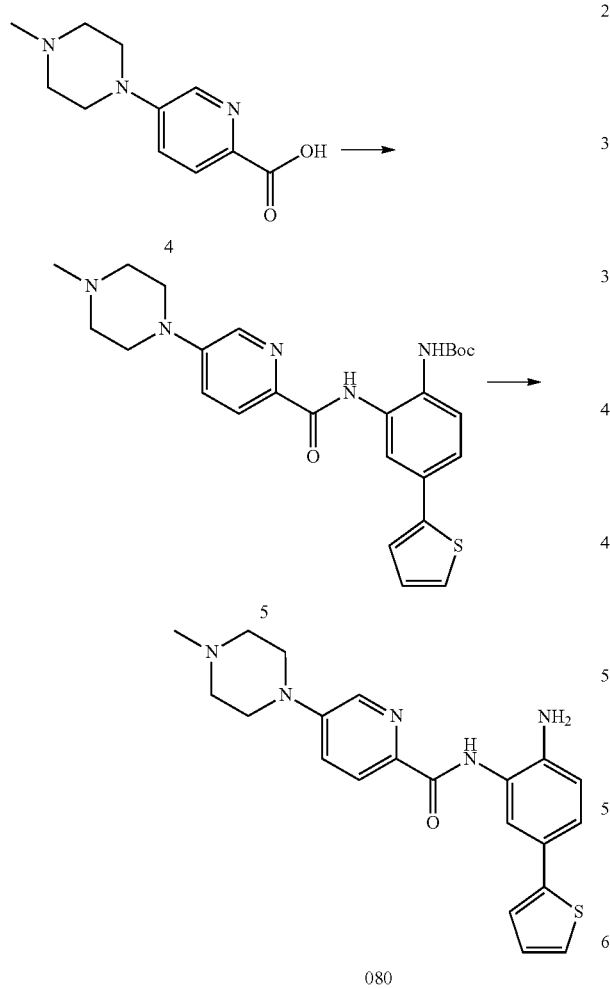

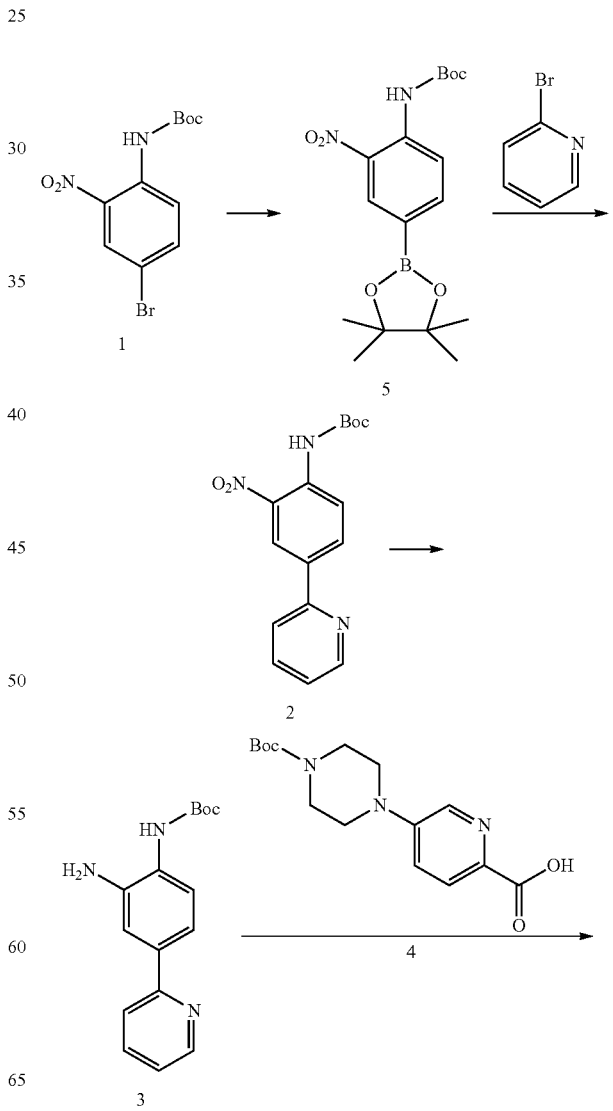

Step 1:

A mixture of lithium 5-(4-methylpiperazin-1-yl)picolinate (0.60 mmol) and HATU (252 mg, 0.66 mmol) in DMF (4 mL) was stirred at room temperature for 15 min. Then -continued

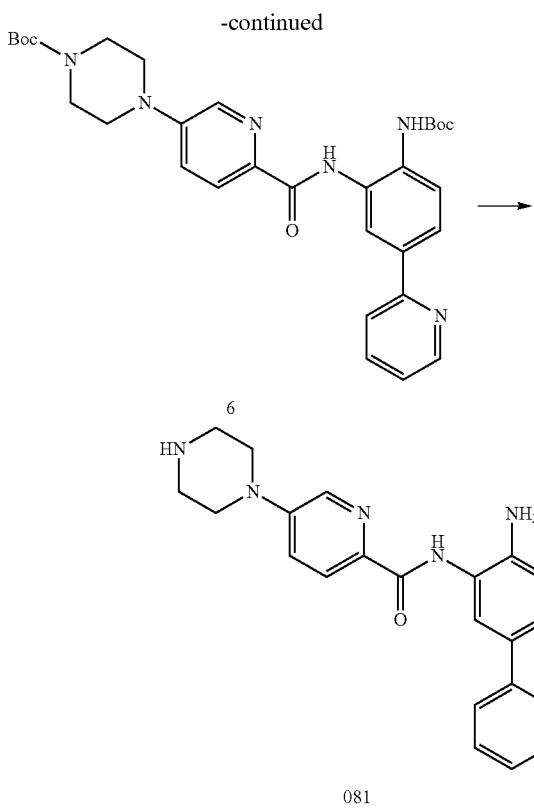

Step 1:

To a solution of tert-butyl 4-bromo-2-nitrophenylcarbamate (8.0 g, 25.2 mmol) and 4,4,4',4',5,5,5',5'-octamethyl-2,2'-bi(1,3,2-dioxaborolane) (7.7 g, 30.3 mmol), KOAc 5.0 g, 51.0 mmol), PdCl₂(dppf-DCM) (922 mg, 1.3 mmol) in 1,4-dioxane (50 ml) under N₂ protection. The mixture was stirred at 80° C. overnight. The mixture was directly purified on column with (PE/EA=50/1) to afford a yellow solid (7.8 g, 80%).

Step 2:

To a solution of tert-butyl 2-nitro-4-(4,4,5,5-tetramethyl-1,3,2-dioxaborolan-2-yl)phenylcarbamate (3.0 g, 8.24 mmol) and 2-bromopyridine (1.3 g, 8.24 mmol) in 1,4-dioxane (15 ml) and H₂O (8 ml) was added K₂CO₃ (1.7 g, 16.48 mmol) and Pd(PPh3)4 (476 mg, 0.41 mmol). The mixture was stirred at 100° C. for overnight. The mixture was directly purified on column with (PE/EA=20/1) to afford a yellow solid (1 g, 38%).

Step 3:

To a solution of tert-butyl 2-nitro-4-(pyridin-2-yl)phenylcarbamate (1.5 g, 4.76 mmol) and FeCl₃ (155 mg, 0.95 mmol) in EtOH (15 ml) was added Carbon (1.5 g, 125 mmol) and drop wise N₂H₄.H₂O (8 ml). The mixture was stirred at 60° C. for 2 h. The aqueous layer was extracted with EA (100 ml). The combined organic layers were washed with brine (50 ml), dried over Na₂SO₄, filtered and concentrated in vacuum to afford a gray solid. (1.1 g, 76%)

Step 4:

To a solution of 5-(4-(tert-butoxycarbonyl)piperazin-1-yl) picolinic acid (216 mg, 0.62 mmol) and HATU (232 mg, 0.62 mmol) in DMF (7 ml) that was stirred at room temperature for 15 min., tert-butyl 2-amino-4-(pyridin-2-yl) phenylcarbamate (100 mg, 0.35 mmol) was added. The mixture was stirred at room temperature for overnight. Water was added at 0° C. The resulting precipitate was collected by filtration and dried in vacuum to afford a white solid (200 mg, 100%).

Step 5:

To a solution of tert-butyl 4-(6-(2-(tert-butoxycarbonylamino)-5-(pyridin-2-yl) phenylcarbamoyl) pyridin-3-yl) piperazine-1-carboxylate (200 mg, 0.35 mmol) in DCM (2 ml) at 0° C. was added TFA (2 ml) dropwise. The resulting solution was stirred at room temperature for 2 h. The crude product was purified by Prep-HPLC to afford a white solid as compound 081 (53 mg, 41% yield, lot SP-0018108-028). LCMS: m/z=375.2 (M+H)⁺. ¹H NMR (400 MHz, DMSO) δ 9.83 (s, 1H), 8.55 (d, J=4.7 Hz, 1H), 8.37 (d, J=2.8 Hz, 1H), 8.27 (d, J=2.0 Hz, 1H), 7.95 (d, J=8.8 Hz, 1H), 7.77 (d, J=3.4 Hz, 2H), 7.72-7.65 (m, 1H), 7.45 (d, J=6.0 Hz, 1H), 7.20 (dd, J=8.6, 4.6 Hz, 1H), 6.88 (d, J=8.4 Hz, 1H), 5.21 (s, 2H), 3.30-3.26 (m, 4H), 2.87-2.81 (m, 4H).

Example 82—Synthesis of Compound 082

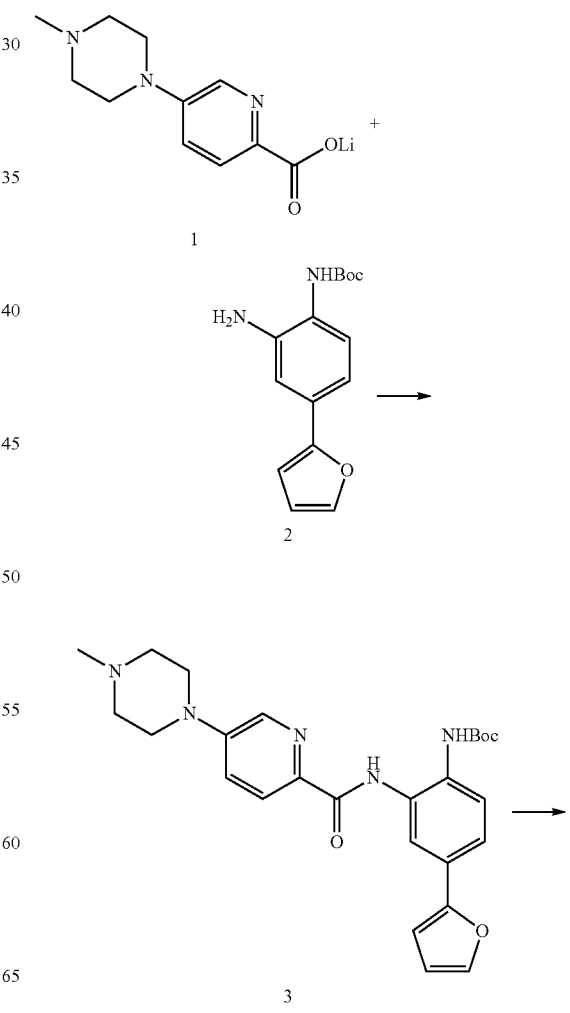

-continued

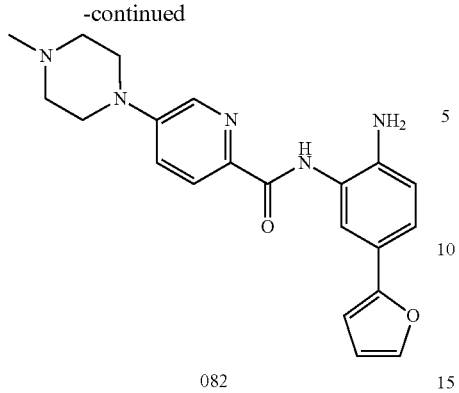

082

Step 1:

A mixture of lithium 5-(4-methylpiperazin-1-yl)picolinate (176 mg, 0.63 mmol) and HATU (240 mg, 0.63 mmol) in DMF (5 mL) was stirred at room temperature for 15 min. Then tert-butyl 2-amino-4-(furan-2-yl) phenylcarbamate (96 mg, 0.35 mmol) was added. It was stirred at room temperature for 18 h. Water was added. The resulting solid was collected by filtration and dried in vacuo to give crude compound.

Step 2:

To a mixture of above tert-butyl 4-(furan-2-yl)-2-(5-(4-methylpiperazin-1-yl) picolinamido) phenylcarbamate (0.35 mmol) in DCM (2 mL) was added TFA (2 mL) at 0° C. It was stirred at 0° C. and then at room temperature until the reaction was complete. It was concentrated in vacuo and the residue was purified by Prep-HPLC to give compound 082 as a white solid (57.0 mg, free amine, yield: 43%, two steps, lot SP-0017146-145). LCMS: m/z=378.1 (M+H)⁺. ¹H NMR (400 MHz, DMSO) δ 9.84 (s, 1H), 8.39 (d, J=2.6 Hz, 1H), 7.93 (dd, J=17.9, 5.2 Hz, 2H), 7.62 (s, 1H), 7.47 (dd, J=8.8, 2.7 Hz, 1H), 7.29 (dd, J=8.3, 1.9 Hz, 1H), 6.85 (d, J=8.3 Hz, 1H), 6.61 (d, J=3.2 Hz, 1H), 6.51 (dd, J=3.2, 1.8 Hz, 1H), 5.08 (s, 2H), 3.42-3.35 (m, 4H), 2.49-2.42 (m, 4H), 2.24 (s, 3H).

Example 83—Synthesis of Compound 083

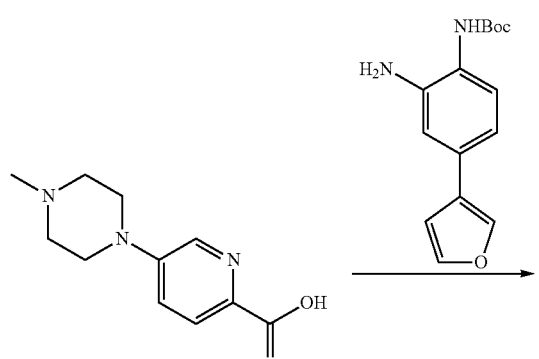

-continued

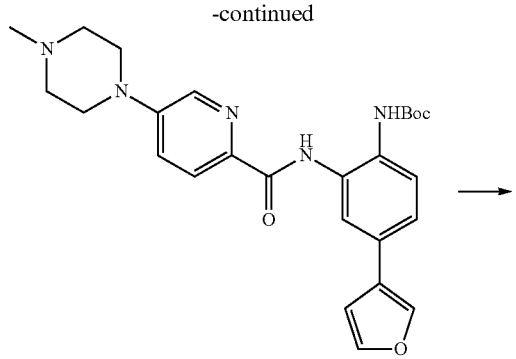

083

Step 1:

To a solution of 5-(4-methylpiperazin-1-yl) picolinic acid (170 mg, 0.77 mmol) and HATU (292 mg, 0.77 mmol) in DMF (5 ml) that was stirred at room temperature for 15 min., tert-butyl 2-amino-4-(furan-3-yl)phenylcarbamate (117 mg, 0.43 mmol) was added. The mixture was stirred at room temperature for overnight. The mixture was added to water, then a white solid formed. It was filtered through a Celite pad, and the filtrate was concentrated to afford a yellow solid (154 mg, 92.2% yield).

Step 2:

To a solution of tert-butyl 4-(furan-3-yl)-2-(5-(4-methylpiperazin-1-yl) picolinamido) phenylcarbamate (154 mg, 0.32 mmol) in DCM (2 ml) at 0° C. was added TFA (2 ml) dropwise. And the resulted was stirred at room temperature for 2 h. The reaction mixture was concentrated in vacuum. The residue was purified by Prep-HPLC. The white solid was re-crystallized from water, dried by lyophilization to afford white solid as compound 083. (62 mg, 51.7% yield, lot SP-0018108-083). LCMS: m/z=378.2 (M+H)⁺. ¹H NMR (400 MHz, DMSO) δ 9.83 (s, 1H), 8.39 (d, J=2.7 Hz, 1H), 8.00-7.89 (m, 2H), 7.74 (d, J=1.7 Hz, 1H), 7.67 (s, 1H), 7.48 (dd, J=8.9, 2.8 Hz, 1H), 7.20 (dd, J=8.2, 1.8 Hz, 1H), 6.88-6.76 (m, 2H), 4.93 (s, 2H), 3.42-3.35 (m, 4H), 2.49-2.45 (m, 4H).

Example 84—Synthesis of Compound 084

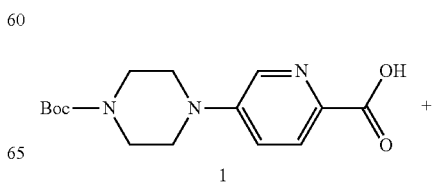

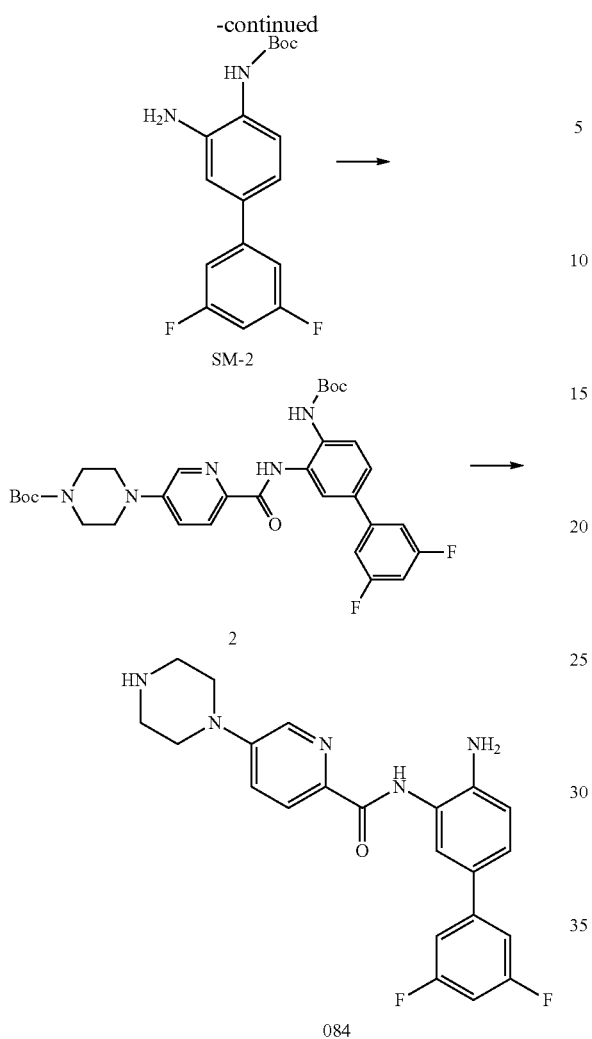

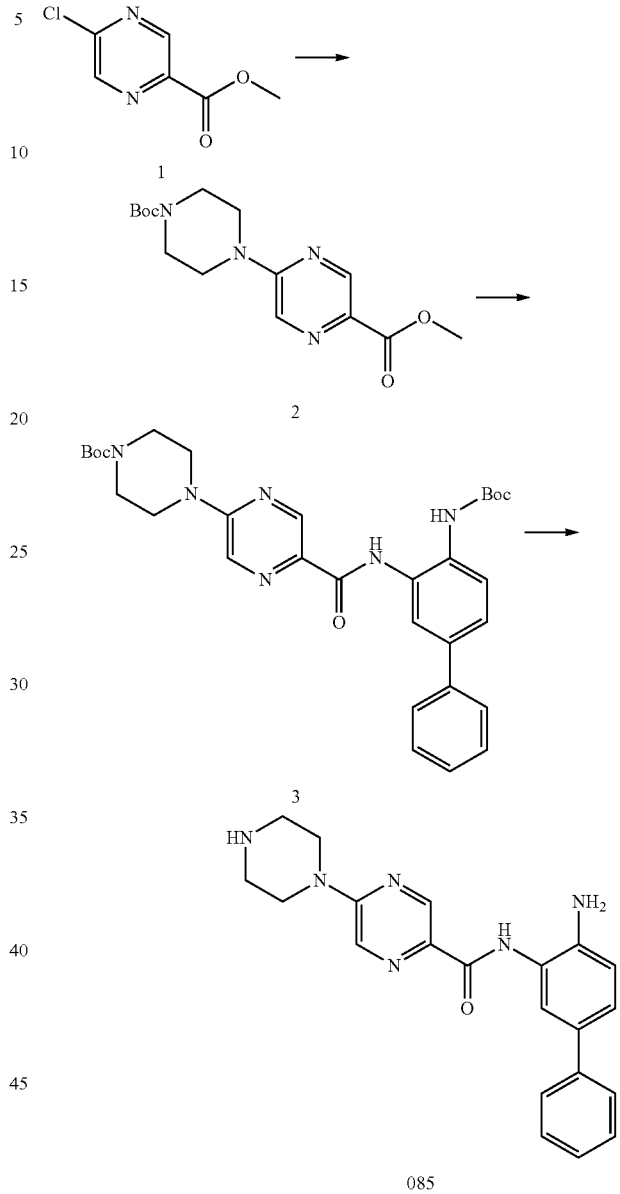

Example 85—Synthesis of Compound 085

Step 1:

A mixture of 5-(4-(tert-butoxycarbonyl) piperazin-1-yl) picolinic acid (100 mg, 0.33 mmol), tert-butyl 3-amino-3',5'-difluorobiphenyl-4-ylcarbamate (106 mg, 0.33 mmol) and EDCl (190 mg, 0.99 mmol) in Py (3 ml) was stirred at room temperature for overnight. It was extracted with EA and purified by column chromatography (PE:EA=2:1). White solid was afforded (175 mg, 69% yield).

Step 2:

To a solution of tert-butyl 4-(6-(4-(tert-butoxycarbonylamino)-3',5'-difluorobiphenyl-3-ylcarbamoyl) pyridin-3-yl) piperazine-1-carboxylate (175 mg, 0.29 mmol) in DCM (4 ml) was added TFA (2 ml). The mixture was stirred at room temperature for 2 h. It was concentrated and neutralized by aqueous NaOH (2 mol/L). White solid was filtered as compound 084. (85 mg, 72% yield, lot SP-0018421-087). LCMS: m/z=410.2 (M+H)+. $^1$H NMR (400 MHz, DMSO) δ 9.87 (s, 1H), 8.38 (d, J=2.6 Hz, 1H), 7.96 (d, J=8.8 Hz, 1H), 7.89 (d, J=2.0 Hz, 1H), 7.46 (dd, J=8.7, 2.7 Hz, 1H), 7.38 (dd, J=8.4, 2.2 Hz, 1H), 7.29 (d, J=7.4 Hz, 2H), 7.08 (t, J=9.2 Hz, 1H), 6.89 (d, J=8.4 Hz, 1H), 5.22 (s, 2H), 2.94-2.84 (m, 4H), 2.58 (m, 4H).

Step 1:

A mixture of methyl 5-chloropyrazine-2-carboxylate (1.72 g, 10 mmol), tert-butyl piperazine-1-carboxylate (3.72 g, 20 mmol) and DIPEA (3.87 g, 30 mmol) in 1,4-dioxane (20 mL) was stirred at 100° C. for overnight. The mixture was concentrated to get a residue, which was purified by silica gel to get compound (3.06 g, 95%).

Step 2:

A mixture of methyl methyl 5-(4-(tert-butoxycarbonyl) piperazin-1-yl)pyrazine-2-carboxylate (322 mg, 1 mmol) and LiOH (126 mg, 3 mmol) in MeOH (20 mL) was stirred at 60° C. for 3 h. The mixture was concentrated to get a residue, which was added tert-butyl 3-aminobiphenyl-4-ylcarbamate (284 mg, 1 mmol), EDCl (573 mg, 3 mmol) and Py (10 mL). The mixture was stirred at room temperature for overnight. The mixture was poured into water (50 mL) and filtered to afford compound (459 mg, 80%).

Step 3:

To a solution of tert-butyl 4-(5-(4-(tert-butoxycarbonylamino)biphenyl-3-ylcarbamoyl)pyrazin-2-yl)piperazine-1-carboxylate (287 mg, 0.5 mmol) in DCM (5 mL) was added TFA (2.5 mL), stirred for 1 h. The mixture was concentrated to get a residue, which was purified by Prep-HPLC to get compound 085 (131 mg, 70%). LCMS: m/z=375.2 (M+H)$^+$. $^1$H NMR (400 MHz, DMSO) δ 9.70 (s, 1H), 8.72 (s, 1H), 8.34 (s, 1H), 7.81 (s, 1H), 7.56 (d, J=7.7 Hz, 2H), 7.40 (t, J=7.6 Hz, 2H), 7.32-7.20 (m, 2H), 6.90 (d, J=8.3 Hz, 1H), 5.06 (s, 2H), 3.72-3.59 (m, 4H), 2.85-2.74 (m, 4H).

Example 86—Synthesis of Compound 086

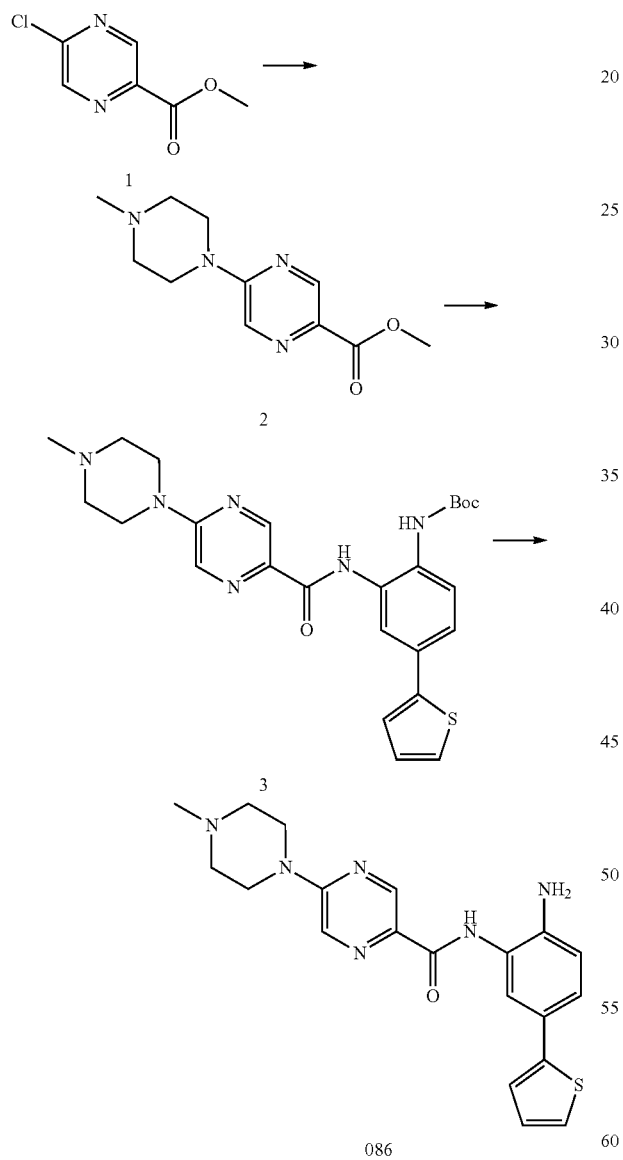

Step 1:

A mixture of methyl 5-chloropyrazine-2-carboxylate (1.72 g, 10 mmol), tert-butyl piperazine-1-carboxylate (2.0 g, 20 mmol) and DIPEA (3.87 g, 30 mmol) in 1,4-dioxane (20 mL) was stirred at 100° C. for overnight. The mixture was concentrated to get a residue, which was purified by silica gel to get compound (1.65 g, 70%).

Step 2:

A mixture of methyl 5-(4-methylpiperazin-1-yl)pyrazine-2-carboxylate (236 mg, 1 mmol) and LiOH (126 mg, 3 mmol) in MeOH (20 mL) was stirred at 60° C. for 3 h. The mixture was concentrated to get a residue, which was added tert-butyl 2-amino-4-(thiophen-2-yl)phenylcarbamate (290 mg, 1 mmol), EDCl (573 mg, 3 mmol) and Py (10 mL). The mixture was stirred at room temperature for overnight. The mixture was poured into water (50 mL), filtered to get compound (420 mg, 85%).

Step 3:

To a solution of tert-butyl 2-(5-(4-methylpiperazin-1-yl)pyrazine-2-carboxamido)-4-(thiophen-2-yl)phenylcarbamate (247 mg, 0.5 mmol) in DCM (5 mL) was added TFA (2.5 mL), stirred for 1 h. The mixture was concentrated to get a residue, which was purified by Prep-HPLC to get compound 086 (138 mg, 70%). LCMS: m/z=395.1 (M+H)$^+$. $^1$H NMR (400 MHz, DMSO) δ 9.69 (s, 1H), 8.73 (s, 1H), 8.37 (s, 1H), 7.78 (d, J=1.7 Hz, 1H), 7.37 (d, J=5.0 Hz, 1H), 7.26 (dd, J=11.4, 2.8 Hz, 2H), 7.09-6.97 (m, 1H), 6.84 (d, J=8.3 Hz, 1H), 5.10 (s, 2H), 3.80-3.66 (m, 4H), 2.46-2.37 (m, 4H), 2.23 (s, 3H).

Example 87—Synthesis of Compound 087

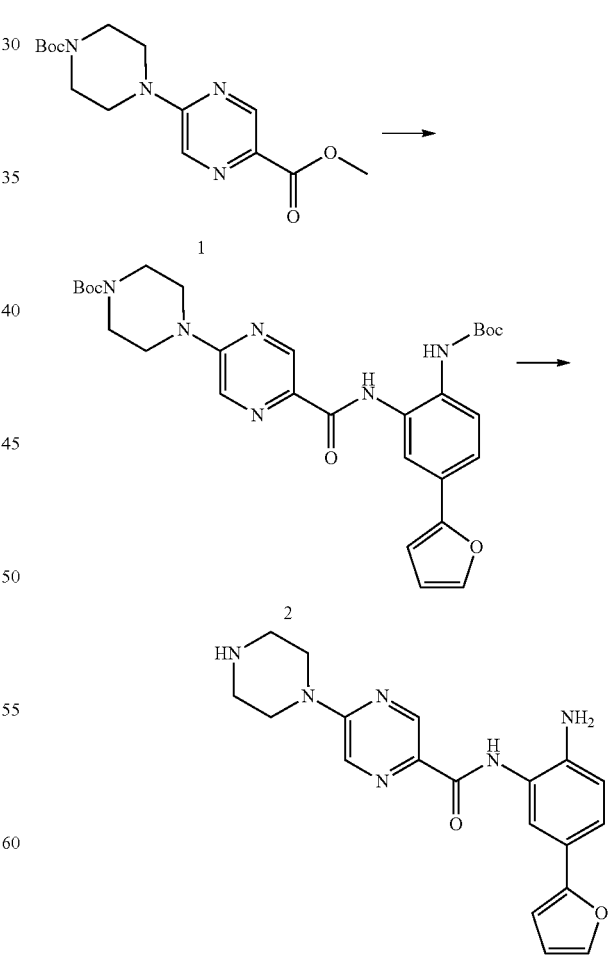

Step 1:

A mixture of methyl 5-(4-(tert-butoxycarbonyl)piperazin-1-yl)pyrazine-2-carboxylate (236 mg, 1 mmol) and LiOH (126 mg, 3 mmol) in MeOH (20 mL) was stirred at 60° C. for 3 h. The mixture was concentrated to get a residue, which was added tert-butyl 2-amino-4-(furan-2-yl)phenylcarbamate (274 mg, 1 mmol), EDCl (573 mg, 3 mmol) and Py (10 mL). The mixture was stirred at room temperature for overnight. The mixture was poured into water (50 mL), filtered to get compound (451 mg, 80%)

Step 2:

To a solution of tert-butyl 4-(5-(2-(tert-butoxycarbonylamino)-5-(furan-2-yl)phenylcarbamoyl)pyrazin-2-yl)piperazine-1-carboxylate (282 mg, 0.5 mmol) in DCM (5 mL) was added TFA (2.5 mL), stirred for 1 h. The mixture was concentrated to get a residue, which was purified by Prep-HPLC to get compound 087 (146 mg, 80%) LCMS: m/z=365.2 (M+H)+. 1H NMR (400 MHz, DMSO) δ 9.65 (s, 1H), 8.71 (s, 1H), 8.34 (s, 1H), 7.83 (s, 1H), 7.62 (s, 1H), 7.30 (d, J=7.4 Hz, 1H), 6.84 (d, J=8.3 Hz, 1H), 6.61 (d, J=2.7 Hz, 1H), 6.51 (s, 1H), 5.10 (s, 2H), 3.66 (s, 4H), 2.80 (s, 4H).

Example 88—Synthesis of Compound 088

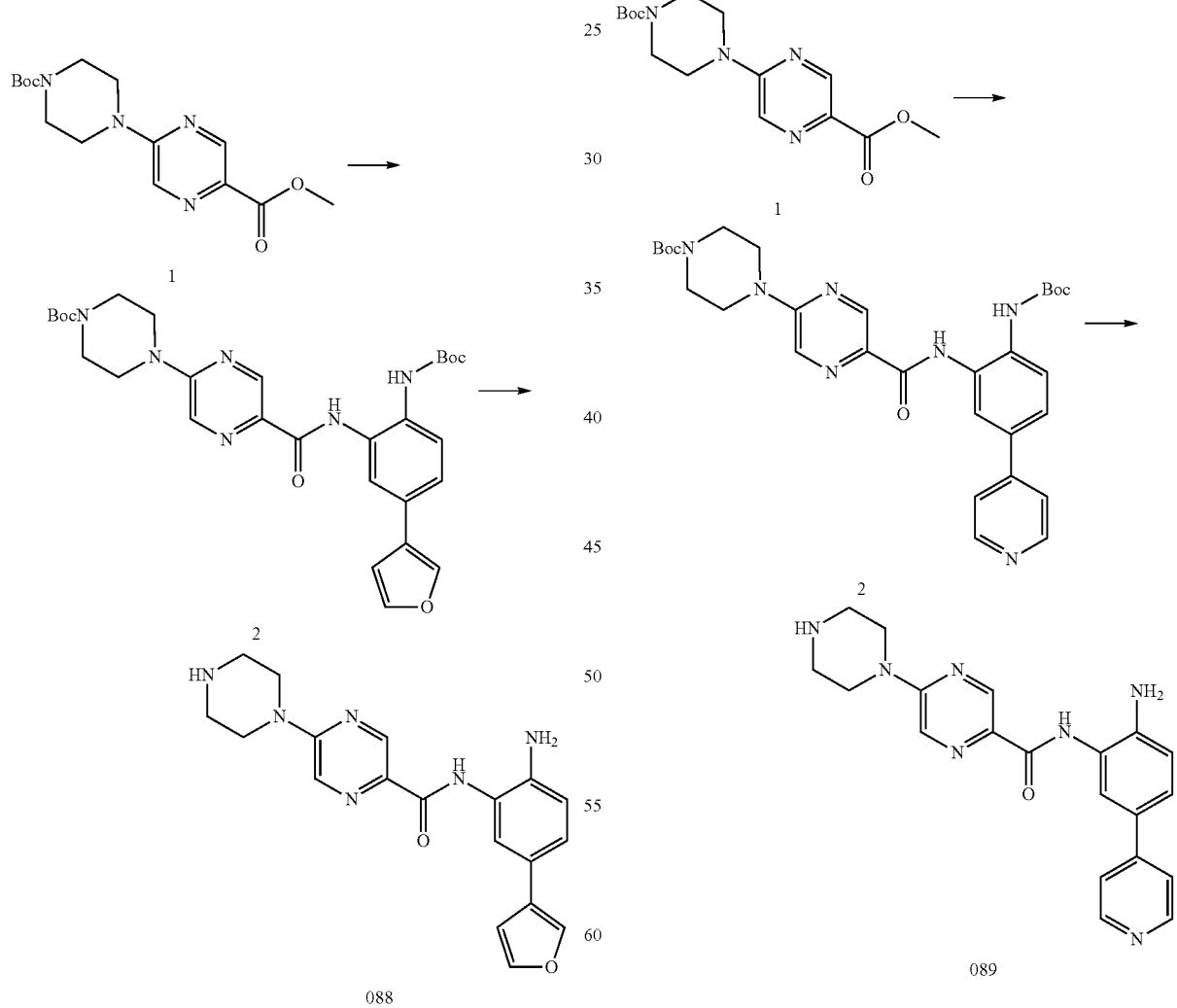

088

Step 1:

A mixture of methyl 5-(4-(tert-butoxycarbonyl)piperazin-1-yl)pyrazine-2-carboxylate (236 mg, 1 mmol) and LiOH (126 mg, 3 mmol) in MeOH (20 mL) was stirred at 60° C. for 3 h. The mixture was concentrated to get a residue, which was added tert-butyl 2-amino-4-(furan-3-yl)phenylcarbamate (274 mg, 1 mmol), EDCl (573 mg, 3 mmol) and Py (10 mL). The mixture was stirred at room temperature for overnight. The mixture was poured into water (50 mL), filtered to get compound 3 (451 mg, 80%)

Step 2:

To a solution of tert-butyl 4-(5-(2-(tert-butoxycarbonylamino)-5-(furan-3-yl)phenylcarbamoyl)pyrazin-2-yl)piperazine-1-carboxylate (282 mg, 0.5 mmol) in DCM (5 mL) was added TFA (2.5 mL), stirred for 1 h. The mixture was concentrated to get a residue, which was purified by Prep-HPLC to get compound 088 (146 mg, 80%). LCMS: m/z=365.1 (M+H)+. 1H NMR (400 MHz, DMSO) δ 9.66 (s, 1H), 8.71 (s, 1H), 8.33 (s, 1H), 7.96 (s, 1H), 7.67 (s, 2H), 7.21 (d, J=8.2 Hz, 1H), 6.87-6.77 (m, 2H), 4.95 (s, 2H), 3.66 (s, 4H), 2.80 (s, 4H).

Example 89—Synthesis of Compound 089

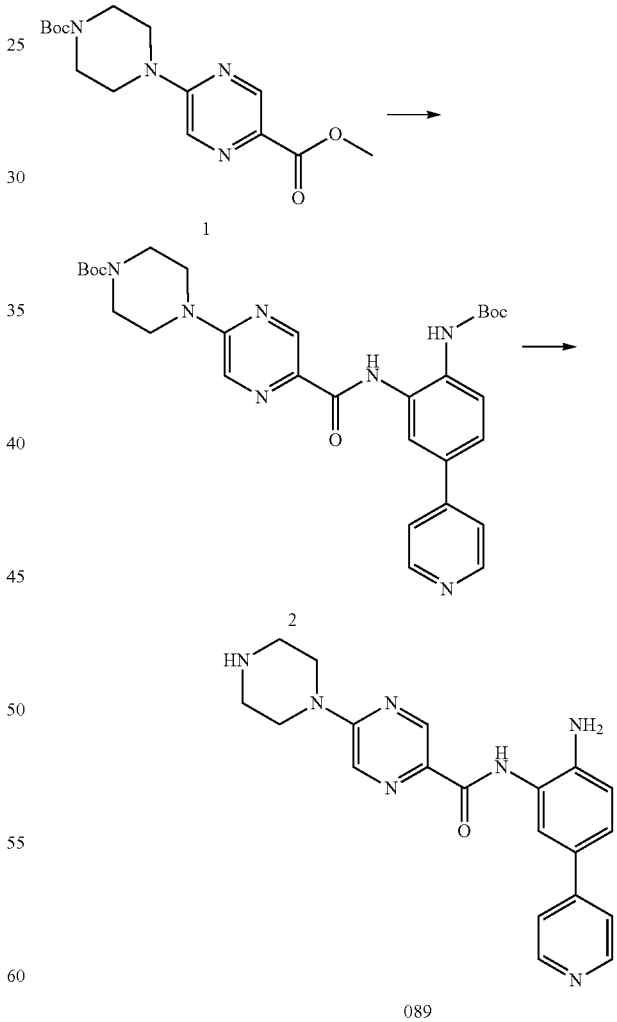

089

Step 1:

A mixture of methyl 5-(4-(tert-butoxycarbonyl)piperazin-1-yl)pyrazine-2-carboxylate (236 mg, 1 mmol) and LiOH (126 mg, 3 mmol) in MeOH (20 mL) was stirred at 60° C.

for 3 h. The mixture was concentrated to get a residue, which was added tert-butyl 2-amino-4-(pyridin-4-yl)phenylcarbamate (285 mg, 1 mmol), EDCl (573 mg, 3 mmol) and Py (10 mL). The mixture was stirred at room temperature for overnight. The mixture was poured into water (50 mL), filtered to get compound (401 mg, 70%)

Step 2:

To a solution of tert-butyl 4-(5-(2-(tert-butoxycarbonylamino)-5-(pyridin-4-yl)phenylcarbamoyl)pyrazin-2-yl)piperazine-1-carboxylate (288 mg, 0.5 mmol) in DCM (5 mL) was added TFA (2.5 mL), stirred for 1 h. The mixture was concentrated to get a residue, which was purified by Prep-HPLC to get compound 089 (150 mg, 80%). LCMS: m/z=376.1 (M+H)+. 1H NMR (400 MHz, DMSO) δ 9.70 (s, 1H), 8.72 (s, 1H), 8.52 (d, J=5.6 Hz, 2H), 8.34 (s, 1H), 7.91 (s, 1H), 7.58 (d, J=5.7 Hz, 2H), 7.48 (d, J=8.5 Hz, 1H), 6.91 (d, J=8.4 Hz, 1H), 5.32 (s, 2H), 3.66 (s, 4H), 2.80 (s, 4H).

Example 90—Synthesis of Compound 090

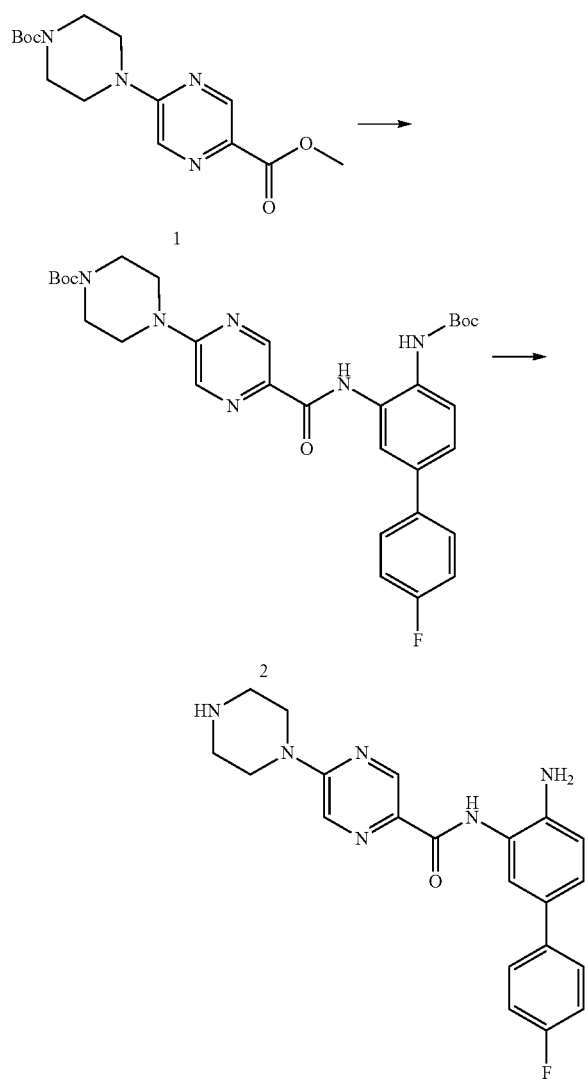

Step 1:

A mixture of methyl 5-(4-(tert-butoxycarbonyl)piperazin-1-yl)pyrazine-2-carboxylate (236 mg, 1 mmol) and LiOH (126 mg, 3 mmol) in MeOH (20 mL) was stirred at 60° C. for 3 h. The mixture was concentrated to get a residue, which was added tert-butyl 3-amino-4'-fluorobiphenyl-4-ylcarbamate (302 mg, 1 mmol), EDCl (573 mg, 3 mmol) and Py (10 mL). The mixture was stirred at room temperature for overnight. The mixture was poured into water (50 mL), filtered to get compound (444 mg, 75%).

Step 2

To a solution of tert-butyl 4-(5-(4-(tert-butoxycarbonylamino)-4'-fluorobiphenyl-3-ylcarbamoyl)pyrazin-2-yl)piperazine-1-carboxylate (296 mg, 0.5 mmol) in DCM (5 mL) was added TFA (2.5 mL), stirred for 1 h. The mixture was concentrated to get a residue, which was purified by Prep-HPLC to get compound 090 (157 mg, 80%). LCMS: m/z=393.2 (M+H)+. 1H NMR (400 MHz, DMSO) δ 9.94 (s, 1H), 9.04 (s, 2H), 8.79 (d, J=1.1 Hz, 1H), 8.46 (s, 1H), 7.79 (d, J=2.1 Hz, 1H), 7.61 (dd, J=8.8, 5.5 Hz, 2H), 7.35 (dd, J=8.3, 2.1 Hz, 1H), 7.25 (t, J=8.9 Hz, 2H), 7.03 (d, J=8.3 Hz, 1H), 4.02-3.92 (m, 4H), 3.26 (s, 4H).

Example 91—Pharmacokinetics

Male SD rats were fasted overnight. Compounds of the invention were dissolved in dimethyl acetamide at 10 times the final concentration, then Solutol HS 15 (BASF) was added to a final concentration of 10%. Finally 80% saline was added and vortexed to achieve a clear solution. For the IV dosing three animals were injected via the foot dorsal vein with 1 mg/kg compound. For the PO dosing 5 mg/kg of compound was delivered by oral gavage. Blood was collected via the tail vein into K2EDTA tubes at 5 minutes, 15 minutes, 30 minutes, 1 hour, 2 hours, 4 hours, 8 hours and 24 hours after dosing. The blood was centrifuged at 2000 g for 5 minutes at 4° C. to obtain plasma. The plasma was extracted with acetonitrile and the level of compound was analyzed by LC/MS/MS. The level of compound in plasma was calculated from a standard curve in rat plasma. The IV clearance (L/h/kg) and area under the curve (h*ng/mL) were calculated using WinNonLin software. The dose adjusted area under the curve for the IV and oral dosing were used to calculate the oral bioavailability.

Pharmacokinetic properties were assessed in a rat cassette dosing experiment. The IV clearance (IV Clr.) is in units of L/hr/kg. The oral maximum plasma concentration (PO Cmax) is in units of ng/ml. The oral plasma half-life (PO T1/2) is in units of hours. The oral area under the curve (PO AUC) is in units of hours*ng/ml. The fraction absorbed by the oral route (F %) is a percentage of the oral area under the curve to the IV area under the curve, dose adjusted. A summary of results is presented in Table 2, below.

TABLE 2

| Compound No. | Structure | IV Clr. | PO T1/2 | PO Cmax | PO AUC | F% |
|---|---|---|---|---|---|---|
| 002 | 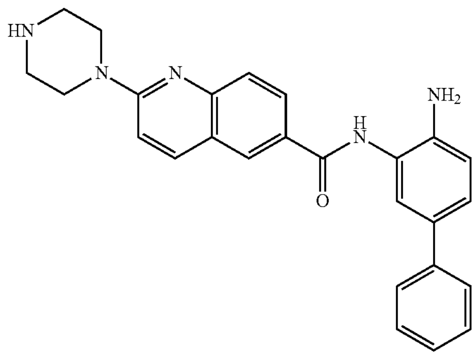 [SMILES: Nc1ccc(-c2ccccc2)cc1NC(=O)c1ccc2nc(N3CCNCC3)ccc2c1] | 0.12 | 5.9 | 3746 | 34597 | 86.1 |
| 003 | 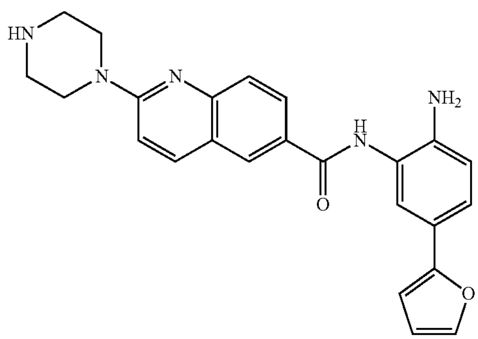 [SMILES: Nc1ccc(-c2ccco2)cc1NC(=O)c1ccc2nc(N3CCNCC3)ccc2c1] | 0.19 | 5.0 | 1910 | 19108 | 77.0 |
| 004 | 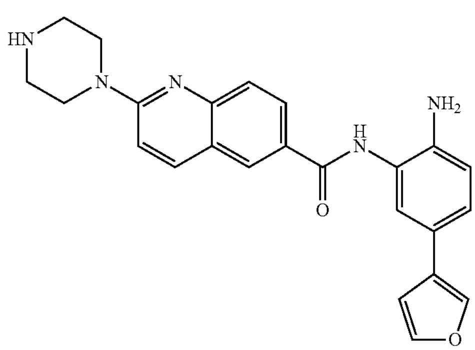 [SMILES: Nc1ccc(-c2ccoc2)cc1NC(=O)c1ccc2nc(N3CCNCC3)ccc2c1] | 0.04 | 4.3 | 10353 | 91943 | 90.8 |
| 008 | 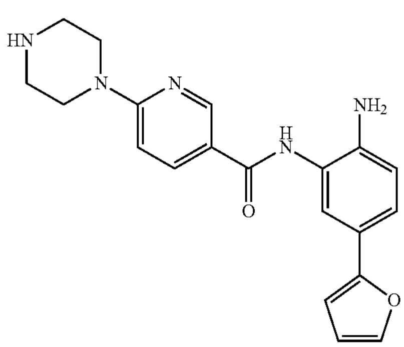 | 0.86 | 5.6 | 536 | 5536 | 100 |

TABLE 2-continued

| Compound No. | Structure | IV Clr. | PO T1/2 | PO Cmax | PO AUC | F% |
|---|---|---|---|---|---|---|
| 010 | 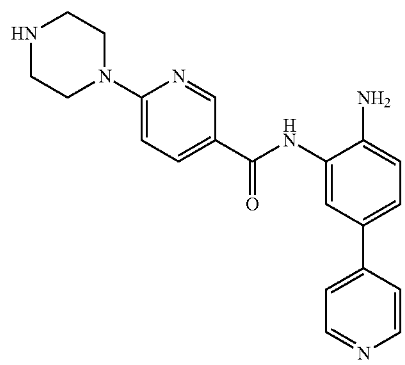 | 1.1 | 4.7 | 164 | 570 | 12.6 |
| 012 | 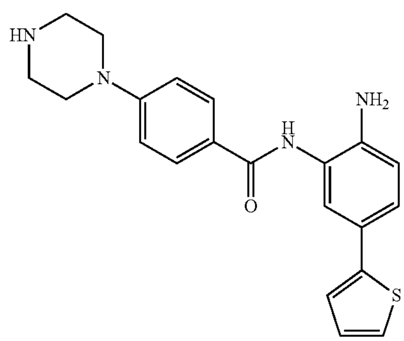 | 0.53 | 7.7 | 534 | 8186 | 93.9 |
| 013 | 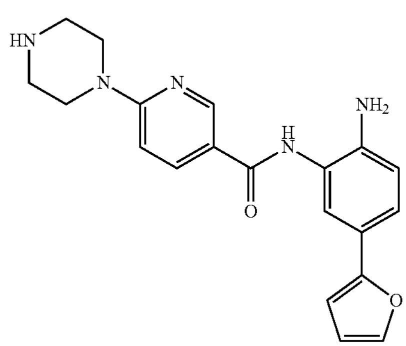 | 0.78 | 8.1 | 425 | 5783 | 105 |
| 014 | 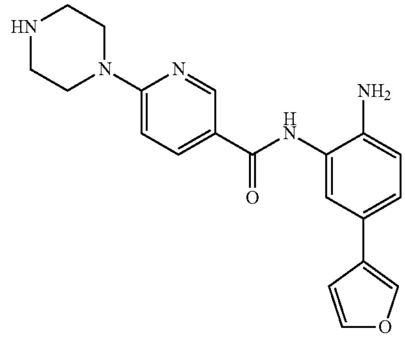 | 0.66 | 4.9 | 727 | 7097 | 97.0 |

TABLE 2-continued

| Compound No. | Structure | IV Clr. | PO T1/2 | PO Cmax | PO AUC | F% |
|---|---|---|---|---|---|---|
| 021 | 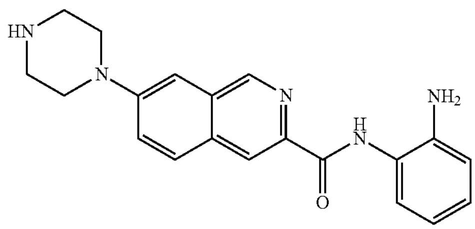 [SMILES: Nc1ccccc1NC(=O)c1cc2ccc(N3CCNCC3)cc2cn1] | 5.66 | 3.2 | 68 | 763 | 89.8 |
| 022 | 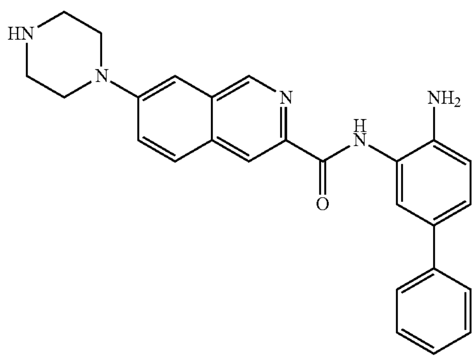 [SMILES: Nc1ccc(-c2ccccc2)cc1NC(=O)c1cc2ccc(N3CCNCC3)cc2cn1] | 0.98 | 13.5 | 517 | 8183 | 195 |
| 023 | 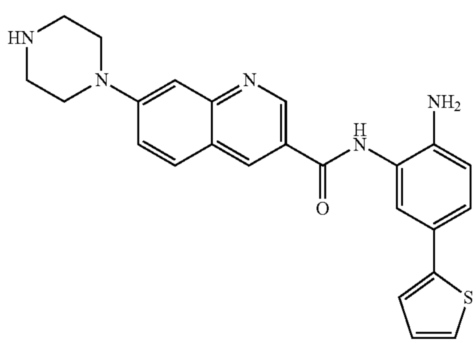 [SMILES: Nc1ccc(-c2cccs2)cc1NC(=O)c1cnc2cc(N3CCNCC3)ccc2c1] | 0.36 | 8.5 | 664 | 6368 | 51.2 |
| 024 | 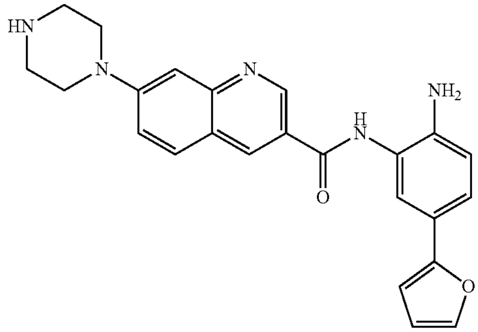 [SMILES: Nc1ccc(-c2ccco2)cc1NC(=O)c1cnc2cc(N3CCNCC3)ccc2c1] | 0.21 | 4.4 | 1000 | 8225 | 36.3 |

TABLE 2-continued
| Compound No. | Structure | IV Clr. | PO T1/2 | PO Cmax | PO AUC | F% |
|---|---|---|---|---|---|---|
| 027 | 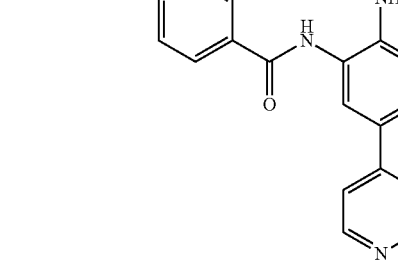 | 0.63 | 3.0 | 839 | 6191 | 78.6 |
| 030 | 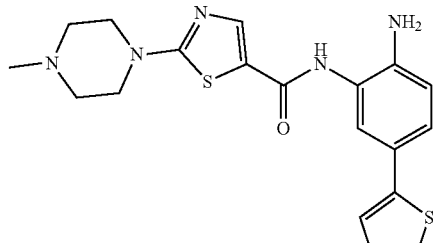 | 0.48 | 12.8 | 944 | 15260 | 170 |
| 032 | 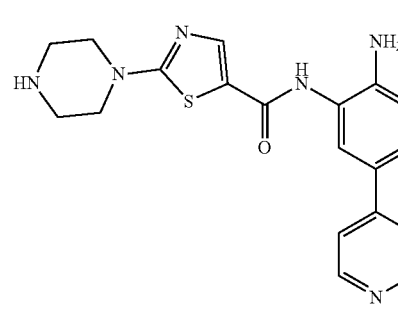 | 1.06 | 4.3 | 173 | 456 | 9.7 |
| 033 | 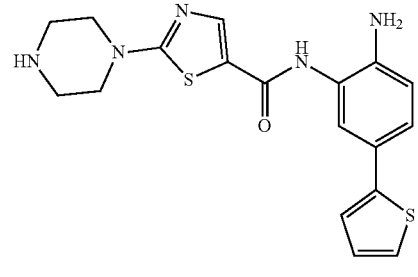 | 0.65 | 13.7 | 614 | 10714 | 191 |
| 035 | 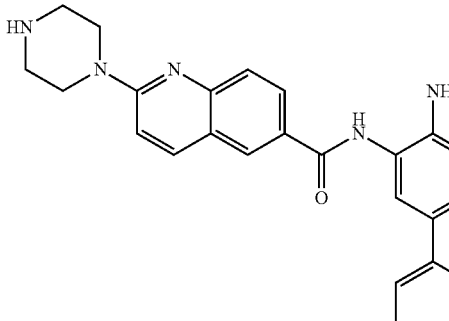 | 0.17 | 4.4 | 1870 | 20150 | 70.5 |

TABLE 2-continued

| Compound No. | Structure | IV Clr. | PO T1/2 | PO Cmax | PO AUC | F% |
|---|---|---|---|---|---|---|
| 036 | 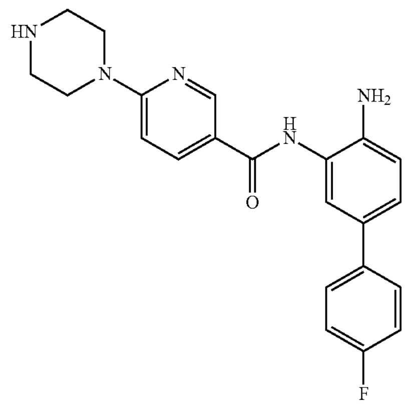 | 0.42 | 7.3 | 500 | 7282 | 69.1 |
| 040 | 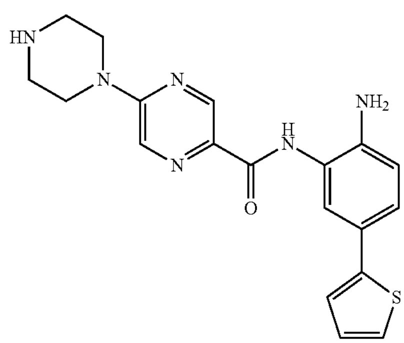 | 1.6 | 16.7 | 211 | 3338 | 151 |

Example 92—hERG and Cyp Inhibition

For hERG inhibition assays, the cells used were HEK293 cells stably transfected with hERG (cell line obtained from Cytocentrics Inc. 3463 Magic Drive San Antonio, Tex. 78229). Composition of External Solution: NaCl, 137 mM; KCl, 4 mM; MgCl2, 1.0 mM; CaCl2, 1.8 mM; HEPES 10 mM; Dextrose 11 mM; Adjusted to a pH of 7.4 with NaOH. Composition of Internal Solution: KCl, 130.0 mM; MgCl2, 1.0 mM; HEPES, 5.0 mM; EGTA, 5.0 mM; NaCl 7.0 mM. Adjusted to a pH of 7.2 using KOH. Test Concentrations: 0.1, 1, 10, 100 μM. Vehicle: DMSO. Experiments were performed at 34+/−1° C. Current was recorded using the whole-cell patch clamp technique on the Cytopatch automated platform. hERG current was elicited with the following voltage protocol: hERG current amplitude was measured as the peak current at −50 mV (tail current). The percent blockade of hERG was measured as current reduction after a steady-state effect had been reached in the presence of drug relative to current amplitude before drug was introduced (control). Each cell served as its own control. Data are presented as the IC50 calculated by non-linear regression analysis.

For Cyp inhibition, human liver microsomes from BD Gentest were incubated with Compound 028 or Compound 032 (10, 3.33, 1.11, 0.37, 0.12, 0.04, 0.01 μM) and substrate (CYP1A2: Phenacetin at 30 μM; CYP2C$_9$: Diclofenac at 10 μM; CYP2C$_{19}$: S-Mephenytoin at 35 μM; CYP3A4: Midazolam at 5 μM and Testosterone at 80 μM; CYP2D6: Bufuralol at 10 μM) for the following incubation times: CYP1A2, 2C9, 2D6: 10 minutes, 37° C.; CYP2C19: 45 minutes, 37° C.; CYP3A4: 5 minutes, 37° C. Substrate conversion was measured by liquid chromatography/mass spectrometry/mass spectrometry (LC/MS/MS). Inhibition was calculated by curve fitting in Graph Pad Prism.

A summary of results is presented in Table 3, below. A -- indicates that the compound was not tested.

TABLE 3

| Compound ID | Structure | hERG (IC$_{50}$) | Cyp (IC$_{50}$) |
|---|---|---|---|
| 001 | 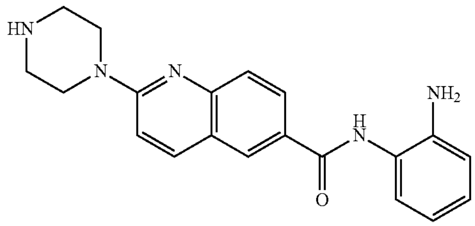 [SMILES: Nc1ccccc1NC(=O)c1ccc2nc(N3CCNCC3)ccc2c1] | >30 μM | — |
| 003 | 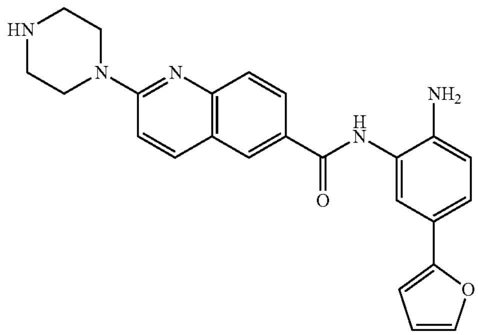 [SMILES: Nc1ccc(-c2ccco2)cc1NC(=O)c1ccc2nc(N3CCNCC3)ccc2c1] | 7.6 μM | >10 μM (all isozymes) |
| 006 | 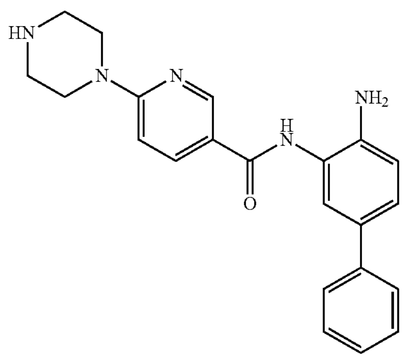 | 5.1 μM | >10 μM (all isozymes) |
| 007 | 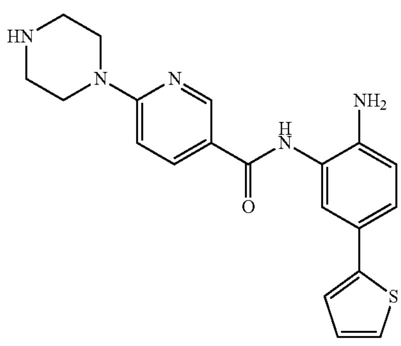 | 8.6 μM | >10 μM (all isozymes) |
| 021 | 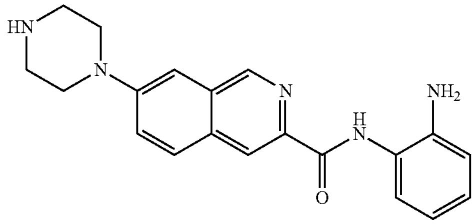 [SMILES: Nc1ccccc1NC(=O)c1cc2ccc(N3CCNCC3)cc2cn1] | 4.2 μM | — |

TABLE 3-continued

| Compound ID | Structure | hERG (IC$_{50}$) | Cyp (IC$_{50}$) |
|---|---|---|---|
| 022 | 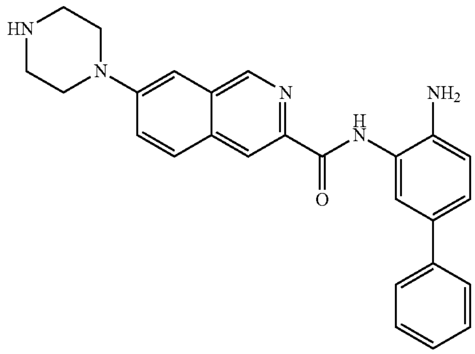 [SMILES: Nc1ccc(-c2ccccc2)cc1NC(=O)c1cc2ccc(N3CCNCC3)cc2cn1] | 0.4 μM | >10 μM (all isozymes) |
| 025 | 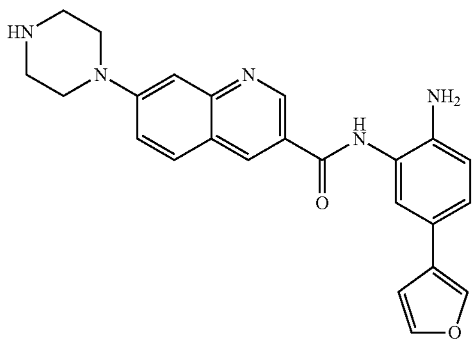 [SMILES: Nc1ccc(-c2ccoc2)cc1NC(=O)c1cnc2cc(N3CCNCC3)ccc2c1] | 8.9 μM | >10 μM (all isozymes) |
| 026 | 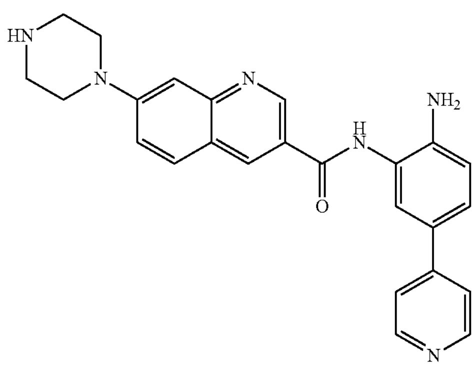 [SMILES: Nc1ccc(-c2ccncc2)cc1NC(=O)c1cnc2cc(N3CCNCC3)ccc2c1] | >100 μM | — |
| 027 | 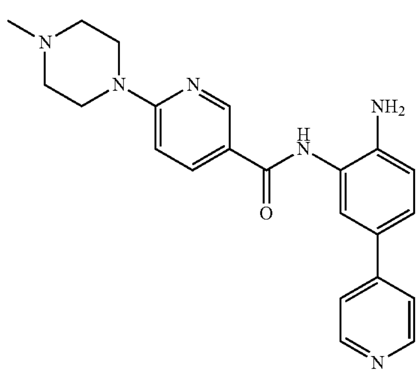 [SMILES: CN1CCN(c2ccc(C(=O)Nc3cc(-c4ccncc4)ccc3N)cn2)CC1] | >100 μM | >10 μM (all isozymes) |

TABLE 3-continued

| Compound ID | Structure | hERG (IC$_{50}$) | Cyp (IC$_{50}$) |
|---|---|---|---|
| 028 | 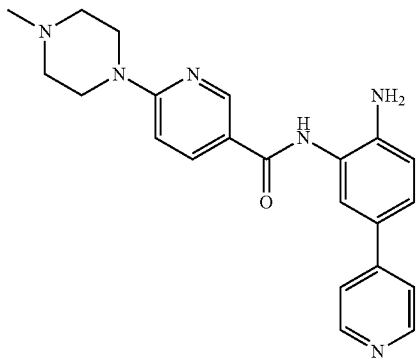 | 38 μM | 5.9 μM (3A4/midazolam) |
| 029 | 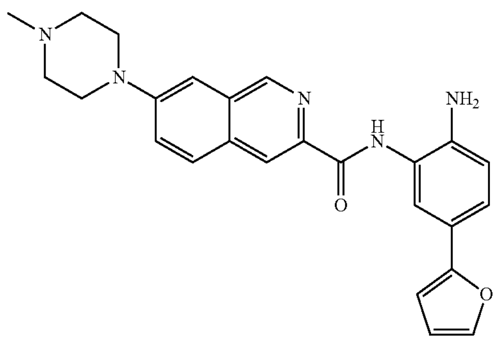 [SMILES: CN1CCN(c2ccc3cc(C(=O)Nc4cc(-c5ccco5)ccc4N)ncc3c2)CC1] | 5.2 μM | — |
| 030 | 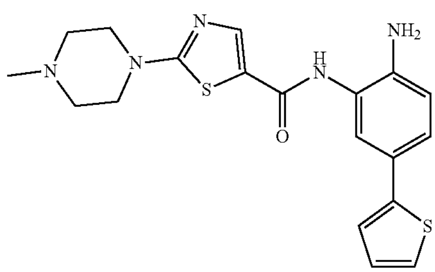 [SMILES: CN1CCN(c2ncc(C(=O)Nc3cc(-c4cccs4)ccc3N)s2)CC1] | 70 μM | >10 μM (all isozymes) |
| 031 | 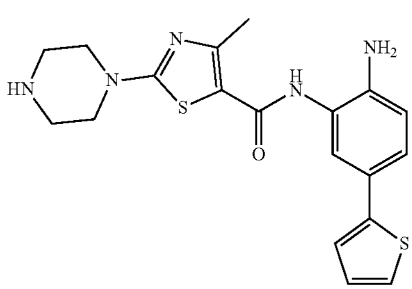 [SMILES: Cc1nc(N2CCNCC2)sc1C(=O)Nc1cc(-c2cccs2)ccc1N] | 12 μM | >10 μM (all isozymes) |
| 032 | 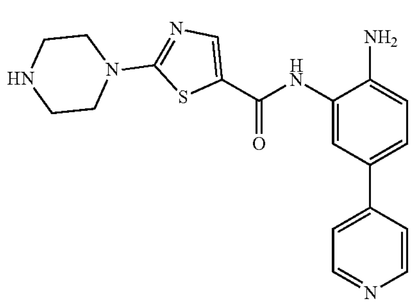 [SMILES: Nc1ccc(-c2ccncc2)cc1NC(=O)c1cnc(N2CCNCC2)s1] | 12 μM | 9.5 μM (3A4/midazolam) |

TABLE 3-continued

| Compound ID | Structure | hERG (IC$_{50}$) | Cyp (IC$_{50}$) |
|---|---|---|---|
| 038 | 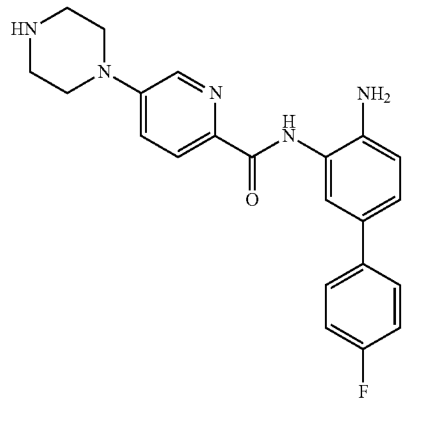 [SMILES: Nc1ccc(-c2ccc(F)cc2)cc1NC(=O)c1ccc(N2CCNCC2)cn1] | 2.5 | — |
| 039 | 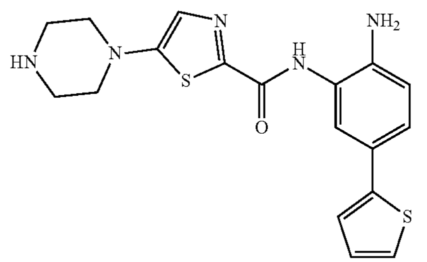 | 3.6 | — |

Example 93—HDAC Enzyme Assays

Compounds for testing were diluted in DMSO to 50 fold the final concentration and a ten-point three-fold dilution series was made. The compounds were diluted in assay buffer (50 mM HEPES, pH 7.4, 100 mM KCl, 0.001% Tween-20, 0.05% BSA, 20 µM TCEP) to 6-fold their final concentration. The HDAC enzymes (purchased from BPS Biosciences) were diluted to 1.5-fold their final concentration in assay buffer. The tripeptide substrate and trypsin at 0.05 µM final concentration were diluted in assay buffer at 6-fold their final concentration. The final enzyme concentrations used in these assays were 3.3 ng/ml (HDAC1), 0.2 ng/ml (HDAC2) and 0.08 ng/ml (HDAC3). The final substrate concentrations used were 16 µM (HDAC1), 10 µM (HDAC2) and 17 µM (HDAC3).

Five µl of compounds and 20 µl of enzyme were added to wells of a black, opaque 384 well plate in duplicate. Enzyme and compound were incubated together at room temperature for 10 minutes. Five µl of substrate was added to each well, the plate was shaken for 60 seconds and placed into a Victor 2 microtiter plate reader. The development of fluorescence was monitored for 60 min and the linear rate of the reaction was calculated. The IC$_{50}$ was determined using Graph Pad Prism by a four parameter curve fit. In Table 4 below, letter designations are defined as follows: A=IC$_{50}$ value<10 nM, B=IC$_{50}$ value between 10 and 500 nM, C=IC$_{50}$ value>500 nM.

TABLE 4

| Compound ID | Structure | HDAC1 | HDAC2 | HDAC3 |
|---|---|---|---|---|
| 034 | 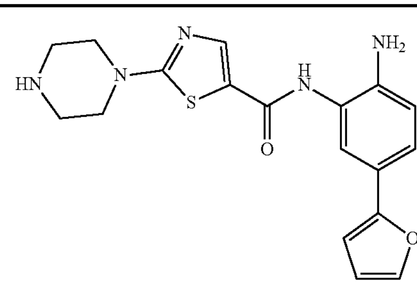 | A | B | B |

| Compound ID | Structure | HDAC1 | HDAC2 | HDAC3 |
|---|---|---|---|---|
| 035 | 2-(piperazin-1-yl)-N-(2-amino-4'-fluoro-[1,1'-biphenyl]-3-yl)quinoline-6-carboxamide | A | B | B |
| 036 | 6-(piperazin-1-yl)-N-(2-amino-4'-fluoro-[1,1'-biphenyl]-3-yl)nicotinamide | A | B | B |
| 037 | 2-(piperazin-1-yl)-N-(2-amino-4'-fluoro-[1,1'-biphenyl]-3-yl)thiazole-5-carboxamide | A | B | B |
| 038 | 5-(piperazin-1-yl)-N-(2-amino-4'-fluoro-[1,1'-biphenyl]-3-yl)picolinamide | A | B | B |

TABLE 4-continued
| Compound ID | Structure | HDAC1 | HDAC2 | HDAC3 |
|---|---|---|---|---|
| 039 | 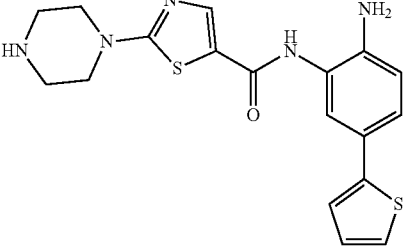 [SMILES: Nc1ccc(-c2cccs2)cc1NC(=O)c1ncc(N2CCNCC2)s1] | A | A | B |
| 040 | 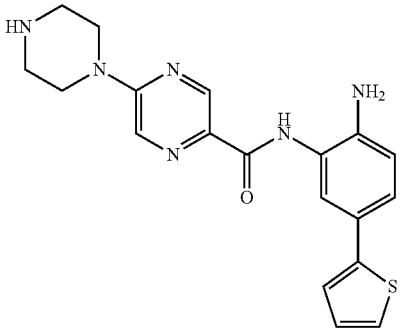 | A | A | B |
| 041 | 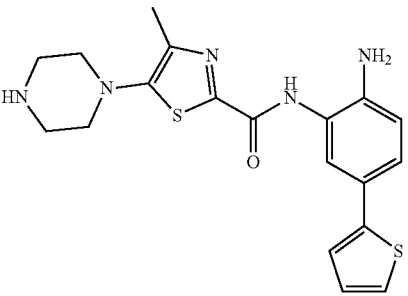 [SMILES: Cc1nc(C(=O)Nc2cc(-c3cccs3)ccc2N)sc1N1CCNCC1] | A | B | B |
| 042 | 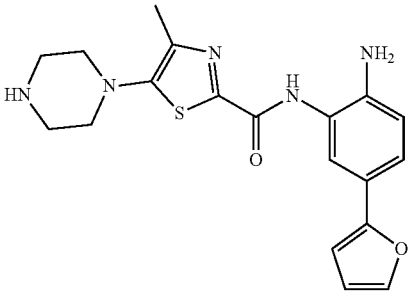 [SMILES: Cc1nc(C(=O)Nc2cc(-c3ccco3)ccc2N)sc1N1CCNCC1] | A | B | B |
| 043 | 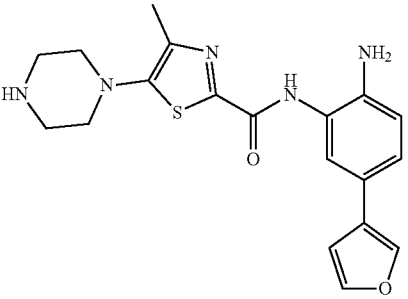 [SMILES: Cc1nc(C(=O)Nc2cc(-c3ccoc3)ccc2N)sc1N1CCNCC1] | A | B | C |

TABLE 4-continued

| Compound ID | Structure | HDAC1 | HDAC2 | HDAC3 |
|---|---|---|---|---|
| 044 | 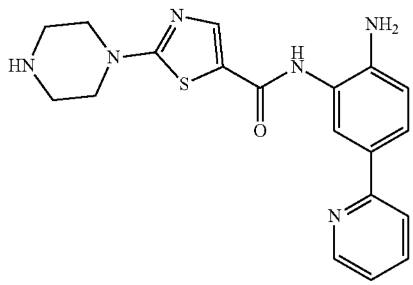 [SMILES: Nc1ccc(-c2ccccn2)cc1NC(=O)c1cnc(N2CCNCC2)s1] | B | B | C |
| 045 | 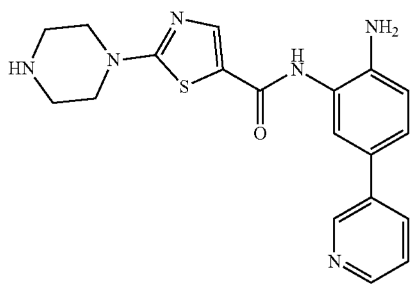 [SMILES: Nc1ccc(-c2cccnc2)cc1NC(=O)c1cnc(N2CCNCC2)s1] | B | B | B |
| 046 | 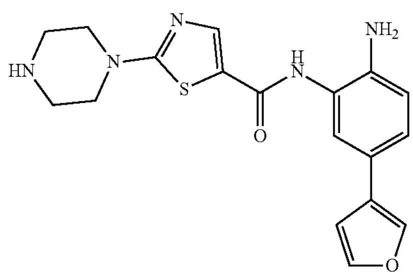 [SMILES: Nc1ccc(-c2ccoc2)cc1NC(=O)c1cnc(N2CCNCC2)s1] | A | B | B |
| 047 | 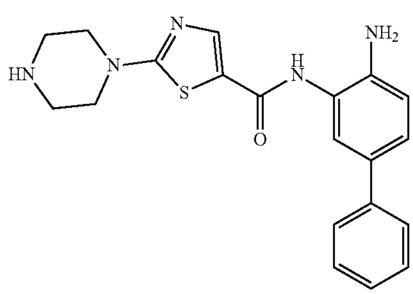 | A | B | C |
| 048 | 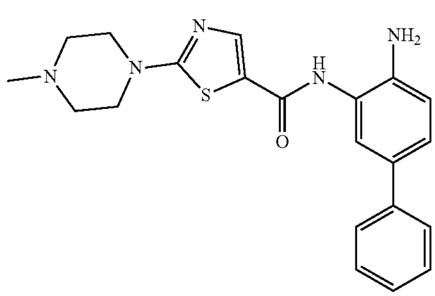 [SMILES: CN1CCN(c2ncc(C(=O)Nc3cc(-c4ccccc4)ccc3N)s2)CC1] | A | B | C |

TABLE 4-continued

| Compound ID | Structure | HDAC1 | HDAC2 | HDAC3 |
| --- | --- | --- | --- | --- |
| 049 | 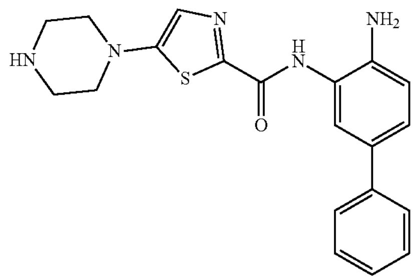 [SMILES: Nc1ccc(-c2ccccc2)cc1NC(=O)c1ncc(N2CCNCC2)s1] | A | B | B |
| 050 | 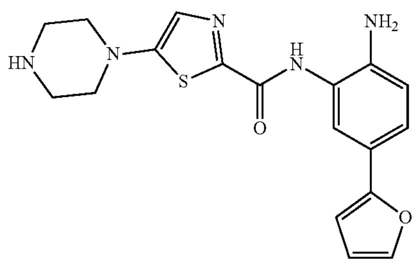 [SMILES: Nc1ccc(-c2ccco2)cc1NC(=O)c1ncc(N2CCNCC2)s1] | A | B | B |
| 051 | 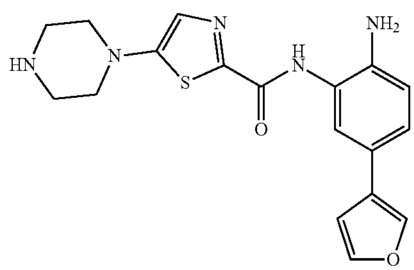 [SMILES: Nc1ccc(-c2ccoc2)cc1NC(=O)c1ncc(N2CCNCC2)s1] | A | A | B |
| 052 | 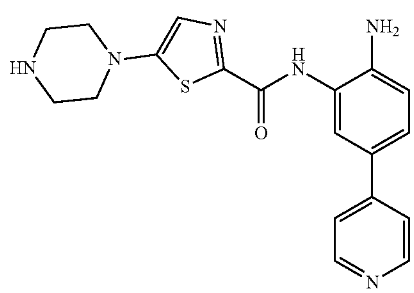 [SMILES: Nc1ccc(-c2ccncc2)cc1NC(=O)c1ncc(N2CCNCC2)s1] | A | B | B |
| 053 | 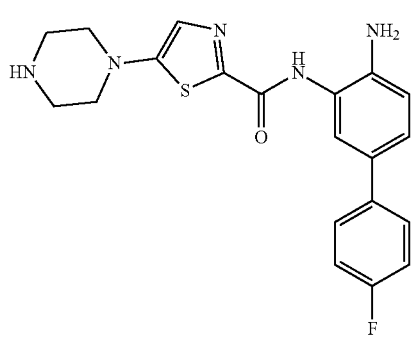 [SMILES: Nc1ccc(-c2ccc(F)cc2)cc1NC(=O)c1ncc(N2CCNCC2)s1] | A | A | B |

TABLE 4-continued
| Compound ID | Structure | HDAC1 | HDAC2 | HDAC3 |
|---|---|---|---|---|
| 054 | 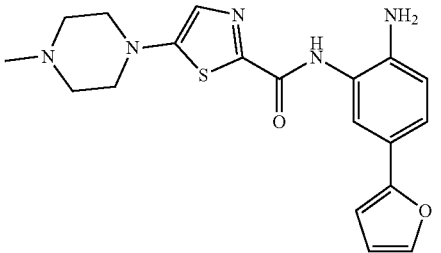 [SMILES: CN1CCN(c2cnc(C(=O)Nc3cc(-c4ccco4)ccc3N)s2)CC1] | A | B | B |
| 055 | 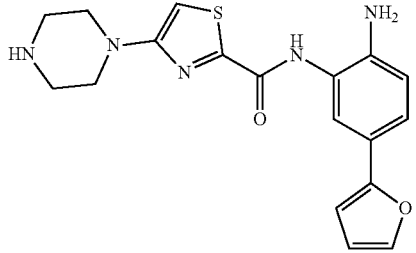 [SMILES: Nc1ccc(-c2ccco2)cc1NC(=O)c1nc(N2CCNCC2)cs1] | C | B | C |
| 056 | 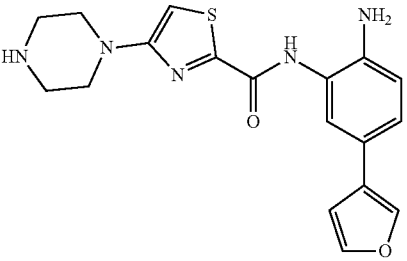 [SMILES: Nc1ccc(-c2ccoc2)cc1NC(=O)c1nc(N2CCNCC2)cs1] | B | B | C |
| 057 | 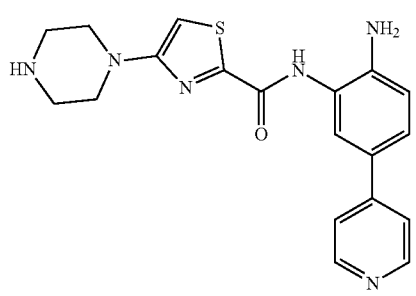 [SMILES: Nc1ccc(-c2ccncc2)cc1NC(=O)c1nc(N2CCNCC2)cs1] | C | B | C |
| 058 | 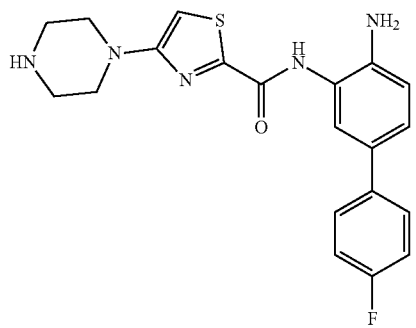 [SMILES: Nc1ccc(-c2ccc(F)cc2)cc1NC(=O)c1nc(N2CCNCC2)cs1] | B | B | B |

TABLE 4-continued
| Compound ID | Structure | HDAC1 | HDAC2 | HDAC3 |
|---|---|---|---|---|
| 059 | 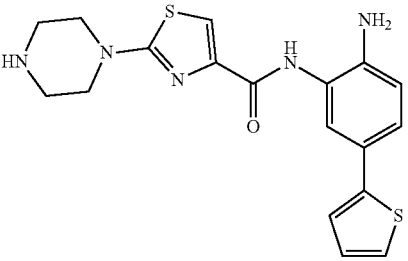 [SMILES: Nc1ccc(-c2cccs2)cc1NC(=O)c1csc(N2CCNCC2)n1] | C | B | B |
| 060 | 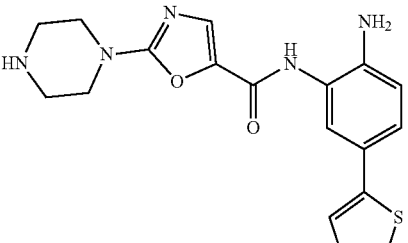 | C | C | C |
| 061 | 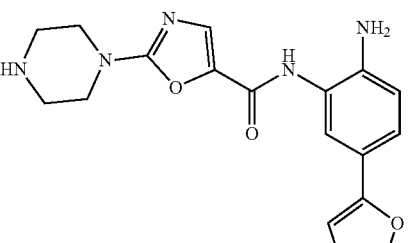 | C | C | C |
| 062 | 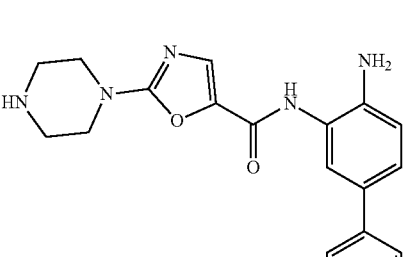 | C | C | C |
| 063 | 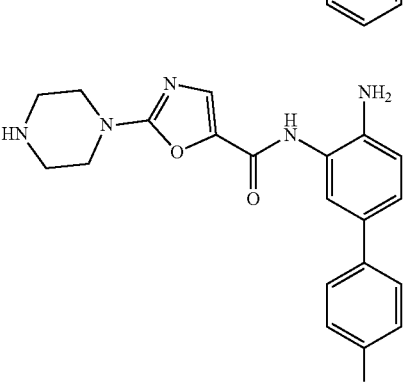 | C | C | C |

TABLE 4-continued

| Compound ID | Structure | HDAC1 | HDAC2 | HDAC3 |
|---|---|---|---|---|
| 064 | 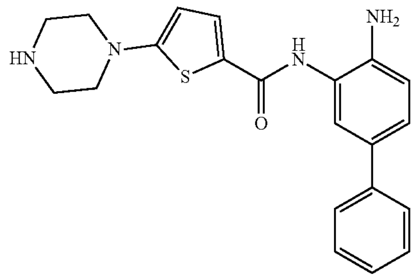 [SMILES: Nc1ccc(-c2ccccc2)cc1NC(=O)c1ccc(N2CCNCC2)s1] | A | B | B |
| 065 | 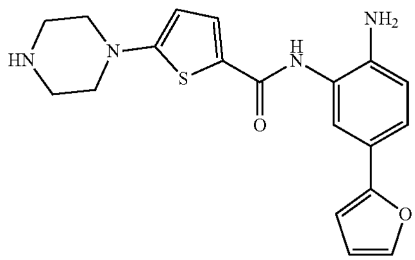 [SMILES: Nc1ccc(-c2ccco2)cc1NC(=O)c1ccc(N2CCNCC2)s1] | A | B | B |
| 066 | 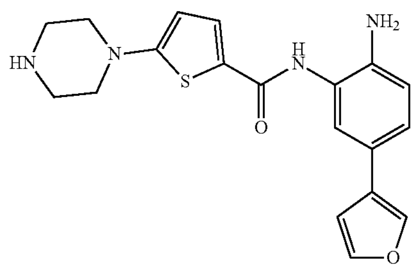 [SMILES: Nc1ccc(-c2ccoc2)cc1NC(=O)c1ccc(N2CCNCC2)s1] | A | B | B |
| 067 | 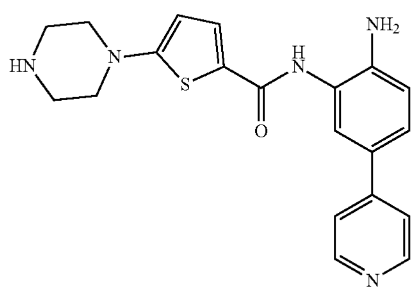 [SMILES: Nc1ccc(-c2ccncc2)cc1NC(=O)c1ccc(N2CCNCC2)s1] | A | B | B |
| 068 | 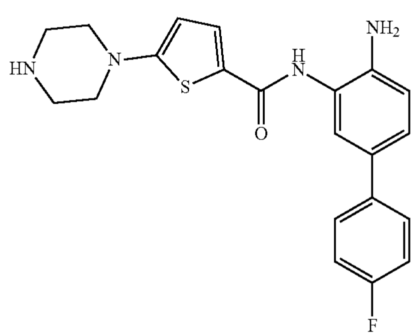 [SMILES: Nc1ccc(-c2ccc(F)cc2)cc1NC(=O)c1ccc(N2CCNCC2)s1] | A | B | B |

TABLE 4-continued

| Compound ID | Structure | HDAC1 | HDAC2 | HDAC3 |
|---|---|---|---|---|
| 069 | 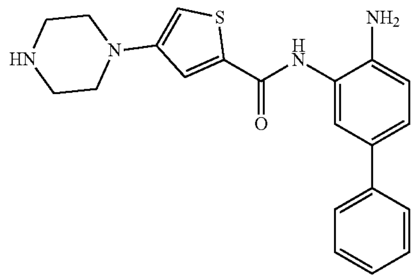 [SMILES: Nc1ccc(-c2ccccc2)cc1NC(=O)c1cc(N2CCNCC2)cs1] | B | B | C |
| 070 | 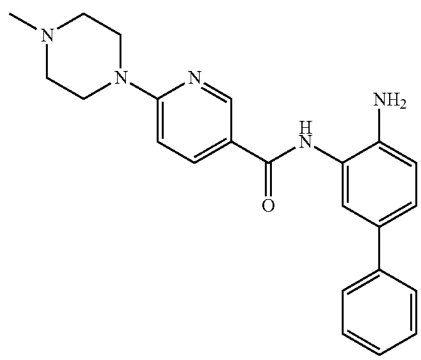 | A | B | B |
| 071 | 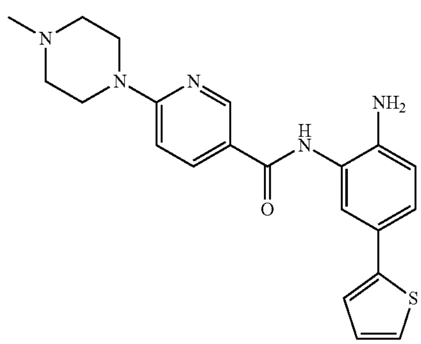 [SMILES: CN1CCN(c2ccc(C(=O)Nc3cc(-c4cccs4)ccc3N)cn2)CC1] | A | B | B |
| 072 | 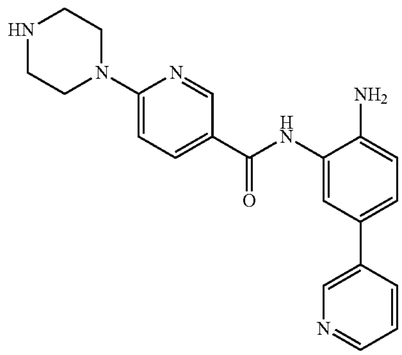 | B | B | B |

TABLE 4-continued

| Compound ID | Structure | HDAC1 | HDAC2 | HDAC3 |
|---|---|---|---|---|
| 073 | 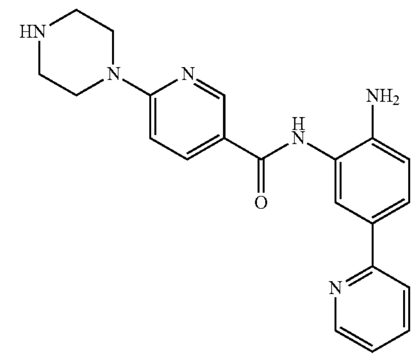 [SMILES: Nc1ccc(-c2ccccn2)cc1NC(=O)c1ccc(N2CCNCC2)nc1] | B | B | C |
| 074 | 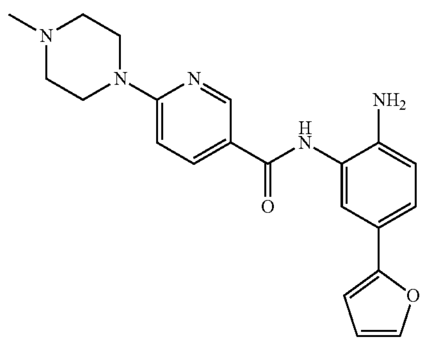 [SMILES: CN1CCN(c2ccc(C(=O)Nc3cc(-c4ccco4)ccc3N)cn2)CC1] | A | B | B |
| 075 | 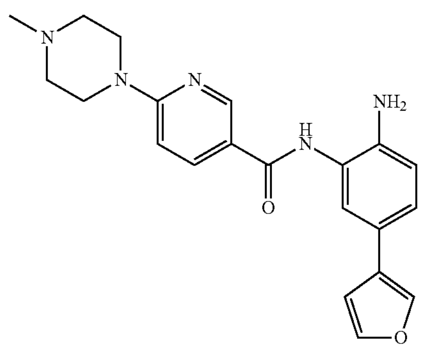 [SMILES: CN1CCN(c2ccc(C(=O)Nc3cc(-c4ccoc4)ccc3N)cn2)CC1] | A | B | B |
| 076 | 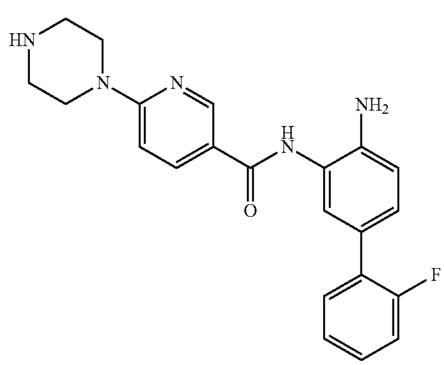 [SMILES: Nc1ccc(-c2ccccc2F)cc1NC(=O)c1ccc(N2CCNCC2)nc1] | A | B | B |

TABLE 4-continued

| Compound ID | Structure | HDAC1 | HDAC2 | HDAC3 |
|---|---|---|---|---|
| 077 | 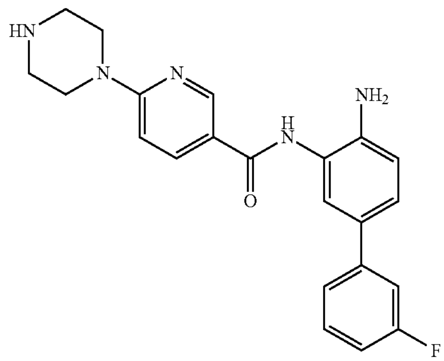 [SMILES: Nc1ccc(-c2cccc(F)c2)cc1NC(=O)c1ccc(N2CCNCC2)nc1] | B | B | B |
| 078 | 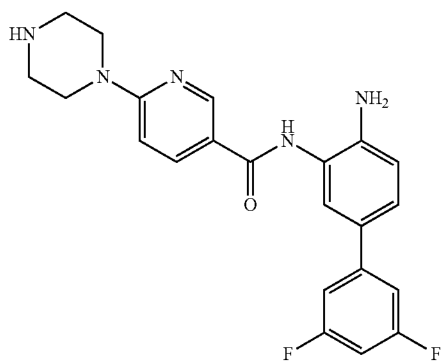 | C | B | C |
| 079 | 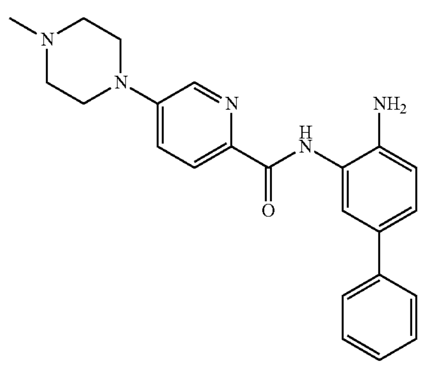 | A | B | B |
| 080 | 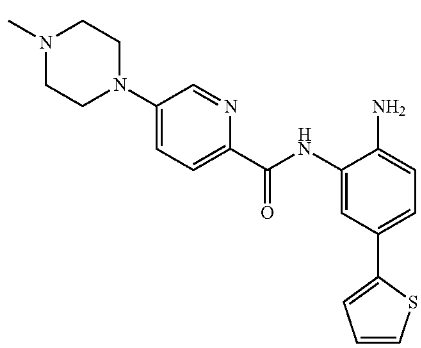 [SMILES: CN1CCN(c2ccc(C(=O)Nc3cc(-c4cccs4)ccc3N)nc2)CC1] | A | A | B |

TABLE 4-continued

| Compound ID | Structure | HDAC1 | HDAC2 | HDAC3 |
|---|---|---|---|---|
| 081 | 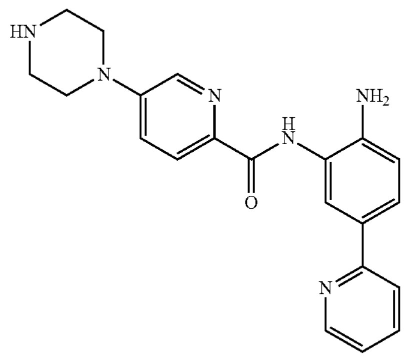 | B | B | C |
| 082 | 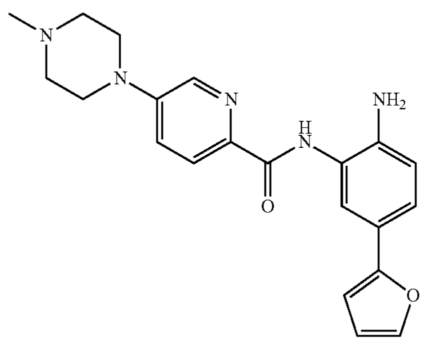 [SMILES: CN1CCN(c2ccc(C(=O)Nc3cc(-c4ccco4)ccc3N)nc2)CC1] | A | B | B |
| 083 | 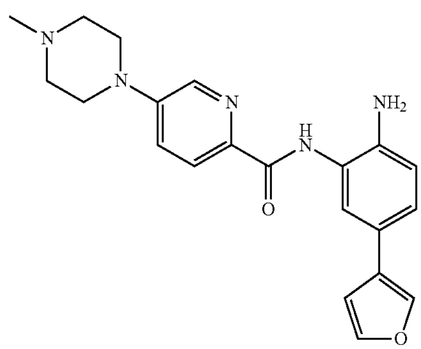 [SMILES: CN1CCN(c2ccc(C(=O)Nc3cc(-c4ccoc4)ccc3N)nc2)CC1] | A | B | B |
| 084 | 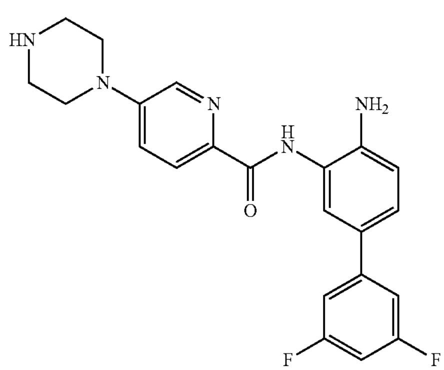 [SMILES: Nc1ccc(-c2cc(F)cc(F)c2)cc1NC(=O)c1ccc(N2CCNCC2)cn1] | C | C | C |

TABLE 4-continued
| Compound ID | Structure | HDAC1 | HDAC2 | HDAC3 |
|---|---|---|---|---|
| 085 | 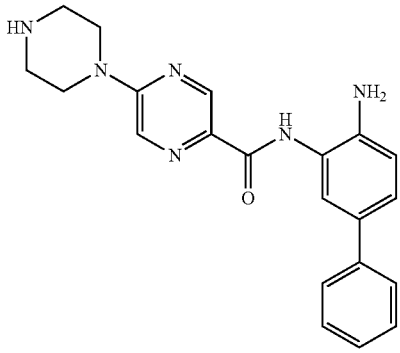 [SMILES: Nc1ccc(-c2ccccc2)cc1NC(=O)c1cnc(N2CCNCC2)cn1] | A | B | B |
| 086 | 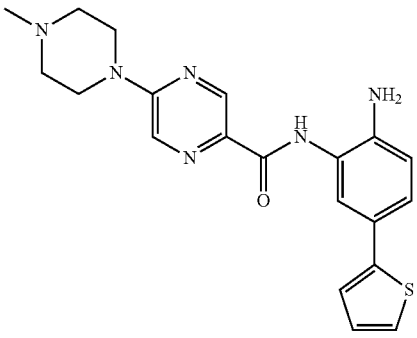 [SMILES: CN1CCN(c2cnc(C(=O)Nc3cc(-c4cccs4)ccc3N)cn2)CC1] | A | A | B |
| 087 | 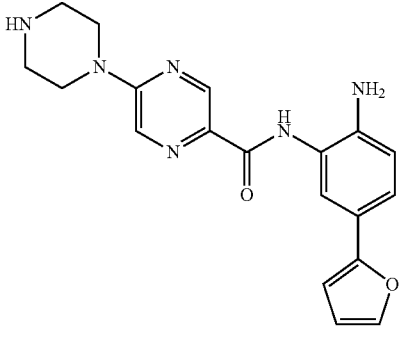 | A | B | B |
| 088 | 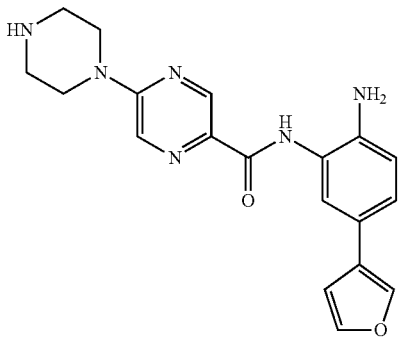 | A | B | B |

TABLE 4-continued

| Compound ID | Structure | HDAC1 | HDAC2 | HDAC3 |
|---|---|---|---|---|
| 089 | 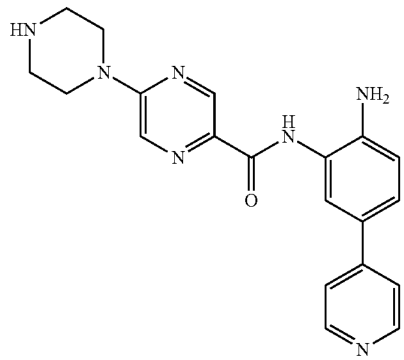 [SMILES: Nc1ccc(-c2ccncc2)cc1NC(=O)c1cnc(N2CCNCC2)cn1] | B | B | B |
| 090 | 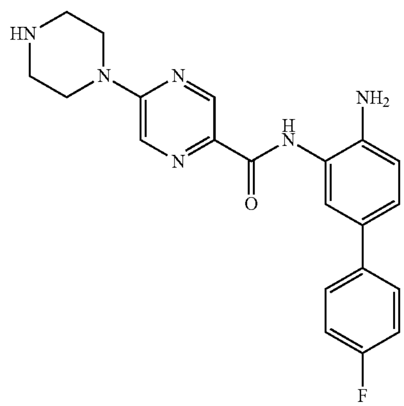 | A | B | B |

The invention claimed is:

1. A compound of Formula (III):

(III)

or a pharmaceutically acceptable salt thereof,
wherein:

$R^5$ is furanyl;

$R^6$ is H or $C_1$-$C_4$ alkyl, wherein the $C_1$-$C_4$ alkyl is optionally substituted with one or more substituents independently selected from the group consisting of halogen, CN, $NO_2$, $C_1$-$C_6$ alkyl, $C_1$-$C_6$ haloalkyl, C(O)—$C_1$-$C_6$ alkyl, and O$C_1$-$C_6$ alkyl;

X is CH;
Y is CH; and
Z is N.

2. The compound of claim 1, or a pharmaceutically acceptable salt thereof, wherein $R^6$ is $CH_3$.

3. The compound of claim 1, wherein the compound is:

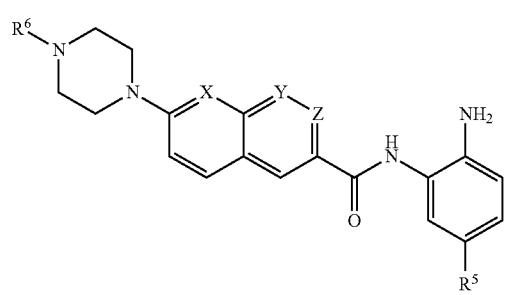

or a pharmaceutically acceptable salt thereof.

4. A pharmaceutical composition comprising a pharmaceutically acceptable carrier together with a compound of claim 1, or a pharmaceutically acceptable salt thereof.

* * * * *